(12) United States Patent
Macdonald et al.

(10) Patent No.: US 11,111,314 B2
(45) Date of Patent: Sep. 7, 2021

(54) NON-HUMAN ANIMALS THAT SELECT FOR LIGHT CHAIN VARIABLE REGIONS THAT BIND ANTIGEN

(71) Applicant: Regeneron Pharmaceuticals, Inc., Tarrytown, NY (US)

(72) Inventors: Lynn Macdonald, Harrison, NY (US); Andrew J. Murphy, Croton-on-Hudson, NY (US); Cagan Gurer, Chappaqua, NY (US); Robert Babb, River Edge, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 357 days.

(21) Appl. No.: 15/559,358

(22) PCT Filed: Mar. 18, 2016

(86) PCT No.: PCT/US2016/023289
§ 371 (c)(1),
(2) Date: Sep. 18, 2017

(87) PCT Pub. No.: WO2016/149678
PCT Pub. Date: Sep. 22, 2016

(65) Prior Publication Data
US 2018/0244804 A1 Aug. 30, 2018

Related U.S. Application Data

(60) Provisional application No. 62/135,419, filed on Mar. 19, 2015.

(51) Int. Cl.
| | | |
|---|---|---|
| *C07K 16/46* | (2006.01) | |
| *C07K 16/00* | (2006.01) | |
| *C07K 16/28* | (2006.01) | |
| *A01K 67/027* | (2006.01) | |

(52) U.S. Cl.
CPC ........ *C07K 16/468* (2013.01); *A01K 67/0278* (2013.01); *C07K 16/00* (2013.01); *C07K 16/28* (2013.01); *C07K 16/462* (2013.01); *A01K 2217/072* (2013.01); *A01K 2217/15* (2013.01); *A01K 2227/105* (2013.01); *A01K 2267/01* (2013.01); *C07K 2317/21* (2013.01); *C07K 2317/24* (2013.01); *C07K 2317/31* (2013.01); *C07K 2317/51* (2013.01); *C07K 2317/515* (2013.01); *C07K 2317/52* (2013.01); *C07K 2317/522* (2013.01); *C07K 2317/524* (2013.01); *C07K 2317/526* (2013.01); *C07K 2317/528* (2013.01); *C07K 2317/53* (2013.01); *C07K 2317/55* (2013.01); *C07K 2317/56* (2013.01); *C07K 2317/565* (2013.01);
(Continued)

(58) Field of Classification Search
CPC ...... C07K 16/468; C07K 16/00; C07K 16/28; C07K 16/462; C07K 2317/52; C07K 2317/21; C07K 2317/24; C07K 2317/55; C07K 2317/565; C07K 2317/567; C07K 2317/622; C07K 2317/51; C07K 2317/515; C07K 2317/522; C07K 2317/524; C07K 2317/526; C07K 2317/528; C07K 2317/53; C07K 2317/56; C07K 2317/569; C07K 2317/92; C07K 2317/31; A01K 67/0278; A01K 2217/072; A01K 2217/15; A01K 2227/105; A01K 2267/01

See application file for complete search history.

(56) References Cited

U.S. PATENT DOCUMENTS

| | | |
|---|---|---|
| 4,977,081 A | 12/1990 | Raybould et al. |
| 5,545,806 A | 8/1996 | Lonberg et al. |
| 5,545,807 A | 8/1996 | Surani et al. |

(Continued)

FOREIGN PATENT DOCUMENTS

| | | |
|---|---|---|
| CN | 1203922 A | 1/1999 |
| CN | 1560081 A | 1/2005 |

(Continued)

OTHER PUBLICATIONS

Gerlai R. "Gene Targeting Using Homologous Recombination in Embryonic Stem Cells: The Future for Behavior Genetics?"Front Genet. Apr. 11, 2016;7:43. (Year: 2016).*

(Continued)

*Primary Examiner* — Titilayo Moloye
(74) *Attorney, Agent, or Firm* — FisherBroyles, LLP; Rita S. Wu; Margarita Zippin

(57) ABSTRACT

Non-human animals, cells, methods and compositions for making and using the same are provided, wherein the non-human animals and cells comprise an immunoglobulin heavy chain locus that includes unrearranged human immunoglobulin light chain gene segments and an immunoglobulin light chain locus that includes a single rearranged human light chain variable region nucleotide sequence. The unrearranged human light chain gene segments may be operably linked to a heavy chain constant region nucleotide sequence and the rearranged human immunoglobulin light chain variable region nucleotide sequence may be operably linked to a light chain constant region nucleotide sequence. Also provided are methods for obtaining nucleic acid sequences that encode immunoglobulin light chain variable domains capable of binding an antigen in the absence of a cognate variable domain, and expressing such nucleic acid sequences in a host cell, e.g., to generate a multispecific antigen-binding protein.

25 Claims, 20 Drawing Sheets

Specification includes a Sequence Listing.

(52) U.S. Cl.
CPC .. *C07K 2317/567* (2013.01); *C07K 2317/569* (2013.01); *C07K 2317/622* (2013.01); *C07K 2317/92* (2013.01)

(56) References Cited

U.S. PATENT DOCUMENTS

| | | |
|---|---|---|
| 5,574,205 A | 11/1996 | Kucherlapati et al. |
| 5,667,988 A | 9/1997 | Barbas et al. |
| 5,770,429 A | 6/1998 | Lonberg et al. |
| 5,789,208 A | 8/1998 | Sharon |
| 5,800,988 A | 9/1998 | Casterman et al. |
| 5,840,526 A | 11/1998 | Casterman et al. |
| 5,874,541 A | 2/1999 | Casterman et al. |
| 5,888,789 A | 3/1999 | Rodriguez |
| 5,939,598 A | 8/1999 | Kucherlapati et al. |
| 5,942,435 A | 8/1999 | Wheeler |
| 6,005,079 A | 12/1999 | Casterman et al. |
| 6,015,695 A | 1/2000 | Casterman et al. |
| 6,075,181 A | 6/2000 | Kucherlapati et al. |
| 6,080,560 A | 6/2000 | Russell et al. |
| 6,096,551 A | 8/2000 | Barbas et al. |
| 6,114,598 A | 9/2000 | Kucherlapati et al. |
| 6,139,835 A | 10/2000 | Kucherlapati et al. |
| 6,150,584 A | 11/2000 | Kucherlapati et al. |
| 6,162,963 A | 12/2000 | Kucherlapati et al. |
| 6,461,818 B1 | 10/2002 | Bradley et al. |
| 6,514,752 B1 | 2/2003 | Kucherlapati et al. |
| 6,551,592 B2 | 4/2003 | Lindhofer et al. |
| 6,586,251 B2 | 7/2003 | Economides et al. |
| 6,596,541 B2 | 7/2003 | Murphy et al. |
| 6,632,976 B1 | 10/2003 | Tomizuka et al. |
| 6,657,103 B1 | 12/2003 | Kucherlapati et al. |
| 6,673,986 B1 | 1/2004 | Kucherlapati et al. |
| 6,713,610 B1 | 3/2004 | Kucherlapati et al. |
| 6,765,087 B1 | 7/2004 | Casterman et al. |
| 6,774,279 B2 | 8/2004 | Dymecki |
| 6,914,128 B1 | 7/2005 | Salfeld et al. |
| 6,998,514 B2 | 2/2006 | Bruggemann |
| 7,052,873 B2 | 5/2006 | Tsuchiya |
| 7,064,244 B2 | 6/2006 | Jakobovits et al. |
| 7,067,284 B1 | 6/2006 | Barbas et al. |
| 7,084,260 B1 | 8/2006 | Lonberg et al. |
| 7,105,348 B2 | 9/2006 | Murphy et al. |
| 7,119,248 B1 | 10/2006 | Rajewsky et al. |
| 7,129,084 B2 | 10/2006 | Buelow et al. |
| 7,183,076 B2 | 2/2007 | Arathoon et al. |
| 7,262,028 B2 | 8/2007 | Van Berkel et al. |
| 7,294,754 B2 | 11/2007 | Poueymirou et al. |
| 7,435,871 B2 | 10/2008 | Green et al. |
| 7,501,552 B2 | 3/2009 | Lonberg et al. |
| 7,534,604 B2 | 5/2009 | Fandl et al. |
| 7,582,298 B2 | 9/2009 | Stevens et al. |
| 7,585,668 B2 | 9/2009 | Buelow et al. |
| 7,605,237 B2 | 10/2009 | Stevens et al. |
| 7,642,228 B2 | 1/2010 | Carter et al. |
| 7,704,498 B2 | 4/2010 | Gerritsen et al. |
| 7,879,985 B2 | 2/2011 | Urso et al. |
| 7,910,798 B2 | 3/2011 | Tanamachi et al. |
| 7,919,257 B2 | 4/2011 | Hoogenboom et al. |
| 7,932,431 B2 | 4/2011 | Bruggemann |
| 8,158,419 B2 | 4/2012 | Lonberg et al. |
| 8,502,018 B2 | 8/2013 | Murphy et al. |
| 8,568,992 B2 | 10/2013 | Walker et al. |
| 8,586,713 B2 | 11/2013 | Davis et al. |
| 8,592,562 B2 | 11/2013 | Kannan et al. |
| 8,629,317 B2 | 1/2014 | Cogne et al. |
| 8,642,835 B2 | 2/2014 | Macdonald et al. |
| 8,697,940 B2 | 4/2014 | Macdonald et al. |
| 8,754,287 B2 | 6/2014 | Macdonald et al. |
| 9,248,182 B2 | 2/2016 | De Kruif et al. |
| 9,315,824 B2 | 4/2016 | Kuroiwa et al. |
| 9,365,655 B2 | 6/2016 | Craig et al. |
| 9,516,868 B2 | 12/2016 | Macdonald et al. |
| 9,686,970 B2 | 6/2017 | Macdonald et al. |
| 2002/0026036 A1 | 2/2002 | Shitara et al. |
| 2002/0088016 A1 | 7/2002 | Bruggemann |
| 2002/0106628 A1 | 8/2002 | Economides et al. |
| 2002/0106629 A1 | 8/2002 | Economides et al. |
| 2003/0017534 A1 | 1/2003 | Buelow et al. |
| 2003/0078385 A1 | 4/2003 | Arathoon et al. |
| 2003/0103970 A1 | 6/2003 | Tsuchiya |
| 2003/0108925 A1 | 6/2003 | Dix et al. |
| 2003/0109021 A1 | 6/2003 | Wu et al. |
| 2003/0138440 A1 | 7/2003 | Fang et al. |
| 2003/0217373 A1 | 11/2003 | Green et al. |
| 2004/0015880 A1 | 1/2004 | Floyd et al. |
| 2004/0018626 A1 | 1/2004 | Murphy et al. |
| 2004/0052773 A1 | 3/2004 | Bogen et al. |
| 2004/0101920 A1 | 5/2004 | Radziejewski et al. |
| 2004/0146991 A1 | 7/2004 | Tsuji et al. |
| 2005/0059082 A1 | 3/2005 | Breitling et al. |
| 2005/0060763 A1 | 3/2005 | Bruggeman et al. |
| 2005/0153392 A1 | 7/2005 | Buelow et al. |
| 2005/0170398 A1 | 8/2005 | Van Berkel et al. |
| 2005/0229263 A1 | 10/2005 | Buelow |
| 2005/0246782 A1 | 11/2005 | Etches et al. |
| 2006/0015949 A1 | 1/2006 | Lonberg et al. |
| 2006/0015957 A1 | 1/2006 | Lonberg et al. |
| 2006/0015958 A1 | 1/2006 | Kuroiwa et al. |
| 2006/0021074 A1 | 1/2006 | Kellermann et al. |
| 2006/0026696 A1 | 2/2006 | Buelow et al. |
| 2006/0083747 A1 | 4/2006 | Winter |
| 2006/0099207 A1 | 5/2006 | Wu et al. |
| 2006/0106203 A1 | 5/2006 | Winter |
| 2006/0117398 A1 | 6/2006 | Buelow et al. |
| 2006/0153826 A1 | 7/2006 | Arnould et al. |
| 2006/0199204 A1 | 9/2006 | Dix et al. |
| 2006/0257406 A1 | 11/2006 | Winter |
| 2006/0280734 A1 | 12/2006 | Winter |
| 2007/0009957 A1 | 1/2007 | Bowdish et al. |
| 2007/0196363 A1 | 8/2007 | Arathoon et al. |
| 2007/0209083 A1 | 9/2007 | Thiam et al. |
| 2007/0275466 A1 | 11/2007 | Economides et al. |
| 2007/0280945 A1 | 12/2007 | Stevens et al. |
| 2008/0069822 A1 | 3/2008 | Jensen et al. |
| 2008/0267982 A1 | 10/2008 | Kiselev et al. |
| 2009/0083871 A1* | 3/2009 | Etches .................. C07K 16/00 800/19 |
| 2009/0083879 A1 | 3/2009 | Dhugga |
| 2009/0092582 A1 | 4/2009 | Bogin et al. |
| 2009/0093059 A1 | 4/2009 | Baszczynski et al. |
| 2009/0181855 A1 | 7/2009 | Vasquez et al. |
| 2009/0258392 A1 | 10/2009 | Gallo et al. |
| 2009/0271880 A1 | 10/2009 | Grosveld et al. |
| 2010/0069614 A1 | 3/2010 | Houtzager et al. |
| 2010/0122358 A1 | 5/2010 | Bruggermann |
| 2010/0146647 A1 | 6/2010 | Logtenberg et al. |
| 2010/0196367 A1 | 8/2010 | Day |
| 2010/0254988 A1 | 10/2010 | Bossenmaier et al. |
| 2010/0254989 A1 | 10/2010 | Bossenmaier et al. |
| 2010/0286374 A1 | 11/2010 | Kannan et al. |
| 2010/0298542 A1 | 11/2010 | Igawa et al. |
| 2010/0310586 A1 | 12/2010 | Dolcetti et al. |
| 2010/0331527 A1 | 12/2010 | Davis et al. |
| 2011/0123527 A1 | 5/2011 | Shizuya et al. |
| 2011/0138489 A1 | 6/2011 | Tanamachi et al. |
| 2011/0145937 A1 | 6/2011 | Macdonald et al. |
| 2011/0195454 A1 | 8/2011 | McWhirter et al. |
| 2011/0236378 A1 | 9/2011 | Green et al. |
| 2011/0283376 A1 | 11/2011 | Murphy et al. |
| 2011/0314563 A1 | 12/2011 | Craig et al. |
| 2012/0021409 A1 | 1/2012 | McWhirter et al. |
| 2012/0047585 A1 | 2/2012 | Rohrer et al. |
| 2012/0070861 A1 | 3/2012 | Macdonald et al. |
| 2012/0073004 A1 | 3/2012 | Macdonald et al. |
| 2012/0096572 A1 | 4/2012 | Macdonald et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2012/0222140 A1 | 8/2012 | Kuroiwa et al. |
| 2012/0272344 A1 | 10/2012 | Tanamachi et al. |
| 2012/0322108 A1 | 12/2012 | Macdonald et al. |
| 2013/0045492 A1 | 2/2013 | Babb et al. |
| 2013/0096020 A1 | 4/2013 | Throsby et al. |

(56) References Cited

U.S. PATENT DOCUMENTS

| | | |
|---|---|---|
| 2013/0096287 A1 | 4/2013 | Macdonald et al. |
| 2013/0145484 A1 | 6/2013 | Logtenberg et al. |
| 2013/0185821 A1 | 7/2013 | Babb et al. |
| 2013/0198879 A1 | 8/2013 | McWhirter et al. |
| 2013/0198880 A1 | 8/2013 | Babb et al. |
| 2013/0212719 A1 | 8/2013 | Macdonald et al. |
| 2013/0243759 A1 | 9/2013 | Friedrich et al. |
| 2013/0243773 A1 | 9/2013 | Van Berkel et al. |
| 2013/0247234 A1 | 9/2013 | McWhirter et al. |
| 2013/0263292 A1 | 10/2013 | Liang et al. |
| 2013/0263293 A1 | 10/2013 | Bradley et al. |
| 2013/0302836 A1 | 11/2013 | McWhirter et al. |
| 2013/0318643 A1 | 11/2013 | Bradley et al. |
| 2013/0323235 A1 | 12/2013 | Craig et al. |
| 2014/0243504 A1 | 8/2014 | Davis et al. |
| 2014/0245468 A1 | 8/2014 | McWhirter et al. |
| 2014/0283150 A1 | 9/2014 | Bradley et al. |
| 2014/0289876 A1 | 9/2014 | Macdonald et al. |
| 2014/0310828 A1 | 10/2014 | Lee et al. |
| 2014/0322756 A1 | 10/2014 | Arathoon et al. |
| 2015/0059009 A1 | 2/2015 | McWhirter et al. |
| 2015/0133641 A1 | 5/2015 | Germaschewski et al. |
| 2015/0196015 A1 | 7/2015 | Macdonald et al. |
| 2015/0197553 A1 | 7/2015 | Macdonald et al. |
| 2015/0197554 A1 | 7/2015 | Macdonald et al. |
| 2015/0197555 A1 | 7/2015 | Macdonald et al. |
| 2015/0197556 A1 | 7/2015 | Macdonald et al. |
| 2015/0197557 A1 | 7/2015 | Macdonald et al. |
| 2015/0201589 A1 | 7/2015 | Macdonald et al. |
| 2015/0210776 A1 | 7/2015 | Macdonald et al. |
| 2015/0250152 A1 | 9/2015 | Jakobovits et al. |
| 2015/0266976 A1 | 9/2015 | Babb et al. |
| 2015/0289489 A1 | 10/2015 | Macdonald et al. |
| 2015/0313193 A1 | 11/2015 | McWhirter et al. |
| 2016/0219847 A1 | 8/2016 | McWhirter et al. |
| 2016/0238600 A1 | 8/2016 | Hoogenboom et al. |
| 2017/0094955 A1 | 4/2017 | Macdonald et al. |
| 2017/0223939 A1 | 8/2017 | Macdonald et al. |
| 2017/0226231 A1 | 8/2017 | Macdonald et al. |
| 2017/0369593 A1 | 12/2017 | McWhirter et al. |
| 2018/0244804 A1 | 8/2018 | Macdonald et al. |
| 2018/0273641 A1 | 9/2018 | Babb et al. |
| 2019/0021295 A1 | 1/2019 | Babb et al. |
| 2019/0040123 A1 | 2/2019 | McWhirter et al. |
| 2019/0071519 A1 | 3/2019 | McWhirter et al. |
| 2019/0077884 A1 | 3/2019 | McWhirter et al. |
| 2019/0090462 A1 | 3/2019 | Babb et al. |

FOREIGN PATENT DOCUMENTS

| | | |
|---|---|---|
| CN | 101962408 A | 2/2011 |
| EP | 0364096 A2 | 4/1990 |
| EP | 0583980 A1 | 8/1993 |
| EP | 0491057 B1 | 12/1998 |
| EP | 1439234 A1 | 7/2004 |
| EP | 1505148 B1 | 4/2009 |
| EP | 2050764 A1 | 4/2009 |
| EP | 1605058 B1 | 5/2009 |
| EP | 1589107 B1 | 12/2009 |
| EP | 2147594 A1 | 1/2010 |
| EP | 2505654 A1 | 10/2012 |
| EP | 2517556 A2 | 10/2012 |
| EP | 2517557 A2 | 10/2012 |
| EP | 2556747 A2 | 2/2013 |
| EP | 2564695 A1 | 3/2013 |
| KR | 1020050042792 A | 5/2005 |
| WO | 1990/004036 A1 | 4/1990 |
| WO | 1991/000906 A1 | 1/1991 |
| WO | 1991/008216 A1 | 6/1991 |
| WO | 1992/003918 A1 | 3/1992 |
| WO | 1994/002602 A1 | 2/1994 |
| WO | 1994/004690 A1 | 3/1994 |
| WO | 1994/012215 A1 | 9/1994 |
| WO | 1994/025585 A1 | 11/1994 |
| WO | 1995/017085 A1 | 6/1995 |
| WO | 1995/017500 A1 | 6/1995 |
| WO | 1996/034103 A1 | 10/1996 |
| WO | 1997/013852 A1 | 4/1997 |
| WO | 1997/016537 A1 | 5/1997 |
| WO | 1997/042313 A1 | 11/1997 |
| WO | 1998/024893 A2 | 6/1998 |
| WO | 1998/039416 A1 | 9/1998 |
| WO | 1998/046645 A2 | 10/1998 |
| WO | 1998/050431 A2 | 11/1998 |
| WO | 1999/018212 A1 | 4/1999 |
| WO | 1999/045962 A1 | 9/1999 |
| WO | 2000/026373 A1 | 5/2000 |
| WO | 2000/063403 A2 | 10/2000 |
| WO | 2000/073323 A2 | 12/2000 |
| WO | 2001/053353 A2 | 7/2001 |
| WO | 2001/064929 A1 | 9/2001 |
| WO | 2002/008409 A2 | 1/2002 |
| WO | 2002/012437 A2 | 2/2002 |
| WO | 2002/018948 A2 | 3/2002 |
| WO | 2002/020767 A2 | 3/2002 |
| WO | 2002/036789 A2 | 5/2002 |
| WO | 2002/046237 A2 | 6/2002 |
| WO | 2002/053596 A2 | 7/2002 |
| WO | 2002/066630 A1 | 8/2002 |
| WO | 2002/085944 A2 | 10/2002 |
| WO | 2002/085945 A2 | 10/2002 |
| WO | 2003/002609 A2 | 1/2003 |
| WO | 2003/029458 A2 | 4/2003 |
| WO | 2003/047336 A1 | 6/2003 |
| WO | 2003/052416 A2 | 6/2003 |
| WO | 2003/061363 A2 | 7/2003 |
| WO | 2003/106495 A2 | 12/2003 |
| WO | 2004/006955 A1 | 1/2004 |
| WO | 2004/009618 A2 | 1/2004 |
| WO | 2004/049794 A2 | 6/2004 |
| WO | 2004/050838 A2 | 6/2004 |
| WO | 2004/058820 A2 | 7/2004 |
| WO | 2004/058822 A2 | 7/2004 |
| WO | 2004/063381 A2 | 7/2004 |
| WO | 2004/106375 A1 | 12/2004 |
| WO | 2005/007696 A2 | 1/2005 |
| WO | 2005/019463 A1 | 3/2005 |
| WO | 2005/028510 A2 | 3/2005 |
| WO | 2005/038001 A2 | 4/2005 |
| WO | 2006/008548 A2 | 1/2006 |
| WO | 2006/047367 A2 | 5/2006 |
| WO | 2006/117699 A2 | 11/2006 |
| WO | 2006/122442 A1 | 11/2006 |
| WO | 2007/012614 A2 | 2/2007 |
| WO | 2007/096779 A2 | 8/2007 |
| WO | 2007/117410 A2 | 10/2007 |
| WO | 2008/022391 A1 | 2/2008 |
| WO | 2008/027986 A2 | 3/2008 |
| WO | 2008/054606 A2 | 5/2008 |
| WO | 2008/076379 A2 | 6/2008 |
| WO | 2008/081197 A1 | 7/2008 |
| WO | 2008/112922 A2 | 9/2008 |
| WO | 2008/151081 A1 | 12/2008 |
| WO | 2009/013620 A2 | 1/2009 |
| WO | 2009/018386 A1 | 2/2009 |
| WO | 2009/026660 A1 | 3/2009 |
| WO | 2009/051974 A1 | 4/2009 |
| WO | 2009/052081 A2 | 4/2009 |
| WO | 2009/089004 A1 | 7/2009 |
| WO | 2009/097006 A2 | 8/2009 |
| WO | 2009/129247 A2 | 10/2009 |
| WO | 2009/143472 A2 | 11/2009 |
| WO | 2009/157771 A2 | 12/2009 |
| WO | 2010/039900 A2 | 4/2010 |
| WO | 2010/053751 A1 | 5/2010 |
| WO | 2010/054007 A1 | 5/2010 |
| WO | 2010/070263 A1 | 6/2010 |
| WO | 2010/097385 A1 | 9/2010 |
| WO | 2010/136598 A1 | 12/2010 |
| WO | 2010/151792 A1 | 12/2010 |
| WO | 2011/004192 A1 | 1/2011 |
| WO | 2011/062207 A1 | 5/2011 |
| WO | 2011/072204 A1 | 6/2011 |
| WO | 2011/097603 A1 | 8/2011 |

(56) References Cited

FOREIGN PATENT DOCUMENTS

| | | |
|---|---|---|
| WO | 2011/143545 A1 | 11/2011 |
| WO | 2011/158009 A1 | 12/2011 |
| WO | 2011/163311 A1 | 12/2011 |
| WO | 2011/163314 A1 | 12/2011 |
| WO | 2012/018764 A1 | 2/2012 |
| WO | 2012/063048 A1 | 5/2012 |
| WO | 2012/116926 A1 | 9/2012 |
| WO | 2012/116927 A1 | 9/2012 |
| WO | 2012/141798 A1 | 10/2012 |
| WO | 2012/148873 A2 | 11/2012 |
| WO | 2013/022782 A1 | 2/2013 |
| WO | 2013/041844 A2 | 3/2013 |
| WO | 2013/041845 A2 | 3/2013 |
| WO | 2013/041846 A2 | 3/2013 |
| WO | 2013/045916 A1 | 4/2013 |
| WO | 2013/059230 A1 | 4/2013 |
| WO | 2013/061078 A1 | 5/2013 |
| WO | 2013/061098 A2 | 5/2013 |
| WO | 2013/079953 A1 | 6/2013 |
| WO | 2013/096142 A1 | 6/2013 |
| WO | 2013/116609 A1 | 8/2013 |
| WO | 2013/134263 A1 | 9/2013 |
| WO | 2013/138680 A1 | 9/2013 |
| WO | 2013/187953 A1 | 12/2013 |
| WO | 2014/121087 A1 | 8/2014 |
| WO | 2014/160179 A1 | 10/2014 |
| WO | 2014/160202 A1 | 10/2014 |
| WO | 2015/143406 A2 | 9/2015 |
| WO | 2015/143414 A2 | 9/2015 |

OTHER PUBLICATIONS

Matsuzawa et al. "Guinea pig immunoglobulin VH and VL naïve repertoire analysis."PLoS One. Dec. 13, 2018;13(12):e0208977. (Year: 2018).*

Ozato et al. "Comment on "Gene Disruption Study Reveals a Nonredundant Role for TRIM21/Ro52 in NF-κB-Dependent Cytokine Expression in Fibroblasts""J Immunol. Dec. 15, 2009; 183(12): 7619-721 (Year: 2009).*

Murphy and Silha."Unexpected and unexplained phenotypes in transgenic models."Growth Horm IGF Res. Oct. 2000;10(5):233-5. (Year: 2000).*

Adams et al. (2005) "A genome-wide, end-sequenced 129Sy BAC library resource for targeting vector construction," Genomics, 86(6):753-758.

Adderson et al. (1991) "Restricted Ig H Chain V Gene Usage in the Human Antibody Response to Haemophilus influenzae Type b Capsular Polysaccharide," The Journal of Immunology, 147:1667-1674.

Adderson et al. (1993) "Restricted Immunoglobulin VH Usage and VDJ Combinations in the Human Response to Haemophilus influenzae Type b Capsular Polysaccharide," J. Clin. Invest., 91:2734-2743.

Al-Lazikani, B. et al., (1997) "Standard conformations for the canonical structures of immunoglobulins," J. Mol. Biol., 273(4):927-48.

Almagro et al. (2004) "Identification of differences in the specificity-determining residues of antibodies that recognize antigens of different size: implications for the rational design of antibody repertoires," Journal of Molecular Recognition, 17(2):132-143.

Almagro and Fransson (2008) "Humanization of antibodies," Frontiers in Bioscience, 13:1619-1633.

Altschul et al. (1990) "Basic local alignment search tool," J. Mol. Biol., 215(3): 403-410.

Altschul et al. (1997) "Gapped BLAST and PSI-BLAST: a new generation of protein database search programs," Nucleic Acids Res. 25:3389-3402.

Altschul et al. Methods in Enzymology.

Amit and Itskovitz-Eldor (2009) "Embryonic Stem Cells: Isolation, Characterization and Culture," Adv. Biochem. Eng. Biotechnol, 114:173-184.

Andris-Widhopf et al. (2000) "Methods for the generation of chicken monoclonal antibody fragments by phage display," J. Immunol. Methods 242:159-181.

Arnaout, R. et al., High-resolution description of antibody heavy-chain repertoires in; humans PLoS One, 6(8):e22365 (2011).

Arnold, L. et al., Development of B-1 cells: segregation of phosphatidyl choline-specific B cells to the B-1 population occurs after immunoglobulin gene expression, J. Exp. Med., 179:1585-1595 (1994).

Askew, G.R. et al., Site-directed point mutations in embryonic stem cells: a gene-targeting tag-and-exchange strategy, Mol. Cell Biol., 13(7):4115-24 (1993).

Astellas Negotiates $295M License Extension to Regeneron's VelocImmune mAb Platform, Genetic Engineering & Biotechnology News, Jul. 28, 2010, 2 pages.

Aucouturier, P.et al., Monoclonal Ig L chain and L chain V domain fragment crystallization in myeloma-associated Fanconi's syndrome, J. Immunol., 150( 8):3561-3568 (1993).

Auerbach et al. (2000) "Establishment and Chimera Analysis of 129/SvEv- and C57BL/6-Derived Mouse Embryonic Stem Cell Lines," BioTechniques, 29(5):1024-1028, 1030, 1032.

Austin et al. (2004) "The Knockout Mouse Project," Nature Genetics, 36(9):921-924.

Author Not Known (2007) "Breeding Strategies for Maintaining Colonies of Laboratory Mice," A Jackson Laboratory Resource Manual, pp. 1-29.

Author Not Known, Additional post-filing data and letter filed by the Applicant/Patentee for corresponding European application 09075279.1, now opposed patent EP 2147594 B1, 4 pages. (Jun. 13, 2013).

Author Not Known, Chapter 6: The Development of B Lymphocytes, Immuno Biology: The Immune System in Health and Disease, 4th Edition, Janeway et al. ed., pp. 195-208 (1999).

Author Not Known, Chapter 8: The Development and Survival of Lymphocytes, Janeway's Immunobiology, 8th Edition, Eds. Kenneth Murphy et al, Garland Science (ISBN: 9780815342434), whole document, in particular p. 279 and Figure 8.4, (2011).

Author Not Known, Mouse strain, document #3 submitted with Third Party Observation, filed in GB2012052956, 4 pages (Mar. 26, 2014).

Author Not Known, Next generation transgenic mice for therapeutic human antibodies, Description of MeMoTM, filed by the Applicant/Patentee in prosecution for corresponding European application 09075279.1, now opposed patent EP 2147594 B1, 2 pages (Dec. 22, 2011).

Author Not Known, V-BASE Sequence Directory, 6 pages, retrieved on Jun. 6, 2016 <http://www2.mrc-lmb.cam.ac.uk/vbase/list2.php.

Azzazy and Highsmith (2002) "Phage display technology: clinical applications and recent innovations," Clin. Biochem. 35:425-445.

Baeuerle, P.A. and Reinhardt, C., Bispecific T-cell engaging antibodies for cancer; therapy, Cancer Res., 69(12):4941-4 (2009).

Baird and Myszka (2001) "Current and emerging commercial optical biosensors," J. Molecular Recognition, 14:261-268.

Bando et al. (2004) "Characterization of VH gene expressed in PBL from children with atopic diseases: detection of homologous VH1-69 derived transcripts from three unrelated patients," Immunology Letters, 94:99-106.

Bankovich et al. (2007) "Structural Insight into Pre-B Cell Receptor Function," Science, 316(5822):291-294.

Baseggio et al. (2010) "CD5 expression identifies a subset of splenic marginal zone lymphomas with higher lymphocytosis: a clinico-pathological, cytogenetic and molecular study of 24 cases," Haematologica, 95(4):604-612.

Bates et al. (2007) "Chromosomal position of a VH gene segment determines its activation and inactivation as a substrate for V(D)J recombination," Journal of Experimental Medicine, 204(13):3247-3256.

Bauer, S. et al., Structure and pre-B lymphocyte restricted expression of the VpreB gene in humans and conservation of its structure in other mammalian species,The EMBO Journal, 7(1):111-116 (1988).

Berberian et al. (1991) "A VH Clonal Deficit in Human Immunodeficiency VirUS Positive Individuals Reflects a B-Cell Maturational Arrest," Blood, 78(1):175-179.

(56) References Cited

OTHER PUBLICATIONS

Billiard, F. et al., Ongoing Dll4-Notch signaling is required for T-cell homeostasis in the adult thymus, Eur. J. Immunol., 41(8):2207-16 (2011).
Bispecific monoclonal antibody, From Wikipedia, the free encyclopedia, pp. 1-5; downloaded on Mar. 19, 2019, https://en.wikipedia.org/wiki/Bispecific monoclonal antibody.
Blaas, L. et al., Bacterial artificial chromosomes improve recombinant protein production in mammalian cells, BMC Biotechnol., 9:3 (2009).
Blankenstein et al. (1987) "Immunoglobulin $V_H$ region genes of the mouse are organized in overlapping clusters*," Eur. J. Immunol., 17:1351-1357.
Bode, J. et al., the transgeneticist's toolbox: novel methods for the targeted modification of eukaryotic genomes, Biol. Chem., 381(9-10):801-13 (2000).
Bot, A. et al., V2-Light Chain Genes Reconstitute Immune Responses to Defined Carbohydrate Antigens or Haptens by Utilizing Different VH Genes, Molecular Immunology, 33(17/18):1359-1368 (1996).
Brevini et al. (2010) "no. shortcuts to pig embryonic stem cells," Theriogenology 74(4):544-550.
Brezinschek et al. (1995) "Analysis of the Heavy Chain Repertoire of Human Peripheral B Cells Using Single-Cell Polymerase Chain Reaction," Journal of Immunology, 155:190-202.
Brezinschek, H. et al., Pairing of variable heavy and variable kappa chains in individual naïve and memory B cells, J. Immunol., 160(10):4762-4767 (1998).
Brezinschek, H.P. et al., Analysis of the human VH gene repertoire. Differential effects of selection and somatic hypermutation on human peripheral CD5(+)/IgM+ and CD5(-)/IgM+ B; Cells, J. Clin. Invest., 99(10):2488-501 (1997).
Brodeur et al. (1984) "The immunoglobulin heavy chain variable region (Igh-V) locus in the mouse I. One hundred IgH-V genes comprise seven families of homologous genes*," Eur. J. Immunol., 14:922-930.
Brouwers et al. (2015) "Unexpected Phenotypes in Mouse Models Carrying the Human Growth Hormone Minigene to Enhance Transgene Expression," Journal of Steroids & Hormonal Science, 6(2):1-2.
Bruchez et al. (1998) "Semiconductor Nanocrystals as Fluorescent Biological Labels," Science 281: 2013-2016.
Bruüggemann et al. (1989) "A repertoire of monoclonal antibodies with human heavy chains from transgenic mice," Proceedings of the National of Academy of Science USA, 86:6709-6713.
Brüggemann and Neuberger (1996) "Strategies for expressing human antibody repertoires in transgenic mice," Review Immunology Today, 192(17):391-397.
Brüggemann (2001) "Human Antibody Expression in Transgenic Mice," Archivum Immunologiae et Therapiae Experimentalis, 49:203-208.
Brüggemann (2004) "Human Monoclonal Antibodies from Translocus Mice," Molecular Biology of B Cells, Eds. Honjo, T. and Neuberger, M.S., New York, NY: Academic Press, pp. 547-561.
Burton (1995) "Phage display," Immunotechnology 1:87-94.
Butler, (1998) "Immunoglobulin diversity, B-cell and antibody repertoire development in large farm animals," Rev. Sco. Tech. Off. Int. Epiz., 17(1):43-70.
Campbell, K.H. et al., Sheep cloned by nuclear transfer from a cultured cell line, Nature, 380(6569):64-6 (1996).
Cao, et al. (2009) Isolation and Culture of Primary Bovine Embryonic Stem Cell Colonies by a Novel Method, Journal of Experimental Zoology, 311A:368-376.
Carbonari et al. (2005) "Hepatitis C Virus Drives the Unconstrained Monoclonal Expansion of VH1-69-Expressing Memory B Cells in Type II Cryoglobulinemia: A Model of Infection-Driven Lymphomagenesis," The Journal of Immunology, 174:6532-6539.
Carmack, C. et al., Influence of a V kappa 8 L chain transgene on endogenous rearrangements and the immune response to the HA(Sb) determinant of influenza virus, J. Immunol., 147(6):2024-2033 (1991).
Carter, P., Bispecific human IgG by design, Journal of Immunological Methods, 248(1-2):7-15 (2001).
Cascalho, M. et al., A quasi-monoclonal mouse, Science, 272(5268):1649-1652 (1996).
Casellas, R. et al., Contribution of receptor editing to the antibody repertoire, Science, 291(5508):1541-4 (2001).
Cavelier et al. (1997) "B lineage-restricted rearrangement of a human Ig kappa transgene," Eur J. Immunol. 27(7):1626-1631.
Chan et al. (2001) "VH1-69 gene is preferentially used by hepatitis C virUS associated B cell lymphomas and by normal B cells responding to the E2 viral antigen," Blood, 97(4):1023-1026.
Chang et al. (1984) "Immunologic memory to phosphocholine. IV. Hybridomas representative of Group I (T15-like) and Group II (non-T15-like) antibodies utilize distinct VH genes," J. Immunol., 132(3):1550-1555.
Charles et al. (2011) "A flow cytometry-based strategy to identify and express IgM from VH1-69+ clonal peripheral B cells," Journal of Immunological Methods, 363:210-220.
Chen, C. et al., Deletion and Editing of B Cells that Express Antibodies to DNA, Journal of Immunology, 152(4):1970-1982 (1994).
Cheval et al. (2012) Of Mice and Men: Divergence of Gene Expression Patterns in Kidney, PLoS One, 7(10):e46876 (12 pages).
Cho, Chunghee, (2012) "Testicular and epididymal ADAMs: expression and function during fertilization," Nature Reviews Urology, 9:550-560.
Choi et al. (2004) "Characterization and comparative genomic analysis of intronless Adams with testicular gene expression," Genomics, 83(4):636-646.
Choi et al. (2011) "Expression of the metabotropic glutamate receptor 5 (mGluR5) induces melanoma in transgenic mice," PNAS, 108(37):15219-15224.
Choi et al. (2013) "Identification and characterizaion of promoter and regulatory regions for mouse Adam2 gene expression," Molecular Biology Reports, 40:787-796.
Chothia, C. and Lesk, A.M., Canonical structures for the hypervariable regions of; Immunoglobulins, J. Mol. Biol., 196(4):901-17 (1987).
Choulika, A. et al., Induction of homologous recombination in mammalian chromosomes by using the I-Sceˇ system of Saccharomyces cerevisiae, Mol. Cell. Biol., 15:4 1968-73 (1995).
Clark and Whitelaw, (2003) "A future for transgenic livestock, National Reviews Genetics," 4(10):825-833.
Cocea et al. (1999) "A targeted deletion of a region upstream from the Jkppa cluster impairs kappa chain rearrangement in cis in mice and in the 103/bcl2 cell line," J. Exp. Med., 189(9):1443-1450.
Cohen-Tannoudji, M. et al., I-Sceˇ-induced gene replacement at a natural locus in; embryonic stem cells, Mol. Cell. Biol., 18(3):1444-8 (1998).
Collins, A. et al., The reported germline repertoire of human immunoglobulin kappa chain genes is relatively complete and accurate, Immunogenetics, 60:669-676 (2008).
Combriato et al. (2002) "Regulation of Human Igl Light Chain Gene Expression," The Journal of Immunology, 168:1259-1266.
Corcos, D. et al, Pre-B-cell development in the absence of lambda 5 in transgenic mice expressing a heavy-chain disease protein, Curr. Biol., 5(10):1140-8 (1995).
Cowen, n. J. et al., Purification and Sequence Analysis of the mRNA Coding for an Immunoglobulin Heavy Chain, European J. of Biochem., 61(2): 355-368 (1976).
Davidkova et al. (1997) "Selective Usage of VH Genes in Adult Human B Lymphocyte Repertoires," Scand. J. Immunol., 45:62-73.
Davies, N. et al., Creation of Mice Expressing Human Antibody Light Chains by Introduction of a Yeast Artificial Chromosome Containing the Core Region of the Human Immunoglobulin ? Locus, Nature Biotechnology 11:911-914, (1993).
De Gensst et al. (2006) Antibody repertoire development in camelids. Dev. Comp. Immunol, 30:187-198.
De Kruif, J. et al., Human Immunoglobulin Repertoires against Tetanus Toxoid Contain a Large and Diverse Fraction of High-Affinity Promiscuous VH Genes, Journal of Molecular Biology, 387:548-558 (2009).

(56) References Cited

OTHER PUBLICATIONS

De Kruif, J. et al., Rapid selection of cell subpopulation-specific human monoclonal antibodies from a synthetic phage antibody library, Proc. Natl. Acad. Sci. U S A, 92(9):3938-42 (1995).
Dennis (2002) "Welfare issues of genetically modified animals," ILAR Journal, 43(2):100-109.
De Wildt, R. et al., Analysis of heavy and light chain pairings indicates that receptor editing shapes the human antibody repertoire, J. Mol. Biol., 285(3):895-901 (1999).
Dechiara, T.M. et al., Chapter 16: VelociMouse: Fully ES Cell-Derived F0 Generation Mice Obtained from the Injection of ES Cells into 8-Cell Stage Embryos, Gene Knockout Protocols: Second Edition, vol. 530, Humana Press (2009).
Deegan (1976) "Bence Jones Proteins: Nature, Metabolism, Detection and Significance," Annals of Clinical and Laboratory Science, 6(1):38-46.
Deisenhofer, J., Crystallographic Refinement and Atomic Models of a Human Fc Fragment and Its Complex with Fragment B of Protein A from *Staphylococcus aureus* at 2.9- and 2.8-? Resolution, Biochemistry, 20(9):2361-2370 (1981).
Desmyter, A. et al., Crystal structure of a camel single-domain VH antibody fragment in complex with lysozyme, Nat. Struct. Biol., 3(9):803-811 (1996).
Dinnyés, A. et al., Somatic cell nuclear transfer: recent progress and challenges, Cloning Stem Cells, 4(1):81-90 (2002).
Donoho, G. et al., Analysis of gene targeting and intrachromosomal homologous recombination stimulated by genomic double-strand breaks in mouse embryonic stem cells, Mol. Cell. Biol., 18(7):4070-8 (1998).
Donohoe, M. et al., Transgenic Human Lambda5 Rescues the Murine Lambda5 Nullizygous Phenotype, Journal of Immunology, 164:5269-5276 (2000).
Echelard, Y., Year of the ox, Nat. Biotechnol., 27(2):146-147 (2009).
Edmundson et al. (1993) "Priniciples and Pitfalls in Designing Site-Directed Peptide Ligands," Proteins: Structure, Function, and Genetics, Wiley-Liss, Inc., 16:246-267.
Edwards et al. (2008) "The ADAM metalloproteinases, Molecular Aspects of Medicine," 29(5):258-289.
Els Conrath, K. et al., Camel single-domain antibodies as modular building units in bispecific and bivalent antibody constructs, J. Biol. Chem., 276(10):7346-50 (2001).
Enever et al. (2009) "Next generation immunotherapeutics- honing the magic bullet. Current Opinion in Biotechnology," 20:405-411.
Engel, P. et al., Abnormal B Lymphocyte Development, Activation, and Differentiation in Mice that Lack or Overexpress the CD19 Signal Transduction Molecule, Immunity, 3:39-50 (1995).
Epinat, J.C., et al. A novel engineered meganuclease induces homologous recombination in yeast and mammalian cells, Nucleic Acids Res., 31(11):2952-62 (2003).
Ewert, S. et al., Biophysical properties of human antibody variable domains, J. Mol. Biol., 325(3):531-53 (2003).
Farner, N.L. et al., Molecular mechanisms and selection influence the generation of the human V lambda J lambda repertoire, J. Immunol., 162(4):2137-45 (1999).
Featherstone, K et al. (2010) "The mouse immunoglobulin heavy chain V-D intergenic sequence contains insulators that may regulate ordered V(D)J recombination," J. Biol. Chem., 285(13): 9327-9338.
Fell, H.P. et al., Homologous recombination in hybridoma cells: heavy chain chimeric antibody produced by gene targeting, Proc. Natl. Acad. Sci. U S A., 86(21):8507-11 (1989).
Female Science Professor https://science-professor.blogspot.com/2009/04/photoshooters.html; posted Apr. 17, 2009; last accessed May 26, 2017.
Festing et al. (1999) "Revised nomenclature for strain 129 mice," Mamm. Genome 10:836.
Fischer, N. and Léger, O., Bispecific antibodies: molecules that enable noveltherapeutic strategies, Pathobiology, 74(1):3-14 (2007).

Fishwild et al., (1996) "High-avidity human IgGk monoclonal antibodies from a novel train of mililocus transgenic mice," Nat. Biotech., 14(7):845-851.
Flavell, D.J., et al., Therapy of human T-cell acute lymphoblastic leukaemia with a combination of anti-CD7 and anti-CD38-SAPORIN immunotoxins is significantly better than therapy with each individual immunotoxin, Br. J. Cancer., 84(4):571-8 (2001).
Fraenkel, S. et al., Allelic 'choice' governs somatic hypermutation in vivo at the immunoglobulin kappa-chain locus, Nat. Immunol., 8(7):715-722 (2007).
Fussenegger, M. et al., Genetic optimization of recombinant glycoprotein production by mammalian cells, Tibtech, 17:35-42 (1999).
Gallo et al. (2000) "The human immunoglobulin loci introduced into mice: V (D) and J gene segment usage similar to that of adult humans," Eur. J. Immunol., 30(2):534-540.
Gama Sosa et al. (2010)"Animal transgenesis: an overview," Brain Structure & Function, 214(2-3):91-109.
Gavilondo and Larrick (2002) BioTechniques 29:128-145.
Gavish et al. (1977) "Comparison of the fine specificity of anti-dinitrophenyl-combining site composed of either VL dimer or VL and VH of protein 315," Biochemistry, 16(14):3154-3159.
Gay, D. et al., Receptor editing: an approach by autoreactive B cells to escape tolerance, J. Exp. Med., 177(4):999-1008 (1993).
GenBank accession No. NT_114985, p. 1, first referenced Dec. 1, 2005, last updated Feb. 9, 2015.
GenBank Accession No. X97051, GI:564822, first referenced Jan. 9, 1997, updated Nov. 14, 2006 (29 pages).
GenBank Accession No. ABA26122, immunoglobulin light chain variable region, partial [*Homo sapiens*], Rabquer et al., 2 pages, first referenced Dec. 31, 2005.
GenBank Accession No. M87478, Human rearranged IgK mRNA VJC region, Aucouturier et al., 1 page, first referenced Mar. 3, 1992, first seen at NBI Apr. 27, 1993.
Giallourakis et al. (2010) "Elements between the IgH variable (V) and diversity (D) clusters influence antisense transcription and lineage-specific V(D)K recombination," PNAS, 107(51):22207-22212.
Giddings, G. et al., Transgenic plants as factories for biopharmaceuticals, Nat. Biotechnol., 18(11):1151-5 (2000).
Goldman et al. (2004) "Transgenic animals in medicine: Integration and expression of foreign genes, theoretical and applied aspects," Med. Sci. Monit., 10(11):RA274-285.
Goletz, S. et al., Selection of Large Diversities of Antiidiotypic Antibody Fragments by Phage Display, J. Mol. Biol. 315:1087-97, (2002).
Goni et al. (1985) "Sequence similarities and cross-idiotypic specificity of L chains among human monoclonal IgMk with anti-gamma-globulin activity," J. Immunol, 135(6):4073-9.
Gonnet et al. (1992) Exhaustive Matching of the Entire Protein Sequence Database, Science 256:1443-45.
Gonzalez-Fernandez, A. and Milstein, C., Analysis of somatic hypermutation in mouse Peyer's patches using immunoglobulin kappa light-chain transgenes, PNAS USA, 90:9862-9866 (1993).
Goodhardt et al., Rearrangement and Expression of rabbit immunoglobulin K light chain gene in transgenic mice; Jun. 1987; PNAS, 84: 4229-4233.
Gorman et al. (1996) "The Ig(kappa) enhancer influences the ratio of Ig(kappa) versus Ig(lambda) B lymphocytes," Immunity, 5(3):241-252.
Goyenechea, B. and Milstein, C., Modifying the sequence of an immunoglobulin V-gene alters the resulting pattern of hypermutation, PNAS USA, 93:13979-13984 (1996).
Goyenechea, B. et al., Cells strongly expressing Ig(kappa) transgenes show clonal recruitment of hypermutation: a role for both MAR and the enhancers, EMBO J., 16(13):3987-94 (1997).
Grawunder et al. (1995) "Induction of sterile transcription from the kappa L chain gene locus in V(D)J recombinase-deficient progenitor B cells," International Immunology, 7(12):1915-1925.
Green, L. and Jakobovits, A., Regulation of B cell development by variable gene complexity in mice reconstituted with human immunoglobulin yeast artificial chromosomes, J. Exp. Med., 188(3):483-495 (1998).

(56) References Cited

OTHER PUBLICATIONS

Green, L. et al. (1994) "Antigen-specific human monoclonal antibodies from mice engineered with human Ig heavy and light chain YACs," Nature Genetics, 7(1):13-21.
Gunther et al. (2007) "SuperHapten: a comprehensive database for small immunogenic compounds," Nucleic Acid Research, 35:D906-D910.
Hagiwara, S., Transgenic expression of VpreB-3 under the control of the immunoglobulin heavy chain enhancer and SV40 promoter, Kobe J. Med. Sci., 42(1):43-59 (1996). Abstract Only.
Haines and Brodeur (1998) Accessibility changes across the mouse Igh-V locus during B cell development, Eur. J. Immunol., 28:4228-4235.
Han et al. (2009) "Comprehensive analysis of reproductive ADAMs: relationship of ADAM4 and ADAM6; with an ADAM complex required for fertilization in mice," Biology of Reproduction, 80(5):1001-1008.
Harding and Lonberg (1995) "Class switching in human immunoglobulin transgenic Mice," Ann. N Y Acad. Sci., 764:536-546.
Hardy, R.R and Hayakawa, K., B cell development pathways, Annu. Rev. Immunol., 19:595-621 (2001).
Hartley, S. and Goodnow, C., Censoring of self-reactive B cells with a range of receptor affinities in transgenic mice expressing heavy chains for a lysozyme-specific antibody, International Immunology, 6:1417-1425 (1994).
Helms and Wetzel (1995) "Destabilizing loop swaps in the CDRs of an immunoglobulin $V_L$ domain," Protein Science, 4:2073-2081.
Hendricks et al. (2010) "Organization of the variable region of the immunoglobulin heavy-chain gene locus of the rat," Immunogenetics, 62(7):479-486.
Hengstschlager, M. et al., A lambda1 transgene under the control of a heavy chain promoter and enhancer does not undergo somatic hypermutation, Eur. J. Immunol., 24:1649-1656 (1994).
Hiatt, A. et al. Production of antibodies in transgenic plants, Nature, 342(6245):76-8 (1989).
Hirabayashi et al. (1995) "Kinetic analysis of the interactions of recombinant human VpreB and Ig V domains," J. Immunol., 155:1218-1228.
Hochedlinger, K. and R. Jaenisch, Monoclonal Mice Generated by Nuclear Transfer from Mature B and T Donor Cells, Nature, 415(6875):1035-1038, (2002).
Hoiruchi and Blobel (2005) Studies from Adam Knockout Mice, in Hooper and Lendeckel, The ADAM Family of proteases, Netherlands 2005, Springer (37 pages).
Hömig-Hölzel, C. et al., Constitutive CD40 signaling in B cells selectively activates the noncanonical NF-kappaB pathway and promotes lymphomagenesis, J. Exp. Med., 205(6):1317-29 (2008).
Hoogenboom (1997) "Designing and optimizing library selection strategies for generating high-affinity antibodies," TIB Tech., 15:62-70.
Hoogenboom and Chames (2000) "Antibodies isolated from an animal (e.g., a mouse) that is transgenic for human immunoglobulin genes," Immunology Today 21:371-378.
Houdebine, L.M. Transgenic Animals: Generation and Use. Amsterdam: Harwood Academic Publishers.pp. 397-403 (1997).
Houdebine et al. "Methods to Generate Transgenic Animals," Genetic Engineering in Livestock, New Applications and Interdisciplinary Perspectives, Engelhard M, et al., 2009, XVI, 146, pp. 31-47.
House mouse (MUS musculus) IGH locus on chromosome 12 (12F2) strain C57BL/6 pp. 1-5; dowloaded Aug. 26, 2016.
Huang et al. (1993) "A Majority of Ig H Chain cDNA of Normal Human Adult Blood Lymphocytes Resembles cDNA for Fegal Ig and Natural Autoantibodies," The Journal of Immunology, 151(10):5290-5300.
Huang et al. (1994) "Comparison of Crystal Structures of Two Homologous Proteins: Structural Origin of Altered Domain Interactions in Immunoglobulin Light-Chain Dimers," Biochemistry, 33:14848-14857.

Huls, G. et al., Antitumor immune effector mechanisms recruited by phage display-derived fully human IgG1 and IgA1 monoclonal antibodies, Cancer Res., 59(22):5778-84 (1999).
Hussack et al. (2012) "A VL single-domain antibody library shows a high-propensity to yield non-aggregating binders," Protein Engineering, Design & Selection, 25(6):313-318.
Ill et al. (1997) "Design and construction of a hybrid immunoglobulin domain with properties of both heavy and light chain variable regions," Protein Engineering, 10(8):949-957.
IMGT V-Quest Analysis of Sequence of Gen Bank M87478, 7 pages.
Inlay, M. et al., Essential roles of the kappa light chain intronic enhancer and 3' enhancer in kappa rearrangement and demethylation, Nat. Immunol., 3(5):463-8 (2002).
Irving, R.A. et al., Ribosome display and affinity maturation: from antibodies to single V-domains and steps towards cancer therapeutics, J. Immunol. Methods, 248(1-2):31-45 (2001).
Jakobovits, A. et al., From XenoMouse technology to panitumumab, the first fully human antibody product from transgenic mice, Nature Biotechnology, 25(10):1134-1143 (2007).
Jakobovits, A., Production of fully human antibodies by transgenic mice, Curr. Opin. Biotechnol., 6(5):561-6 (1995).
Jakobovits, Therapeutic Antibodies from XenoMouse Transgenic Mice, Recombinant Antibodies for Immunotherapy, Ed. Little, M., New York, NY: Cambridge University Press, Chapter 7, pp. 89-99 (2009).
Janeway's Immunobiology, Seventh Edition, Murphy, Travers and Walpot, eds., Garland Science, New York and London, Ch. 4, pp. 145-155, and Ch. 7, pp. 266-267 (2008).
Janssens et al. (2006) "Generation of heavy-chain-only antibodies in mice," Proc. Nat'l. Acad. Sci., 103(41):15130-15135; including 7 additional pages of supporting information (Figures 7, 8, 9 and Supporting Methods).
Jendeberg, L. et al., Engineering of Fc1 and Fc3 from human immunoglobulin G to analyse subclass specificity for staphylococcal protein A1, Journal of Immunological Methods, 201:25-34 (1997).
Jendreyko, N. et al., Intradiabodies, bispecific, tetravalent antibodies for the simultaneous functional knockout of two cell surface receptors, J. Biol. Chem., 278(48):47812-9 (2003).
Jensen, et al. (2007) One Step Generation of Fully Chimeric Antibodies Using Cγt-and Cκ Mutant Mice, J. Immunother., 30(3):338-349.
Johnson et al. (1997) "Ig VH1 Genes Expressed in B Cell Chronic Lymphocytic Leukemia Exhibit Distinctive Molecular Features," The Journal of Immunology, 158:235-246.
Johnston et al. (2006) "Complete Sequence Assembly and Characterization of the C57BL/6 Mouse Ig Heavy Chain V Region[1]," J. Immunol., 176:4221-4234.
Jolly, C. et al., Rapid methods for the analysis of immunoglobulin gene hypermutation: application to transgenic and gene targeted mice, Nucleic Acids Research, 25(10):1913-1919 (1997).
Jones, D. et al., High-level expression of recombinant IgG in the human cell line per.c6, Biotechnol. Prog., 19(1):163-8 (2003).
Joyner, A.L. ed., Gene Targeting: A Practical Approach, Second Edition, Oxford University Press, entire book, 193 pages (2000).
Kaartinen et al. (1988) "Combinatorial association of V genes: One VH gene codes for three non-cross-reactive monoclonal antibodies each specific for a different antigen (phOXAZOLONE, NP or GAT)," Mol. Immunol., 25(9):859-865.
Kabat and Wu, (1991) "Identical V region amino acid sequences and segments of sequences in antibodies of different specificities. Relative contributions of VH and VL genes, minigenes, and complementarity-determining regions to binding of antibody-combining sites," J. Immunol., 147(5):1709-1719.
Kantor et al. (1997) "An Unbiased Analysis of VH-D-JH Sequences from B-1a, B-1b, and Conventional B Cells," The Journal of Immunology, 158: 1175-1186.
Kasprzyk, P.G. et al., Therapy of an animal model of human gastric cancer using a combination of anti-erbB-2 monoclonal antibodies, Cancer Res., 52(10):2771-6 (1992).

(56) References Cited

OTHER PUBLICATIONS

Kaushik et al, "Stochastic pairing of heavy-chain and k light-chain variable gene families occurs in polyclonally activated B cells," Proc. Natl. Acad. Sci. USA, vol. 87: 4932-4936 (1990).

Kaushik et al. (2002) "Novel insight into antibody diversification from cattle," Veterinary Immunology and Immunopathology, 87(3-4):347-350.

Kellermann and Green (2002) "Antibody discovery: the use of transgenic mice to generate human monoclonal antibodies for therapeutics ," Current Opinion in Biotechnology 13:593-597.

Kim et al. (2006) "Expression and relationship of male reproductive ADAMs in mouse," Biology of Reproduction, 74(4):744-750.

Kingzette et al.(1998) "Trans-chromosomal recombination within the Ig heavy chain switch region in B lymphocytes," PNSA, 95(20):11840-11845.

Klebig, (1995) "Ectopic Expression of the Agouti Gene in Transgenic Mice Causes Obesity," Features fo Type II Diabetes, and Yellow Fur, PNAS 92:4728-4732.

Klöhn, P.C. et al., IBC's 23rd Annual Antibody Engineering, 10th Annual Antibody Therapeutics international conferences and the 2012 Annual Meeting of the Antibody Society: Dec. 3-6, 2012, San Diego, CA, Mabs, 5(2):178-201 (2013).

Klotz, E. et al., Somatic hypermutation of a lambda2 transgene under the control of the lambda enhancer or the heavy chain intron enhancer, J. Immunol., 157:4458-4463 (1996).

Klotz, E. et al., Somatic hypermutation of an artificial test substrate within an Ig kappa transgene, J. Immunol., 161:782-790 (1998).

Knappik, A. et al., Fully synthetic human combinatorial antibody libraries (HuCAL) based on modular consensus frameworks and CDRs randomized with trinucleotides, J. Mol. Biol., 296(1):57-86 (2000).

Kobayashi and Oyama (2011) "Antibody engineering toward high-sensitivity high-throughput immunosensing of small molecules," The Royal Society of Chemistry, Analyst, 136:642-651 (DOI: 10.1039/c0an00603c).

Kong et al. (2009) "Transgene expression is associated with copy number and cytomegalovirus promoter methylation in transgenic pigs," PLoS One 4(8):1-10.

Kong, Q. et al., a lambda 3' enhancer drives active and untemplated somatic hypermutation of a lambdal transgene, J. Immunol., 161:294-301 (1998).

Kontermann, R.E., Dual targeting strategies with bispecific antibodies, MAbs., 4(2):182-97 (2012).

Korhonen, J.M, https://jmkorhonen.net/2012/06/25/is-it-ok-to-record-conferencepresentations-reconsidering-fair-use-and-electronic-note-taking; posted Jun. 25, 2012; last accessed May 26, 2017.

Kroesen, B.J. et al., Bispecific antibodies for treatment of cancer in experimental animal models and man, Adv. Drug Deliv. Rev., 31(1-2):105-129 (1998).

Kunert et al. (2004) "Characterization of Molecular Features, Antigen-Binding, and in Vitro Properties of IgG and IgM Variants of 4E10, an Anti-HIV Type 1 Neutralizing Monoclonal Antibody," Aids ReSearch and Human Retroviruses, 20(7):755-762.

Kuroiwa et al. (2002) "Cloned transchromosomic calves producing human immunoglobulin," Nat. Biotechnol., 20(9):889-894.

Kuroiwa et al. (2004) "Sequential targeting of the genes encoding immunoglobulin-µ and prion protein in cattle," Nature Genetics, 36:775-780.

Lam, K. et al., In Vivo Ablation of Surface Immunoglobulin on Mature B Cells by Inducible Gene Targeting Results in Rapid Cell Death, Cell, 90:1073-1083 (1997).

Lantto, J. et al., Capturing the natural diversity of the human antibody response against vaccinia virus, J Virol, 85(4):1820-33 (2011).

Larrick, J.W. and Thomas, D.W., Producing proteins in transgenic plants and animals, Curr. Opin. Biotechnol., 12(4):411-8 (2001).

Lavial and Pain, (2010) "Chicken embryonic stem cells as a non-mammalian embryonic stem cell model" Develop. Groth Diff., 52(1):101-114.

Le Gall, F. et al., Effect of linker sequences between the antibody variable domains on the formation, stability and biological activity of a bispecific tandem diabody, Protein Eng. Des. Sel., 17(4):357-66 (2004).

Leclercq et al. (1989) "A novel germ-like JK transcript starting immediately upstream of JK1," Nucleic Acids Research, 17(17):6809-6819.

Lee, H. et al., Human C5aR knock-in mice facilitate the production and assessment of anti-inflammatory monoclonal antibodies, Nat. Biotechnol., 24(10):1279-84 (2006).

Lee et al. (2014) "Complete humanization of the mouse immunoglobulin loci enables efficient therapeutic antibody discovery," Nature Biotechnology, 32(4):356-363.

Lefranc, (2000) "Nomoclature of the Human Immunoglobulin Genes Current Protocols in Immunology," Supplement 40:1.1P.1-A.1P.37.

Lefranc, (2001) "Nomeclature of the human immunoglobulin lambda (IGL) genes," Experimental and Clinical Immunogenetics, S. Karger Basel C.H., 18(4):242-254.

Lefranc, M.P. Nomenclature of the human immunoglobulin heavy (IGH) genes, Exp. Clin. Immunogenet., 18(2):100-16 (2001).

Lefranc, M.P., Nomenclature of the human immunoglobulin kappa (IGK) genes, Exp. Clin. Immunogenet., 18(3):161-74 (2001).

Lefranc, M-P. and Lefranc, G., The Immunoblobulin Facts Books-,San Diego/San Francisco/New York/Boston/London/Sydney/ Tokyo: Academic Press, entire book, pp. 1-457 (2001).

Lefranc, (2004) Molecular Biology of B Cells. London: Elsevier Academic Press, Ed. Honjo, Chapter 4 pp. 37-59.

Leitzgen et al. (1997) "Assembly of Immunoglobulin Light Chains as a Prerequisite for Secretion," Journal Biological Chemistry., 272(5):3117-3123.

Liao, M.J. and Van Dyke, T., Critical role for Atm in suppressing V(D)J recombination-driven thymic lymphoma, Genes Dev., 13(10):1246-50 (1999).

Lie and Petropoulos, 1998. Curr. Opin. Biotechnology 9:43-48.

Lin et al. (1990) "Research of Immune Globulin in Mice," Guangzhou Medical Journal, 1:49-50 and English translation.

Lindhofer, H. et al., Preferential Species-Restricted Heavy/Light Chain Pairing in Rat/Mouse Quadromas, The Journal of Immunology, 155:219-225 (1995).

Little et al. (2000) "Of mice and men: hybridoma and recombinant antibodies.," Immunology Today 21:364-370.

Liu et al. (2014) "Primary Genetic Investigation of a Hyperlipidemia Model: Molecular Characteristics and Variants of the Apolipoprotein E Gene in Mongolian Gerbil," Biomed. Research International, (9 pages).

Logtenberg, T., Antibody cocktails: next-generation biopharmaceuticals with improved potency, Trends Biotechnol., 25(9):390-4 (2007).

Lonberg, (2005) "Human antibodies from transgenic animals, Nature Biotechnology," 23(9):1117-1125.

Lonberg, N. et al., Antigen-specific Human Antibodies from Mice Comprising Four Distinct Genetic Modifications, Nature, 368:856-859, (1994).

Lonberg, N., Fully human antibodies from transgenic mouse and phage display platforms, Curr. Opin. Immunol., 20(4):450-9, and supplemental material, 16 pages (2008).

Lonberg, N., Human Monoclonal Antibodies from Transgenic Mice, Therapeutic Antibodies, Handbook of Experimental Pharmacology, Eds. Chernajovsky, Y and Nissim, A., Berlin Heidelberg: Springer-Verlag, 181: 69-97 (2008).

Longo et al., (2008) "Characterization of immunoglobulin gene somatic hypermutation in the absence of activation-induced cytidine deaminase," J. Immunol., 181(2):1299-1306.

Lovell-Badge (2007) "Many ways to pluripotency," Nature Biotechnology, 25:1114-1116.

Luby, T.M. et al., The mu Switch Region Tandem Repeats Are Important, but Not Required, for Antibody Class Switch Recombination, J. Exp. Med., 193(2):159-168 (2001).

Macdonald et al. (2006) "Velocigene Technology Extended to Humanization of Several Megabases of complex Gene Loci," First International MUGEN Conference of Animal Models for Human Immunological Disease, Sep. 10-13, 2006—Athens, Greece, Abstract 21 and Poster, 11 pages.

(56) References Cited

OTHER PUBLICATIONS

Macdonald et al. (2014) "Precise and in situ genetic humanization of 6 Mb of mouse immunoglobulin genes," PNAS, 111(14):5147-5152.
Mageed et al. (2001) "Rearrangement of the human heavy chain variable region gene V3-23 in transgenic mice generates antibodies reactive with a range of antigens on the basis of VhCDR3 and residues intrinsic to the heavy chain variable region," Clin Exp Immunol, 123:1-8.
Mahmoud et al. (2011) "Limiting CDR-H3 Diversity Abrogates the Antibody Response to the Bacterial Polysaccharide α 1 →3 Dextran," The Journal of Immunology, 187: 879-886.
Mahmoudi et al. "V region gene analysis of human IgM hybridoma monoclonal anti-Sm antibodies," Lupus, 6:578-589, 1997.
Manis et al. (2002) "Mechanism and control of class-switch recombination," Trends in Immunology, 23(1):31-39.
Marasca et al. (2001) "Immunoglobulin Gene Mutations and Frequent Use of VH1-69 and VH4-34 Segments in Hepatitis C VirUS Positive and Hepatitis C VirUS Negative Nodal Marginal Zone B-Cell Lymphoma," American Journal of Pathology, 159(1): 253-261.
Martin and Van Ness, (1989) "Identification of a Germ Line Transcript from the Unrearranged Kappa Gene in Human B Cells," Molecular and Cellular Biology, 9(10):4560-4562.
Martin and Van Ness, (1990) "Initiation and Processing ofTwo Kappa Immunoglobulin Germ Line Transcripts in Mouse B cells," Molecular and Cellular Biology, 10(5):1950-1958.
Martinez-Jean, C. et al., Nomenclature and overview of the mouse (Mus musculus and Mus sp.) immunoglobulin kappa (IGK) genes, Exp. Clin. Immunogenet., 18(4):255-79 (2001).
Marvin, J. and Zhu, Z., Recombinant approaches to IgG-like bispecific antibodies, Acta Pharmacologica Sinica, 26(6):649-658 (2005).
Matsuda, F. et al., The Complete Nucleotide Sequence of the Human Immunoglobulin Heavy Chain Variable Region Locus, J. Exp. Med., 188(11): 2151-2162 (1998).
McGoldrick et al. (2013) "Rodent models of amyotrophic lateral sclerosis," Biochimica et Biophysica Acta, 1832:1421-1436.
Mei et al. (1991) "Vasoactive intestinal peptide hydrolysis by antibody light chains," J. Biol. Chem., 266(24):15571-4.
Melton (2002) Chapter 8: Gene-Targeting Strategies, Methods in Molecular Biology, Transgenesis Techniques, 2nd Edition, Priciples and Protocols, 180:19 pages.
Mendez M.J., et al., Functional transplant of megabase human immunoglobulin loci recapitulates human antibody response in mice, Nat Genet. 15(2):146-56 (1997).
Merchant, A. et al., An efficient route to human bispecific IgG, Nature Biotechnology, 16(7):677-681 (1998).
Miklos et al. (2000) "Salivary gland mucosa-associated lymphoid tissue lymphoma immunoglobulin VH genes show frequent use of V1-69 with distinctive CDR3 features," Blood, 95:3878-3884.
Miller et al. (2003) "Design, Constructio, and In Vitro Analyses of Multivalent Antibodies," J. Immunol., 170:4854-4861.
Mills et al. (1997) "Enhancer complexes located downstream of both human immunoglobulin Calpha genes, Journal of Experimental Medicine,"186(6):845-858.
Mirzabekov et al. (1996) Nucleic Acids Res 24(15): 2998-3004.
Montaño and Morrison, (2002) "Influence of the Isotype of the Light Chain on the Properties of IgG," Journal of Immunology, 168:224-231.
Moran, (2013) "Mouse platforms jostle for slice of humanized antibody market," Nature Biotechnology, 31(4):267-268.
Morrison et al. (1998) "Variable region domain exchange influences the functional properties of igG," J. Immunol., 160:2802-2808.
Mortari et al. (1993) "Human Cord Blood Antibody Repertoire," The Journal of Immunology, 150(4):1348-1357.
Muller et al. (1993) "B-Cell Abnormalities in AIDSs: Stable and Clonally-Restricted Antibody Response in HIV-1 Infection," Scand. J. Immunol., 38:327-334.

Muñoz et al. (2008) "Conventional pluripotency markers are unspecific for bovine embryonic-derived cell-lines," Theriogenology, 69(9):1159-1164.
Murphy and Silha (2000) "Unexpected and unexplained phenotypes in transgenic models," Growth Hormone & IGF Research, 10:233-235.
Murphy, A., VelocImmune: Immunoglobulin Variable Region Humanized Mice, Recombinant Antibodies for Immunotherapy, Ed. Little, M., New York, NY: Cambridge University Press, Chapter 8, pp. 100-107 (2009).
Murphy Slide Deck, Slide Presentation dated Nov. 3, 2009, "BAC-based Modifications of the Mouse Genome: The Big and the Backward," slides 1-57.
Murphy (2012) Kenneth, Janeway's Immunobiology 8th Edition. New York: Garland Science, Printed in USA., Chapter 5, Sections 5-1 to 5-4, pp. 157-162.
Murphy et al. (2014) "Mice with megabase humanization of their immunoglobulin genes generate antibodies as efficiently as normal mice," PNAS, pp. 1-12, www.pnas.org/cgi/doi/10.1073/pnas.1324022111.
Muyldermans, S. et al., Sequence and structure of VH domain from naturally occurring camel heavy chain immunoglobulins lacking light chains, Protein Eng., 7(9):1129-1135 (1994).
Muyldermans (2001) "Single domain camel antibodies: current status," Rev. Mol. Biotech., 74:277-302.
Myszka (1999) "Improving biosensor analysis," J. Mol. Recogn. 12:279-284.
Nagle (2007) Regeneron helps make Sanofi VelocImmune to its "weak pipeline", <http://www.outsourcing-pharma.com/Preclinical-Research/Regeneron-helps-make-Sanofi-VelocImmune-to-its-weak-pipeline>—Published Dec. 3, 2007.
Nelson, A.L. et al., Development trends for human monoclonal antibody therapeutics, Nat. Rev. Drug. Discov., 9(10):767-74 (2010).
Nemazee, D., Receptor editing in B cells, Adv. Immunol., 74:89-126 (2000).
Nemazee, D., Receptor editing in lymphocyte development and central tolerance, Nat. Rev. Immunol., 6(10):728-40 (2006).
News in Brief Article. Big Pharma views for mice, Nature Biotechnology 2007(June);25(6):613.
Nguyen, V.K. et al., Heavy-chain only antibodies derived from dromedary are secreted and displayed by mouse B cells, Immunology, 109(1):93-101 (2003).
Nicholson et al. (1999) "Antibody Repertoires of four-and Five-Feature Translocus Mice Carrying Human Immunoglobulin Heavy Chain and kappa and lambda light chain Yeast Artificial Chromosomes," Journal of Immunology, 163(12):6898-6906.
Niemann et al. (2005) "Transgenic farm animals: present and future, Review of Science Technology," 24(1):285-298.
Nishimura et al. (2004) "Possible Function of the ADAM1a/ADAM2 Fertilin Complex in the Appearance of ADAM 3 on the Sperm Surface," The Journal of Biological Chemistry, 279(33):34957-34962.
Nissim et al., Antibody fragments from a 'single pot' phage display library as immunochemical reagents, EMBO J., 13(3): 692-698 (1994).
Nitschke et al. (2001) "Deletion of the DQ52 element with the Ig heavy chain locus leads to a selective reduction in VDJ recombination and altered D gene usage," J. Immunol., 166:2540-52.
Novotny et al. (1985) "Structural Invariants of Antigen Binding: Comparison of Immunoglobulin VL-VH and VL-VL Domain Dimers," Proc. Nat. Acad. Sci., 82:4592-4596.
Oberdoerffer et al. (2003) "Unidirectional Cre-mediated genetic inversion in mice using the mutant loxP pair lox66/lox71," Nucleic Acids Research, 31(22)(e140):1-7.
O'Brien, R. et al., Somatic hypermutation of an immunoglobulin transgene in kappa mice, Nature, 326(6111):405-409 (1987).
Oddo et al. (2003) "Triple-Transgenic Model of Alzheimer's Disease with Plaques and Tangles: Intracellular A and Synaptic Dysfunction," Neuron, 39:409-421.
Orban, P.C. et al., Tissue- and site-specific DNA recombination in transgenic mice, Proc. Natl. Acad. Sci. U S A., 89(15):6861-5 (1992).

(56) References Cited

OTHER PUBLICATIONS

Paris and Stout, (2010) "Equine embryos and embryonic stem cells: defining reliable markers of pluripotency," Theriogenology, 74(4):516-524.
Parng et al. (1996) "Gene conversion contributes to the Ig light chain diversity in cattle," The Journal of Immunology, 157(12):5478-5486.
Pasqualini and Arap (2004) "Hybridoma-free generation of monoclonal antibodies," Proceedings of the National Academy of Sciences USA, 101(1):257-259.
Peeters, K. et al., Production of antibodies and antibody fragments in plants, Vaccine, 19(17-19):2756-61 (2001).
Pelanda, R. et al., A prematurely expressed Ig(kappa) transgene, but not V(kappa)J(kappa) gene segment targeted into the Ig(kappa) locus, can rescue B cell development in lambda5-deficient mice, Immunity, 5(3):229-239 (1996).
Pereira et al. (1998) "Cardiolipin binding a light chain from lupus-prone mice," Biochemistry, 37:1430-7.
Perez et al. (2010) "Primary cutaneous B-cell lymphoma is associated with somatically hypermutated immunoglobulin variable genes and frequent use of VH1-69 and VH4-59 segments," British Journal of Dermatology, 162:611-618.
Petitte et al. (2004) "Avian pluripotent stem cells," Mech. of Develop., 121(9):1159-1168.
Pettersson et al. (1990) "A second B cell-specific enhancer 3' of the immunoglobulin heavy-chain locus," Nature, 344(6262):165-168.
Phan, T. et al., Altered Migration, Recruitment, and Somatic Hypermutation in the Early Response of Marginal Zone B Cells to T Cell-Dependent Antigen, The Journal of Immunology, 174(8):4567-78 (2005).
Phan, T. et al., B Cell Receptor-independent Stimuli Trigger Immunoglobulin (Ig) Class Switch Recombination and Production of IgG Autoantibodies by Anergic Self-Reactive B Cells, The Journal of Experimental Medicine, 197(7):845-860 (2003).
Phan, T.G. et al., High affinity germinal center B cells are actively selected into the plasma cell compartment, J. Exp. Med., 203(11):2419-24 (2006).
Phelps, J. et al. (1990) Expression and Characterization of a Chimeric Bifunctional Antibody with Therapeutic Applications, The Journal of Immunology, 145:1200-1204 (1990).
Pollock, D.P. et al., Transgenic milk as a method for the production of recombinant antibodies, J. Immunol. Methods., 231(1-2):147-57 (1999).
Popov et al. (1999) "A Human Immunoglobulin lambda locus is Similarly Well Expressed in Mice and Humans," J. Exp. Med., 189(10):1611-1619.
Porteus, M.H. and Carroll, D., Gene targeting using zinc finger nucleases, Nat.; Biotechnol., 23(8):967-73 (2005).
Pos et al. (2008) "VH1-69 germline encoded antibodies directed towards ADAMTSI3 in patients with acquired thrombotic thrombocytopenic purpura," Journal of Thrombosis & Haemostasis, 7:421-428.
Poueymirou et al (2007) "F0 generation mice fully derived from gene-targeted embryonic stem cells allowing immediate phenotypic analyses," Nat Biotechnol 25, 91-99.
Prak, E. and Weigert, M., Light chain replacement: a new model for antibody gene rearrangement, J. Exp. Med., 182(2):541-548 (1995).
Prelle, K. et al., Pluripotent stem cells—model of embryonic development, tool for gene targeting, and basis of cell therapy, Anat. Histol. Embryol., 31(3):169-86 (2002).
Qi et al. (2005) "A new transgenic rat model of hepatic steatosis and the metabolic syndrome," Hypertension, 45(5):1004-1011.
Radic, M.Z. et al., Ig H and L chain contributions to autoimmune specificities, J. Immunol., 146(1):176-82 (1991).
Ramírez-Solis et al. (1995) "Chromosome engineering in mice," Nature, 378(6558):720-724.
Ramsden et al. (1994) "Conservation of sequence in recombination signal sequence spacers," Nucleic Acids Res., 22(10):1785-1796.

Ravetch et al. (1981) "Structure of the human immunoglobulin mu locus: characterization of embryonic and rearranged J and D genes," Cell, 27:583-591.
Ray (1991) "Ectopic expression of a c-kitW42 minigene in transgenic mice: recapitulation of W phenotypes and evidence for c-kit function in melanoblast progenitors," Genes Dev., 5(12A): 2265-2273.
Reineke (2004) "Antibody Epitope Mapping Using Arrays of Synthetic Peptides," Methods Mol Biol 248:443-463.
Ren e al. (2004) "Silencing of the immunoglobulin heavy chain locus by removal of all eight constant-region genes in a 200-kb region," Genomics, 84:686-695.
Reusch, et al., Beyond mAbs with TandAbs, Innovations in Pharmaceutical Technology, 4 pages (Jun. 2011).
Rich et al. (2000) "Advances in surface plasmon resonance biosensor analysis," Curr. Opin. Biotechnol. 11:54-61.
Rickert, R. et al., Impairment of T-cell-dependent B-cell responses and B-1 cell development in CD19-deficient mice, Nature, 376(6538):352-5 (1995).
Rickert, R.C. et al., B lymphocyte-specific, Cre-mediated mutagenesis in mice, Nucleic Acids Res., 25(6):1317-8 (1997).
Riechmann, L. and Muyldermans, S., Single domain antibodies: comparison of camel VH and camelised human VH domains, J. Immunol. Methods., 231(1-2):25-38 (1999).
Ristevski (2005) "Making better transgenic models: conditional, temporal, and spatial approaches," Molecular Biotechnology, 29(2):153-163.
Ritchie, K. et al., Allelic exclusion and control of endogenous immunoglobulin gene rearrangement in kappa transgenic mice, Nature, 312:517-520 (1984).
Rocca-Serra et al. (1983) "Two monoclonal antibodies against different antigens using the VH germ-line gene," Nature 304:353-5.
Rodriguez et al. (2000) "High-efficiency deleter mice show that FLPe is an alternative to Cre-loxP," Nature Genetics, 25:139-140.
Roebroek et al. (2003) "Chapter 10: Knockin Approaches," Methods in Molecular Biology, Transgenic Mouse Methods and Protocols, 209:16 pages.
Rojas et al. (2002) "Phage antibody fragments library combining a single human light chain variable region with immune mouse heavy chain variable regions," Biotechnol., 94(3):287-298.
Rosner, K. et al., Third complementarity-determining region of mutated VH immunoglobulin genes contains shorter V, D, J, P, and N components than non-mutated genes, Immunology, 103(2):179-87 (2001).
Rouet, P., et al. Introduction of double-strand breaks into the genome of mouse cells by expression of a rare-cutting endonuclease, Mol. Cell. Biol., 14:12 8096-8106 (1994).
Roussel et al. (1999) "The structure of an entire noncovalent immunoblobulin kappa light-chain dimer (Bence-Jones protein) reveals a weak and unusual constant domains association," Eur. J. Biochem., 260:192-199.
Rudikoff et al. (1982) "Single amino acid substitution altering antigen-binding specificity," PNAS 79:1979-1983.
Sapparapu et al. (2009) "Antigen-specific proteolysis by hybrid antibodies containing promiscuous proteolytic light chains paired with an antigen-binding heavy chain," J. Biol. Chem., 284(36):24622-24633.
Sasaki et al., "Canonical NF-kB Activity, Dispensable for B Cell Development, Replaces BAFF-Receptor Signals and Promotes B Cell Proliferation upon Activation," Immunity 24: 729-739 (2006).
Sasso et al., (1990) "Prevalence and Polymorphism of Human $V_h3$ Genes," Journal of Immunology, 145(8):2751-2757.
Sasso et al. (1993) "A Fetally Expressed Immunoglobulin $V_H1$ Gene Belongs to a Complex Set of Alleles," Journal of Clinical Investigation, 91:2358-2367.
Sasso et al. (1996) "Expression of the Immunoglobulin VH Gene 51p1 Is Proportional to Its Germline Gene Copy Number" Journal of Clinical Investigation, 97(9):2074-2080.
Schelonka et al. (2005) "A Single DH Gene Segment Creates Its Own Unique CDR-H3 Repertoire and Is Sufficient for B cell Development and Immune Functions," Journal of Immunology, 175:6624-6632.

(56) References Cited

OTHER PUBLICATIONS

Schiffer et al. (1973) "Structure of a λ-Type Bence-Jones Protein at 3.5-Å," Biochemistry, 12:4620-4631.
Schlissel and Baltimore (1989) "Activation of Immunoglobulin Kappa Gene Rearrangement Correlates with Induction of Germline Kappa Gene Transcription," Cell, 58:1001-1007.
Schnieke, A.E. et al., Human factor IX transgenic sheep produced by transfer of nuclei from transfected fetal fibroblasts, Science, 278(5346):2130-3 (1997).
Schroeder, H.W. Jr., Similarity and divergence in the development and expression; of the mouse and human antibody repertoires, Dev. Comp. Immunol., 30(1-2):119-35 (2006).
Schultz et al. (2012) "Humanized mice for immune system investigation: progress, promise and challenges," Nature Reviews Immunology, 12:786-798.
Schulze et al. (2006) "Derivation, Maintenance, and Characterization of Rat Embryonic Stem Cells in Vitro," Methods in Molecular Biology, 329:45-58.
Schwartz and Cantor (1984) "Separation of Yeast Chromosome-Sized DNAs by Pulsed Field Gradient Gel Electrophoresis," Cell, 37:67-75.
Science Magazine Careers http://www.sciencemag.org/careers/2007/03/mastering-your-phdmaking-most-conference, last accessed Nov. 15, 2016.
Scott (2007) "Mice with a human touch," Nature Biotechnology, 25(10):1075-1077.
Seals and Courtneidge (2003) "The ADAMs family of metalloproteases: multidomain; proteins with multiple functions," Genes and Development, 17(1):7-30.
Segal, D. et al., Introduction: bispecific antibodies, Journal of Immunological Methods, 248(1-2):1-6 (2001).
Sekiguchi, et al. Mechanism of V(D)J Recombination, Molecular Biology of B Cells, Eds. Honjo, Alt, and Neuberger, London, UK: Elsevier Academic Press, pp. 61-82 (2004).
Sen and Baltimore (1986) "Multiple nuclear factors interact with the immunoglobulin enhancer sequences," Cell, 46(5):705-716.
Sepulveda et al. (2003) "Binders Based on Dimerised Immunoglobulin VH Domains," J. Mol. Biol., 333:355-365.
Sharpe, M.J. et al., Somatic hypermutation of immunoglobulin kappa may depend on sequences 3' of C kappa and occurs on passenger transgenes, EMBO J., 10(8):2139-45 (1991).
Shi et al. (2006) J. Immunol. Methods 314:9-20.
Shih, H.H., Discovery Process for Antibody-Based Therapeutics, Development of Antibody-Based Therapeutics 426, Eds. Tabrizi, M.A. et al., Springer New York, pp. 9-32 (2012).
Shmerling et al. (2005) "Strong and ubiquitous expression of transgenes targeted into the β-actin locus by Cre/lox cassette replacement," Genesis, 42(5):229-235.
Sibilia et al. (1997) "Structural Analysis of Human Antibodies to Proteinase 3 from Patients with Wegener Granulomatosis," Journal of Immunology, 159:712-719.
Sigmund (2000) "Viewpoint: Are Studies in Genetically Altered Mice Out of Control?" Arterioscler. Thomb. Vasc. Biol., 20(6):1425-1429.
Simon and Rajewsky (1990) "Antibody domain mutants demonstrate autonomy of the antigen binding site," EMBO Journal., 9(4):1051-1056.
Sirac, C. et al., Light chain inclusion permits terminal B cell differentiation and does not necessarily result in autoreactivity, Proc. Natl. Acad. Sci, U S A, 103(20):7747-52 (2006), and Supplemental information, 4 pages, retrieved Jul. 7, 2016: <http://www.pnas.org/content/103/20/7747.long?tab=ds#F6>.
Sirac, C. et al., Role of the monoclonal kappa chain V domain and reversibility of renal damage in a transgenic model of acquired Fanconi syndrome, Blood, 108(2):536-543 (2006).
Sirac, C. et al., Toward understanding renal Fanconi syndrome: step by step advances through experimental models, Contrib. Nephrol., 169:247-61 (2011).
Smith, (2002) "Gene transfer in higher animals: theoretical considerations and key concepts," Journal of Biotechnology, 99(1):1-22.
Smith, B. et al., The unique and immunoglobulin-like regions of surrogate light chain component lambda5 differentially interrogate immunoglobulin heavy-chain structure, Molecular Immunology, 47:1195-1206 (2010).
Smith, E.J. et al., A novel, native-format bispecific antibody triggering T-cell killing of B-cells is robustly active in mouse tumor models and cynomolgus monkeys, Sci. Rep., 5:17943 (2015).
Solomon et al. (1998) "Light chain-associated amyloid deposits comprised of a novel κ constant domain," PNAS, 95:9547-9551.
Song et al. (2000) "Light chain of natural antibody plays a dominant role in protein antigen binding," Biochem. Biophys. Res. Comm., 268:390-394.
Soriano, P., Generalized lacZ expression with the ROSA26 Cre reporter strain, Nat. Genet., 21(1):70-1 (1999).
Sorrell and Kolb (2004) "Chapter XI: Targeted Modification of Mammalian Genomes," Focus on Genome Research, 6 pages.
Souroujon et al. (1989) "Polymorphisms in Human H Chain V Region Genes From The VHIII Gene Family," Journal of Immunology, 143(2):706-711.
Stamatopoulos et al. (1997) "Follicular lymphoma immunoglobulin κ light chains are affected by the antigen selection process, but to a lesser degree than their partner heavy chains," British J. Haematology, 96:132-146.
Steipe, B., et al. Sequence statistics reliably predict stabilizing mutations in a protein domain, J. Mol. Biol., 240(3):188-92 (1994).
Stevens et al. (2006) "Velocimmune: Humanization of Immunoglobulin Loc Using Velocigene Technology," First International MUGEN Conference of Animal Models for Human Immunological Disease, Sep. 10-13, 2016—Athens, Greece, Abstract 4 and Poster, 11 pages.
Stevens et al., Human Antibody Discovery, VelocImmune—A novel platform, Pharma Focus Asia, Issue 8: 72-74 (2008).
Storb, U. et al., Transgenic Mice with μ and ? Genes Encoding Antiphosphorycholine Antibodies, J. Exp Med, 164:627-41 (1986).
Su, Q. et al., A DNA transposon-based approach to validate oncogenic mutations in the mouse, Proc. Natl. Acad. Sci. USA, 105(50):19904-9 (2008).
Sui et al. (2009) "Structural and functional bases for broad-spectrum neutralization of avian and human influenza A viruses," Nature Structural & Molecular Biology, 16(3):265-273.
Sun et al. (1994) "Antigen recognition by an antibody light chain," J. Biol. Chem., 269(1):734-738.
Suzuki et al. (1995) "Representation of Rearranged $V_H$ Gene Segments in the Human Adult Antibody Repertoire," Journal of Immunology, 154:3902-3911.
Swarthout et al. (2011) "Zinc Finger Nucleases: A new era for transgeenic animals," Annals of Neurosciences, 18(1):25-28.
Szent-Gyorgy et al. (2013) "Malachite Green Mediates Homodimerization of Antibody $V_L$ Domains to Form a Fluorescent Ternary Complex with Singular Symmetric Interfaces," J. Mol. Biol., 425:4595-4613.
Tada, H. et al., Expression and characterization of a chimeric bispecific antibody against fibrin and against urokinase-type plasminogen activator, Journal of Biotechnology, 33:157-174 (1994).
Taki et al. (1993) "Targeted Insertion of a Variable Region Gene into the Immunoglobuliin Heavy Chain Locus," Science, 262:1268-1271.
Tanha, J. et al., Optimal design features of camelized human single-domain antibody libraries, J. Biol. Chem., 276(27):24774-80 (2001).
Taylor (1992) "A transgenic mouse that expresses a diversity of human sequence heavy and light chain immunoglobulins," Nucl. Acids Res. 20:6287-6295).
Taylor L.D. et al., Human immunoglobulin transgenes undergo rearrangement, somatic mutation and class switching in mice that lack endogenous IgM, Int Immunol. 6(4):579-91 (1994).
Tiegs, S. et al., Receptor Editing in Self-reactive Bone Marrow B Cells,The Journal of Experimental Medicine, 177:1009-1020 (1993).
Timetable for Mouse ES Cells course at Wellcome Trust Sanger Institute Oct. 26-Nov. 8, 2009 (black and white), 5 pges original (pp. 6-13 are pp. 1-5 of the original, enlarged).

(56) References Cited

OTHER PUBLICATIONS

Timetable for Mouse ES Cells course at Wellcome Trust Sanger Institute Oct. 26-Nov. 8, 2009 (greyscale), 5 pages original (pp. 6-13 are pp. 1-5 of the original, enlarged).
Tomer (2000) "Characterization of a discontinuous epitope of the human immunodeficiency virus ~HIV! core protein p24 by epitope excision and differential chemical modification followed by mass spectrometric peptide mapping analysis," Protein Science: 9:487-496 (first named author is Hochleitner).
Tomizuka, K. et al., Double trans-chromosomic mice: maintenance of two individual human chromosome fragments containing Ig heavy and kappa loci and expression of fully human antibodies, Proc. Natl. Acad. Sci. U S A., 97(2):722-7 (2000).
Tonegawa (1983) "Somatic generation of antibody diversity," Nature, 302(5909):575-581.
Torres and Kuhn (1997) Laboratory Protocols for Conditional Gene Targeting, 37-40.
Tsubata, T. and Reth, M., The Products of the Pre-B Cell-specific Genes(Lambda5 and VpreB) and the Immunoglobulin mu Chain Form a Comples that is Transported onto the Cell Surface, Journal of Experimental Medicine, 172:973-976 (1990).
Tsybovsky et al. (2004) "Folding and stabiilty of chimeric immunofusion VL-barstar," Biochem (Moscow), 69(9):939-948.
Tuaillon (2000) "Repertoire analysis in human immunoglobulin heavy chain minilocus transgenic, [mu]MT/ [mu]MT mice," Molecular Immunology, 37(5):221-231.
Tuaillon et al. (1993) "Human immunoglobulin heavy-chain minilocus recombination in transgenic mice: Gene-segment use in μ and y transcripts," PNAS, 90:2734-2743.
UniProt Entry Q5QGZ9, retrieved Jan. 21, 2015 from <http://www.uniprot.org/uniprot/Q5QGZ9> (16 pages).
V-Base Sequence Directory http://www2.mrc-lmb-cam.ac.uk/vbase/list2.php.
Valenzuela et al (2003) "High-throughput engineering of the mouse genome coupled with high-resolution expression analysis," Nat. Biotechnol. 21:652-659.
Van Den Beucken et al. (2001) "Building novel binding ligands to B7.1 and B7.2 based on human antibody single variable light chain domains," J. Mol. Immunol., 310:591-601.
Van Ness et al. (1981) "Transcription of the unrearranged mouse C kappa locus: sequence of the initiation region and comparison of activity with a rearranged V kappa-C kappa gene," Cell, 27:593-602.
Van Spriel, A.B. et al., Immunotherapeutic perspective for bispecific antibodies, Immunol. Today, 21(8):391-7 (2000).
Vasquez, K.M. et al., Manipulating the mammalian genome by homologous recombination, Proc. Natl. Acad. Sci. U S A., 98(15):8403-10 (2001).
Vaughan, T.J. et al., Human antibodies with sub-nanomolar affinities isolated from a large non-immunized phage display library, Nat. Biotechnol., 14(3):309-14 (1996).
Verkoczy et al. (2010) "Autoreactivity in an HIV-1 broadly reactive neutralizing antibody variable region heavy chain induces immunologic tolerance," Proc. Natl. Acad. Sci. U.S.A., 107(1): 181-186.
Verma, R. et al., Antibody engineering: Comparison of bacterial, yeast, insect and mammalian expression systems, Journal of Immunological Methods, 216:165-181 (1998).
Vettermann and Schlissel (2010) "Allelic eclusion of immunoglobulin genes: models and mechanisms," Immunological Reviews, 237:22-42.
Vieira, P. and Rajewsky, K., The half-lives of serum immunoglobulins in adult mice,; Eur. J. Immunol., 18(2):313-6 (1988).
Wagner et al. (1994) "Antibodies generated from human immunoglobulin miniloci in transgenic mice," Nucleic Acids Research, 22(8):1389-1393.
Wagner et al. (1994) "The diversity of antigen-specific monoclonal antibodies form transgenic mice bearing human immunoglobulin gene miniloci," Eur. J. Immunol., 24:2673-2681.
Wallace et al. (2007) "Manipulating the mouse genome to engineer precise functional syntenic replacements with human sequence," Cell, 128(1):197-209.
Wang et al. (2000) "Human immunoglobulin variable region gene analysis by single cell RT-PCR," J. Immunol. Methods, 244(1-2):217-225.
Wang and Palese (2009) "Universal epitopes of influenza virus hemagglutinins?," Nature Structural & Molecular Biology, 16(3):233-234.
Warren and Nie (1998) Science 281: 2016-2018.
Waterfield, M.D. et al., Restricted Structural Heterogeneity in Antibodies: Might Different Heavy Chains have a Common Light Chain? Nature New Biology, vol. 240:215-217 (1972).
Watson and Crick (2002) Molekulyarnaya biotekhnologiya. Printsipy i primeneniye, Moscow Mir., 45-47 and English translation.
Williams et al. (1996) "Sequence Evolution of the Human Germline V lambda Repertoire," J. Mol. Biol., 264(2):220-232.
Wilmut, I. and Clark, A.J., Basic techniques for transgenesis, J. Reprod. Fertil. Suppl., 43:265-75 (1991).
Wilmut, I. et al., Viable offspring derived from fetal and adult mammalian cells, Nature, 385(6619):810-3 (1997).
Winter, D.B. et al., Insertion of 2 kb of bacteriophage DNA between an immunoglobulin promoter and leader exon stops somatic hypermutation in a kappa transgene, Mol. Immunol., 34(5):359-66 (1997).
Wu, H. et al., Double replacement: strategy for efficient introduction of subtle mutations into the murine Col1a-1 gene by homologous recombination in embryonic stem cells, Proc. Natl. Acad. Sci. U S A., 91(7):2819-23 (1994).
Xu and Davis (2000) "Diversity in the CDR3 Region of VHIs Sufficient for Most Antibody Specificities," Immunity, 13:37-45.
Xu, L. et al., Combinatorial surrobody libraries, Proceedings of the National Academy of Sciences (USA), 105(31):10756-10761 (2008).
Yamada et al. (1991) "Preferential Utilization of Specific Immunoglobulin Heavy Chain Diversity and Joining Segments in Adult Human Peripheral Blood B Lymphocytes," Journal of Experimental Medicine, 173:395-407.
Yang, X.W. et al., Homologous recombination based modification in *Escherichia coli* and germline transmission in transgenic mice of a bacterial artificial chromosome, Nat. Biotechnol. 15(9):859-65 (1997).
Yantha et al. (2010) "Unexpected Acceleration of Type 1 Diabetes by Transgenic Expression of B7-H1 in NOD Mouse Peri-Islet Glia," Diabetes, 59:2588-2596.
Yarilin A.A. "Osnovy immunologii", M.: Meditsina, 1999, p. 172-174 (with English translation).
Yu et al. (2008) "Interaction between Bevacizumab and Murine VEGF-A: A Reassessment," Investigative Ophthalmology & Visual Science, 49(2):522-527.
Zemlin, M. et al., Expressed Murine and Human CDR-H3 Intervals of Equal Length Exhibit Distinct Repertoires that Differ in their Amino Acid Composition and Predicted Range of Structures, JMB, 334:733-749 (2003).
Zhang et al. (1998) "A new logic for DNA engineering using recombination in *Escherichia coli*," Nature Genetics, 20:123-138.
Zheng et al. (2000) "Engineering mouse chromosomes with Cre-loxP: range, efficiency, and somatic applications," Molecular and Cellular Biology, 20(2):648-655.
Zheng, J. et al., Immunoglobulin gene transcripts have distinct VHDJH recombination characteristics in human epithelial cancer cells, J. Biol. Chem., 284(20):13610-9 (2009).
Zhou et al., (2009) "Developing tTA transgenic rats for inducible and reversible gene expression," International Journal of Biological Sciences, 5:171-181.
Zou et al. (1994) Cre-loxP-mediated gene replacement: a mouse strain producing humanized antibodies, Current Biology, 4:1099-1103.
Zou et al. (2007) "Heavy chain-only antibodies are spontaneously produced in light chain-deficient mice," J. Exp. Med. 204(13):3271-3283.
After Final Consideration Pilot Program Request as filed in U.S. Appl. No. 13/798,310, filed Jul. 18, 2014 (2 pages).
Applicant's Written Submissions for AU2009263082, 49 pages (Sep. 6, 2016).

(56) References Cited

OTHER PUBLICATIONS

Brief comments on third party observations, EP 11703799.1-1410, submitted to EPO by David Power, 3 pages (Apr. 20, 2015).
Communication in Cases for which No Other Form is Applicable for PCT/US2012/026416, 9 pages (Jun. 7, 2013).
Communication in Cases for Which No Other Form Is Applicable for PCT/US2012/069981 , 18 pages (Jul. 3, 2013).
Communication pursuant to Article 94(3) EPC for EP 11 703 799.4, 6 pages (dated Oct. 9, 2012).
Communication pursuant to Article 94(3) EPC for EP 12 173 456.0, 5 pages (dated Dec. 5, 2012).
Corrected Claims in JP5749161 (English and Japanese), 6 pages.
Cover Letter—Applicant Post-Hearing Submissions in AU2009263082, 1 page (Oct. 19, 2016).
Declaration Appendix as filed in U.S. Appl. No. 13/798,310, filed Jul. 18, 2014 (7 pages).
Declaration of Andrew M. Scharenberg, M.D., filed in prosecution of U.S. Appl. No. 12/130,818, 21 pages, signed Oct. 4, 2010.
Declaration of Brink dated Apr. 30, 2015, as filed in AU Application No. 2009263082, 34 pages.
Declaration of Brink dated Jun. 2, 2015, as filed in AU Application No. 2009263082, 38 pages.
Declaration of Brink dated Sep. 27, 2016, as filed against EP Patent No. 2,147,594 B1 (European patent application No. 09075279.1), 33 pages.
Declaration of DeFranco dated Dec. 21, 2014, as filed in AU Application No. 2009263082, 56 pages.
Declaration of DeFranco dated Oct. 19, 2015, as filed in AU Application No. 2009263082, 31 pages.
Declaration of Denley dated May 1, 2015, as filed in AU Application No. 2009263082, 493 pages.
Declaration of Dr. Joel Martin, Opposition filed against European Patent No. EP 2314629 B1, 13 pages (May 18, 2016).
Declaration of Dr. Ton Logtenberg filed in U.S. Appl. No. 13/750,753, 10 pages (Dec. 18, 2015).
Declaration of Dr. Ton Logtenberg filed in U.S. Appl. No. 13/750,753, 4 pages (Sep. 15, 2015).
Declaration of Goodnow dated Oct. 19, 2015, as filed in AU Application No. 2009263082, 81 pages.
Declaration of Hudson dated Jun. 2, 2015, as filed in AU Application No. 2009263082, 81 pages.
Declaration of Hudson dated May 1, 2015, as filed in AU Application No. 2009263082, 52 pages.
Declaration of Lynn E. Macdonald, including Annexes 1-4, as together made publicly available at least upon submission to and online publication by the European Patent Office on Mar. 12, 2015, 13 pages, signed Mar. 3, 2015.
Declaration of Murphy dated Dec. 19, 2014, as filed in AU Application No. 2009263082, 18 pages.
Declaration of Professor Ton Logtenberg for EP2314629, 7 pages (May 4, 2016).
Declaration of Robert Brink in AU 2009263082, 19 pages (Oct. 19, 2016).
Declaration of Tarlinton dated Dec. 21, 2014, as filed in AU Application No. 2009263082, 40 pages.
Declaration of Tarlinton dated Oct. 19, 2015, as filed in AU Application No. 2009263082, 24 pages.
Declaration under 37 CFR 1.131 as filed in U.S. Appl. No. 13/798,310, filed Jul. 18, 2014 (21 pages).
Declaration Under C.F.R. § 1.131 Inventors: Lynn Macdonald, Cagan Gurer, Karolina Hosiawa, Sean Stevens, and Andrew Murphy Dated Dec. 1, 2015.
Declaration Under C.F.R. § 1.132 Dr. Andrew Murphy Dated Jul. 16, 2014.
Declaration Under C.F.R. § 1.132 Dr. Jürgen Roes Dated Jul. 19, 2014.
EP Examination Report with respect to EP 11741730.3 dated Jan. 23, 2015.
English Translation of Arguments dated Jan. 14, 2014, as filed in Merus Japanese Patent No. 5749161, 6 pages.
English Translation of Arguments dated Jan. 5, 2015, as filed in Merus Japanese Patent No. 5749161, 9 pages.
European Search Report with respect to EP12192727, dated Mar. 7, 2013.
European Search Report with respect to EP12195716, dated Jan. 29, 2013.
Exhibit A as filed in U.S. Appl. No. 13/798,310, filed Jul. 18, 2014 (2 pages).
Exhibit B as filed in U.S. Appl. No. 13/798,310, filed Jul. 18, 2014 (2 pages).
Exhibit C as filed in U.S. Appl. No. 13/798,310, filed Jul. 18, 2014 (1 page).
Exhibit D as filed in U.S. Appl. No. 13/798,310, filed Jul. 18, 2014 (1 page).
Exhibit E as filed in U.S. Appl. 13/798,310, filed Jul. 18, 2014 (3 pages).
Extended European Search Report for 12 173 456.0, 9 pages (dated Aug. 21, 2012).
Extended European Search Report for EP 15186515.1, 8 pages (dated Feb. 3, 2016).
Extended European Search Report with respect to EP14154918.8, dated Aug. 27, 2014.
Extended European Search Report with respect to EP14176593.3, dated Nov. 19, 2014.
Extended European Search Report with respect to EP15173007.4, dated Oct. 5, 2015.
Final Office Action with Respect to U.S. Appl. No. 13/756,889, dated Nov. 6, 2015.
Final Post-Hearing Submission—DeFranco Declaration Annexure in AU2009263082, 10 pages (Oct. 18, 2016).
Final Post-Hearing Submission—Opponent in AU2009263082, 4 pages (Oct. 19, 2016).
Final Response to Opposition in EP2501817, 27 pages (Dec. 23, 2016).
Final Written Submissions for Oral Proceedings Scheduled for Jun. 22, 2016, Opposition to Merus B.V.'s EP 2314629 B1, 13 pages (May 20, 2016).
Final Written Submissions Oral Proceedings Scheduled for Oct. 28, 2016 in EP2147594, 40 pages.
Forrest, K. B., Opinion of the United States District Court, *Regeneron Pharmaceuticals, Inc.* v. *Merus B.V.*, 114 pages (Nov. 2, 2015).
Initial Determination in EP Application No. 10186063.3, 11 pages (Nov. 19, 2015).
Initial Post-Hearing Submissions—DeFranco Declaration Annexure for Australian patent application No. 2009263082, 41 pages (Oct. 4, 2016).
Initial Post-Hearing Submissions—Goodnow Declaration Annexure for Australian patent application No. 2009263082, 13 pages (Oct. 4, 2016).
Initial Post-Hearing Submissions (Applicant) Brink Declaration Annex for Australian patent application No. 2009263082, 36 pages (Oct. 4, 2016).
Initial Post-Hearing Submissions (Applicant) for Australian patent application No. 2009263082, 5 pages (Oct. 5, 2016).
Initial Post-Hearing Submissions (Opponent's Initial Supplementary Submissions) for Australian patent application No. 2009263082, 7 pages (Oct. 5, 2016).
International Search Report & Written Opinion with respect to PCT/US2011/041366, dated Sep. 22, 2011.
International Search Report & Written Opinion with respect to PCT/US2011/041370, dated Sep. 22, 2011.
International Search Report & Written Opinion with respect to PCT/US2011/046196, dated Oct. 17, 2011.
International Search Report & Written Opinion with respect to PCT/US2012/026416, dated Jun. 25, 2012.
International Search Report & Written Opinion with respect to PCT/US2012/060487, dated Feb. 1, 2013.
International Search Report & Written Opinion with respect to PCT/US2012/069981, dated Mar. 20, 2013.
International Search Report & Written Opinion with respect to PCT/US2013/024295, dated Apr. 24, 2013.
International Search Report & Written Opinion with respect to PCT/US2015/021884, dated Oct. 13, 2015.

(56) References Cited

OTHER PUBLICATIONS

International Search Report & Written Opinion with respect to PCT/US2015/021892, dated Nov. 4, 2015.
International Search Report and Written Opinion with respect to PCT/US2016/023289, dated May 30, 2016.
International Search Report and Written Opinion for PCT Application No. PCT/US2013/044257 dated Sep. 4, 2013.
International Search Report for PCT/US2011/023971, 5 pages (dated Apr. 11, 2011).
International Search Report for PCT/US2012/034737 (dated Dec. 6, 2012).
International Search Report for PCT/US2012/049600 (7 pages), dated Nov. 23, 2012.
International Search Report for PCT/US2013/029125 (dated Jun. 20, 2013).
International Search Report for PCT/US2013/044257, 4 pages (dated Sep. 4, 2013).
International Search Report for PCT/US2014/025982 dated Jul. 22, 2014 (6 pages).
International Search Report for PCT/US2014/026040 dated Jul. 29, 2014 (5 pages).
Invitation to Pay Additional Fees and, Where Applicable, Protest Fee for PCT/US2015/021892, mailed Aug. 10, 2015.
JP Opposition Decision in JP5749161 (English and Japanese), 54 pages (Sep. 7, 2016).
Letter Accompanying Initial Post-Hearing Submissions (Applicant) for Australian patent application No. 2009263082, 1 page (Oct. 5, 2016).
Letter in Reply to Merus Response in EP2147594, 9 pages (Aug. 20, 2015).
Merus Final Written Submissions as filed in EP2147594 / 09075279.1-1405, 32 pages (Aug. 26, 2016).
Merus Response to REGN Opposition in EP2147594, 35 pages (Apr. 2, 2015).
Non-Final Office Action with Respect to U.S. Appl. No. 13/756,889, dated Dec. 1, 2016.
Notice of Opposition for EP 2501817, 28 pages (May 25, 2016).
Notice of Opposition in EP2701499, 27 pages (Nov. 10, 2016).
Notice of Opposition in JP5749161 (English and Japanese), 188 pages (Jan. 15, 2016).
Notice of Opposition to a European patent for EP 2314629, *Merus B.V. v. Regeneron Pharmaceuticals, Inc.*, 38 pages (Jul. 15, 2014).
Notice of Reasons for Revocation in JP5749161, (English and Japanese), 18 pages (Mar. 17, 2016).
Notice of Receipt of Correction Request in JP5749161 (English and Japanese), 2 pages (Jul. 1, 2016).
Nucleotide Sequence RID Y55HBK1 W114, last accessed Aug. 6, 2014 (2 pages).
Office Action for CN Application 201180013714.0, 19 pages (dated May 15, 2013).
Opposition dated Aug. 11, 2014, in EP Application No. 09075279.1, 983 pages.
Opposition dated Aug. 20, 2015, in EP Application No. 09075279.1, 25 pages.
Opposition dated Jan. 15, 2016, in JP Patent No. 5749161 and English translation, 188 pages.
Opposition dated Sep. 22, 2014, in AU Application No. 2009263082, 35 pages.
Opposition filed in European Application No. 10186063.3, 1351 pages (Jul. 15, 2014).
Opposition's rebuttal to Proprietor's submissions in Opposition No. 700031/2016 (English and Japanese), 64 pages (Aug. 22, 2016).
Patent Owner Final Submissions in response to the Summons to attend Oral Proceedings dated Nov. 19, 2015 and in preparation of the Hearing of Jun. 22, 2016 for EP2314629, 16 pages (May 20, 2016).
Patentee's Arguments against Opposition No. 700031/2016 (English and Japanese), 29 pages (Jun. 21, 2016).
Patentee's Exhibit 1 submitted with Argument against Opposition No. 700031/2016 on Jun. 21, 2016, "Really Essential Medical Immunology", Blackwell Science Ltd. Cover, colophon, Contents and Chapter 3 (pp. 23-25) (English and Japanese), 17 pages (2000).
Patentee's Exhibit 2 submitted with Argument against Opposition No. 700031/2016 on Jun. 21, 2016, Communication to the EPO submitted by the Opponent in connection with prosecution of EP2505654 (English and Japanese), 7 pages (Sep. 29, 2014).
Patentee's Exhibit 3 submitted with Argument against Opposition No. 700031/2016 on Jun. 21, 2016, Declaration of Peter Hudson (English and Japanese), 15 pages (Jun. 17, 2016).
Preliminary Opinion of the Opposition Division in EP2147594, 11 pages (Jan. 19, 2016).
Reply to Communication in EP12173456.0, 12 pages (dated Apr. 12, 2013).
Reply to Third Party Observations on EP2501817 (May 20, 2013).
Request for Correction in JP5749161 (English and Japanese), 29 pages (Jun. 21, 2016).
Request to provoke an interference U.S. Appl. No. 13/750,753, filed Jan. 25, 2013.
Response Post-Hearing Submissions by Applicant in AU2009263082, 15 pages (Oct. 19, 2016).
Response to Notice of Opposition dated Aug. 22, 2014 for EP2314629, 20 pages (Feb. 24, 2015).
Response to Opponent's Submission dated Aug. 26, 2016 and in Preparation of the Hearing scheduled for Oct. 28, 2016 in EP2147594, 14 pages (Sep. 28, 2016).
Statement of Facts and Arguments in Support of Opposition for EP2147594, 57 pages (Aug. 11, 2014).
Summary of Opponent's Submissions for AU2009263082, 35 pages (Aug. 30, 2016).
Summons to Attend Oral Proceedings Arranged in Connection with EP2147594 (Mar. 6, 2013).
Summons to attend oral proceedings dated Jan. 19, 2016, in EP Application 09075279.1, 20 pages.
Summons to Attend Oral Proceedings with respect to EP 11741730.3 mailed Sep. 28, 2015.
Third Party Observation dated Apr. 8, 2014, in CA Application No. 2729095, 16 pages.
Third Party Observation dated Apr. 10, 2015, in EP Application No. 11703799.4, 248 pages.
Third Party Observation dated Apr. 25, 2012, in EP Application No. 09075279.1, 145 pages.
Third Party Observation dated Feb. 28, 2013, in EP Application No. 11703799.4, 43 pages.
Third Party Observation dated Jul. 1, 2013, in EP Application No. 09075279.1, 6 pages.
Third Party Observation dated Jun. 24, 2013, in EP Application No. 09075279.1, 15 pages.
Third Party Observation dated May 16, 2013, in EP Application No. 09075279.1, 82 pages.
Third Party Observation dated May 4, 2015, in EP Application No. 12717033.0, 151 pages.
Third Party Observation dated Nov. 18, 2014, in EP Application No. 11703799.4, 132 pages.
Third Party Observation dated Nov. 3, 2014, in EP Application No. 12173456.0, 274 pages.
Third Party Observation dated Oct. 3, 2013, in EP Application No. 09075279.1, 3 pages.
Third Party Observation dated Oct. 21, 2013, in AU Application No. 2009263082, 24 pages.
Third Party Observation dated Oct. 25, 2012, in EP Application No. 09075279.1, 27 pages.
Third Party Observation dated Sep. 12, 2013, in EP Application No. 09075279.1, 5 pages.
Third Party Observation dated Sep. 16, 2015, in CA Application No. 2729095, 15 pages.
Third Party Observation dated Sep. 5, 2013, in EP Application No. 09075279.1, 11 pages.
Third Party Observation dated Sep. 7, 2015, in EP Application No. 12173456.0, 68 pages.
Third Party Observation pursuant to Article 115 EPC for EP 14170196.1, 6 pages (Jul. 1, 2015).
Third Party Observations on EP2501817 (Feb. 28, 2013).

(56) References Cited

OTHER PUBLICATIONS

Third Party Observations pursuant to Art. 115 EPC and R. 114 EPC against EP Application No. 12717033.0, 11 pages (May 4, 2015).
Third Party Observations pursuant to Article 115 EPC and R. 114 EPC against European Application No. 11703799.4, 5 pages (Apr. 10, 2015).
Third Party Observations Under Article 115 EPC against European Application No. 09075279.1 in the name of Merus BV, 12 pages (Oct. 25, 2012).
Third Party Observations under Article 115 EPC for EP 12 173 456.0, 8 pages (Nov. 3, 2014).
Third Party Submission dated Feb. 18, 2013, in U.S. Appl. No. 13/093,156, 179 pages.
Third Party Submission dated Feb. 19, 2014, in U.S. Appl. No. 13/750,753, 282 pages.
Third Party Submission dated Feb. 24, 2014, in U.S. Appl. No. 13/750,753, 97 pages.
Third Party Submission dated Feb. 27, 2014, in U.S. Appl. No. 13/948,818, 10 pages.
Third Party Submission dated Jan. 28, 2013, in U.S. Appl. No. 12/589,181, 13 pages.
Third Party Submission dated Jun. 12, 2013, in U.S. Appl. No. 13/750,753, 100 pages.
Third Party Submission filed in U.S. Appl. No. 13/795,637, 117 pages (Mar. 18, 2014).
U.S. Non-Final Office Action for U.S. Appl. No. 13/022,759 (dated Sep. 7, 2012).
U.S. Non-Final Office Action for U.S. Appl. No. 13/093,156 (dated Sep. 6, 2012).
U.S. Non-Final Office Action for U.S. Appl. No. 13/412,936 (dated Sep. 6, 2012).
Written Opinion for PCT/US2011/023971 (dated Apr. 11, 2011).
Written Opinion for PCT/US2012/034737, (dated Dec. 6, 2012).
Written Opinion for PCT/US2012/049600 (8 pages), dated Nov. 23, 2012.
Written Opinion for PCT/US2013/029125 (dated Jun. 20, 2013).
Written Opinion for PCT/US2013/044257, 5 pages (dated Sep. 4, 2013).
Written Opinion for PCT/US2014/025982 dated Jul. 22, 2014 (7 pages).
Written Opinion for PCT/US2014/026040 dated Jul. 29, 2014 (8 pages).
Statement of relatedness with respect to U.S. Appl. No. 15/559,358 dated Apr. 30, 2019.
Giraldo and Montoliu (2001) "Size matters: use of YACs, BACs and PACs in transgenic animals," Transgenic Research, 18:83-103.
Statement of relatedness with respect to U.S. Appl. No. 15/559,358 dated Jan. 30, 2020.
Chen and Murawsky "Strategies for Generating Diverse Antibody Repertoires Using Transgenic Animals Expressing Human Antibodies," Frontiers in Immunology, 9(460):1-7 https://www.frontiersin.org/articles/10.3389/fimmu.2018.00460/full#B22)/.
Wang, X. et al., Ab-origin: an enhanced tool to identify the sourcing gene segments in germline for rearranged antibodies. BMC Bioinformatics, 9(Suppl 12), 9 pages (2008).
Declaration of Professor Dr. Roland Kontermann, Ph.D. for EP2505654 B1, 4 pages (May 19, 2017).
Declaration of Professor Michel Cogné, 26 pages (Jul. 17, 2017).
Notice of Opposition in EP2505654, 39 pages (May 24, 2017).
Opponent Reply to Patentee Submissions in EP2501817, 5 pages (Mar. 17, 2017).
Patent Oppositions—Decision in for AU2009263082, 53 pages (May 5, 2017).
Response to Opposition in EP2701499, 22 pages (Apr. 28, 2017).
Statement of Grounds of Appeal for U.S. Pat. No. 2,147,594, 82 pages (2017).
Summons to Opposition in EP2501817, 12 pages (May 17, 2017).
Statement of relatedness with respect to U.S. Appl. No. 15/559,358 dated Sep. 8, 2020.
Brüggemann et al. "Immunoglobulin heavy chain locus of the rat: Striking homology to mouse antibody genes," Proc. Natl. Acad. Sci. U.S.A., 83:6075-6079 (1986).
Chen and Murawsky "Strategies for Generating Diverse Antibody Repertoires Using Transgenic Animals Expressing Human Antibodies," Frontiers in Immunology, 9(460):1-7 (2018) https://www.frontiersin.org/articles/10.3389/fimmu.2018.00460/full#B22)/.
Statement of relatedness with respect to U.S. Appl. No. 15/559,358 dated Nov. 5, 2020.

\* cited by examiner

| Antibody | Vκ | V_H | Antigen 3 (pH 7.4) | | | | | | Antigen 2 (pH 7.4) | | | | | |
|---|---|---|---|---|---|---|---|---|---|---|---|---|---|---|
| | | | mab capture (RU) | Antigen 3 100nM (RU) | ka (1/Ms) | kd (1/s) | $K_D$ (M) | T½ (min) | mab capture (RU) | Antigen 2 1 µM (RU) | ka (1/Ms) | kd (1/s) | $K_D$ (M) | T½ (min) |
| A | Vκ from anti-Antigen 2 KOH | Anti-Antigen 3 VH | 156 | 0 | | NB | | | 329 | 68 | 9.21E+04 | 2.80E-02 | 304 nM | 0.4 |
| B | Vκ from anti-Antigen 2 KOH | Anti-Antigen 3 VH | 148 | 0 | | NB | | | 136 | 32 | 4.80E+05 | 3.60E-01 | 750 nM | 0.03 |
| C | Cognate Vκ Anti-Antigen 3 VH | Anti-Antigen 3 VH | 201 | 34 | 1.73E+05 | 1.39E-03 | 8.1 nM | 8.3 | 140 | -4 | | NB | | |

FIG. 18

| Ab Name | Anti-A Ab Arm | Anti-B Ab Arm | Antibody type | Affinity to Antigen A at 25°C ||||| Affinity to Antigen B at 25°C |||||
|---|---|---|---|---|---|---|---|---|---|---|---|
| | | | | mAb captured | Antigen A bound – 100 nM | $K_D$ | | $t_{1/2}$ | mAb captured | Antigen B bound – 90 nM | $K_D$ | | $t_{1/2}$ |
| | | | | (RU) | (RU) | (mol/l) | | (min) | (RU) | (RU) | (mol/l) | | (min) |
| B1 | KOH1 | VH | anti-AxB Bispecific | 250.1±0.6 | 230 | 9.6E-09 | | 1.1 | 249.5±0.8 | 31 | 5E-09 | | 31 |
| B2 | KOH2 | VH | anti-AxB Bispecific | 259.5±1.4 | 211 | 8.2E-09 | | 0.9 | 257.9±0.5 | 29 | 9.3E-09 | | 25 |
| B3 | KOH3 | VH | anti-AxB Bispecific | 252.3±0.9 | 228 | 6.8E-09 | | 2.3 | 251.4±0.6 | 28 | 1.1E-08 | | 23 |
| C$_{KOH}$1 | KOH1 | NA | anti-A bivalent mAb | 262 | 288 | 2E-10 | | 149.75 | NA | NA | NT | | NT |
| C$_{KOH}$2 | KOH2 | NA | anti-A bivalent mAb | 163 | 123 | 2.3E-09 | | 18.41 | NA | NA | NT | | NT |
| C$_{KOH}$3 | KOH3 | NA | anti-A bivalent mAb | 113 | 118 | 8.2E-10 | | 36.68 | NA | NA | NT | | NT |
| C$_{VH}$ | NA | VH | anti-B bivalent mAb | NA | NA | NA | | NA | 483 | 53 | 5.21E-09 | | 41.1 |
| C$_I$ | NA | NA | hIgG1 isotype control | 236.5±1.0 | 18 | NB | | NB | 236.1±0.8 | 7 | NB | | NB |
| C | NA | NA | Anti-B hIgG1 control | 166.2±0.3 | 1 | NB | | NB | 159.5±0.2 | 78 | 1.4E-09 | | 52 |

FIG. 20

SEQUENCE LISTING

```
<160> NUMBER OF SEQ ID NOS: 2

<210> SEQ ID NO 1
<211> LENGTH: 3155
<212> TYPE: DNA
<213> ORGANISM: Artificial
<220> FEATURE:
<223> OTHER INFORMATION: Synthetic

<400> SEQUENCE: 1
ggcgcgccgt agctttgaat tttaaacatc tatttgacaa gaaatgcata gttccttctc      60
tttaaaataa tgtaatgttt ctttcaagaa taagcttggt ttgatgcctc tctccccaac     120
atgatagaag tgtagcataa atctatgaaa aattccattt ccctgtgcct acaacaacta     180
cctgggattg aaaacttctt cccttgctct agtcctttct tctacaccta cttccacatc     240
atctgtgact caaaacaata cttgtcagga aagatcccgg aaagagcaaa aaagacttcc     300
ttagaggtgt cagagattcc tatgccacta tctgtcatct ctagaagggg ttgtgagtat     360
gaggaagagc agagcttgta aattttctac ttgctttgac ttccactgta tttcctaaca     420
acaacaacca cagcaacacc cataacatca caggacaaac ttctagtact tccaaggctt     480
tagtctcagt aaatcttctc tacctccatc acagcagcta gaaggtttga tactcataca     540
aatagtactg tagctttctg ttcataattg gaaaaataga caagacccaa tgtaatacag     600
gctttccttc agccagttag cgttcagttt ttggatcacc attgcacaca tatacccagc     660
atatgtctaa tatatatgta gaaatccgtg aagcaagagt tataatagct tgtgtttttct    720 attgtattgt attttcctct tatatcatct tcttcttcgt tcattaaaaa aaaaccgttc     780
aagtaggtct aaattaatta ttggatcata agtagataaa atattttatt tcataacaca     840
ttgacccgat gaatatgttt ctttgccaga catagtcctc atttccaagg taacaagcct     900
gaaaaaatta tactggagca agtcaacagg taatgatggt agcttttcct tattgtcctg     960
gggcaagaat aagacaaaag ataacagggt agaataaaga ttgtgtaaga aagaaggaca    1020
gcaacaggac atgggaacct tttatagagt aacattttga taatggatga tgagaattaa    1080
tgagttagac agggatgggt gggaatgatt gaaggtgtga gtactttagc acagattaag    1140
accaaatcat taggatttaa agagttgtgt agagttagtg aaggaaaagc cttagaatta    1200
aatttggctg cggataaaac attcttggat tagactgaag actctttttct gtgctaagta    1260 agtatattta tgataatgat gatgactgta gtgctgaata tttaataaat aaaaacaaaa    1320
```

```
ttaattgccg catacataat gtcctgaata ctattgtaaa tgttttatct tatttccttt    1380
aaactgtcta cagcactata aggtaggtac cagtattgtc acagttacac agatatggaa    1440
accgagacac agggaagtta agttacttga tcaatttcaa gcaatcggca agccatggag    1500
catctatgtc agggctgcca ggacatgtga ctgtaaacag aagttttca ctttttaact     1560 caaagagggt atgtggctgg gttaatggaa agcttcagga ccctcagaaa acattactaa    1620
caagcaaatg aaaggtgtat ctggaagatt aagttttaac agactcttca tttccatcga    1680
tccaataatg cacttaggga gatgactggg catattgagg ataggaagag agaagtgaaa    1740
acacagcttt ttatattgtt cttaacaggc ttgtgccaaa catcttctgg gtggatttag    1800
gtgattgagg agaagaaaga cacaggagcg aaattctctg agcacaaggg aggagttcta    1860
cactcagact gagccaacag acttttctgg cctgacaacc agggcggcgc aggatgctca    1920
gtgcagagag gaagaagcag gtggtctttg cagctgaaag ctcagctgat ttgcatatgg    1980
agtcattata caacatccca gaattcttta agggcagctg ccaggaagct aagaagcatc    2040
ctctcttcta gctctcagag atggagacag acacactcct gctatgggtg ctgctgctct    2100
gggttccagg tgagggtaca gataagtgtt atgagcaacc tctgtggcca ttatgatgct    2160
ccatgcctct ctgttcttga tcactataat tagggcattt gtcactggtt ttaagtttcc    2220
ccagtcccct gaattttcca ttttctcaga gtgatgtcca aaattattct taaaaattta    2280
aatgaaaagg tcctctgctg tgaaggcttt taaagatata taaaaataat ctttgtgttt    2340
atcattccag gtgccagatg tgacatccag atgacccagt ctccatcctc cctgtctgca    2400
tctgtaggag acagagtcac catcacttgc cgggcaagtc agagcattag cagctattta    2460
aattggtatc agcagaaacc agggaaagcc cctaagctcc tgatctatgc tgcatccagt    2520
ttgcaaagtg gggtcccatc aaggttcagt ggcagtggat ctgggacaga tttcactctc    2580
accatcagca gtctgcaacc tgaagatttt gcaacttact actgtcaaca gagttacagt    2640
acccctccga tcaccttcgg ccaagggaca cgactggaga ttaaacgtaa gtaattttc     2700 actattgtct tctgaaattt gggtctgatg ccagtattg acttttagag gcttaaatag     2760
gagtttggta aagattggta aatgagggca tttaagattt gccatgggtt gcaaaagtta    2820
aactcagctt caaaaatgga tttggagaaa aaaagattaa attgctctaa actgaatgac    2880
acaaagtaaa aaaaaaagt gtaactaaaa aggaaccctt gtatttctaa ggagcaaaag     2940
taaatttatt tttgttcact cttgccaaat attgtattgg ttgttgctga ttatgcatga    3000
tacagaaaag tggaaaaata catttttag tctttctccc ttttgtttga taaattattt     3060
tgtcagacaa caataaaaat caatagcacg ccctaagatc tagatgcatg ctcgagtgcc    3120
atttcattac ctctttctcc gcacccgaca tagat                              3155
```

<210> SEQ ID NO 2
<211> LENGTH: 3166
<212> TYPE: DNA
<213> ORGANISM: Artificial
<220> FEATURE:
<223> OTHER INFORMATION: Synthetic

<400> SEQUENCE: 2

```
ggcgcgccgt agctttgaat tttaaacatc tatttgacaa gaaatgcata gttccttctc      60
tttaaaataa tgtaatgttt ctttcaagaa taagcttggt ttgatgcctc tctccccaac     120
atgatagaag tgtagcataa atctatgaaa aattccattt ccctgtgcct acaacaacta    180
cctgggattg aaaacttctt cccttgctct agtcctttct tctacaccta cttccacatc    240
```

```
atctgtgact caaaacaata cttgtcagga aagatcccgg aaagagcaaa aaagacttcc    300
ttagaggtgt cagagattcc tatgccacta tctgtcatct ctagaagggg ttgtgagtat    360
gaggaagagc agagcttgta aattttctac ttgctttgac ttccactgta tttcctaaca    420
acaacaacca cagcaacacc cataacatca caggacaaac ttctagtact tccaaggctt    480
tagtctcagt aaatcttctc tacctccatc acagcagcta gaaggtttga tactcataca    540
aatagtactg tagcttttctg ttcataattg gaaaaataga caagacccaa tgtaatacag    600
gctttccttc agccagttag cgttcagttt ttggatcacc attgcacaca tacccagc      660 atatgtctaa tatatatgta gaaatccgtg aagcaagagt tataatagct tgtgttttct    720
attgtattgt attttcctct tatatcatct tcttcttcgt tcattaaaaa aaaaccgttc    780
aagtaggtct aaattaatta ttggatcata agtagataaa atattttatt tcataacaca    840
ttgacccgat gaatatgttt ctttgccaga catagtcctc atttccaagg taacaagcct    900
gaaaaaatta tactggagca agtcaacagg taatgatgag agcttttcct tattgtcctg    960
gggcaagaat aagacaaaag ataacagggt agaataaaga ttgtgtaaga aagaaggaca   1020
gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagttttttca cttttttaact   1560 caaagagggt atgtggctgg gttaatggaa agcttcagga ccctcagaaa acattactaa   1620
caagcaaatg aaaggtgtat ctggaagatt aagtttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtcccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tataccaccg gagaaattgt gttgacgcag tctccaggca   2400
ccctgtcttt gtctccaggg gaaagagcca ccctctcctg cagggccagt cagagtgtta   2460
gcagcagcta cttagcctgg taccagcaga aacctggcca ggctcccagg ctcctcatct   2520
atggtgcatc cagcagggcc actggcatcc cagacaggtt cagtggcagt gggtctggga   2580
```

```
cagacttcac tctcaccatc agcagactgg agcctgaaga ttttgcagtg tattactgtc    2640
agcagtatgg tagctcacct tggacgttcg gccaagggac caaggtggaa atcaaacgta    2700
agtaattttt cactattgtc ttctgaaatt tgggtctgat ggccagtatt gacttttaga    2760
ggcttaaata ggagtttggt aaagattggt aaatgagggc atttaagatt tgccatgggt    2820
tgcaaaagtt aaactcagct tcaaaaatgg atttggagaa aaaaagatta aattgctcta    2880
aactgaatga cacaaagtaa aaaaaaaaag tgtaactaaa aaggaaccct tgtatttcta    2940
aggagcaaaa gtaaatttat ttttgttcac tcttgccaaa tattgtattg gttgttgctg    3000
attatgcatg atacagaaaa gtggaaaaat acatttttta gtctttctcc cttttgtttg    3060
ataaattatt ttgtcagaca acaataaaaa tcaatagcac gccctaagat ctagatgcat    3120
gctcgagtgc catttcatta cctctttctc cgcacccgac atagat                  3166
```

NON-HUMAN ANIMALS THAT SELECT FOR LIGHT CHAIN VARIABLE REGIONS THAT BIND ANTIGEN

CROSS-REFERENCE TO RELATED APPLICATIONS

This application is a U.S. National Phase Application filed under 35 U.S.C. § 371 of PCT Application No. PCT/US2016/023289, filed 18 Mar. 2016, which claims the benefit under 35 U.S.C. § 119(e) of U.S. Provisional Application Ser. No. 62/135,419, filed 19 Mar. 2015, which applications are hereby incorporated by reference in their entireties.

SEQUENCE LISTING

An official copy of the sequence listing is submitted concurrently with the specification electronically via EFS-Web as an ASCII formatted sequence listing with a file name of 2016-03-28-1150WO01-CORRECTED-SEQ-LIST_ST25.txt, a creation date of Mar. 28, 2016, and a size of about 9 kilobytes. The sequence listing contained in this ASCII formatted document is part of the specification and is herein incorporated by reference in its entirety.

FIELD OF INVENTION

Provided herein are immunoglobulin light chain variable ($V_{L/CH \times ULC}$) domains that are derived from a immunoglobulin hybrid chain that is cognate to a universal light chain, and that may bind antigen independently (e.g., in absence of) a cognate variable domain of the universal light chain, genetically modified non-human animals and cells that express $V_{L/CH \times ULC}$ domains, nucleic acids that encode $V_{L/CH \times ULC}$ domains, antigen-binding proteins (e.g., multispecific antigen-binding proteins) comprising one or more $V_{L/CH \times ULC}$ domains, and in vitro methods of generating antigen-binding protein (e.g., multispecific antigen-binding proteins) comprising one or more $V_{L/CH \times ULC}$ domains.

BACKGROUND

A number of promising novel diagnostics and therapies are biologics, commonly based on a traditional antibody format. However, traditional antibody-based design may be limited as antigen binding typically requires an antibody molecule that includes four polypeptides: two identical immunoglobulin heavy chains and two identical immunoglobulin light chains. The present invention encompasses the recognition that there remains a need for improvement and diversification of immunoglobulin-based therapeutic design.

SUMMARY

The present invention provides improved technologies for the development, production, and/or use of antigen-binding proteins based on immunoglobulin format. The present invention encompasses the recognition that conventional antibody-based format imposes certain constraints on the technology. For example, the present invention recognizes that requiring an antigen-binding site to be comprised of heavy and light chain variable domains can restrict the available affinity and/or specificity that can be achieved with respect to some antigenic determinants.

The present invention provides technologies that solve these problems. Among other things, the present invention provides genetically engineered non-human animals that express a "universal" or "common" immunoglobulin light chain variable domain and are useful, for example, in the development and/or production of novel antigen-binding protein formats. Moreover, the present invention surprisingly demonstrates that use of such an animal expressing a universal immunoglobulin light chain can direct selection of partner immunoglobulin chains whose variable domain binding characteristics can dominate within an antigen-binding site, even when the partner (or cognate) immunoglobulin chain's variable domain is a light chain variable domain. Thus, contrary to expectations in the art, the present invention demonstrates that it is possible to develop immunoglobulin light chain variable regions that determine or control specificity and/or affinity of antigen-binding sites in which they participate, e.g., that bind antigen when associated with a universal light chain variable domain and/or in the absence of, i.e., independently of, a cognate universal light chain variable domain.

Thus, in some embodiments, the present invention provides antigen-binding proteins, including multispecific antigen-binding proteins, comprising one or more imunoglobulin light chain variable domains that bind antigen when associated with a universal light chain variable domain and/or independently of a cognate universal light chain variable domain. Also provided are technologies, e.g., non-human animals and in vitro recombinant methods, for the development, production, and or use of such immunoglobulin light chain variable domain sequences in which antigen specificity and affinity results solely or primarily from, and/or resides solely or primarily in, immunoglobulin light chain variable domain diversity.

Various aspects and embodiments described herein are based in part on the surprising discovery that genetically modified non-human animals that express binding proteins that contain immunoglobulin light chain variable domains that are operably linked to a heavy chain constant region and immunoglobulin light chain variable domains encoded by a rearranged light chain variable gene sequence (e.g., a rearranged light chain $V_L J_L$ sequence) can solve various problems recognized herein and/or can provide surprising results. Non-human animals whose genome includes (i) a hybrid immunoglobulin chain locus containing unrearranged human light chain gene segments (e.g., $V_L$ and $J_L$ gene segments) operably linked to a heavy chain constant region sequence, e.g., at an endogenous heavy chain locus; and (ii) an immunoglobulin light chain locus containing a rearranged immunoglobulin light chain variable sequence (e.g., a single rearranged immunoglobulin light chain variable region sequence, such as for example a universal light chain variable region sequence) operably linked to a light chain constant gene can focus the mechanisms of antibody diversification on the unrearranged (i.e., diversifiable) immunoglobulin light chain variable gene segment(s) operably linked to the heavy chain constant region. Upon rearrangement, the unrearranged human light chain gene segments form a light chain variable region gene sequence that is operably linked to a heavy chain constant region gene sequence to form a sequence that encodes a immunoglobulin hybrid chain, i.e., an immunoglobulin polypeptide comprising a light chain variable domain fused with a heavy chain constant region. Non-human animals with the genomes described herein are able to generate antigen-binding proteins comprising dimeric immunoglobulin hybrid chains, each associated with cognate universal light chains in typical tetrameric antibody format, wherein the immunoglobulin hybrid chains comprise a light chain variable domain that is cognate with the light chain variable domain of the universal light chain, e.g., a $V_{L/CHxULC}$ variable domain.

As shown herein, a light chain variable $V_{L/CHxULC}$ domain that is derived from an immunoglobulin hybrid chain (e.g., is encoded by a $V_L/J_L$ gene sequence that encodes a variable domain of an immunoglobulin hybrid chain) and that is cognate to a universal light chain variable domain is capable of binding an antigen of interest in the presence or absence of the cognate universal light chain variable domain. The immunoglobulin hybrid chain from which the $V_{L/CHxULC}$ domain is derived is preferably somatically hypermutated and is not a single domain antibody, e.g., preferably has a heavy chain constant region that has an isotype selected from the group consisting of IgD, IgG, IgE and IgA and comprises a functional $C_H1$ domain. Such a variable $V_{L/CHxULC}$ domain is also able to bind antigen when associated with a second and noncognate variable domain specific for a different epitope, and regardless of whether the variable $V_{L/CHxULC}$ domain is operably fused to a a heavy chain constant region or a light chain constant region.

Accordingly, provided herein are antigen-binding proteins comprising at least a first binding component comprising an immunoglobulin light chain variable domain, e.g., a light chain variable $V_{L/CHxULC}$ domain, wherein the $V_{L/CHxULC}$ domain is (1) derived from a immunoglobulin hybrid chain encoded by a light chain sequence operably linked to one or more heavy chain constant region genes, e.g., Igµ, Igδ, Igγ, Igα and/or Igε, each of which comprises a nucleotide sequence that encodes a functional $C_H1$ domain, and (2) cognate to a universal light chain encoded by a rearranged light chain sequence operably linked to a light chain constant region gene.

In some embodiments, the a light chain variable $V_{L/CHxULC}$ domain is a $V_{κOHxULC}$ domain, e.g., is derived from and/or encoded by, a κ light chain variable region nucleotide sequence, e.g., a human κ light chain variable region nucleotide sequence, e.g., a Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, or Vκ7-3 gene segment sequence, which may be rearranged with a (human) Jκ1, Jκ2, Jκ3, Jκ4, or Jκ5 gene segment, or somatically hypermutated variant thereof. In some embodiments, the light chain variable $V_{L/CHxULC}$ domain is a $V_{λOHxULC}$ domain, e.g., is derived from and/or encoded by, a λ light chain variable region nucleotide sequence, e.g., a human λ light chain variable region nucleotide sequence, e.g., a Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 or Vλ4-69 gene segment sequence, which may be rearranged with a (human) Jλ1, Jλ2, Jλ3 or Jλ7 gene segment sequence, or a somatically hypermutated variant thereof.

Notably, rearrangement in a hybrid immunoglobulin locus of the unrearranged immunoglobulin $V_L$ and $J_L$ gene segments may result in a rearranged immunoglobulin light chain variable $V_{L/CHxULC}$ domain encoding gene sequence comprising 1, 2, 3, 4, 5, 6, 7, 8, 9, 10 or more N additions. In one embodiment, the N additions and/or the somatic mutations observed in the rearranged immunoglobulin light chain gene encoding a $V_{L/CHxULC}$ domain are 1.5-fold, 2-fold, 2.5-fold, 3-fold, 3.5-fold, 4-fold, 4.5-fold, or at least 5-fold more than the number of N additions and/or somatic mutations observed in a rearranged light chain variable sequence (derived from the same $V_L$ gene segment and the same $J_L$ gene segment) that is rearranged at an endogenous light chain locus. The increased N additions in the $V_{L/CHxULC}$ encoding gene sequence may encode a light chain variable $V_{L/CHxULC}$ domain having more amino acids in the CDR3 compared to a light chain variable $V_L$ domain encoded by a $V_L/J_L$ gene sequence recombined at an endogenous light chain locus. Accordingly, in some embodiments, an antigen-binding protein provided herein comprises an immunoglobulin light chain variable $V_{L/CHxULC}$ domain, wherein the variable $V_{L/CHxULC}$ domain comprises a CDR3 having a length of 9, 10, 11, 12 or more amino acids. In some embodiments, the $V_{L/CHxULC}$ domain comprises a CDR3 that is 9 amino acids in length. In some embodiments, the $V_{L/CHxULC}$ domain comprises a CDR3 that is 10 amino acids in length. In some embodiments, the $V_{L/CHxULC}$ domain comprises a CDR3 that is 11 amino acids in length. In some embodiments, the $V_{L/CHxULC}$ domain comprises a CDR3 that is 12 amino acids in length.

In preferred embodiments, an antigen-binding protein as described herein is not a single domain binding protein, e.g., is not a heavy chain only binding protein. Accordingly, in some embodiments, a first binding component as described comprises a light chain variable $V_{L/CHxULC}$ domain fused to a constant region, e.g., a heavy chain constant region comprising at least a functional $C_H1$ domain or a light chain constant domain, wherein the variable $V_{L/CHxULC}$ domain is derived from a immunoglobulin hybrid chain that (1) comprises a functional $C_H1$ domain and (2) is cognate to a universal light chain, e.g., wherein the immunoglobulin light chain variable $V_{L/CHxULC}$ domain is a $V_{κOHxULC}$ or $V_{λOHxULC}$ domain (respectively encoded by a rearranged (human) Vλ/Jκ or Vλ/Jλ sequence) that is or was operably linked to a heavy chain constant region gene sequence encoding at least a functional $C_H1$ domain, and thus, may comprise a CDR3 that is 9, 10, 11, 12 or more amino acids in length.

Accordingly, in some embodiments, an antigen-binding protein as described herein comprises at least a first binding component comprising an immunoglobulin light chain variable $V_{L/CHxULC}$ domain fused to a heavy chain constant region comprising at least a functional $C_H1$ domain (e.g., the immunoglobulin light chain $V_{L/CHxULC}$ domain is fused to a $C_H1$ domain capable of forming a disulfide bond with a light chain constant region) and optionally further comprising a hinge region, a $C_H2$ domain, a $C_H3$ domain, a $C_H4$ domain or a combination thereof. In some embodiments, the heavy chain constant region is a non-human heavy chain constant region comprising at least a functional $C_H1$ domain. In some embodiments, the non-human heavy chain constant region is a rodent (e.g., rat or mouse) or chicken heavy chain constant region comprising at least a functional $C_H1$ domain. In some embodiments, the heavy chain constant region is a human heavy chain constant region comprising at least a functional $C_H1$ domain. In some embodiments, the heavy chain constant region (or $C_H1$ domain) has an isotype selected from the group consisting of IgM, IgD, IgG, IgE and IgA. In some embodiments, the variable $V_{L/CHxULC}$ domain is fused to an IgG heavy chain constant region (or $C_H1$ domain) having a subclass selected from the group consisting of IgG1, IgG2, IgG3, and IgG4. In some embodiments, the variable $V_{L/CHxULC}$ domain is fused to a human and mutated IgG1, IgG2, or IgG4 heavy chain constant region (or $C_H1$ domain) comprising a $C_H3$ domain, wherein the mutation is in the $C_H3$ domain of the IgG1, IgG2 or IgG4 heavy chain constant region and reduces or eliminates binding of the $C_H3$ domain to Protein A, e.g., wherein the mutation is selected from the group consisting of (a) 95R, and (b) 95R and 96F in the IMGT numbering system, or (a') 435R, and (b') 435R and 436F in the EU numbering system. In some embodiments, the human and mutated heavy chain constant region is a human and mutated IgG1 constant region and, in addition to the (a) 95R or (b) 95R and 96F mutation (in the IMGT numbering system), further comprises one to five modifications selected from the group consisting of 16E, 18M, 44S, 52N, 57M, and 82I in the IMGT exon numbering system, or 356E, 358M, 384S, 392N, 397M, and 422I in the EU numbering system. In some embodiments, the human heavy chain constant region is a human IgG2 constant region and, in addition to the (a) 95R or (b) 95R and 96F mutation (in the IMGT numbering system), further comprises one or two modifications selected from the group consisting of 44S, 52N, 82I in the IMGT exon numbering system, or 348S, 392N and 422I in the EU numbering system. In other embodiments, the human heavy chain constant region is a human IgG4 constant region and, in addition to the (a) 95R or (b) 95R and 96F mutation (in the IMGT numbering system), further comprises one to seven modifications selected from the group consisting of 15R, 44S, 52N, 57M, 69K, 79Q and 82I in the IMGT exon numbering system or 355R, 384S, 392N, 397M, 409K, 419Q and 422I in the EU numbering system and/or the modification 105P in the IGMT exon numbering system or 445P in the EU numbering system.

Additionally, in some embodiments, an antigen-binding protein as described herein comprises at least a first binding component comprising an immunoglobulin light chain variable $V_{L/CHxULC}$ domain fused to a light chain constant domain. In some embodiments, the light chain constant domain is a non-human light chain constant domain. In some embodiments, the non-human light chain constant domain is a rodent (e.g., rat or mouse) or chicken light chain constant domain. In some embodiments, the light chain constant domain is a human light chain constant domain. In some embodiments, the light chain constant domain is a light chain κ constant domain. In some embodiments, the light chain constant domain is a light chain λ constant domain.

In some embodiments, an immunoglobulin light chain variable $V_{L/CHxULC}$ (e.g., $V_{\kappa OHxULC}$ or $V_{\lambda OHxULC}$) domain as described herein binds an antigen of interest in the absence of a cognate universal light chain. Accordingly, a first binding component as described herein may consist essentially or consist of the immunoglobulin light chain variable $V_{L/CHxULC}$ domain or the immunoglobulin light chain variable $V_{L/CHxULC}$ domain fused to a constant region, e.g., a heavy chain constant region comprising at least a functional $C_H1$ domain or a light chain constant region, wherein the variable $V_{L/CHxULC}$ domain is derived from a immunoglobulin hybrid chain that is cognate to a universal light chain, e.g., the immunoglobulin light chain variable $V_{L/CHxULC}$ domain is encoded by a rearranged (human) Vκ/Jκ or Vλ/Jλ sequence that is or was operably linked to a heavy chain constant region gene sequence, and thus, may comprise a CDR3 that is 9, 10, 11, 12 or more amino acids in length.

In other embodiments, the first binding component further comprises a cognate universal light chain variable domain in association with the immunoglobulin light chain $V_{L/CHxULC}$ variable domain, wherein the variable $V_{L/CHxULC}$ domain is derived from a immunoglobulin hybrid chain (e.g., the immunoglobulin light chain variable $V_{L/CHxULC}$ domain is encoded by a rearranged (human) Vκ/Jκ or Vλ/Jλ sequence that is or was operably linked to a heavy chain constant region gene sequence, and thus, may comprise a CDR3 that is 9, 10, 11, 12 or more amino acids in length), and wherein the immunoglobulin hybrid chain is cognate to a universal light chain encoded by a rearranged $V_L/J_L$ gene sequence and wherein the universal light chain variable domain is encoded by the rearranged $V_L/J_L$ gene sequence or a somatically hypermutated variant thereof.

In some embodiments, the universal light chain variable domain is encoded by or derived from a κ sequence, e.g., a human κ sequence, e.g., a Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, or Vκ7-3 gene segment sequence rearranged with a (human) Jκ1, Jκ2, Jκ3, Jκ4, or Jκ5 gene segment sequence, or a somatically hypermutated variant thereof. In some embodiments, the universal light chain variable domain is encoded by or derived from a nucleotide sequence comprising a human Vκ1-39 gene segment sequence rearranged with a human Jκ5 gene segment sequence, or a somatically hypermutated variant thereof. In some embodiments, the universal light chain variable domain is encoded by or derived from a nucleotide sequence comprising a human Vκ3-20 gene segment sequence rearranged with a human Jκ1 gene segment sequence, or a somatically hypermutated variant thereof. In some embodiments, the universal light chain variable domain is encoded by or derived from a lambda sequence, e.g., a human Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 or Vλ4-69 gene segment sequence rearranged with a (human) Jλ1, Jλ2, Jλ3 or Jλ7 gene segment sequence, or a somatically hypermutated variant thereof. In some embodiments the universal light chain variable domain is encoded by or derived from a nucleotide sequence comprising a Vλ2-14 gene segment sequence rearranged with a Jλ3 gene segment sequence, or a somatically hypermutated variant thereof. In some embodiments the universal light chain variable domain is encoded by or derived from a nucleotide sequence comprising a Vλ2-14 gene segment sequence rearranged with a Jλ7 gene segment sequence, or a somatically hypermutated variant thereof.

A first binding component as described herein may comprise the immunoglobulin light chain variable $V_{L/CH \times ULC}$ (e.g., $V_{\kappa OH \times ULC}$ or $V_{\lambda OH \times ULC}$) domain and the cognate universal light chain variable domain associated, e.g., linked, by a disulfide bond or a peptide linker. In some embodiments, a first binding component as described herein comprises a $V_{L/CH \times ULC}$ variable domain linked to a cognate universal light chain variable domain via a peptide linker, e.g., in an scFv-type format. In some embodiments, a first binding component as described herein comprises (i) an immunoglobulin light chain variable $V_{L/CH \times ULC}$ (e.g., $V_{\kappa OH \times ULC}$ or $V_{\lambda OH \times ULC}$) domain fused to a heavy chain constant region comprising at least a functional $C_H 1$ domain, e.g., the immunoglobulin light chain variable $V_{L/CH \times ULC}$ (e.g., $V_{\kappa OH \times ULC}$ or $V_{\lambda OH \times ULC}$) domain fused to the functional $C_H 1$ domain and (ii) a universal light chain variable domain fused to a light chain constant domain, wherein the $C_H 1$ domain is linked to the light chain constant domain by a disulfide bond or a peptide linker. In one embodiment, the $V_{L/CH \times ULC}$ variable domain is fused to heavy chain constant region comprising at least a functional $C_H 1$ domain (and optionally further comprising a hinge region, a $C_H 2$ domain, a $C_H 3$ domain, a $C_H 4$ domain, or a combination thereof), the universal light chain variable domain is fused to a light chain constant domain, and the functional $C_H 1$ domain is linked to the light chain constant domain by a disulfide bond. In another embodiment, the first binding component is in an scFab format, e.g., the $V_{L/CH \times ULC}$ variable domain is fused to heavy chain constant region comprising at least a functional $C_H 1$ domain, the universal light chain variable domain is fused to a light chain constant domain, and the functional $C_H 1$ domain is linked to the light chain constant domain by a peptide linker.

In some embodiments, a first binding component comprises a human $V_{L/CH \times ULC}$ (e.g., a human $V_{\kappa OH \times ULC}$ or a human $V_{\lambda OH \times ULC}$) domain, optionally fused with a human heavy chain comprising a $C_H 1$ domain or a human light chain constant domain. In one embodiment, an antigen-binding protein provided herein consists essentially or consists of only a first binding component as described herein, wherein the first binding component binds an antigen of interest.

Also provided are an antigen-binding proteins that, in addition to comprising a first binding component comprising a $V_{L/CH \times ULC}$ (e.g., $V_{\kappa OH \times ULC}$ or $V_{\lambda OH \times ULC}$) variable domain as described herein, further comprise a second binding component that comprises a second immunoglobulin variable domain that is derived from a heavy or hybrid chain, wherein both the $V_{L/CH \times ULC}$ variable domain of the first component and the second variable domain of second binding component may be, and preferably are, cognate to a universal light chain variable domain derived from, e.g., encoded by, an identical rearranged light chain variable region gene sequence. As such, any differences in the universal light chain variable domains to which the $V_{L/CH \times ULC}$ and second variable domains are respectively cognate are the result of somatic hypermutation(s), e.g., may be determined to have arisen from somatic hypermutation or affinity maturation processes.

An antigen-binding protein as provided herein may comprise first and second binding components as described herein, wherein the first and second binding components comprise identical $V_{L/CH \times ULC}$ variable domains, and wherein the antigen-binding protein is monospecific, e.g., may specifically bind a single epitope of interest.

In some embodiments, the first and second binding components are not identical, e.g., bind different epitopes, which may be on the same antigen or may be on different antigens. Accordingly, an antigen-binding protein as described herein may be a multi-specific antigen-binding protein and comprise a (i) first binding component comprising a first variable domain, e.g., a $V_{L/CH \times ULC}$ domain (e.g., $V_{\kappa OH \times ULC}$ or $V_{\lambda OH \times ULC}$), specific for a first epitope; and (ii) a second binding component comprising a second variable domain specific for a second epitope, wherein the second variable domain is either a second $V_{L/CH \times ULC}$ domain or a $V_{H \times ULC}$ domain (a heavy chain variable domain derived from a heavy chain encoded by $V_H D J_H$ gene sequence operably linked to a heavy chain constant region gene, wherein the heavy chain variable domain is cognate to a universal light chain variable domain), wherein the first and second epitopes are not identical, and wherein the first and second variable domains are each cognate to universal light chain variable domains that are derived from the same single rearranged light chain variable region gene sequence, and thus, are identical or are somatically hypermutated variants, e.g., differ in amino acid sequence only through somatic hypermutation. In some embodiments, the second variable domain is a second $V_{L/CH \times ULC}$ (e.g., $V_{\kappa OH \times ULC}$ or $V_{\lambda OH \times ULC}$) domain that binds a second epitope that is different than the first epitope, although the first and second variable $V_{L/CH \times ULC}$ domains are cognate to universal light chain variable domains that are derived from the same single rearranged light chain variable region gene sequence, and thus, are identical or somatically hypermutated variants. In some embodiments, the second variable domain is an immunoglobulin heavy chain variable ($V_{H \times ULC}$) domain that binds a second epitope different than the first epitope, wherein the $V_{L/CH \times ULC}$ variable domain of the first binding component and the $V_{H \times ULC}$ variable domain of the second binding component are cognate to universal light chain variable domains that are derived from same single rearranged light chain variable region gene sequence, and thus, are identical or somatically hypermutated variants. A multispecific antigen-binding protein provided herein comprising first and second binding components that are not identical may specifically bind more than one epitope of interest.

In some embodiments, wherein the second binding component comprises a second variable domain that is a $V_{H \times ULC}$ domain, the $V_H$ domain is encoded by a heavy chain variable region nucleotide sequence, e.g., a human heavy chain variable region nucleotide sequence, e.g., any human $V_H$, D, and $J_H$ gene segment sequence present in the human repertoire, e.g., any human heavy chain variable gene segments described in IMGT database, www.imgt.org, or somatically hypermutated variants thereof.

Additionally, the first binding component and the second binding component may be associated by one or more peptide linkers, one or more disulfide bonds and/or one or more leucine zippers such that a multiple specific antigen-binding protein provided herein is in a form selected from the group consisting of a Fab-like structure, an scFab-like structure, a diabody-like structure, an scFv-like structure, an scFv-Fc like structure, an scFv-zipper like structure, or a tetrameric structure that is similar to a typical antibody that includes the cognate universal light chain. Accordingly, in some embodiments, either or both the $V_{L/CH \times ULC}$ (e.g., $V_{\kappa OH \times ULC}$ or $V_{\lambda OH \times ULC}$) and second variable domains may be or may not be fused to a constant region (e.g., a heavy chain constant region comprising a functional $C_H 1$ domain or a light chain constant domain) and/or may or may not be associated with a cognate universal light chain variable domain.

In some embodiments, the variable $V_{L/CH\times ULC}$ (e.g., $V_{\kappa OH\times ULC}$ or $V_{\lambda OH\times ULC}$) domain of the first component is linked to the second variable ($V_{L/CH\times ULC}$ or $V_{H\times ULC}$) domain of second binding component by a peptide linker such that the antigen-binding protein may have a diabody-like structure, an scFv-like structure, an scFv-Fc like structure, or an scFv-zipper like structure. In some embodiments, (1) at least one of (a) the $V_{L/CH\times ULC}$ variable domain of the first component or (b) the second variable domain of second binding component is fused to a (non-human or human) heavy chain constant region comprising at least a functional $C_H1$ domain (and optionally further comprising a hinge region, a $C_H2$ domain, a $C_H3$ domain, a $C_H4$ domain, or a combination thereof) and (2) the other of (a) the $V_L IC_{H\times ULC}$ variable domain of the first component or (b) the second variable domain of second binding component is fused to a (non-human or human) light chain constant ($C_L$) domain, wherein the $C_H1$ domain is linked to the $C_L$ domain by a disulfide bond such that the antigen-binding protein has a Fab-like structure, or wherein the $C_H1$ domain is linked to the $C_L$ domain by a peptide linker such that the antigen-binding protein may have a scFab-like structure.

In some embodiments, both the first $V_{L/CH\times ULC}$ ($V_{\kappa OH\times ULC}$ or $V_{\lambda OH\times ULC}$) and second ($V_{L/CH\times ULC}$ or $V_{H\times ULC}$) variable domains are respectively fused to a first and second heavy chain constant regions, wherein each of the first and second heavy chain constant regions respectively comprises a first functional $C_H1$ domain and a second functional $C_H1$ domain (each heavy chain constant region optionally further comprising a hinge region, a $C_H2$ domain, a $C_H3$ domain, a $C_H4$ domain, or a combination thereof), and wherein the first and second heavy chain constant regions are linked, e.g., by a disulfide bond or a peptide linker. In some embodiments, at least one (or both) of the heavy chain constant regions is a non-human heavy chain constant region, e.g., a rodent (e.g., rat or mouse) or chicken heavy chain constant region. In some embodiments, at least one (or both) of the heavy chain constant regions is a human heavy chain constant region. In some embodiments, at least one (or both) of the heavy chain constant regions has an isotype selected from the group consisting of IgM, IgD, IgG, IgE and IgA. In some embodiments, at least one (or both) of the first variable $V_{L/CH\times ULC}$ and the second variable domains is fused to an IgG heavy chain constant region having a subclass selected from the group consisting of IgG1, IgG2, IgG3, and IgG4. In some embodiments, the first variable $V_{L/CH\times ULC}$ and the second variable domains are fused to heavy chain constant regions having an identical isotype and/or subclass, but optionally, wherein the heavy chain constant regions differ in their affinity to Protein A. In some embodiments, wherein both the first variable $V_{L/CH\times ULC}$ and the second variable domains are fused to a human IgG1, IgG2, or IgG4 heavy chain constant region, only one of the first variable $V_{L/CH\times ULC}$ and the second variable domain is fused to a human IgG1, IgG2, or IgG4 heavy chain constant region comprising a mutation in the $C_H3$ domain that reduces or eliminates binding of the $C_{H3}$ domain to Protein A, e.g., a mutation selected from the group consisting of (a) 95R, and (b) 95R and 96F in the IMGT numbering system, or (a') 435R, and (b') 435R and 436F in the EU numbering system. In some embodiments, the human heavy chain constant region is a human IgG1 constant region and further comprises one to five modifications selected from the group consisting of 16E, 18M, 44S, 52N, 57M, and 82I in the IMGT exon numbering system, or 356E, 358M, 384S, 392N, 397M, and 422I in the EU numbering system. In some embodiments, the human heavy chain constant region is a human IgG2 constant region and further comprises one or two modifications selected from the group consisting of 44S, 52N, 82I in the IMGT exon numbering system, or 348S, 392N and 422I in the EU numbering system. In other embodiments, the human heavy chain constant region is a human IgG4 constant region and further comprises one to seven modifications selected from the group consisting of 15R, 44S, 52N, 57M, 69K, 79Q and 82I in the IMGT exon numbering system or 355R, 384S, 392N, 397M, 409K, 419Q and 422I in the EU numbering system and/or the modification 105P in the IGMT exon numbering system or 445P in the EU numbering system.

In some embodiments, the first and second binding components may each respectively further comprise a first and second universal light chain variable domain respectively fused to a first and second light chain constant ($C_L$) domain, wherein the first and second $C_L$ domains are respectively linked, e.g., by a disulfide bond, to the first and second $C_H1$ domains of the first and second heavy chain constant regions, wherein the first and second universal light chain variable domains are derived from same single rearranged light chain variable region gene sequence, and thus, are identical or somatically hypermutated variants.

In some embodiments, an antigen-binding protein as described herein comprises a first binding component comprising a human $V_{L/CH\times ULC}$ ($V_{\kappa OH\times ULC}$ or $V_{\lambda OH\times ULC}$) domain, optionally fused with a human heavy chain comprising at least a $C_H1$ domain or a human light chain constant domain, a second binding component comprising a second human $V_{L/CH\times ULC}$ or a human $V_{H\times ULC}$ domain, optionally fused with a human heavy chain comprising a $C_H1$ domain or a human light chain constant domain, and optionally, a human universal light chain comprising a human universal light chain variable domain fused with a human light chain constant domain.

Non-human animals include, e.g., mammals and, in particular embodiments, rodents (e.g., mice, rats, or hamsters). In some embodiments, non-human animals include birds, e.g., chickens. The present invention provides non-human animals engineered to contain (e.g., in their germline genome and/or in genomes of their B cells) nucleic acid sequences as described herein and/or to express antigen-binding proteins (e.g., immunoglobulin chains and/or antibodies) as described herein, are provided by the present invention.

In some embodiments, the present invention particularly encompasses the recognition that it is desirable to engineer non-human animals to provide improved in vivo systems for the generation of immunoglobulin light chain domains in which antigen specificity and affinity is dominated by (e.g., results solely or primarily from, and/or resides solely or primarily in), immunoglobulin light chain variable domain diversity. In some embodiments, the present invention encompasses the recognition that it is desirable to engineer non-human animals to permit improved in vivo affinity maturation and/or selection for immunoglobulin light chain variable domains that bind antigen independent from an immunoglobulin heavy chain variable domain. In some embodiments, the present invention encompasses the recognition that non-human animals whose genome comprises unrearranged human light chain variable region gene segments operably linked to a heavy chain constant region and a rearranged human light chain variable region nucleic acid sequence are desirable, for example for use in selection immunoglobulin light chain variable domains ($V_{\kappa OH\times ULC}$ or $V_{\lambda OH\times ULC}$) having some or all of the aforementioned characteristics.

In some embodiments, the present invention provides a non-human animal capable of generating a $V_{L/CH \times ULC}$ variable domain, wherein the non-human animal comprises in its germline genome (a) a first hybrid immunoglobulin locus, e.g., at an endogenous non-human heavy chain locus, comprising unrearranged (human) immunoglobulin light chain ($V_L$ and $J_L$) gene segments capable of rearranging to form a rearranged (human) $V_L/J_L$ gene sequence operably linked to an immunoglobulin heavy chain constant region nucleic acid sequence comprising one or more heavy chain constant region genes each one comprising a sequence encoding a functional $C_H1$ domain, e.g., an intact Igμ gene and at least one of an intact Igδ gene, an intact Igγ gene, an intact Igε gene, and an intact Igα gene, wherein the rearranged human $V_L/J_L$ gene sequence operably linked to an immunoglobulin heavy chain constant region nucleic acid sequence encodes a hybrid immunoglobulin chain; and (b) a second light chain immunoglobulin locus, e.g., at an endogenous non-human light chain locus, comprising a rearranged human immunoglobulin light chain variable region nucleotide sequence operably linked to an immunoglobulin light chain constant region nucleic acid sequence, wherein the rearranged human immunoglobulin light chain variable region nucleotide sequence operably linked to an immunoglobulin light chain constant region nucleic acid sequence encodes a universal light chain, and wherein the non-human animal is capable of producing or does produce a cell, e.g., a lymphocyte, e.g., a B cell that expresses an antigen-binding protein comprising the immunoglobulin hybrid chain and the universal light chain, and wherein an immunoglobulin light chain variable domain of the immunoglobulin hybrid chain is a $V_{L/CH \times ULC}$ domain. In some embodiments, the non-human animal is a mammal or a bird. In some certain embodiments, the bird is a chicken. In some certain embodiments, the mammal is a rodent. In some embodiments, the rodent is selected from the group consisting of a mouse, a rat, and a hamster.

In some embodiments, a non-human animal of the present invention is homozygous for the rearranged human immunoglobulin light chain variable region nucleotide sequence. In some embodiments, a non-human animal of the present invention is heterozygous for the rearranged human immunoglobulin light chain variable region nucleotide sequence. In some embodiments, a non-human animal of the present invention is homozygous for the hybrid immunoglobulin locus. In some embodiments, a non-human animal of the present invention is heterozygous for the hybrid immunoglobulin locus. In some embodiments, the unrearranged (human) immunoglobulin light chain variable gene segments are operably linked to a non-human heavy chain constant region nucleic acid sequence comprising one or more heavy chain constant region genes each one comprising a sequence encoding a functional $C_H1$ domain, e.g., an intact Igμ gene and at least one of an intact Igδ gene, an intact Igγ gene, an intact IgE gene, and an intact Igα gene. In some embodiments, the non-human heavy chain constant region nucleic acid sequence is a mouse, rat, or chicken heavy chain constant region nucleic acid sequence comprising one or more heavy chain constant region genes each one comprising a sequence encoding a functional $C_H1$ domain, e.g., an intact Igμ gene and at least one of an intact Igδ gene, an intact Igγ gene, an intact Igε gene, and an intact Igα gene. In some embodiments, the non-human animal is a rodent, and the unrearranged human immunoglobulin light chain variable gene segments are operably linked to a human heavy chain constant region nucleic acid sequence comprising one or more heavy chain constant region genes each one comprising a sequence encoding a functional $C_H1$ domain, e.g., an intact Igμ gene and at least one of an intact Igδ gene, an intact Igγ gene, an intact Igε gene, and an intact Igα gene.

In some embodiments, the rearranged human immunoglobulin light chain variable region nucleotide sequence is operably linked to a non-human light chain constant region nucleic acid sequence. In some certain embodiments, the non-human light chain constant region nucleic acid sequence is a mouse or a rat light chain constant region nucleic acid sequence. In some embodiments, the non-human animal is a rodent, and the rearranged human immunoglobulin light chain variable region nucleotide sequence is operably linked to a human light chain constant region nucleic acid sequence.

In some certain embodiments, the light chain constant region nucleic acid sequence is a kappa sequence. In some certain embodiments, the light chain constant region nucleic acid sequence is a lambda sequence.

In some embodiments, the second immunoglobulin locus is a light chain kappa locus. In some embodiments, the second immunoglobulin locus is a light chain lambda locus.

In some embodiments, the unrearranged human immunoglobulin $V_L$ and $J_L$ gene segments are Vκ and Jκ gene segments. In some embodiments, the unrearranged human immunoglobulin $V_L$ and $J_L$ gene segments are Vλ and Jλ gene segments.

In some embodiments, the rearranged human immunoglobulin light chain variable region nucleotide sequence comprises a human κ light chain variable region nucleotide sequence. In some embodiments, the rearranged human immunoglobulin light chain variable region nucleotide sequence comprises a human λ light chain variable region nucleotide sequence.

In some embodiments, the first locus comprises one or more unrearranged human immunoglobulin $V_L$ gene segments selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the first locus comprises unrearranged human immunoglobulin $J_L$ gene segments that include Jκ1, Jκ2, Jκ3, Jκ4, and Jκ5.

In some embodiments, the $V_κ$ gene segment in the rearranged human immunoglobulin light chain variable region nucleotide sequence is a (human germline) Vκ gene segment selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some certain embodiments, the $V_L$ gene segment is selected from the group consisting of Vκ1-39 and Vκ3-20. In some embodiments, the $V_κ$ gene segment is selected from the group consisting of a human germline Vκ1-39 gene segment and a human germline Vκ3-20 gene segment.

In some embodiments, the $J_L$ gene segment in the rearranged human immunoglobulin light chain variable region nucleotide sequence is selected from the group consisting of Jκ1, Jκ2, Jκ3, Jκ4, and Jκ5, e.g., a human germline Jκ1 gene segment, a human germline Jκ2 gene segment, a human germline Jκ3 gene segment, a human germline Jκ4 gene segment, and a human germline Jκ5 gene segment.

In some certain embodiments, the rearranged human immunoglobulin light chain variable region nucleotide sequence comprises Vκ1-39 and Jκ5. In some certain embodiments, the Vκ1-39 is rearranged with the Jκ5. In some embodiments, the rearranged human immunoglobulin light chain variable region nucleotide sequence is set forth as SEQ ID NO: 1. In some certain embodiments, the rearranged human immunoglobulin light chain variable region nucleotide sequence comprises Vκ3-20 and Jκ1. In some certain embodiments, the Vκ3-20 is rearranged with Jκ1. In some embodiments, the rearranged human immunoglobulin light chain variable region nucleotide sequence is set forth as SEQ ID NO:2.

In some embodiments the non-human animal is a rodent, and wherein the light chain constant region nucleic acid sequence is a rat or a mouse Cκ constant region nucleic acid sequence.

In some embodiments, the non-human animal is a rodent, and wherein the heavy chain constant region nucleic acid sequence is a rat or mouse constant region sequence selected from the group consisting of Igμ, Igδ, Igγ, Igε, Igα, each of which encodes a functional $C_H1$ domain.

In some embodiments, the first locus comprises one or more unrearranged human immunoglobulin $V_L$ gene segments selected from the group consisting of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 and Vλ4-69. In some embodiments, the first locus comprises unrearranged human immunoglobulin $J_L$ gene segment that include Jλ1, Jλ2, Jλ3 and Jλ7.

In some embodiments, the $V_L$ gene segment in the rearranged human immunoglobulin light chain variable region nucleotide sequence is a (human germline) Vλ gene segment selected from the group consisting of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 and Vλ4-69. In some certain embodiments the $V_L$ gene segment is Vλ2-14, e.g., a human germline Vλ2-14 gene segment.

In some embodiments, the $J_L$ gene segment in the rearranged human immunoglobulin light chain variable region nucleotide sequence is selected from the group consisting of Jλ1, Jλ2, Jλ3 and Jλ7.

In some certain embodiments, the rearranged human immunoglobulin light chain variable region nucleotide sequence comprises Vλ2-14Jλ1. In some certain embodiments, the rearranged human immunoglobulin light chain variable region nucleotide sequence is Vλ2-14Jλ2. In some certain embodiments, the rearranged human immunoglobulin light chain variable region nucleotide sequence is Vλ2-14Jλ3. In some certain embodiments, the rearranged human immunoglobulin light chain variable region nucleotide sequence is Vλ2-14Jλ7. In some embodiments, the non-human animal is a rodent, and wherein the light chain constant region nucleic acid sequence is a rat or a mouse Cλ constant region nucleic acid sequence.

In some embodiments, the non-human animal is a rodent, and wherein the heavy chain constant region nucleic acid sequence is a rat or mouse constant region sequence selected from the group consisting of Igμ, Igδ, Igγ, Igε, Igα, and a combination thereof, each of which encodes a functional $C_H1$ domain.

In some embodiments, substantially all endogenous functional variable heavy chain $V_H$, D, and $J_H$ gene segments are deleted from an endogenous immunoglobulin heavy chain locus of the non-human animal or rendered non-functional. In some embodiments, substantially all endogenous functional light chain $V_L$ and $J_L$ gene segments are deleted from an endogenous immunoglobulin light chain locus of the non-human animal or rendered non-functional.

In some embodiments, the non-human animal comprises an integrated Adam6a gene, an Adam6b gene, or both. In some embodiments, a non-human animal comprises a functional ectopic mouse Adam6 gene.

In some embodiments, the first immunoglobulin locus comprises a plurality of copies of the rearranged human immunoglobulin light chain variable nucleotide sequence.

In some embodiments, the present invention provides a method of making a non-human animal, the method generally comprising modifying a germline genome of the non-human animal to comprise (i) a rearranged human immunoglobulin light chain variable region nucleotide sequence operably linked to an immunoglobulin light chain constant region nucleic acid sequence; and (ii) unrearranged human immunoglobulin light chain variable region gene segments ($V_L$ and $J_L$) capable of rearranging to form a rearranged human $V_L/J_L$ gene sequence operably linked to an immunoglobulin heavy chain constant region nucleic acid sequence. In some embodiments, the method comprises (a) modifying a genome of a non-human animal to delete or render non-functional all or substantially all (i) endogenous functional immunoglobulin heavy chain $V_H$, D, and $J_H$ gene segments and (ii) endogenous functional light chain $V_L$ and $J_L$ gene segments; (b) placing unrearranged human immunoglobulin $V_L$ and $J_L$ gene segments in the genome so that the unrearranged light chain variable gene segments are operably linked to a heavy chain constant region nucleic acid sequence; and (c) placing a rearranged human immunoglobulin light chain variable region nucleotide sequence in the genome so that the rearranged human immunoglobulin light chain variable region nucleotide sequence is operably linked to a light chain constant region nucleic acid sequence. In some embodiments, the method comprises (a) replacing all endogenous functional immunoglobulin heavy chain $V_H$, D, and $J_H$ gene segments at an endogenous heavy chain locus with unrearranged human immunoglobulin $V_L$ and $J_L$ gene segments so that the unrearranged light chain variable gene segments are operably linked to an endogenous heavy chain constant region nucleic acid sequence, and (b) replacing all endogenous functional light chain $V_L$ and $J_L$ gene segments at an endogenous light chain locus with a rearranged human immunoglobulin light chain variable region nucleotide sequence so that the rearranged human immunoglobulin light chain variable region nucleotide sequence is operably linked to an endogenous light chain constant region nucleic acid sequence.

In some embodiments, the non-human animal is a mammal or a bird. In some certain embodiments, the bird is a chicken. In some certain embodiments, the mammal is a rodent. In some embodiments, the rodent is selected from the group consisting of a mouse, a rat, and a hamster.

In some embodiments, the unrearranged human immunoglobulin $V_L$ and $J_L$ gene segments are operably linked to a non-human immunoglobulin heavy chain constant region nucleic acid sequence. In some embodiments, the non-human immunoglobulin heavy chain constant region nucleic acid sequence is a mouse or rat immunoglobulin heavy chain constant region nucleic acid sequence. In some embodiments, the non-human animal is a rodent, and the unrearranged human immunoglobulin light chain variable $V_L$ and $J_L$ gene segments are operably linked to a human heavy chain constant region nucleic acid sequence.

In some embodiments, the rearranged human immunoglobulin light chain variable region nucleotide sequence is operably linked to a non-human light chain constant region nucleic acid sequence. In some embodiments, the non-human light chain constant region nucleic acid sequence is a mouse or a rat light chain constant region nucleic acid sequence. In some embodiments, the non-human animal is a rodent, and the rearranged human immunoglobulin light chain variable region nucleotide sequence is operably linked to a human light chain constant region nucleic acid sequence. In some certain embodiments, the light chain constant region nucleic acid sequence is a kappa sequence. In some certain embodiments, the light chain constant region nucleic acid sequence is a lambda sequence. In some embodiments, the rearranged human immunoglobulin light chain variable region nucleotide sequence is placed in a kappa light chain locus. In some certain embodiments, the rearranged human immunoglobulin light chain variable region nucleotide sequence is placed in a lambda light chain locus.

In some certain embodiments, the unrearranged human immunoglobulin $V_L$ and $J_L$ gene segments are Vκ and Jκ gene segments. In some certain embodiments, the unrearranged human immunoglobulin $V_L$ and $J_L$ gene segments are Vλ and Jλ gene segments.

In some embodiments, the rearranged human immunoglobulin light chain variable region nucleotide sequence comprises a human κ light chain variable region nucleotide sequence. In some embodiments, the rearranged human immunoglobulin light chain variable region nucleotide sequence comprises a human λ light chain variable region nucleotide sequence.

In some embodiments, the unrearranged human immunoglobulin $V_L$ gene segments include one or more of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the unrearranged human immunoglobulin $J_L$ gene segments include Jκ1, Jκ2, Jκ3, Jκ4, and Jκ5.

In some embodiments, the rearranged human immunoglobulin light chain variable region nucleotide sequence comprises $V_L$ and $J_L$ gene segments. In some embodiments, the $V_L$ gene segment in the rearranged human immunoglobulin light chain variable region is a (human germline) Vκ gene segment selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some certain embodiments, the $V_L$ gene segment is selected from the group consisting of Vκ1-39 and Vκ3-20. In some embodiments, the Vκ gene segment is a human germline Vκ gene segment, e.g., a human germline Vκ1-39 gene segment or a human germline Vκ3-20 gene segment. In some embodiments, the $J_L$ gene segment is selected from the group consisting of Jκ1, Jκ2, Jκ3, Jκ4, and Jκ5, e.g., the group consisting of a human germline Jκ1 gene segment, a human germline Jκ2 gene segment, a human germline Jκ3 gene segment, a human germline Jκ4 gene segment, and a human germline Jκ5 gene segment. In some certain embodiments, the rearranged human immunoglobulin light chain variable nucleotide sequence comprises Vκ1-39 and Jκ5 (e.g., the Vκ1-39 is rearranged with the Jκ5). In some embodiments, the rearranged immunoglobulin light chain variable region nucleotide sequence comprises the sequence set forth as SEQ ID NO: 1. In some certain embodiments, the rearranged human immunoglobulin light chain variable nucleotide sequence comprises Vκ3-20 and Jκ1 (e.g., the Vκ3-20 is rearranged with the Jκ1). In some embodiments, the rearranged human immunoglobulin light chain variable region nucleotide sequence comprises the sequence set forth as SEQ ID NO:2.

In some embodiments, the non-human animal is a rodent, and wherein the light chain constant region nucleic acid sequence is a rat or a mouse Cκ constant region nucleic acid sequence. In some embodiments, the non-human animal is a rodent, and wherein the heavy chain constant region nucleic acid sequence is a rat or mouse constant region sequence selected from the group consisting of Igμ, Igδ, Igγ, Igε, Igα, and a combination thereof, each of which encodes a functional $C_H1$ domain.

In some embodiments, the non-human animal comprises one or more unrearranged human immunoglobulin $V_L$ gene segments selected from the group consisting of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 and Vλ4-69. In some embodiments, the non-human animal comprises unrearranged human immunoglobulin $J_L$ gene segments that include Jλ1, Jλ2, Jλ3 and Jλ7.

In some embodiments, the $V_L$ gene segment in the rearranged human immunoglobulin light chain variable region nucleotide sequence is a (human germline) Vλ gene segment selected from the group consisting of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 and Vλ4-69. In some certain embodiments, the $V_L$ gene segment is Vλ2-14, e.g., a human germline Vλ2-14 gene segment. In some embodiments, the $J_L$ gene segment in the rearranged human immunoglobulin light chain variable region nucleotide sequence is selected from the group consisting of Jλ1, Jλ2, Jλ3 and Jλ7. In some certain embodiments, the rearranged human immunoglobulin light chain variable region nucleotide sequence is Vλ2-14Jλ1. In some certain embodiments, the rearranged human immunoglobulin light chain variable region nucleotide sequence comprises Vλ2-14Jλ2. In some certain embodiments, the rearranged human immunoglobulin light chain variable region nucleotide sequence comprises Vλ2-14Jλ3. In some certain embodiments, the rearranged human immunoglobulin light chain variable region nucleotide sequence comprises Vλ2-14Jλ7.

In some embodiments, the non-human animal is a rodent, and wherein the light chain constant region nucleic acid sequence is a rat or a mouse Cλ constant region nucleic acid sequence.

In some embodiments, the non-human animal is a rodent, and wherein the heavy chain constant region nucleic acid sequence is a rat or mouse constant region sequence selected from the group consisting of Igμ, Igδ, Igγ, Igε, Igα, and a combination thereof, each of which encodes a functional $C_H1$ domain.

In some embodiments, the rearranged human immunoglobulin light chain variable region nucleotide sequence is placed at an endogenous immunoglobulin light chain locus in the genome. In some embodiments, the rearranged human immunoglobulin light chain variable region nucleotide sequence is present in a germline genome of the non-human animal. In some embodiments, the rearranged human immunoglobulin light chain variable region nucleotide sequence is placed at an ectopic locus in the genome. In some embodiments, the non-human animal comprises a plurality of copies of the rearranged human immunoglobulin light chain variable region nucleotide sequence.

In some embodiments, the non-human animal comprises an Adam6a gene, an Adam6b gene or both. In some embodiments, a non-human animal comprises a functional ectopic mouse Adam6 gene.

In some embodiments, the nucleic acid sequence encoding the universal light chain comprises one or more histidine codons that are not encoded by a corresponding human germline light chain variable gene segment.

In some embodiments, the present invention provides methods of using a genetically modified non-human animal provided herein or made according to a method disclosed herein, wherein the methods generally comprise isolating from the non-human animal a cell, e.g., a lymphocyte, e.g., a B cell, that expresses a hybrid immunoglobulin chain that comprises a $V_{L/CH \times ULC}$ domain fused to a heavy chain constant region, wherein the hybrid immunoglobulin chain is cognate to a universal light chain and/or obtaining from cell a nucleic acid encoding the $V_{L/CH \times ULC}$ domain of the hybrid immunoglobulin chain. In some embodiments, a method for obtaining a nucleic acid sequence that encodes an immunoglobulin light chain variable $V_{L/CH \times ULC}$ domain comprises (a) optionally immunizing a non-human animal with an antigen that comprises an epitope or immunogenic portion thereof, wherein the non-human animal comprises in its genome (i) a rearranged human immunoglobulin light chain variable region nucleotide sequence operably linked to an immunoglobulin light chain constant region nucleic acid sequence, and (ii) unrearranged human immunoglobulin light chain variable region gene segments ($V_L$ and $J_L$) operably linked to an immunoglobulin heavy chain constant region nucleic acid sequence such that the non-human animal mounts an immune response; and isolating from the immunized non-human animal a cell that expresses a nucleic acid sequence that encodes a light chain variable $V_{L/CH \times ULC}$ domain that can bind the antigen and/or the nucleic acid sequence that encodes a light chain variable $V_{L/CH \times ULC}$ domain that can bind the antigen.

In some embodiments, the nucleic acid sequence that encodes the light chain variable $V_{L/CH \times ULC}$ domain that can bind the antigen is derived from the unrearranged human immunoglobulin light chain variable region gene segments ($V_L$ and $J_L$) operably linked to a heavy chain constant region nucleic acid sequence.

In some embodiments, the isolating step is carried out via fluorescence-activated cell sorting (FACS) or flow cytometry. In some embodiments, the isolating step comprises obtaining from the immunized non-human animal a cell and obtaining from said cell the nucleic acid sequence that encodes the light chain $V_{L/CH \times ULC}$ domain that can bind the antigen, and wherein the cell is a lymphocyte. In some certain embodiments, the lymphocyte comprises natural killer cells, T cells, or B cells.

In some embodiments, the method further comprises fusing the lymphocyte with a cancer cell to form a hybridoma. In some certain embodiments, the cancer cell is a myeloma cell.

In some embodiments, the isolated nucleic acid sequence is fused with a nucleic acid sequence encoding an immunoglobulin constant region nucleic acid sequence.

In some embodiments, the non-human animal is a mammal or a bird. In some certain embodiments, the bird is a chicken. In some certain embodiments, the mammal is a rodent. In some embodiment, the rodent is selected from the group consisting of a mouse, a rat, and a hamster.

In some embodiments, the unrearranged human immunoglobulin light chain variable $V_L$ and $J_L$ gene segments are operably linked to a non-human immunoglobulin heavy chain constant region nucleic acid sequence. In some embodiments, the non-human immunoglobulin heavy chain constant region nucleic acid sequence is a mouse or rat immunoglobulin heavy chain constant region nucleic acid sequence, e.g., comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene.

In some embodiments, the non-human animal is a rodent, and the unrearranged human immunoglobulin light chain variable $V_L$ and $J_L$ gene segments are operably linked to a human heavy chain constant region nucleic acid sequence, e.g., comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene.

In some embodiments, the rearranged human immunoglobulin light chain variable region nucleotide sequence is operably linked to a non-human light chain constant region nucleic acid sequence. In some embodiments, the non-human light chain constant region nucleic acid sequence is a mouse or a rat light chain constant region nucleic acid sequence.

In some embodiments, the non-human animal is a rodent, and the rearranged human immunoglobulin light chain variable region nucleotide sequence is operably linked to a human light chain constant region nucleic acid sequence. In some certain embodiments, the light chain constant region nucleic acid sequence is a kappa sequence. In some certain embodiments, the light chain constant region nucleic acid sequence is a lambda sequence.

In some embodiments, the unrearranged human immunoglobulin $V_L$ and $J_L$ gene segments are human Vκ and Jκ gene segments. In some embodiments, the unrearranged human immunoglobulin $V_L$ and $J_L$ gene segments are human Vλ and Jλ gene segments.

In some embodiments, the rearranged human immunoglobulin light chain variable region nucleotide sequence comprises a human κ light chain variable region nucleotide sequence. In some embodiments, the rearranged human immunoglobulin light chain variable region nucleotide sequence comprises a human λ light chain variable region nucleotide sequence.

In some embodiments, the unrearranged human immunoglobulin $V_L$ gene segments include one or more of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the unrearranged human immunoglobulin $J_L$ gene segments include one or more of Jκ1, Jκ2, Jκ3, Jκ4, and Jκ5.

In some embodiments, the $V_L$ gene segment in the rearranged human immunoglobulin light chain variable region is a (human germline) Vκ gene segment selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some certain embodiments, the $V_L$ gene segment is selected from the group consisting of Vκ1-39 (e.g., a human germline Vκ1-39 gene segment) and Vκ3-20 (e.g., a human germline Vκ3-20 gene segment). In some embodiments, the $J_L$ gene segment is selected from the group consisting of Jκ1 (e.g., a human germline Jκ1 gene segment), Jκ2 (e.g., a human germline Jκ2 gene segment), Jκ3 (e.g., a human germline Jκ3 gene segment), Jκ4 (e.g., a human germline Jκ4 gene segment), and Jκ5 (e.g., a human germline Jκ5 gene segment). In some certain embodiments, the rearranged human immunoglobulin light chain variable nucleotide sequence comprises Vκ1-39 and Jκ5 (e.g., the Vκ1-39 is rearranged with the Jκ5, e.g., a human germline Vκ1-38 gene segment is rearranged with a human germline Jκ5 gene segment). In some embodiments, the rearranged human immunoglobulin light chain variable region nucleotide sequence comprises a sequence set forth as SEQ ID NO:1. In some certain embodiments, the rearranged human immunoglobulin light chain variable nucleotide sequence comprises Vκ3-20 and Jκ1 (e.g., the Vκ3-20 is rearranged with the Jκ1, e.g., a human germline Vκ3-20 gene segment rearranged with a human germline Jκ1 gene segment). In some embodiments, the rearranged human immunoglobulin light chain variable region nucleotide sequence comprises a sequence set forth as SEQ ID NO:2. In some embodiments, the non-human animal is a rodent, and wherein the light chain constant region nucleic acid sequence is a rat or a mouse Cκ constant region nucleic acid sequence.

In some embodiments, the non-human animal is a rodent, and wherein the heavy chain constant region nucleic sequence is a rat or mouse constant region sequence selected from the group consisting of Igμ, Igδ, Igγ, Igε, Igα, and a combination thereof, each of which encodes a functional $C_H1$ domain.

In some embodiments, the unrearranged human immunoglobulin $V_L$ gene segments include one or more of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 and Vλ4-69. In some embodiments, the non-human animal comprises unrearranged human immunoglobulin $J_L$ gene segments that include Jλ1, Jλ2, Jλ3 and Jλ7.

In some embodiments, the $V_L$ gene segment in the rearranged human immunoglobulin light chain variable region nucleotide sequence is a (human germline) Vλ gene segment selected from the group consisting of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 and Vλ4-69. In some certain embodiments the $V_L$ gene segment is Vλ2-14, e.g., a human germline Vλ2-14 gene segment. In some embodiments, the $J_L$ gene segment in the rearranged human immunoglobulin light chain variable region nucleotide sequence is selected from the group consisting of Jλ1, Jλ2, Jλ3 and Jλ7. In some certain embodiments, the rearranged human immunoglobulin light chain variable region nucleotide sequence comprises Vλ2-14Jλ1. In some certain embodiments, the rearranged human immunoglobulin light chain variable region nucleotide sequence comprises Vλ2-14Jλ2. In some certain embodiments, the rearranged human immunoglobulin light chain variable region nucleotide sequence comprises Vλ2-14Jλ3. In some certain embodiments, the rearranged human immunoglobulin light chain variable region nucleotide sequence comprises Vλ2-14Jλ7. In some embodiments, the non-human animal is a rodent and the light chain constant region nucleic acid sequence is a rat or a mouse Cλ constant region nucleic acid sequence.

In some embodiments, the non-human animal is a rodent, and wherein the heavy chain constant region nucleic acid sequence is a rat or mouse constant region sequence selected from the group consisting of Igμ, Igδ, Igγ, Igε, Igα, and a combination thereof, each of which encodes a functional $C_H1$ domain.

In some embodiments, the rearranged human immunoglobulin light chain variable region nucleotide sequence is at an endogenous immunoglobulin light chain locus in the genome. In some embodiments, the rearranged human immunoglobulin light chain variable region nucleotide sequence is present in a germline genome of the non-human animal. In some embodiments, the rearranged human immunoglobulin light chain variable region nucleotide sequence is integrated into a transcriptionally active locus in the genome. In some embodiments, the non-human animal comprises a plurality of copies of the rearranged human immunoglobulin light chain variable region nucleotide sequence.

In some embodiments, the non-human animal comprises an integrated Adam6a gene, an Adam6b gene or both. In some embodiments, a non-human animal comprises a functional ectopic mouse Adam6 gene.

In some embodiments, the nucleic acid sequence encoding the universal light chain comprises one or more histidine codons that are not encoded by a corresponding human germline light chain variable gene segment.

In some embodiments, the present invention provides a method for making an antigen-binding protein that comprises a $V_{L/CH \times ULC}$ ($V_{\kappa OH \times ULC}$ or $V_{\lambda OH \times ULC}$) domain, the method generally comprising expressing in a host cell a first nucleic acid comprising a nucleic acid sequence that encodes a $V_{L/CH \times ULC}$ domain, optionally operably linked with a heavy chain constant region gene comprising a functional $C_H1$ domain encoding sequence or a light chain constant region gene, wherein the $V_{L/CH \times ULC}$ domain is cognate to a universal light chain variable domain, and wherein the antigen-binding protein is not a single domain antigen binding protein. In some embodiments, the nucleic acid sequence that encodes the $V_{L/CH \times ULC}$ domain is isolated from non-human animal comprising in its genome (i) a rearranged human immunoglobulin light chain variable region nucleotide sequence operably linked to an immunoglobulin light chain constant region nucleic acid sequence; and (ii) unrearranged human immunoglobulin light chain variable region gene segments ($V_L$ and $J_L$) operably linked to an immunoglobulin heavy chain constant region nucleic acid sequence, wherein the nucleic acid sequence that encodes the $V_{L/CH \times ULC}$ domain is derived from the unrearranged human immunoglobulin light chain variable region gene segments ($V_L$ and $J_L$) operably linked to an immunoglobulin heavy chain constant region nucleic acid sequence, e.g., comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene. In some embodiments, the method further comprises (a) optionally immunizing a non-human animal with an antigen that comprises an epitope or immunogenic portion thereof, wherein the non-human animal comprises in its genome (i) a rearranged human immunoglobulin light chain variable region nucleotide sequence operably linked to an immunoglobulin light chain constant region nucleic acid sequence; and (ii) unrearranged human immunoglobulin light chain variable region gene segments ($V_L$ and $J_L$) capable of rearranging to form a rearranged $V_L/J_L$ gene sequence operably linked to an immunoglobulin heavy chain constant region nucleic acid sequence, such that the non-human animal mounts an immune response to the epitope or immunogenic portion thereof prior to (b) isolating from the non-human animal a nucleic acid sequence that encodes a light chain variable domain that specifically binds the epitope or immunogenic portion thereof and is derived from the rearranged $V_L/J_L$ gene sequence, which is operably linked to an immunoglobulin heavy chain constant region nucleic acid. Additional embodiments include methods comprising (c) employing the isolated nucleic acid sequence in an expression construct optionally operably linked to a human immunoglobulin constant region nucleic acid sequence; prior to (d) expressing the nucleic acid sequence or expression construct comprising same in a production cell line, e.g., a host cell, to obtain an antigen-binding protein.

In some embodiments, the method for making an antigen-binding protein that comprises a $V_{L/CH \times ULC}$ domain comprises co-expressing in a host cell (i) a first nucleic acid comprising a nucleic sequence that encodes a first binding component comprising a first variable domain, e.g., a $V_{L/CH \times ULC}$ domain, specific for a first epitope, optionally operably linked with a first heavy chain constant region gene comprising a functional $C_H1$ domain encoding sequence or a first light chain constant region gene, and (ii) a second nucleic acid encoding a second component comprising a second variable domain specific for a second epitope, wherein the second variable domain is either a second $V_{L/CH \times ULC}$ domain or a $V_{H \times ULC}$ domain, wherein the first and second epitopes are not identical, and wherein the first and second variable domains are each cognate to universal light chain variable domains that are derived from the same single rearranged light chain variable region gene sequence, and thus, are identical or are somatically hypermutated variants, e.g., differ in amino acid sequence only through somatic hypermutation.

Thus, in some embodiments, the method comprises (a) immunizing a second non human animal with an antigen that comprises an epitope or immunogenic portion thereof, wherein the second non-human animal comprises in its genome (i) a rearranged human immunoglobulin light chain variable region nucleotide sequence operably linked to an immunoglobulin light chain constant region nucleic acid sequence; and (ii) either unrearranged human immunoglobulin light chain variable region gene segments ($V_L$ and $J_L$) capable of rearranging to form a rearranged $V_L/J_L$ gene sequence (that encodes the second $V_{L/CH \times ULC}$ domain of the second binding component) or unrearranged human immunoglobulin heavy chain variable region gene segments ($V_H$, D and $J_H$) capable of rearranging to form a rearranged $V_H/D/J_H$ gene sequence (that encodes the $V_{H \times ULC}$ domain of the second binding component) operably linked to an immunoglobulin heavy chain constant region nucleic acid sequence such that the non-human animal mounts an immune response to the epitope or immunogenic portion thereof prior to (b) isolating from the non-human animal a second nucleic acid sequence that encodes the second $V_{L/CH \times ULC}$ or $V_{H \times ULC}$ domain that specifically binds the second epitope or immunogenic portion thereof. Additional embodiments include methods comprising (c) employing the isolated second nucleic acid sequence in an expression construct, optionally operably linked to a human immunoglobulin constant region nucleic acid sequence; prior to (d) expressing of the first and second nucleic acid sequences or expression construct(s) comprising same in a production cell line, e.g., a host cell, to obtain an antigen-binding protein, wherein the antigen binding protein is not a single domain antigen binding protein.

In additional embodiments, the methods further comprise co-expressing in the production host cell the first nucleic acid encoding a first $V_{L/CH \times ULC}$ domain (or expression construct comprising same), optionally the second nucleic acid encoding a second $V_{L/CH \times ULC}$ domain or $V_{Hx ULC}$ domain (or expression construct comprising same) and a nucleotide sequence comprising a rearranged $V_L/J_L$ gene sequence that encodes a human universal light chain variable domain, or somatically hypermutated variant thereof, that is cognate to the $V_{L/CH \times ULC}$ domain and the optional second $V_{L/CH \times ULC}$ domain or $V_{Hx ULC}$ domain. In some embodiments, the nucleotide sequence encodes the universal light chain variable domain fused to a human light chain constant domain.

The first nucleic acid sequence, and either or both the second nucleic acid sequence and the nucleotide sequence comprising a rearranged $V_L/J_L$ gene sequence encoding the human universal light chain variable domain, may be employed in the same or different expression constructs, wherein the one or more expression constructs express the antigen binding protein, e.g., the first binding component, and either or both the second binding component and universal light chain, in a format selected from the group consisting of a Fab-like structure, an scFab-like structure, a diabody like structure, an scFv-like structure, an scFv-Fc like structure, an scFv-zipper like structure, and a tetrameric structure that is similar to a typical antibody and that includes the cognate universal light chain. Accordingly, in some embodiments, either or both the first and second nucleic acid sequences may respectively encode the first variable $V_{L/CH \times ULC}$ and second variable ($V_{L/CH \times ULC}$ or $V_{Hx ULC}$) domain fused or not fused to a constant region, e.g., a (human) heavy chain constant region comprising a functional $C_H1$ domain or a (human) light chain constant domain.

In some embodiments, either or both first and second nucleic acid sequences comprise a heavy chain constant region nucleic acid that encodes a human heavy chain constant region having an isotype selected from the group consisting of IgM, IgD, IgG, Igε and IgA, e.g., an IgG heavy chain constant region having a subclass selected from the group consisting of IgG1, IgG2, IgG3, and IgG4. In some embodiments, the first and second nucleic acid sequence encode the first variable $V_{L/CH \times ULC}$ and the second variable ($V_{L/CH \times ULC}$ or $V_{Hx ULC}$) domain fused to heavy chain constant regions having an identical isotype and/or subclass, but optionally, wherein the heavy chain constant regions differ in their affinity to Protein A. In some embodiments, wherein both the first variable $V_{L/CH \times ULC}$ and the second variable ($V_{L/CH \times ULC}$ or $V_{Hx ULC}$) domains are fused to a human IgG1, IgG2, or IgG4 heavy chain constant region, only one of the first variable $V_{L/CH \times ULC}$ and the second variable ($V_{L/CH \times ULC}$ or $V_{Hx ULC}$) domain is fused to a human IgG1, IgG2, or IgG4 heavy chain constant region comprising a mutation in the $C_H3$ domain that reduces or eliminates binding of the $C_H3$ domain to Protein A, e.g., a mutation selected from the group consisting of (a) 95R, and (b) 95R and 96F in the IMGT numbering system, or (a') 435R, and (b') 435R and 436F in the EU numbering system. In some embodiments, the human heavy chain constant region is a human IgG1 constant region and further comprises one to five modifications selected from the group consisting of 16E, 18M, 44S, 52N, 57M, and 82I in the IMGT exon numbering system, or 356E, 358M, 384S, 392N, 397M, and 422I in the EU numbering system. In some embodiments, the human heavy chain constant region is a human IgG2 constant region and further comprises one or two modifications selected from the group consisting of 44S, 52N, 82I in the IMGT exon numbering system, or 348S, 392N and 422I in the EU numbering system. In other embodiments, the human heavy chain constant region is a human IgG4 constant region and further comprises one to seven modifications selected from the group consisting of 15R, 44S, 52N, 57M, 69K, 79Q and 82I in the IMGT exon numbering system or 355R, 384S, 392N, 397M, 409K, 419Q and 422I in the EU numbering system and/or the modification 105P in the IGMT exon numbering system or 445P in the EU numbering system.

In some embodiments, at least one of the unrearranged human immunoglobulin light chain $V_L$ or $J_L$ gene segments encode one or more histidine residues that are not encoded by a corresponding human germline light chain variable gene segment.

In some embodiments, the first and/or second non-human animal from which the first and second nucleic acid sequences are derived is a mammal or a bird. In some certain embodiments, the bird is a chicken. In some certain embodiments, the mammal is a rodent. In some embodiments, the rodent is selected from the group consisting of a mouse, a rat, and a hamster.

In some embodiments, the human immunoglobulin light chain variable $V_L$ and $J_L$ gene segments are operably linked to a non-human immunoglobulin heavy chain constant region nucleic acid sequence, e.g., comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene. In some embodiments, the non-human immunoglobulin heavy chain constant region nucleic acid sequence is a mouse or rat immunoglobulin heavy chain constant region nucleic acid sequence, e.g., comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene. In some embodiments, the non-human animal is a rodent, and the human immunoglobulin light chain variable $V_L$ and $J_L$ gene segments are operably linked to a human heavy chain constant region nucleic acid sequence, e.g., comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene.

In some embodiments, the heavy chain constant region nucleic acid sequence comprises a nucleotide sequence that encodes a $C_H1$, a hinge, a $C_H2$, a $C_H3$, or a combination thereof. In some embodiments, heavy chain constant region nucleic acid sequence comprises a sequence that encodes a functional $C_H1$ domain.

In some embodiments, the rearranged human immunoglobulin light chain variable region nucleotide sequence is operably linked to a non-human light chain constant region nucleic acid sequence. In some embodiments, the non-human light chain constant region nucleic acid sequence is a mouse or a rat light chain constant region nucleic acid sequence. In some embodiments, the non-human animal is a rodent, and the rearranged human immunoglobulin light chain variable region nucleotide sequence is operably linked to a human light chain constant region nucleic acid sequence. In some certain embodiments, the light chain constant region nucleic acid sequence is a kappa sequence. In some certain embodiments, the light chain constant region nucleic acid sequence is a lambda sequence.

In some embodiments, the unrearranged human immunoglobulin light chain variable $V_L$ and $J_L$ gene segments are Vκ and Jκ gene segments. In some embodiments, the unrearranged human immunoglobulin light chain variable $V_L$ and $J_L$ gene segments are Vλ and Jλ gene segments.

In some embodiments, the rearranged human immunoglobulin light chain variable region nucleotide sequence comprises a human κ light chain variable region nucleotide sequence. In some embodiments, the rearranged human immunoglobulin light chain variable region nucleotide sequence comprises a human λ light chain variable domain gene sequence.

In some embodiments, the unrearranged human immunoglobulin $V_L$ gene segments include one or more of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the unrearranged human immunoglobulin $J_L$ gene segments include Jκ1, Jκ2, Jκ3, Jκ4, and Jκ5.

In some embodiments, the rearranged human immunoglobulin light chain variable region nucleotide sequence comprises $V_L$ and $J_L$ gene segments. In some embodiments, the $V_L$ gene segment in the rearranged human immunoglobulin light chain variable region is a (human germline) Vκ gene segment selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some certain embodiments, the $V_L$ gene segment is selected from the group consisting of Vκ1-39 (e.g., a human germline Vκ1-39 gene segment) and Vκ3-20 (e.g., a human germline Vκ3-20 gene segment). In some embodiments, the $J_L$ gene segment is selected from the group consisting of Jκ1, Jκ2, Jκ3, Jκ4, and Jκ5. In some certain embodiments, the rearranged human immunoglobulin light chain variable nucleotide sequence comprises Vκ1-39 and Jκ5 (e.g., the Vκ1-39 is rearranged with the Jκ5, e.g., a human germline Vκ1-39 gene segment is rearranged with a human germline Jκ5 gene segment). In some embodiments, the rearranged human immunoglobulin light chain variable region gene sequence comprises a sequence set forth as SEQ ID NO:1. In some certain embodiments, the rearranged human immunoglobulin light chain variable nucleotide sequence comprises Vκ3-20 and Jκ1 (e.g., the Vκ3-20 is rearranged with the Jκ1, e.g., a human germline Vκ3-20 gene segment is rearranged with a human germline Jκ1 gene segment). In some embodiments, the rearranged human immunoglobulin light chain variable region nucleotide sequence comprises a sequence set forth as SEQ ID NO:2.

In some embodiments, the non-human animal is a rodent, and wherein the light chain constant region nucleic acid sequence is a rat or a mouse Cκ constant region nucleic acid sequence. In some embodiments, the non-human animal is a rodent, and wherein the heavy chain constant region nucleic sequence is a rat or mouse constant region sequence selected from the group consisting of Igμ, Igδ, Igγ, Igε, Igα, and a combination thereof, each of which encodes at least a functional $C_H1$ domain.

In some embodiments, the rearranged human immunoglobulin light chain variable region nucleotide sequence is at an endogenous immunoglobulin light chain locus in the genome. In some embodiments, the rearranged human immunoglobulin light chain variable region nucleotide sequence is present in a germline genome of the non-human animal. In some embodiments, the rearranged human immunoglobulin light chain variable region nucleotide sequence is at a transcriptionally active locus in the genome.

In some embodiments, the non-human animal comprises a plurality of copies of the rearranged human immunoglobulin light chain variable region nucleotide sequence.

In some embodiments, the non-human animal comprises an Adam6a gene, an Adam6b gene or both. In some embodiments, a non-human animal comprises a functional ectopic mouse Adam6 gene.

In some embodiments, the present invention provides a non-human animal whose genome comprises (a) a first immunoglobulin locus comprising unrearranged human immunoglobulin light chain variable $V_L$ and $J_L$ gene segments operably linked to an immunoglobulin heavy chain constant region nucleic acid sequence; and (b) a second immunoglobulin locus comprising a rearranged non-human immunoglobulin light chain variable region nucleotide sequence operably linked to an immunoglobulin light chain constant region nucleic acid sequence.

In some embodiments, the non-human animal is a mammal or a bird. In some certain embodiments, the bird is a chicken. In some certain embodiments, the mammal is a rodent. In some certain embodiments, the rodent is selected from the group consisting of a mouse, a rat, and a hamster.

In some embodiments, the rearranged non-human immunoglobulin light chain variable region nucleotide sequence comprises rodent immunoglobulin Vκ and Jκ gene segments. In some certain embodiments, the rodent immunoglobulin Vκ and Jκ gene segments are mouse gene segments. In some certain embodiments, the rodent immunoglobulin Vκ and Jκ gene segments are rat gene segments.

In some embodiments, the present invention provides a method of making a non-human animal, the method comprising (a) modifying a genome of a non-human animal to delete or render non-functional all or substantially all (i) endogenous functional immunoglobulin heavy chain $V_H$, D, and $J_H$ gene segments and (ii) endogenous functional light chain $V_L$ and $J_L$ gene segments; (b) placing unrearranged human immunoglobulin light chain variable $V_L$ and $J_L$ gene segments in the genome so that the unrearranged light chain variable gene segments are operably linked to a heavy chain constant region nucleic acid sequence; and (c) placing a rearranged non-human immunoglobulin light chain variable region nucleotide sequence in the genome so that the rearranged human immunoglobulin light chain variable region nucleotide sequence is operably linked to a light chain constant region nucleic acid sequence.

In some embodiments, the present invention provides a method for obtaining a nucleic acid sequence that encodes an immunoglobulin light chain variable domain ($V_L$) capable of binding an antigen independently from a heavy chain variable domain, the method comprising (a) immunizing a non-human animal with an antigen that comprises an epitope or immunogenic portion thereof, wherein the non-human animal comprises in its genome (i) a rearranged non-human immunoglobulin light chain variable region nucleotide sequence operably linked to an immunoglobulin light chain constant region nucleic acid sequence, and (ii) unrearranged human immunoglobulin light chain variable region gene segments ($V_L$ and $J_L$) operably linked to an immunoglobulin heavy chain constant region nucleic acid sequence; (b) allowing the non-human animal to mount an immune response; and (c) obtaining from the immunized non-human animal a nucleic acid sequence that encodes the light chain variable domain ($V_L$ domain) that can bind the antigen.

In some embodiments, the present invention provides a method for making an antigen-binding protein that comprises an immunoglobulin light chain variable domain that can bind an antigen independently from a heavy chain variable domain, the method comprising (a) immunizing a non-human animal with an antigen that comprises an epitope or immunogenic portion thereof, wherein the non-human animal comprises in its genome (i) a rearranged non-human immunoglobulin light chain variable region nucleotide sequence operably linked to an immunoglobulin light chain constant region nucleic acid sequence; and (ii) unrearranged human immunoglobulin light chain variable region gene segments ($V_L$ and $J_L$) operably linked to an immunoglobulin heavy chain constant region nucleic acid sequence; (b) allowing the non-human animal to mount an immune response to the first epitope or immunogenic portion thereof; (c) obtaining from the non-human animal a nucleic acid sequence that encodes the light chain variable domain that specifically binds the epitope or immunogenic portion thereof; (d) employing the nucleic acid sequence of (c) in an expression construct, fused to a human immunoglobulin constant region nucleic acid sequence; and (e) expressing the nucleic acid sequence of (c) in a production cell line to form an antigen-binding protein whose light chain is encoded by the nucleic acid of (c) and that binds the epitope or immunogenic portion thereof independently from a heavy chain.

In some embodiments, the present invention provides a non-human animal that comprises in its germline genome (a) a hybrid immunoglobulin chain locus comprising unrearranged human immunoglobulin light chain variable $V_L$ and $J_L$ gene segments operably linked to a heavy chain constant region nucleic acid sequence; and (b) an immunoglobulin light chain locus comprising two or more but less than the wild type number of human immunoglobulin light chain variable region gene segments operably linked to an immunoglobulin light chain constant region nucleic acid sequence.

In some embodiments, the non-human animal is a mammal or a bird. In some certain embodiments, the bird is a chicken. In some certain embodiments, the mammal is a rodent. In some embodiments, the rodent is selected from the group consisting of a mouse, a rat, and a hamster.

In some embodiments, the non-human animal is homozygous for the two or more but less than the wild type number of human immunoglobulin light chain variable region gene segments operably linked to an immunoglobulin light chain constant region nucleic acid sequence.

In some embodiments, the unrearranged human immunoglobulin light chain variable gene segments are operably linked to a non-human heavy chain constant region nucleic acid sequence. In some certain embodiments, the non-human heavy chain constant region nucleic acid sequence is a mouse or a rat heavy chain constant region nucleic acid sequence. In some embodiments, the non-human animal is a rodent, and the unrearranged human immunoglobulin light chain variable gene segments are operably linked to a human heavy chain constant region nucleic acid sequence. In some embodiments, the heavy chain constant region nucleic acid sequence comprises a nucleotide sequence that encodes a $C_H1$, a hinge, a $C_H2$, a $C_H3$, or a combination thereof.

In some embodiments, the two or more but less than the wild type number of human immunoglobulin light chain variable region gene segments are operably linked to a non-human light chain constant region nucleic acid sequence. In some embodiments, the non-human light chain constant region nucleic acid sequence is a mouse or a rat light chain constant region nucleic acid sequence.

In some embodiments, the non-human animal is a rodent and the two or more but less than the wild type number of human immunoglobulin light chain variable region gene segments are operably linked to a human light chain constant region nucleic acid sequence. In some embodiments, the light chain constant region nucleic acid sequence is a kappa sequence. In some embodiments, the light chain constant region nucleic acid sequence is a lambda sequence. In some embodiments, the immunoglobulin light chain locus is a kappa locus. In some embodiments, the immunoglobulin light chain locus is a lambda locus.

In some embodiments, the unrearranged human immunoglobulin $V_L$ and $J_L$ gene segments are human Vκ and Jκ gene segments. In some embodiments, the unrearranged human immunoglobulin $V_L$ and $J_L$ gene segments are human Vλ and Jλ gene segments.

In some embodiments, the two or more but less than the wild type number of human immunoglobulin light chain variable region gene segments comprise a human κ light chain variable region nucleotide sequence. In some embodiments, the two or more but less than the wild type number of human immunoglobulin light chain variable region gene segments comprise a human λ light chain variable region nucleotide sequence.

In some embodiments, the unrearranged human immunoglobulin light chain variable $V_L$ gene segment is selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the unrearranged human immunoglobulin light chain variable $J_L$ gene segment is selected from the group consisting of Jκ1, Jκ2, Jκ3, Jκ4, and Jκ5.

In some embodiments, the two or more but less than the wild type number of human immunoglobulin light chain variable region gene segments comprises $V_L$ and $J_L$ gene segments.

In some embodiments, the $V_L$ gene segments of the two or more variable region gene segments are selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some certain embodiments, the $V_L$ gene segments are selected from the group consisting of Vκ1-39, Vκ3-20, and a combination thereof. In some embodiments, the $J_L$ gene segment is selected from the group consisting of Jκ1, Jκ2, Jκ3, Jκ4, Jκ5, and a combination thereof.

In some embodiments, the two or more but less than the wild type number of human immunoglobulin light chain variable region gene segments comprise two or more but less than wild type number of human $V_L$ gene segments and one or more human $J_L$ gene segments. In some certain embodiments, the two or more but less than the wild type number of $V_L$ gene segments comprises Vκ1-39 and Vκ3-20 gene segments and one or more $J_L$ gene segments comprises Jκ1, Jκ2, Jκ3, Jκ4, Jκ5, or a combination thereof.

In some embodiments, the non-human animal is a rodent, and wherein the light chain constant region nucleic acid sequence is a rat or a mouse Cκ constant region nucleic acid sequence.

In some embodiments, the non-human animal is a rodent, and wherein the heavy chain constant region nucleic acid sequence is a rat or mouse constant region sequence selected from the group consisting of Igμ, Igδ, Igγ, Igε, Igα, and a combination thereof, each of which encodes a functional $C_H1$ domain.

In some embodiments, substantially all endogenous variable heavy chain $V_H$, D, and $J_H$ gene segments are deleted from the immunoglobulin heavy chain locus of the non-human animal or rendered non-functional.

In some embodiments, substantially all endogenous light chain $V_L$ and $J_L$ gene segments are deleted from the immunoglobulin light chain locus of the non-human animal or rendered non-functional.

In some embodiments, the non-human animal comprises an Adam6a gene, an Adam6b gene, or both. In some embodiments, a non-human animal comprises a functional ectopic mouse Adam6 gene.

In some embodiments, the immunoglobulin light chain locus comprises a plurality of copies of the two or more but less than the wild type number of human immunoglobulin light chain variable region gene segments ($V_L$ and $J_L$).

In some embodiments, the present invention provides a method of making a non-human animal, the method comprising (a) modifying a genome of a non-human animal to delete or render non-functional all or substantially all (i) endogenous immunoglobulin heavy chain $V_H$, D, and $J_H$ gene segments and (ii) endogenous light chain $V_L$ and $J_L$ gene segments; (b) placing unrearranged human immunoglobulin light chain variable $V_L$ and $J_L$ gene segments in the genome such that the unrearranged light chain variable gene segments are operably linked to a heavy chain constant region nucleic acid sequence; and (c) placing two or more but less than the wild type number of human immunoglobulin light chain variable region gene segments in the genome such that the human immunoglobulin light chain variable region gene segments are operably linked to a light chain constant region nucleic acid sequence.

In some embodiments, the non-human animal is a mammal or a bird. In some certain embodiments, the bird is a chicken. In some certain embodiments, the mammal is a rodent. In some embodiments, the rodent is selected from the group consisting of a mouse, a rat, and a hamster.

In some embodiments, the unrearranged human immunoglobulin light chain variable $V_L$ and $J_L$ gene segments are operably linked to a non-human immunoglobulin heavy chain constant region nucleic acid sequence. In some certain embodiments, the non-human immunoglobulin heavy chain constant region nucleic acid sequence is a mouse or rat immunoglobulin heavy chain constant region nucleic acid sequence.

In some embodiments, the non-human animal is a rodent, and the unrearranged human immunoglobulin light chain variable $V_L$ and $J_L$ gene segments are operably linked to a human heavy chain constant region nucleic acid sequence. In some embodiments, the heavy chain constant region nucleic acid sequence comprises a nucleotide sequence that encodes a $C_H1$, a hinge, a $C_H2$, a $C_H3$, or a combination thereof. In some embodiments, the heavy chain constant region nucleic acid sequence comprises a nucleotide sequence that encodes a functional $C_H1$ domain.

In some embodiments, the two or more but less than the wild type number of human immunoglobulin light chain variable region gene segments are operably linked to a non-human light chain constant region nucleic acid sequence. In some embodiments, the non-human light chain constant region nucleic acid sequence is a mouse or a rat light chain constant region nucleic acid sequence.

In some embodiments, the non-human animal is a rodent and the two or more but less than the wild type number of human immunoglobulin light chain variable region gene segments are operably linked to a human light chain constant region nucleic acid sequence. In some embodiments, the light chain constant region nucleic acid sequence is a kappa sequence. In some embodiments, the light chain constant region nucleic acid sequence is a lambda sequence.

In some embodiments, the two or more but less than the wild type number of human immunoglobulin light chain variable region gene segments are placed in a kappa light chain locus. In some embodiments, the two or more but less than the wild type number of human immunoglobulin light chain variable region gene segments are placed in a lambda light chain locus.

In some embodiments, the unrearranged human immunoglobulin $V_L$ and $J_L$ gene segments are human Vκ and Jκ gene segments. In some embodiments, the unrearranged human immunoglobulin $V_L$ and $J_L$ gene segments are human Vλ and Jλ gene segments.

In some embodiments, the two or more but less than the wild type number of human immunoglobulin light chain variable region gene segments comprise a human κ light chain variable region nucleotide sequence. In some embodiments, the two or more but less than the wild type number of human immunoglobulin light chain variable region gene segments comprise a human λ light chain variable region nucleotide sequence.

In some embodiments, the unrearranged human immunoglobulin light chain variable $V_L$ gene segment is selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the unrearranged human immunoglobulin $J_L$ gene segment is selected from the group consisting of Jκ1, Jκ2, Jκ3, Jκ4, and Jκ5.

In some embodiments, the two or more but less than the wild type number of human immunoglobulin light chain variable region gene segments comprise $V_L$ and $J_L$ gene segments.

In some embodiments, the $V_L$ gene segments of the two or more human immunoglobulin light chain variable region gene segments are selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some certain embodiments, the $V_L$ gene segments are selected from the group consisting of Vκ1-39, Vκ3-20, and a combination thereof. In some embodiments, the $J_L$ gene segment is selected from the group consisting of Jκ1, Jκ2, Jκ3, Jκ4, Jκ5, and a combination thereof.

In some embodiments, the two or more but less than wild type number of human immunoglobulin light chain variable region gene segments comprises two or more but less than wild type number of human $V_L$ gene segments and one or more $J_L$ gene segments. In some certain embodiments, the two or more but less than the wild type number of human $V_L$ gene segments comprises Vκ1-29 and Vκ3-20 gene segments.

In some embodiments, the non-human animal is a rodent, and wherein the light chain constant region nucleic acid sequence is a rat or a mouse Cκ constant region nucleic acid sequence.

In some embodiments, the non-human animal is a rodent, and wherein the heavy chain constant region nucleic acid sequence is a rat or mouse constant region sequence selected from the group consisting of Igμ, Igδ, Igγ, Igε, Igα, each of which encodes a functional $C_H1$ domain.

In some embodiments, the two or more but less than the wild type number of human immunoglobulin light chain variable region gene segments are placed at an endogenous immunoglobulin light chain locus in the genome. In some embodiments, the two or more but less than the wild type number of human immunoglobulin light chain variable region gene segments are present in a germline genome of the non-human animal. In some embodiments, the two or more but less than the wild type number of human immunoglobulin light chain variable region gene segments are present at an ectopic locus in the genome.

In some embodiments, the non-human animal comprises an Adam6a gene, an Adam6b gene or both. In some embodiments, a non-human animal comprises a functional ectopic mouse Adam6 gene.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The Drawings included herein, which is comprised of the following Figures, is for illustration purposes only not for limitation.

Figure 1:
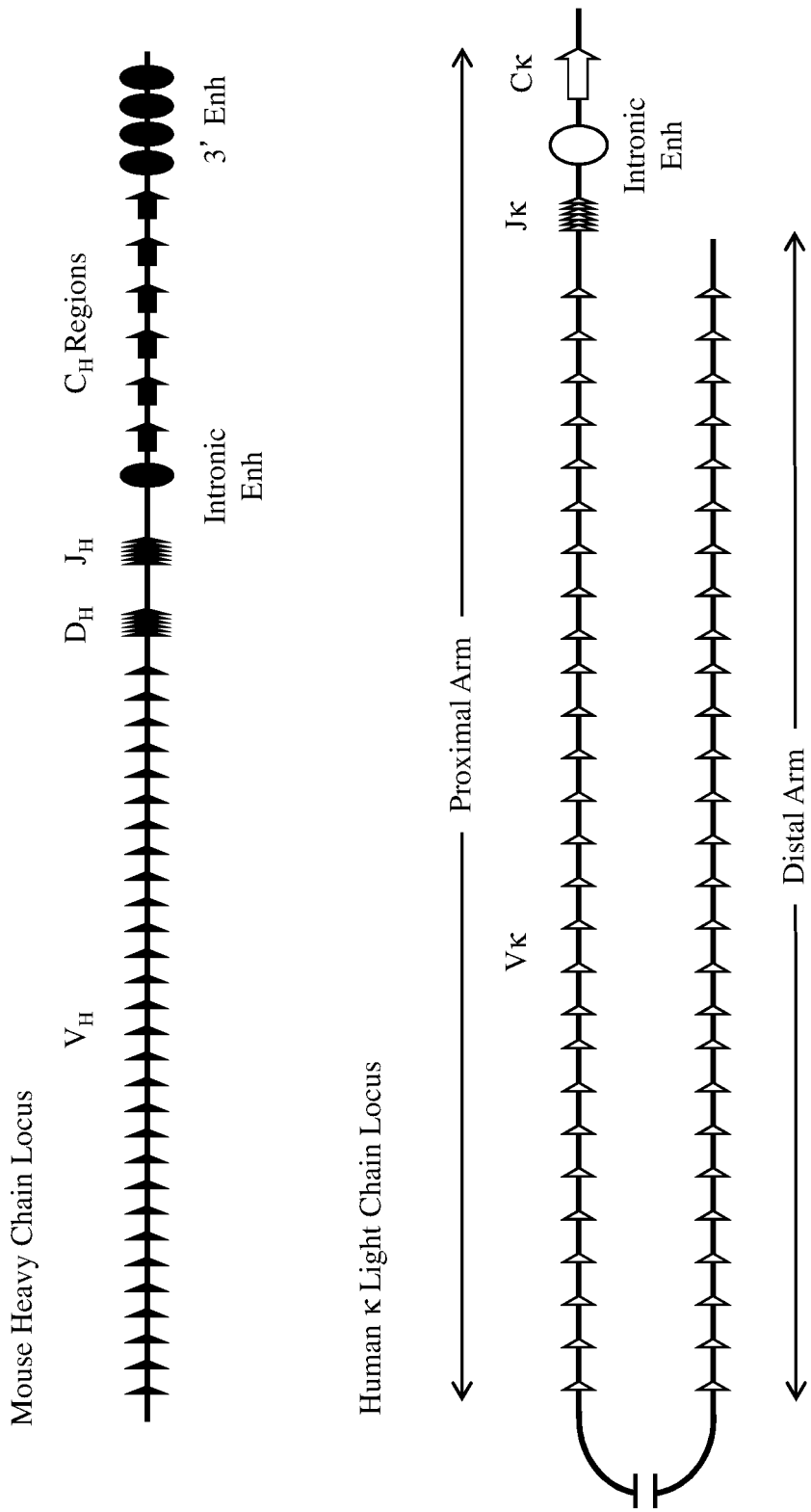
FIG. 1 illustrates a schematic (not to scale) of the mouse heavy chain locus (at top), and a schematic (not to scale) of the human κ light chain locus (at bottom). The mouse heavy chain locus is about 3 Mb in length and contains approximately 200 heavy chain variable ($V_H$) gene segments, 13 heavy chain diversity ($D_H$) gene segments and 4 heavy chain joining ($J_H$) gene segments as well as enhancers (Enh) and heavy chain constant ($C_H$) regions. The human κ light chain locus is duplicated into distal and proximal contigs of opposite polarity spanning about 440 kb and 600 kb, respectively. Between the two contigs is about 800 kb of DNA that is believed to be free of Vκ gene segments. The human κ light chain locus contains about 76 Vκ gene segments, 5 Jκ gene segments, an intronic enhancer (Enh) and a single constant region (Cκ).

KOH-CH1 Fab was transfected with human Vκ3-20 germ line (GL) ULC. Fabs were assayed by ELISA and BIACORE™ for binding to Antigen 2, cell surface protein. A number of antigen specific binders were identified by ELISA and BIACORE™ assays. Fourteen (14) samples bound antigen 2 at neutral pH as determined by ELISA. Binding was confirmed by BIACORE™ for 13 of the 14 ELISA binders.

FIG. 18 shows a Table with BIACORE™ binding data for representative $V_L$ domains that retain binding to Antigen 2 when paired with a $V_{HxULC}$ domain from an antibody to an unrelated enzyme, anti-Antigen 3 antibody. The data shows that binding proteins from KOH×ULC mice have specificity solely in a single $V_L$ domain.

FIG. 19 shows schematic representation of different multispecific antigen-binding protein formats. (A) shows a schematic of a the generation of a multispecific antigen-binding protein comprising (1) a first heavy chain that has a human $V_κ$ ($hVκ_{/CHxULC}$) domain fused with a human heavy chain constant region, the $hVκ_{/CHxULC}$ being cognate to a first universal light chain variable domain and capable of binding a first antigen A (Ag A) and (2) a second heavy chain that has a human $V_H$ ($hV_{HxULC}$) domain fused with a second human heavy chain constant region, the $hV_{HxULC}$ domain being cognate to a second universal light chain variable domain and capable of binding a second antigen B (Ag B), each of which heavy chains is paired with an identical universal light chain that comprises a third universal light chain variable domain fused with a human light chain constant region, wherein the third universal light chain is encoded by a rearranged $V_L/J_L$ gene sequence from which the first and second universal light chains were derived. The $hVκ_{/CHxULC}$ domain of the final multispecific antigen binding protein is derived from antigen-binding protein raised against antigen A in a KOH×ULC mouse, which generates the $hVκ_{/CHxULC}$ domain fused to a mouse heavy chain constant region and paired with a universal light chain comprising a human universal light chain variable domain fused with a mouse light chain constant domain. The $hV_{HxULC}$ domain of the final multispecific antigen binding protein is derived from antigen-binding protein raised against antigen B in a ULC mouse, which generates the $hV_{HxULC}$ domain fused to a mouse heavy chain constant region and paired with a universal light chain comprising a human universal light chain variable domain fused with a mouse light chain constant domain. (B) shows a schematic of a the generation of a multispecific antigen-binding protein comprising (1) a first heavy chain that has a first human $V_κ$ ($hVκ_{/CHxULC}$) domain fused with a human heavy chain constant region, the first $hVκ_{/CHxULC}$ being cognate to a first universal light chain variable domain and capable of binding a first antigen A (Ag A) and (2) a second heavy chain that has a second human $V_κ$ ($hVκ_{/CHxULC}$) domain fused with a second human heavy chain constant region, the second $hVκ_{/CHxULC}$ domain being cognate to a second universal light chain variable domain and capable of binding a second antigen B (Ag B), each of which heavy chains is paired with an identical universal light chain that comprises a third universal light chain variable domain fused with a human light chain constant region, wherein the third universal light chain is encoded by a rearranged $V_L/J_L$ gene sequence from which the first and second universal light chains were derived. The first $hVκ_{/CHxULC}$ domain of the final multispecific antigen binding protein is derived from antigen-binding protein raised against antigen A in a KOH×ULC mouse, which generates the first $hVκ_{/CHxULC}$ domain fused to a mouse heavy chain constant region and paired with a universal light chain comprising a human universal light chain variable domain fused with a mouse light chain constant domain. The second $hVκ_{/CHxULC}$ domain of the final multispecific antigen binding protein is derived from antigen-binding protein raised against antigen B in a KOH×ULC mouse (e.g., second KOH×ULC mouse), which generates the second $hVκ_{/CHxULC}$ domain fused to a mouse heavy chain constant region and paired with a universal light chain comprising a human universal light chain variable domain fused with a mouse light chain constant domain.

FIG. 20 shows a Table with BIACORE™ binding data for representative antigen-binding proteins having a structure depicted in FIG. 19A (B1-B3). Binding data for control antibodies ($C_{KOH}1$-$C_{KOH}2$, $C_{VH}$, $C_1$, and C) are also included. NT=not tested, NA=not applicable, NB=not bound.

DEFINITIONS

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The term "antibody", as used herein, includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises several domains, e.g., $C_H1$, a hinge region, $C_H2$, $C_H3$ and, optionally $C_H4$. Each light chain comprises a light chain variable domain and a light chain constant region (CL). The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of 10-9 M or lower (e.g., about $1\times10^{-9}$ M, $1\times10^{-10}$ M, $1\times10^{-11}$ M, or about $1\times10^{-12}$ M). In one embodiment, $K_D$ is measured by surface plasmon resonance, e.g., BIACORE™; in another embodiment, $K_D$ is measured by ELISA.

The term "biologically active" as used herein includes a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The phrase "antigen-binding protein" includes a monospecific, a bi-specific or higher order antigen-binding protein that respectively and selectively binds one, two or more antigenic determinants. Bispecific antigen-binding proteins generally comprise two nonidentical binding components, with each binding component specifically binding a different epitope—either on two different molecules (e.g., different epitopes on two different immunogens) or on the same molecule (e.g., different epitopes on the same immunogen). If a bispecific antigen-binding protein is capable of selectively binding two different epitopes (a first epitope and a second epitope), the affinity of the first binding component for the first epitope will generally be at least one to two or three or four or more orders of magnitude lower than the affinity of the first binding component for the second epitope, and vice versa. Epitopes specifically bound by a bispecific antigen-binding protein can be on the same or a different target (e.g., on the same or a different protein). Exemplary bispecific antigen-binding protein include those with a first binding component specific for a tumor antigen and a second binding component specific for a cytotoxic marker, e.g., an Fc receptor (e.g., FcγRI, FcγRII, FcγRIII, etc.) or a T cell marker (e.g., CD3, CD28, etc.). Further, the second binding component can be substituted with a binding component having a different desired specificity. For example, a bispecific antigen-binding protein with a first binding component specific for a tumor antigen and a second binding component specific for a toxin can be paired so as to deliver a toxin (e.g., saporin, *vinca* alkaloid, etc.) to a tumor cell. Other exemplary bispecific antigen-binding protein include those with a first binding component specific for an activating receptor (e.g., B cell receptor, FcγRI, FcγRIIA, FcγRIIIA, FcγRI, FcεRI, T cell receptor, etc.) and a second binding component specific for an inhibitory receptor (e.g., FcγRIIB, CD5, CD22, CD72, CD300a, etc.). Such bispecific antigen-binding proteins can be constructed for therapeutic conditions associated with cell activation (e.g. allergy and asthma). Bispecific antigen-binding proteins can be made, for example, by combining binding components that recognize different epitopes of the same immunogen. For example, nucleic acid sequences encoding binding components (e.g., light or heavy chain variable sequences) that recognize different epitopes of the same immunogen can be fused to nucleic acid sequences encoding the same or different heavy chain constant regions, the same or different light chains, or respectively a heavy chain constant region and a light chain constant region, and such sequences can be expressed in a cell as a multispecific antigen-binding protein in a format that is similar to a Fab structure, scFab structure, a diabody structure, an scFv structure, an scFv-Fc structure, an scFv-zipper structure, or a tetrameric structure similar to a typical antibody that includes the cognate universal light chain. An exemplary bispecific antigen-binding protein has two heavy chains each having three light chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each light chain, or that can associate with each light chain and that can bind one or more of the epitopes bound by the light chain epitope-binding regions, or that can associate with each light chain and enable binding of one or both of the light chains to one or both epitopes. Similarly, the term "trispecific antibody" includes an antigen-binding protein capable of selectively binding three or more epitopes.

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germ line sequence or a rearranged or unrearranged sequence, and, for example, by a naive or a mature B cell or a T cell. A CDR can be somatically mutated (e.g., vary from a sequence encoded in an animal's germ line), humanized, and/or modified with amino acid substitutions, additions, or deletions. In some circumstances (e.g., for a CDR3), CDRs can be encoded by two or more sequences (e.g., germ line sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "comparable", as used herein, includes two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative" as used herein to describe a conservative amino acid substitution includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is one that that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, a substitution is deemed to be "moderately conservative" if it has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The term "disruption" as used herein includes the result of an event that interrupts (e.g., via homologous recombination) a DNA. In some embodiments, a disruption may achieve or represent a deletion, insertion, inversion, modification, replacement, substitution, or any combination thereof, of a DNA sequence(s). In some embodiments, a disruption may achieve or represent introduction of a mutation, such as a missense, nonsense, or frame-shift mutation, or any combination thereof, in a coding sequence(s) in DNA. In some embodiments, a disruption may occur in a gene or gene locus endogenous to a cell. In some embodiments, insertions may include the insertion of entire genes or fragments of genes, e.g. exons, into an endogenous site in a cell or genome. In some embodiments, insertions may introduce sequences that are of an origin other than that of an endogenous sequence into which they are inserted. In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or gene product (e.g., an encoded protein). In some embodiments, a disruption may truncate or fragment a gene or gene product (e.g., an encoded protein). In some embodiments, a disruption may extend a gene or gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The phrase "endogenous locus" or "endogenous gene" as used herein includes a genetic locus found in a parent or reference organism prior to introduction of a disruption (e.g., deletion, insertion, inversion, modification, replacement, substitution, or a combination thereof as described herein). In some embodiments, an endogenous locus has a sequence found in nature. In some embodiments, an endogenous locus is wild type. In some embodiments, a reference organism that contains an endogenous locus as described herein is a wild-type organism. In some embodiments, a reference organism that contains an endogenous locus as described herein is an engineered organism. In some embodiments, a reference organism that contains an endogenous locus as described herein is a laboratory-bred organism (whether wild-type or engineered).

The phrase "endogenous promoter" includes a promoter that is naturally associated, e.g., in a wild-type organism, with an endogenous gene.

The phrase "epitope-binding protein" includes a protein having at least one CDR and that is capable of selectively recognizing an epitope, e.g., is capable of binding an epitope with a KD that is at about one micromolar or lower (e.g., a $K_D$ that is about $1\times10^{-6}$M, $1\times10^{-7}$ M, $1\times10^{-8}$ M, $1\times10^{-9}$ M, $1\times10^{-10}$ M, $1\times10^{-11}$ M, or about $1\times10^{-12}$ M). Therapeutic epitope-binding proteins (e.g., therapeutic antibodies) frequently require a $K_D$ that is in the nanomolar or the picomolar range.

"Functional" as used herein, e.g., in reference to a functional polypeptide, includes a polypeptide that retains at least one biological activity normally associated with the native protein. In another instance, a functional immunoglobulin gene segment may include a variable gene segment that is capable of productive rearrangement to generate a rearranged immunoglobulin gene sequence.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "germ line" in reference to an immunoglobulin nucleic acid sequence includes a nucleic acid sequence that can be passed to progeny.

The term "heterologous" as used herein includes an agent or entity from a different source. For example, when used in reference to a polypeptide, gene, or gene product present in a particular cell or organism, the term clarifies that the relevant polypeptide, gene, or gene product 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell", as used herein, includes a cell into which a heterologous (e.g., exogenous) nucleic acid or protein has been introduced. Persons of skill upon reading this disclosure will understand that such terms refer not only to a particular subject cell, but also are used to refer to progeny of that cell. Because certain modifications may occur in succeeding generations due to either mutation or environmental influences, such progeny may not, in fact, be identical to the parent cell, but are still understood by those skilled in the art to be included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells that may be utilized as host cells in accordance with the present disclosure include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The term "humanized" is used herein in accordance with its art-understood meaning and includes nucleic acids or proteins whose structures (i.e., nucleotide or amino acid sequences) include portions that correspond substantially or identically with versions of the relevant nucleic acids or proteins that are found in nature in non-human animals and that are distinguishable from corresponding versions that are found in nature in humans, and also include portions whose structures differ from those present in the non-human-animal versions and instead correspond more closely with comparable structures found in the human versions. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide with an extracellular portion whose amino acid sequence is identical or substantially identical to that of a human extracellular portion, and whose remaining sequence is identical or substantially identical to that of a non-human (e.g., mouse) polypeptide. In some embodiments, a humanized gene comprises at least a portion of a DNA sequence of a human gene. In some embodiment, a humanized gene comprises an entire DNA sequence found in a human gene. In some embodiments, a humanized protein has an amino acid sequence that comprises a portion that appears in a human protein. In some embodiments, a humanized protein has an amino acid sequence whose entire sequence is found in a human protein. In some embodiments (including, for example, some in which a humanized protein has an amino acid sequence whose entire sequence is found in a human protein), a humanized protein is expressed from an endogenous locus of a non-human animal, which endogenous locus corresponds to the homolog or ortholog of the relevant human gene encoding the protein.

The term "identity" as used herein in connection with a comparison of sequences, includes identity as determined by any of a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

The term "isolated", as used herein, includes a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

The phrase "light chain" includes an immunoglobulin light chain sequence from any organism, and unless otherwise specified includes human κ and λ light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region. A light chain variable domain is encoded by a light chain variable region gene sequence, which generally comprises $V_L$ and $J_L$ segments, derived from a repertoire of V and J segments present in the germ line. Sequences, locations and nomenclature for V and J light chain segments for various organisms can be found in IMGT database, www.imgt.org. Light chains include those, e.g., that do not selectively bind either a first or a second epitope selectively bound by the epitope-binding protein in which they appear. Light chains also include those that bind and recognize, or assist the heavy chain or another light chain with binding and recognizing, one or more epitopes selectively bound by the epitope-binding protein in which they appear. Common or universal light chains include those derived from a human Vκ1-39Jκ gene or a human Vκ3-20Jκ gene, and include somatically mutated (e.g., affinity matured) versions of the same. Exemplary human $V_L$ segments include a human Vκ1-39 gene segment, a human Vκ3-20 gene segment, a human Vλ1-40 gene segment, a human Vλ1-44 gene segment, a human Vλ2-8 gene segment, a human Vλ2-14 gene segment, and human Vλ3-21 gene segment, and include somatically mutated (e.g., affinity matured) versions of the same. Light chains can be made that comprise a variable domain from one organism (e.g., human or rodent, e.g., rat or mouse; or bird, e.g., chicken) and a constant region from the same or a different organism (e.g., human or rodent, e.g., rat or mouse; or bird, e.g., chicken).

"Neutral pH" includes pH between about 7.0 and about 8.0, e.g., pH between about 7.0 and about 7.4, e.g., between about 7.2 and about 7.4, e.g., physiological pH. "Acidic pH" includes pH of 6.0 or lower, e.g., pH between about 5.0 and about 6.0, pH between about 5.75 and about 6.0, e.g., pH of endosomal or lysosomal compartments.

The phrase "non-human animal" as used herein includes a vertebrate organism that is not a human. In some embodiments, a non-human animal is a cyclostome, a bony fish, a cartilaginous fish (e.g., a shark or a ray), an amphibian, a reptile, a mammal (e.g., a rodent, e.g., a mouse or a rat), or a bird (e.g., a chicken). In some embodiments, a non-human mammal is a primate, a goat, a sheep, a pig, a dog, a cow, or a rodent. In some embodiments, a non-human animal is a rodent such as a rat or a mouse.

The phrase "operably linked", as used herein, includes a physical juxtaposition (e.g., in three-dimensional space) of components or elements that interact, directly or indirectly with one another, or otherwise coordinate with each other to participate in a biological event, which juxtaposition achieves or permits such interaction and/or coordination. To give but one example, a control sequence (e.g., an expression control sequence) in a nucleic acid is said to be "operably linked" to a coding sequence when it is located relative to the coding sequence such that its presence or absence impacts expression and/or activity of the coding sequence. In many embodiments, "operable linkage" involves covalent linkage of relevant components or elements with one another. Those skilled in the art will readily appreciate, however, that in some embodiments, covalent linkage is not required to achieve effective operable linkage. For example, in some embodiments, nucleic acid control sequences that are operably linked with coding sequences that they control are contiguous with the gene of interest. Alternatively or additionally, in some embodiments, one or more such control sequences acts in trans or at a distance to control a coding sequence of interest. In some embodiments, the term "expression control sequence" as used herein refers to polynucleotide sequences which are necessary and/or sufficient to effect the expression and processing of coding sequences to which they are ligated. In some embodiments, expression control sequences may be or comprise appropriate transcription initiation, termination, promoter and/or enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and/or, in some embodiments, sequences that enhance protein secretion. In some embodiments, one or more control sequences are preferentially or exclusively active in a particular host cell or organism, or type thereof. To give but one example, in prokaryotes, control sequences typically include promoter, ribosomal binding site, and transcription termination sequence; in eukaryotes, in many embodiments, control sequences typically include promoters, enhancers, and/or transcription termination sequences. Those of ordinary skill in the art will appreciate from context that, in many embodiments, the term "control sequences" refers to components whose presence is essential for expression and processing, and in some embodiments includes components whose presence is advantageous for expression (including, for example, leader sequences, targeting sequences, and/or fusion partner sequences).

The term "recombinant", as used herein, includes polypeptides (e.g., B cell activating factor proteins as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein includes a process through which a "replaced" nucleic acid sequence (e.g., a gene) found in a host locus (e.g., in a genome) is removed from that locus and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a variable domain, and the DNA fragment encodes one or more human variable domains). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The term "heavy chain only antibody," "heavy chain only antigen binding protein," "single domain antigen binding protein," "single domain binding protein" or the like refers to a monomeric or homodimeric immunoglobulin molecule comprising an immunoglobulin-like chain comprising a variable domain operably linked to a heavy chain constant region, that is unable to associate with a light chain because the heavy chain constant region typically lacks a functional $C_H1$ domain. Accordingly, the term "heavy chain only antibody," "heavy chain only antigen binding protein," "single domain antigen binding protein," "single domain binding protein" or the like encompasses a both (i) a monomeric single domain antigen binding protein comprising one of the immunoglobulin-like chain comprising a variable domain operably linked to a heavy chain constant region lacking a functional $C_H1$ domain, or (ii) a homodimeric single domain antigen binding protein comprising two immunoglobulin-like chains, each of which comprising a variable domain operably linked to a heavy chain constant region lacking a functional $C_H1$ domain. In various aspects, a homodimeric single domain antigen binding protein comprises two identical immunoglobulin-like chains, each of which comprising an identical variable domain operably linked to an identical heavy chain constant region lacking a functional $C_H1$ domain. Additionally, each immunoglobulin-like chain of a single domain antigen binding protein comprises a variable domain, which may be derived from heavy chain variable region gene segments (e.g., $V_H$, $D_H$, $J_H$), light chain gene segments (e.g., $V_L$, $J_L$), or a combination thereof, linked to a heavy chain constant region ($C_H$) gene sequence comprising a deletion or inactivating mutation in a $C_H1$ encoding sequence (and, optionally, a hinge region) of a heavy chain constant region gene, e.g., IgG, IgA, IgE, IgD, or a combination thereof. A single domain antigen binding protein comprising a variable domain derived from heavy chain gene segments may be referred to as a "$V_H$-single domain antibody" or "$V_H$-single domain antigen binding protein", see, e.g., U.S. Pat. No. 8,754,287; U.S. Patent Publication Nos. 20140289876; 20150197553; 20150197554; 20150197555; 20150196015; 20150197556 and 20150197557, each of which is incorporated in its entirety by reference. A single domain antigen binding protein comprising a variable domain derived from light chain gene segments may be referred to as a or "$V_L$-single domain antigen binding protein," see, e.g., U.S. Publication No. 20150289489, incorporated in its entirety by reference.

"Somatically mutated" includes reference to nucleic acid or amino acid sequences from affinity-matured B cells that are not identical to corresponding immunoglobulin variable region sequences in B cells that are not affinity-matured (i.e., sequences in the genome of germline cells). The phrase "somatically mutated" also includes reference to an immunoglobulin variable region nucleic acid or amino acid sequence from a B cell after exposure of the B cell to an epitope of interest, wherein the nucleic acid or amino acid sequence differs from the corresponding nucleic acid or amino acid sequence prior to exposure of the B cell to the epitope of interest. The phrase "somatically mutated" refers to sequences from binding proteins that have been generated in an animal, e.g., a mouse having human immunoglobulin variable region nucleic acid sequences, in response to an immunogen challenge, and that result from the selection processes inherently operative in such an animal.

The term "substantially" as used herein includes the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology" as used herein includes a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

The phrase "substantial identity" as used herein includes a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct" as used herein includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein in whole or in part that has a similar function as a protein encoded by an endogenous sequence.

The term "unrearranged," with reference to a nucleic acid sequence, includes nucleic acid sequences that exist, e.g., in a wild-type germ line of an animal cell.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

The term "variant", as used herein, includes an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector", as used herein, includes a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type", as used herein, includes an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

The present invention provides, among other things, improved and/or engineered non-human animals having human genetic material encoding light chain variable domains (e.g., $V_L$ regions). In certain embodiments, such non-human animals are useful, for example, for the production and isolation of (human) $V_L$ domains that bind antigen independently. It is contemplated that such non-human animals provide a novel in vivo system for the generation and affinity maturation of human $V_L$ domains that exhibit unique antigen-binding characteristics. Therefore, the present invention is particularly useful for the development of unique antigen-binding proteins in non-human animals. In particular, the present invention encompasses the humanization of a rodent immunoglobulin loci resulting in expression of antigen-binding proteins that resemble naturally occurring immunoglobulins in structure yet differ in binding characteristics, and resulting in expression of said antigen-binding proteins on the membrane surface of cells of the non-human animal. Such antigen-binding proteins have the capacity to recognize foreign antigens that may elude natural immunoglobulins in the generation of unique binding surfaces provided by the antigen-binding proteins. In some embodiments, non-human animals of the present invention are capable of generating (human) $V_{L/CH \times ULC}$ domains that bind to antigen independent of a cognate variable domain (e.g., a heavy chain variable domain); in some embodiments, such non-human animals develop and/or have a B cell population that express binding proteins that resemble immunoglobulins in structure yet are devoid of any heavy chain variable sequences. In some embodiments, antigen-binding proteins expressed by such non-human animals are characterized in that the antigen-binding portion comprises exclusively of (human) $V_{Lx ULC}$ domains. In some embodiments, non-human animals of the present invention comprise an endogenous immunoglobulin heavy chain locus that contains genetic material from the non-human animal and a heterologous species (e.g., a human) and comprise an endogenous immunoglobulin light chain locus that contains genetic material from the non-human animal and a heterologous species (e.g., human). In some embodiments, non-human animals of the present invention comprise a hybrid immunoglobulin chain locus that includes unrearranged human $V_L$ and $J_L$ gene segments operably linked to a heavy chain constant region encoding sequence and an immunoglobulin light chain locus that includes a single rearranged human or non-human $V_L J_L$ sequence. In some embodiments, the expression of the antigen-binding proteins is under the control of non-human immunoglobulin genetic material (e.g., a non-human immunoglobulin promoter and/or enhancer).

Various aspects of the invention are described in detail in the following sections. The use of sections is not meant to limit the invention. Each section can apply to any aspect of the invention.

Non-Human Animals Comprising a High Diversity Hybrid Chain Locus Containing Unrearranged Light Chain Variable Region Gene Segments and a Low Diversity Light Chain Locus Containing a Rearranged Light Chain Variable Region Sequence Generation of light chain variable regions that have an ability to bind an antigen independently from a cognate chain variable region can be useful for making light chain variable domains ($V_L$S) for use in antigen-binding molecules.

One approach to produce such light chain variable domains that can bind to an antigen independently from a cognate chain variable region is to apply a selective pressure on nucleotide sequences that encode a variable region or domain of a light chain ($V_L$) to generate light chain CDR3s with more diverse antigenic binding repertoire. As disclosed herein, this can be achieved by generating a genetically modified non-human animal that contains, in its genome, an immunoglobulin hybrid chain locus that contains a high diversity of unrearranged light chain gene segments, see, e.g., U.S. Patent Publication No. 20120096572, incorporated herein by reference, and an immunoglobulin light chain locus that has a low diversity in that the locus contains a single rearranged human immunoglobulin light chain variable region nucleotide sequence. Alternatively, in some embodiments, non-human animals as described herein contain an immunoglobulin light chain locus that has a low diversity in that the locus contains two or more but less than the wild type number of unrearranged human $V_L$ gene segments (e.g., 2, 3 or 4). Since the light chain sequence (or the limited number of $V_L$ gene segments) at the immunoglobulin light chain locus is restricted to a common or universal (i.e., the same or a very similar) sequences in these animals, the unrearranged light chain variable region nucleotide sequences (i.e., genes) at the hybrid locus will be forced to make light chain CDR3s with more diverse and efficient antigenic binding properties, which can bind an antigenic determinant independently from the cognate variable regions. Furthermore, as disclosed herein, the precise replacement of germ line variable region gene segments (e.g., by homologous recombination-mediated gene targeting) allows for making animals (e.g., mice, rats, or chickens) that have partly human immunoglobulin loci. Because the partly human immunoglobulin loci rearrange, hypermutate, and somatically mutate (e.g., class switch) normally, the partly human immunoglobulin loci generate binding proteins in the animal that comprise human variable domains (i.e., human $V_L$ domains). These animals exhibit a humoral immune system that is substantially similar to wild type animals, and display normal cell populations and normal lymphoid organ structures-even where the animals lack a full repertoire of human variable region gene segments (at an immunoglobulin light chain locus). Immunizing these animals (e.g., mice, rats, or chickens) results in robust humoral responses that display a wide diversity of light chain variable gene segment usage. Nucleotide sequences that encode the variable regions can be identified and cloned, then fused (e.g., in an in vitro system) with any sequences of choice, e.g., any immunoglobulin isotype suitable for a particular use, resulting in an antibody or antigen-binding protein derived wholly from human sequences.

In addition, by utilizing animals (e.g., mice or rats or chickens) that have a restricted (limited) immunoglobulin light chain locus, e.g., a restricted immunoglobulin light chain locus comprising a rearranged light chain variable region nucleotide sequence (e.g., a universal light chain or "ULC," US Patent Application Publication No. 2011-0195454 A1, US 2012-0021409A1, US 2012-0192300A1, US 2013-0045492A1, US 2013-0185821A1 and US 2013-0302836A1, incorporated by reference herein in their entireties) or a restricted (limited) immunoglobulin light chain variable region gene segment repertoire (e.g., a restricted immunoglobulin light chain variable segment repertoire comprising two or more but less than the wild type number of human $V_L$ gene segments; for example, a dual light chain, or "DLC", U.S. Patent Application Publication No. US-2013-0198880-A1, incorporated by reference herein in its entirety) in combination with a high diversity hybrid immunoglobulin chain locus containing unrearranged light chain variable region gene segments described above, an immunoglobulin light chain variable ($V_{L/CH \times ULC}$) domain that binds antigen in the absence of a heavy chain variable domain can be produced. Furthermore, by introducing histidine codons, e.g., via addition of one or more histidine codons or substitution of one or more non-histidine codons with histidine codons, into the rearranged light chain variable region nucleotide sequence (or into the limited $V_L$ gene segments) in the genome of the non-human animals described herein, light chain variable region amino acid sequences that can confer improved pH-dependent recyclability to the antigen-binding proteins can be generated.

In some embodiments, the genetically modified non-human animals as described herein provide a greater yield of binding proteins, while limiting diversity at the same time, thereby increasing the probability of successful production of light chain variable domains from the hybrid locus that bind antigen independent of a cognate variable domain. In some embodiments, the light chains may themselves exhibit antigen-binding properties. In some embodiments, the non-human animal may be induced to produce antigen-binding proteins exhibiting antigen specificity that resides in their light chains (e.g., by limiting a mouse or rat's immunoglobulin light chain repertoire and maximizing the immunoglobulin hybrid chain repertoire; e.g., by creating a hybrid immunoglobulin chain repertoire, e.g., by replacing the mouse or rat heavy chain variable region locus with a locus comprising a high diversity of unrearranged human $V_L$ and $J_L$ gene segments and replacing the mouse or rat light chain variable region locus a single rearranged human immunoglobulin light chain variable region nucleotide sequence). In some embodiments, antigen-binding proteins (e.g., antibodies) produced in such animals will be specific for a particular epitope (e.g., effector antigens, cytotoxic molecules, Fc receptors, toxins, activating or inhibitory receptors, T cell markers, immunoglobulin transporters, etc.) through their light chain binding.

In various aspects, a non-human animal is provided comprising in its germ line genome a hybrid immunoglobulin chain locus that comprises unrearranged (human) $V_L$ and $J_L$ gene segments operably linked to a heavy chain constant region encoding sequence and an immunoglobulin light chain locus that comprises a rearranged human or non-human immunoglobulin light chain variable region nucleotide sequence (i.e., a rearranged light chain VJ sequence). In some embodiments, the unrearranged (human) $V_L$ and $J_L$ gene segments are operably linked to a human or non-human heavy chain constant region sequence comprising one or more heavy chain constant region genes, each of which encodes at least a functional $C_H1$ domain, and the rearranged (human) immunoglobulin light chain variable region nucleotide sequence is operably linked to a human or a non-human light chain constant region sequence. In some embodiments, an immunoglobulin light chain variable domain encoded by the rearranged light chain variable region nucleotide sequence is not immunogenic to the non-human animal. In some embodiments, the non-human animal is modified to comprise a nucleotide sequence that encodes two copies, three copies, four copies or more of the rearranged light chain variable domain operably linked to a light chain constant domain. In some embodiments, the nucleotide sequence encodes a plurality of copies of the rearranged (human) immunoglobulin light chain variable region nucleotide sequence. For example, the nucleotide sequence can encode at least one, two, three, four, five copies of the rearranged human immunoglobulin light chain variable region nucleotide sequence. In some embodiments, the nucleotide sequence encodes 1, 2, 3, 4, 5, 6, 7, 8, 9, or 10 copies of the rearranged (human) immunoglobulin light chain variable region nucleotide sequence. In some embodiments, the immunoglobulin light chain locus comprises a plurality of copies of the rearranged (human) immunoglobulin light chain variable region nucleotide sequence operably linked to a light chain constant region gene sequence.

In various aspects, the immunoglobulin light chain locus of the non-human animals described herein comprises a single rearranged human immunoglobulin light chain variable region nucleotide sequence, e.g., a rearranged human $V_L J_L$ sequence, operably linked to a non-human light chain constant region nucleotide sequence (e.g., a non-human light chain constant region nucleic acid sequence). Thus, genetically modified non-human animals are provided comprising in their genomes: (i) a hybrid immunoglobulin chain locus that comprises unrearranged human $V_L$ and $J_L$ gene segments operably linked to a human or non-human heavy chain constant region nucleic acid sequence; and (ii) an immunoglobulin light chain locus comprising a rearranged human light chain variable region nucleotide sequence operably linked to a light chain constant region nucleic acid sequence. In some embodiments, the light chain constant region is a rat or a mouse constant region, e.g., a rat or a mouse Cκ constant region. In some embodiments, the human $V_L$ and $J_L$ gene segments at an immunoglobulin heavy chain locus (e.g., hybrid immunoglobulin chain locus) are present as a plurality of gene segments (more than one human $V_L$ and more than one human $J_L$ gene segment) and capable of rearranging and encoding human $V_L$ domains in the context of heavy chain constant regions of an antibody, and the non-human animal does not comprise an endogenous $V_H$ and/or $V_L$ gene segment. In some embodiments, the non-human animal comprises six, 16, 30, 40 or more unrearranged human Vκ gene segments at an immunoglobulin heavy chain locus (e.g., hybrid immunoglobulin chain locus). In some embodiments, the non-human animal comprises five unrearranged human Jκ gene segments, e.g., Jκ1, Jκ2, Jκ3, Jκ4, and Jκ5 gene segments at an immunoglobulin heavy chain locus (e.g., hybrid immunoglobulin chain locus). In some embodiments, the non-human animal comprises 12, 28, 40 or more unrearranged human Vλ gene segments at an immunoglobulin heavy chain locus (e.g., hybrid immunoglobulin chain locus). In some embodiments, the non-human animal comprises 1, 2, 3, 4 or more unrearranged human Jλ gene segments, e.g., Jλ1, Jλ2, Jλ3, Jλ7, etc., at an immunoglobulin heavy chain locus (e.g., hybrid immunoglobulin chain locus).

In some embodiments, the immunoglobulin light chain locus of the non-human animals described herein comprises a rearranged human VκJκ nucleotide sequence. In some embodiments, the immunoglobulin light chain locus comprises a rearranged human VλJλ nucleotide sequence. In some embodiments, the rearranged human VκJκ nucleotide sequence or rearranged human VλJλ nucleotide sequence is present at an endogenous light chain locus, e.g., at an endogenous κ light chain locus. In some embodiments, the mouse comprises a functional λ light chain locus. In some embodiments, the mouse comprises a non-functional λ light chain locus. In some embodiments, the one or more human $V_L$ and one or more human $J_L$ gene segments at the immunoglobulin heavy chain locus are operably linked to a mouse or a rat heavy chain constant region sequence (e.g., in a hybrid immunoglobulin chain locus). In some embodiments, the rearranged human VκJκ nucleotide sequence is a rearranged human Vκ1-39Jκ nucleotide sequence, e.g., Vκ1-39Jκ5 sequence (e.g., as set forth in SEQ ID NO:1). In some embodiments, the rearranged human VκJκ nucleotide sequence is a rearranged human Vκ3-20Jκ nucleotide sequence, e.g., Vκ3-20Jκ1 sequence (e.g., as set forth in SEQ ID NO:2). In some embodiments, the rearranged human VλJλ nucleotide sequence is a rearranged human Vλ2-14Jλ1 nucleotide sequence. As persons of skill will recognize the use of other $J_L$ sequences may be employed in a rearranged light chain sequence.

In various aspects, the immunoglobulin light chain locus of the non-human animals described herein comprises a limited repertoire of immunoglobulin light chain variable gene segments, e.g., one or more but less than the wild type number of human $V_L$ gene segments; and one or more human $J_L$ gene segments, operably linked to a non-human light chain constant region nucleotide sequence. Thus, genetically modified non-human animals are provided comprising in their genomes: (i) an immunoglobulin heavy chain locus (e.g., hybrid immunoglobulin chain locus) that comprises unrearranged human $V_L$ and $J_L$ gene segments operably linked to a human or non-human heavy chain constant region nucleic acid sequence (e.g., a non-human heavy chain constant region nucleic acid sequence encoding a CH1, hinge, CH2, CH3, CH4, or a combination thereof, e.g., a CH1, a hinge, an CH2, and a CH3); and (ii) an immunoglobulin light chain locus comprising two or more but less than the wild type number of human immunoglobulin $V_L$ and $J_L$ gene segments operably linked to a light chain constant region nucleic acid sequence. In some embodiments, the light chain constant region is a rat or a mouse constant region, e.g., a rat or a mouse Cκ constant region. In some embodiments, the human $V_L$ and $J_L$ gene segments at an immunoglobulin heavy chain locus (e.g., hybrid immunoglobulin chain locus) are present as a plurality of gene segments (more than one human $V_L$ and more than one human $J_L$ gene segment) and capable of rearranging and encoding human $V_L$ domains in the context of heavy chain constant regions of an antibody, and the non-human animal does not comprise an endogenous $V_H$ and/or $V_L$ gene segment. In some embodiments, the non-human animal comprises six, 16, 30, 40 or more unrearranged human Vκ gene segments at an immunoglobulin heavy chain locus (e.g., hybrid immunoglobulin chain locus). In some embodiments, the non-human animal comprises five unrearranged human Jκ gene segments, e.g., Jλ1, Jκ2, Jκ3, Jκ4, and Jκ5 gene segments at an immunoglobulin heavy chain locus (e.g., hybrid immunoglobulin chain locus). In some embodiments, the non-human animal comprises 12, 28, 40 or more unrearranged human Vλ gene segments at an immunoglobulin heavy chain locus (e.g., hybrid immunoglobulin chain locus). In some embodiments, the non-human animal comprises 1, 2, 3, 4 or more unrearranged human Jλ gene segments, e.g., Jλ1, Jλ2, Jλ3, Jλ7, etc., at an immunoglobulin heavy chain locus (e.g., hybrid immunoglobulin chain locus). In some embodiments, the non-human animal comprises two unrearranged human Vκ gene segments at an immunoglobulin light chain locus. In some embodiments, the non-human animal comprises two unrearranged human Vλ gene segments at an immunoglobulin light chain locus.

In some embodiments, genetically modified mice comprising in their genomes (i) an immunoglobulin heavy chain locus (e.g., hybrid immunoglobulin chain locus) that comprises unrearranged human $V_L$ and $J_L$ gene segments operably linked to a human or non-human heavy chain constant region nucleic acid sequence, and (ii) an immunoglobulin light chain locus comprising rearranged human light chain variable region nucleic acid sequence operably linked to a light chain constant region nucleic acid sequence, demonstrate CD19[+]B cell numbers and mature B cell numbers that are substantially the same as the numbers observed in wild type mice or mice containing other modifications of their immunoglobulin loci (i.e., genetically modified control mice; e.g., VELOCIMMUNE® humanized mice, in which the humoral immune system of the mouse functions like that of a wild type mouse). In some embodiments, such mice also demonstrate a functional silencing of endogenous lambda light chains in splenic B cells. In some embodiments, the mice exhibit normal or nearly normal B cell development in the bone marrow and the spleen. In some embodiments, such mice exhibit a lack of detectable expression and/or usage (or functional silencing) of lambda light chains compared to genetically modified control mice.

In another aspect, a non-human animal is provided comprising (a) a genetically modified immunoglobulin heavy chain locus comprising: a first nucleotide sequence that encodes a light chain variable domain (e.g., where the first nucleotide sequence contains unrearranged human immunoglobulin light chain variable region gene segments), wherein the first nucleotide sequence is operably linked to a heavy chain constant region gene sequence comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene (thus, resulting in, e.g., a hybrid immunoglobulin chain locus); and (b) genetically modified immunoglobulin light chain locus comprising a second nucleotide sequence that encodes a human light chain variable domain (e.g., where the second nucleotide sequence is a rearranged human immunoglobulin light chain variable region nucleotide sequence or where the second nucleotide sequence contains a limited number of human $V_L$ gene segments; e.g., two or more but less than the wild type number of human $V_L$ gene segments), wherein the second nucleotide sequence is operably linked to a light chain constant region gene sequence. For example, in some embodiments, a rearranged light chain from a pre-designed VJ region (i.e., a rearranged human immunoglobulin light chain variable region nucleotide sequence; i.e., a common or universal light chain sequence) or a limited number of human $V_L$ gene segments (e.g., two or more but less than the wild type number of human $V_L$ gene segments) can be operably linked to a light chain constant region gene sequence by targeting the rearranged light chain sequence into a mouse light chain locus, either κ or λ. Thus, as in other embodiments, this genetically engineered immunoglobulin light chain locus may be present in the germ line genome of the non-human animal. Genetically modified non-human animals comprising unrearranged human immunoglobulin light chain variable region nucleotide sequences in operable linkage with a heavy chain constant region gene sequences are described in U.S. Patent Application Publication No. 2012-0096572 A1, which is incorporated herein by reference. In some embodiments, the second nucleotide sequence that encodes the human light chain variable domain is operably linked to a κ light chain constant (i.e., Cκ) region gene sequence. In some embodiments, the second nucleotide sequence that encodes the human light chain variable domain is operably linked to a mouse or rat Cκ region gene sequence. In some embodiments, the second nucleotide sequence that encodes the light chain variable domain is operably linked to a human Cκ region gene sequence. In some embodiments, the second nucleotide sequence that encodes the human light chain variable domain is operably linked to a Cλ region gene sequence. In some embodiments, the second nucleotide sequence that encodes the human light chain variable domain is operably linked to a mouse or rat Cλ region gene sequence. In some embodiments, the second nucleotide sequence that encodes the human chain variable domain is operably linked to a human Cλ region gene sequence.

In some embodiments, the non-human animal is a mammal. Although embodiments employing a rearranged human light chain variable region (or a limited number of human $V_L$ gene segments) and unrearranged human light chain variable region gene segments in a mouse (i.e., a mouse with an immunoglobulin light locus comprising a rearranged human immunoglobulin light chain variable region nucleotide sequence (or a limited number of human $V_L$ gene segments) and an immunoglobulin heavy chain locus (e.g., hybrid immunoglobulin chain locus) comprising unrearranged human light chain variable region gene segments) are extensively discussed herein, other non-human animals that comprise a genetically modified immunoglobulin heavy and light chain loci as described herein are also provided. Such non-human animals include any of those which can be genetically modified to express the rearranged human immunoglobulin light chain variable region nucleotide sequence (or a human light chain variable domain from the limited number of human $V_L$ gene segments) as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo. Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include an immunoglobulin light chain locus that contains a rearranged human immunoglobulin light chain variable region nucleotide sequence (or a limited number of human $V_L$ gene segments, e.g., two or more but less than the wild type number of human $V_L$ gene segments) and an immunoglobulin heavy chain locus (e.g., hybrid immunoglobulin chain locus) that contains unrearranged human light chain variable region gene segments.

In some embodiments, the non-human animal is a small mammal, e.g., of the superfamily Dipodoidea or Muroidea. In some embodiments, the genetically modified animal is a rodent. In some embodiments, the rodent is selected from a mouse, a rat, and a hamster. In some embodiments, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, *Malagasy* rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In some embodiments, the genetically modified mouse is from a member of the family Muridae. In some embodiments, the animal is a rodent. In specific embodiments, the rodent is selected from a mouse and a rat. In some embodiments, the non-human animal is a mouse.

In some embodiments, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6N, C57BL/6NJ, C57BL/10, C57BL/10ScSn, C57BL/10Cr, and C57BL/Ola. In another embodiment, the mouse is a 129 strain. In some embodiments, the 129 strain is selected from the group consisting of 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In some embodiments, the genetically modified mouse is a mix of an aforementioned 129 strain and an aforementioned C57BL strain (e.g., a C57BL/6 strain). In another embodiment, the mouse is a mix of aforementioned 129 strains, or a mix of aforementioned C57BL/6 strains. In some embodiments, the 129 strain of the mix is a 129S6 (129/SvEvTac) strain. In another embodiment, the mouse is a mix of a 129/SvEv- and a C57BL/6-derived strain. In a specific embodiment, the mouse is a mix of a 129/SvEv- and a C57BL/6-derived strain as described in Auerbach et al. 2000 BioTechniques 29:1024-1032. In another embodiment, the mouse is a BALB strain, e.g., BALB/c strain. In another embodiment, the mouse is a mix of a BALB strain (e.g., BALB/c strain) and another aforementioned strain.

In some embodiments, the non-human animal is a rat. In some embodiments, the rat is selected from a Wistar rat, an LEA strain, a Sprague Dawley strain, a Fischer strain, F344, F6, ACI, and Dark Agouti (DA). In some embodiments, the rat strain is a mix of two or more of a strain selected from the group consisting of Wistar, LEA, Sprague Dawley, Fischer, F344, F6, ACI and Dark Agouti (DA).

In some embodiments, such a genetically modified mouse uses lambda gene sequences with a frequency that is half or less than half of the frequency that lambda gene sequences are used in wild type.

In various embodiments, as described herein, the rearranged light chain variable domain is derived from a human $V_L$ and $J_L$ gene sequence or segment. In other embodiments, the rearranged light chain variable domain is derived from a non-human $V_L$ and $J_L$ gene sequence or segment. In some embodiments, the rearranged light chain variable domain is derived from a human germ line $V_L$ segment and a human germ line $J_L$ segment. In some embodiments, the human $V_L$ segment corresponds to observed variants in the human population.

In various embodiments, as described herein, the human $V_L$ gene segment of the rearranged light chain variable region nucleotide sequence is a human Vκ gene segment. In some embodiments, the human Vκ gene segment is selected from the group consisting of Vκ4-1, Vκ5-2, Vκ7-3, Vκ2-4, Vκ1-5, Vκ1-6 Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, and a polymorphic variant thereof. In some embodiments, the human Vκ segment is Vκ1-39 or polymorphic variant thereof. In some embodiments, the human Vκ gene segment is Vκ3-20.

In various embodiments, as described herein, the human $V_L$ gene segments of the restricted (limited) immunoglobulin light chain variable region gene segment repertoire (e.g., a restricted immunoglobulin light chain variable segment repertoire comprising two or more but less than the wild type number of human $V_L$ gene segments) are human Vκ gene segments. In some embodiments, the human Vκ gene segments are selected from human Vκ gene segments described herein. In some certain embodiments, the human Vκ gene segments of the restricted (limited) immunoglobulin light chain variable region gene segment repertoire include a human Vκ1-39 gene segment and a human Vκ3-20 gene segment. In various embodiments of the restricted (limited) immunoglobulin light chain variable gene segment non-human animal, the restricted light chain variable gene segments (e.g., a human Vκ1-39 gene segment and a human Vκ3-20 gene segment) are operably linked to one, two, three, four, or more human $J_L$ gene segments; such that the restricted immunoglobulin light chain variable gene segments recombine with one of the one or two or three or four or more human $J_L$ gene segments (i.e., Jκ gene segments) to form a rearranged VκJκ light chain variable gene.

In various embodiments, as described herein, the human $V_L$ gene segment of the rearranged light chain variable region nucleotide sequence is a human Vλ gene segment. In some embodiments, the human Vλ gene segment is selected from the group consisting of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61, Vλ4-69, and a polymorphic variant thereof. In some embodiments, the human Vλ segment is Vλ2-14.

In various embodiments, as described herein, the human $V_L$ gene segments of the restricted (limited) immunoglobulin light chain variable region gene segment repertoire (e.g., a restricted immunoglobulin light chain variable segment repertoire comprising two or more but less than the wild type number of human $V_L$ gene segments) are human Vλ gene segments. In some embodiments, the human Vλ gene segments are selected from human Vλ gene segments described herein. In some certain embodiments, the human Vλ gene segments of the restricted (limited) immunoglobulin light chain variable region gene segment repertoire include a human Vλ2-14 gene segment.

In various embodiments, as described herein, the human $J_L$ gene segment of the rearranged light chain variable region nucleotide sequence is selected from the group consisting of Jκ1, Jκ2, Jκ3, Jκ4, Jκ5, Jλ1, Jλ2, Jλ3, Jλ7, and a polymorphic variant thereof.

In various embodiments, as described herein, the human $J_L$ gene segments of the restricted (limited) immunoglobulin light chain variable region gene segment repertoire include human Jκ1, Jκ2, Jκ3, Jκ4, Jκ5, and a polymorphic variant thereof. In various embodiments, as described herein, the human $J_L$ gene segments of the restricted (limited) immunoglobulin light chain variable region gene segment repertoire include human Jλ1, Jλ2, Jλ3, Jλ7, and a polymorphic variant thereof.

In some embodiments, the human or non-human animal light chain constant region sequence comprises a sequence selected from a Cκ and a Cλ region.

Various embodiments utilize or encompass features or sequence information derived from VELOCIMMUNE® humanized mice. VELOCIMMUNE® humanized mice contain a precise, large-scale replacement of germ line variable regions of mouse immunoglobulin heavy chain (IgH) and immunoglobulin light chain (e.g., κ light chain, Ig) with corresponding human immunoglobulin variable regions, at the endogenous loci (see, e.g., U.S. Pat. Nos. 6,596,541 and 8,502,018, the entire contents of which are incorporated herein by reference). In total, about six megabases of mouse loci are replaced with about 1.5 megabases of human genomic sequence. This precise replacement results in a mouse with hybrid immunoglobulin loci that make heavy and light chains that have a human variable regions and a mouse constant region. The precise replacement of mouse $V_H$-D-$J_H$ and Vκ-Jκ segments leave flanking mouse sequences intact and functional at the hybrid immunoglobulin loci. The humoral immune system of the mouse functions like that of a wild type mouse. B cell development is unhindered in any significant respect and a rich diversity of human variable regions is generated in the mouse upon antigen challenge. Moreover, VELOCIMMUNE® humanized mice display an essentially normal, wild-type response to immunization that differs only in one significant respect from wild type mice—the variable regions generated in response to immunization are fully human. VELOCIMMUNE® humanized mice are possible because immunoglobulin gene segments for heavy and κ light chains rearrange similarly in humans and mice. Although the loci are not identical, they are similar enough that humanization of the heavy chain variable gene locus can be accomplished by replacing about three million base pairs of contiguous mouse sequence that contains all the $V_H$, D, and $J_H$ gene segments with about one million bases of contiguous human genomic sequence covering basically the equivalent sequence from a human immunoglobulin locus.

In particular embodiments, a humanized mouse comprising an immunoglobulin heavy chain locus that contains unrearranged human light chain variable region gene segments (i.e., comprising an immunoglobulin heavy chain locus that comprises unrearranged human immunoglobulin $V_L$ and $J_L$ gene segments) is provided. A humanized mouse so modified comprises a replacement of mouse immunoglobulin heavy chain variable region gene segments with unrearranged human immunoglobulin light chain variable region gene segments (i.e., unrearranged $V_L$ and $J_L$ gene at an endogenous heavy chain locus), and a replacement of mouse immunoglobulin light chain variable gene segments with a rearranged human $V_L J_L$ nucleotide sequence or a replacement of mouse immunoglobulin light chain variable gene segments with a restricted (limited) immunoglobulin light chain variable region gene segment repertoire (e.g., two or more but less than the wild type number of human $V_L$ gene segments).

In some embodiments, the mouse so modified comprises a replacement of mouse immunoglobulin heavy chain variable region gene segments with at least 40 unrearranged human Vκ gene segments and five unrearranged human Jκ gene segments. In some embodiments, the unrearranged human Vκ gene segments are selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the human Vκ gene segments comprise Vκ4-1, Vκ5-2, Vκ7-3, Vκ2-4, Vκ1-5, and Vκ1-6. In one embodiment, the Vκ gene segments comprise Vκ3-7, Vκ1-8, Vκ1-9, Vκ2-10, Vκ3-11, Vκ1-12, Vκ1-13, Vκ2-14, Vκ3-15 and Vκ1-16. In some embodiments, the human Vκ gene segments comprise Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, and Vκ2-30. In some embodiments, the human Vκ gene segments comprise Vκ3-31, Vκ1-32, Vκ1-33, Vκ3-34, Vκ1-35, Vκ2-36, Vκ1-37, Vκ2-38, Vκ1-39, and Vκ2-40. In specific embodiments, the Vκ gene segments comprise contiguous human immunoglobulin κ gene segments spanning the human immunoglobulin κ light chain locus from Vκ4-1 through Vκ2-40, and the Jκ gene segments comprise contiguous gene segments spanning the human immunoglobulin κ light chain locus from Jκ1 through Jκ5. In some embodiments, the rearranged human light chain variable region nucleotide sequence (i.e., rearranged human VκJκ nucleotide sequence) is operably linked to a mouse light chain constant region sequence (e.g., a Cκ sequence). A humanized mouse comprising an immunoglobulin heavy chain locus encoding human light chain variable domains (i.e., comprising an immunoglobulin heavy chain locus that comprises unrearranged human immunoglobulin light chain variable region gene segments) can be used in any of the aspects, embodiments, methods, etc. described herein.

In some embodiments, the mouse so modified comprises a replacement of mouse immunoglobulin heavy chain variable region gene segments with at least 40 unrearranged human Vλ gene segments and one or more unrearranged human Jλ gene segments; in some certain embodiments, at least 40 unrearranged human Vλ gene segments and four unrearranged human Jλ gene segments. In some embodiments, the unrearranged human Vκ gene segments are selected from the group consisting of Vλ3-1, Vλ4-3, Vλ2-8, Vλ3-9, Vλ3-10, Vλ2-11, Vλ3-12, Vλ2-14, Vλ3-16, Vλ2-18, Vλ3-19, Vλ3-21, Vλ3-22, Vλ2-23, Vλ3-25, Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61, Vλ4-69, and a polymorphic variant thereof. In some embodiments, the unrearranged human Vλ gene segments include Vλ3-1, Vλ4-3, Vλ2-8, Vλ3-9, Vλ3-10, Vλ2-11 and Vλ3-12. In some embodiments, the unrearranged human Vλ gene segments include V Vλ2-14, Vλ3-16, Vλ2-18, Vλ3-19, Vλ3-21, Vλ3-22, Vλ2-23, Vλ3-25 and Vλ3-27. In some embodiments, the unrearranged human Vλ gene segments include V Vλ1-36, Vλ5-37, Vλ5-39, Vλ1-40, Vλ7-43, Vλ1-44, Vλ5-45, Vλ7-46, Vλ1-47, Vλ9-49, Vλ1-51, Vλ5-52, Vλ6-57, Vλ4-60, Vλ8-61 and Vλ4-69. In specific embodiments, the Vλ gene segments comprise contiguous human immunoglobulin λ gene segments spanning the human immunoglobulin λ light chain locus from Vλ3-1 through Vλ3-12, and the Jλ gene segments include Jλ1. In specific embodiments, the Vλ gene segments comprise contiguous human immunoglobulin λ gene segments spanning the human immunoglobulin λ light chain locus from Vλ3-12 through Jλ1. In specific embodiments, the Vλ gene segments comprise contiguous human immunoglobulin λ gene segments spanning the human immunoglobulin λ light chain locus from Vλ3-1 through Vλ3-12, and the Jλ gene segments include Jλ1, Jλ2, Jλ3 and Jλ7. In specific embodiments, the Vλ gene segments comprise contiguous human immunoglobulin λ gene segments spanning the human immunoglobulin λ light chain locus from Vλ3-12 through Vλ3-27, and the Jλ gene segments include Jλ1 or Jλ1, Jλ2, Jλ3 and Jλ7. In specific embodiments, the Vλ gene segments comprise contiguous human immunoglobulin λ gene segments spanning the human immunoglobulin λ light chain locus from Vλ1-40 through Vλ5-52, and the Jλ gene segments include Jλ1 or Jλ1, Jλ2, Jλ3 and Jλ7. In some embodiments, the rearranged human light chain variable region nucleotide sequence is a rearranged human VλJλ nucleotide sequence and is operably linked to a mouse light chain constant region sequence (e.g., a Cλ sequence). A humanized mouse comprising an immunoglobulin heavy chain locus encoding human light chain variable domains (i.e., comprising an immunoglobulin heavy chain locus that comprises unrearranged human immunoglobulin light chain variable region gene segments) can be used in any of the aspects, embodiments, methods, etc. described herein.

In various embodiments, the unrearranged human immunoglobulin light chain variable region gene segments are operably linked to a human or mouse heavy chain constant region gene sequence (e.g., a heavy chain constant region gene sequence that encodes an immunoglobulin isotype selected from IgM, IgD, IgA, IgE, IgG, and combinations thereof, wherein each heavy chain constant region gene encodes a functional $C_H1$ domain). For example, genetically modified non-human animals are provided comprising (a) an immunoglobulin heavy chain locus (e.g., hybrid immunoglobulin chain locus) that contains a first nucleotide sequence which contains unrearranged human light chain variable region gene segments (i.e., where the first nucleotide sequence comprises at least 40 human Vκ gene segments and 5 human Jκ gene segments), wherein the first nucleotide sequence is operably linked to a human or non-human heavy chain constant region gene sequence; and (b) an immunoglobulin light chain locus that contains a second nucleotide sequence that encodes a light chain variable domain (i.e., where the second nucleotide sequence is a rearranged human immunoglobulin light chain variable region nucleotide sequence or where the second nucleotide sequence contains a limited number of human $V_L$ gene segments; e.g., two or more but less than the wild type number of human $V_L$ gene segments), wherein the second nucleotide sequence is operably linked to a human or non-human light chain constant region gene sequence comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene. In some embodiments, the human heavy chain constant region gene further encodes a hinge, a $C_H2$, a $C_H3$, and combinations thereof. In some embodiments, a mouse heavy chain constant region gene further encoedes a hinge, a $C_H2$, a $C_H3$, and combinations thereof. In some embodiments, further replacement of certain non-human animal constant region gene sequences with human gene sequences (e.g., replacement of mouse $C_H1$ sequence with human $C_H1$ sequence, and replacement of mouse $C_L$ sequence with human $C_L$ sequence) results in genetically modified non-human animals with chimeric (and hybrid) immunoglobulin loci that make antibodies that have human variable regions and partly human constant regions, suitable for, e.g., making fully human antibody fragments, e.g., fully human Fab's. In some embodiments, the unrearranged human light chain variable region gene segments are operably linked to a rat heavy chain constant region gene sequence comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene. In some embodiments, the rat heavy chain constant region gene further encodes a $C_H2$, a $C_H3$, and combinations thereof. In some embodiments, the rearranged human immunoglobulin light chain variable region nucleotide sequence (or a limited number of human $V_L$ gene segments) is operably linked with a human Cκ region sequence. In some embodiments, the rearranged human immunoglobulin light chain variable region nucleotide sequence (or a limited number of human $V_L$ gene segments) is operably linked with a mouse or rat Cκ region sequence. In various embodiments, the genetically modified immunoglobulin light chain locus of the non-human animal comprises two copies, three copies, four copies or more of the rearranged human immunoglobulin light chain variable region nucleotide sequence operably linked to a light chain constant region gene sequence. In particular embodiments, the immunoglobulin light chain locus comprises a plurality of copies of the rearranged human immunoglobulin light chain variable region nucleotide sequence operably linked to a light chain constant region gene sequence.

In various embodiments, a (human) IgG1, IgG2, or IgG4 heavy chain constant region gene (e.g., cloned in an expression vector, at an endogenous locus) etc., comprises one or more modification(s) in a $C_H3$ encoding sequence of the gene, wherein the modification reduces or eliminates affinity of the $C_H3$ domain encoded by the modified encoding sequence to Protein A (see, e.g., U.S. Pat. No. 8,586,713, incorporated herein in its entirety by reference). Such modification includes, but is not limited to a mutation selected from the group consisting of (a) 95R, and (b) 95R and 96F in the IMGT numbering system, or (a') 435R, and (b') 435R and 436F in the EU numbering system. In some embodiments, the (human and) mutated heavy chain constant region is a (human and) mutated IgG1 constant region and, in addition to the (a) 95R or (b) 95R and 96F mutation (in the IMGT numbering system), further comprises one to five modifications selected from the group consisting of 16E, 18M, 44S, 52N, 57M, and 82I in the IMGT exon numbering system, or 356E, 358M, 384S, 392N, 397M, and 422I in the EU numbering system. In some embodiments, the heavy chain constant region gene is a (human) IgG2 constant gene and, in addition to the (a) 95R or (b) 95R and 96F mutation in the IMGT numbering system), further comprises one or two modifications selected from the group consisting of 44S, 52N, 82I in the IMGT exon numbering system, or 348S, 392N and 422I in the EU numbering system. In other embodiments, the (human) heavy chain constant gene is a (human) IgG4 constant gene and, in addition to the (a) 95R or (b) 95R and 96F mutation (in the IMGT numbering system), further comprises one to seven modifications selected from the group consisting of 15R, 44S, 52N, 57M, 69K, 79Q and 82I in the IMGT exon numbering system or 355R, 384S, 392N, 397M, 409K, 419Q and 422I in the EU numbering system and/or the modification 105P in the IGMT exon numbering system or 445P in the EU numbering system.

In various embodiments, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0). In some embodiments, the heavy chain constant region nucleotide sequence encodes a human heavy chain constant region amino acid sequence comprising a modification at position 250 by EU numbering (263 by Kabat numbering) (e.g., E or Q); 250 by EU numbering (263 by Kabat numbering) and 428 by EU numbering (459 by Kabat numbering) (e.g., L or F); 252 by EU numbering (265 by Kabat numbering) (e.g., L/Y/F/W or T), 254 by EU numbering (267 by Kabat numbering) (e.g., S or T), and 256 by EU numbering (269 by Kabat numbering) (e.g., S/R/Q/E/D or T); or a modification at position 428 by EU numbering (459 by Kabat numbering) and/or 433 by EU numbering (464 by Kabat numbering) (e.g., L/R/S/P/Q or K) and/or 434 by EU numbering (465 by Kabat numbering) (e.g., H/F or Y); or a modification at position 250 by EU numbering (263 by Kabat numbering) and/or 428 by EU numbering (459 by Kabat numbering); or a modification at position 307 by EU numbering (326 by Kabat numbering) or 308 by EU numbering (327 by Kabat numbering) (e.g., 308F, V308F), and 434 by EU numbering (465 by Kabat numbering). In one embodiment, the modification comprises a 428L (e.g., M428L) and 434S (e.g., N434S) modification by EU numbering (a 459, e.g., M459L, and 465S (e.g., N465S) modification by Kabat numbering); a 428L, 259I (e.g., V259I), and 308F (e.g., V308F) modification by EU numbering (a 459L, 272I (e.g., V272I), and 327F (e.g., V327F) modification by Kabat numbering; a 433K (e.g., H433K) and a 434 (e.g., 434Y) modification by EU numbering (a 464K (e.g., H464K) and a 465 (e.g., 465Y) modification by Kabat numbering; a 252, 254, and 256 (e.g., 252Y, 254T, and 256E) modification by EU numbering (a 265, 267, 269 (e.g., 265Y, 267T, and 269E) modification by Kabat numbering; a 250Q and 428L modification (e.g., T250Q and M428L) by EU numbering (a 263Q and 459L modification, e.g., T263Q and M459L, by Kabat numbering); and a 307 and/or 308 modification (e.g., 307F or 308P) by EU numbering (326 and/or 327 modification, e.g., 326F or 308P, by Kabat numbering), wherein the modification increases the affinity of the heavy chain constant region amino acid sequence to FcRn in an acidic environment (e.g., in an endosome where pH ranges from about 5.5 to about 6.0). In some embodiments, the heavy chain constant region nucleotide sequence encodes a human $C_H2$ amino acid sequence comprising at least one modification between amino acid residues at positions 252 and 257 by EU numbering (i.e., at least one modification between amino acid positions 265 and 270 by Kabat numbering), wherein the modification increases the affinity of the human $C_H2$ amino acid sequence to FcRn in an acidic environment (e.g., in an endosome where pH ranges from about 5.5 to about 6.0). In some embodiments, the heavy chain constant region nucleotide sequence encodes a human $C_H2$ amino acid sequence comprising at least one modification between amino acid residues at positions 307 and 311 (i.e., at least one modification between amino acid positions 326 and 330 by Kabat numbering), wherein the modification increases the affinity of the $C_H2$ amino acid sequence to FcRn in an acidic environment (e.g., in an endosome where pH ranges from about 5.5 to about 6.0). In some embodiments, the heavy chain constant region nucleotide sequence encodes a human $C_H3$ amino acid sequence, wherein the $C_H3$ amino acid sequence comprises at least one modification between amino acid residues at positions 433 and 436 by EU numbering (i.e., at least one modification between amino acid residues at positions 464 and 467 by Kabat numbering), wherein the modification increases the affinity of the $C_H3$ amino acid sequence to FcRn in an acidic environment (e.g., in an endosome where pH ranges from about 5.5 to about 6.0). In some embodiments, the heavy chain constant region nucleotide sequence encodes a human heavy chain constant region amino acid sequence comprising a mutation selected from the group consisting of M428L by EU numbering (459 by Kabat numbering), N434S by EU numbering (465 by Kabat numbering), and a combination thereof. In some embodiments, the heavy chain constant region nucleotide sequence encodes a human heavy chain constant region amino acid sequence comprising a mutation selected from the group consisting of M428L by EU numbering (M459L by Kabat numbering), V259I by EU numbering (V272I by Kabat numbering), V308F by EU numbering (V327 by Kabat numbering), and a combination thereof. In some embodiments, the heavy chain constant region nucleotide sequence encodes a human heavy chain constant region amino acid sequence comprising an N434A mutation by EU numbering (an N465A mutation by Kabat numbering). In some embodiments, the heavy chain constant region nucleotide sequence encodes a human heavy chain constant region amino acid sequence comprising a mutation selected from the group consisting of M252Y by EU numbering (M265Y by Kabat numbering), S254T by EU numbering (S267T by Kabat numbering), T256E by EU numbering (T269E by Kabat numbering), and a combination thereof. In some embodiments, the heavy chain constant region nucleotide sequence encodes a human heavy chain constant region amino acid sequence comprising a mutation selected from the group consisting of T250Q by EU numbering (T263Q by Kabat numbering), M428L by EU numbering (M459L by Kabat numbering), and a combination thereof. In some embodiments, the heavy chain constant region nucleotide sequence encodes a human heavy chain constant region amino acid sequence comprising a mutation selected from the group consisting of H433K by EU numbering (H464K by Kabat numbering), N434Y by EU numbering (N465Y by Kabat numbering), and a combination thereof.

In various embodiments, a non-human animal as described herein is immunized with an antigen of interest, and a B cell expressing an antigen-binding protein that specifically binds the antigen of interest is identified, and a nucleic acid sequence of the B cell which encodes a light chain variable domain in a polypeptide comprising a heavy chain constant region is identified and determined. The nucleic acid sequence of the light chain variable domain is expressed, in a suitable cell and employing a suitable expression vector, with a heavy chain constant region nucleic acid sequence comprising one, two, three, or more modifications. In some embodiments, the light chain variable region is human, and the heavy chain sequence is human. In some embodiments, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0). In some embodiments, the heavy chain constant region nucleotide sequence encodes a human heavy chain constant region amino acid sequence comprising a modification at position 250 by EU numbering (263 by Kabat numbering) (e.g., E or Q); 250 by EU numbering (263 by Kabat numbering) and 428 by EU numbering (459 by Kabat numbering) (e.g., L or F); 252 by EU numbering (265 by Kabat numbering) (e.g., L/Y/F/W or T), 254 by EU numbering (267 by Kabat numbering) (e.g., S or T), and 256 by EU numbering (269 by Kabat numbering) (e.g., S/R/Q/E/D or T); or a modification at position 428 by EU numbering (459 by Kabat numbering) and/or 433 by EU numbering (464 by Kabat numbering) (e.g., L/R/S/P/Q or K) and/or 434 by EU numbering (465 by Kabat numbering) (e.g., H/F or Y); or a modification at position 250 by EU numbering (263 by Kabat numbering) and/or 428 by EU numbering (459 by Kabat numbering); or a modification at position 307 by EU numbering (326 by Kabat numbering) or 308 by EU numbering (327 by Kabat numbering) (e.g., 308F, V308F), and 434 by EU numbering (465 by Kabat numbering). In one embodiment, the modification comprises a 428L (e.g., M428L) and 434S (e.g., N434S) modification by EU numbering (a 459, e.g., M459L, and 465S (e.g., N465S) modification by Kabat numbering); a 428L, 259I (e.g., V259I), and 308F (e.g., V308F) modification by EU numbering (a 459L, 272I (e.g., V272I), and 327F (e.g., V327F) modification by Kabat numbering; a 433K (e.g., H433K) and a 434 (e.g., 434Y) modification by EU numbering (a 464K (e.g., H464K) and a 465 (e.g., 465Y) modification by Kabat numbering; a 252, 254, and 256 (e.g., 252Y, 254T, and 256E) modification by EU numbering (a 265, 267, 269 (e.g., 265Y, 267T, and 269E) modification by Kabat numbering; a 250Q and 428L modification (e.g., T250Q and M428L) by EU numbering (a 263Q and 459L modification, e.g., T263Q and M459L, by Kabat numbering); and a 307 and/or 308 modification (e.g., 307F or 308P) by EU numbering (326 and/or 327 modification, e.g., 326F or 308P, by Kabat numbering), wherein the modification increases the affinity of the heavy chain constant region amino acid sequence to FcRn in an acidic environment (e.g., in an endosome where pH ranges from about 5.5 to about 6.0). In some embodiments, the heavy chain constant region nucleotide sequence encodes a human $C_H2$ amino acid sequence comprising at least one modification between amino acid residues at positions 252 and 257 by EU numbering (i.e., at least one modification between amino acid positions 265 and 270 by Kabat numbering), wherein the modification increases the affinity of the human $C_H2$ amino acid sequence to FcRn in an acidic environment (e.g., in an endosome where pH ranges from about 5.5 to about 6.0). In some embodiments, the heavy chain constant region nucleotide sequence encodes a human $C_H2$ amino acid sequence comprising at least one modification between amino acid residues at positions 307 and 311 (i.e., at least one modification between amino acid positions 326 and 330 by Kabat numbering), wherein the modification increases the affinity of the $C_H2$ amino acid sequence to FcRn in an acidic environment (e.g., in an endosome where pH ranges from about 5.5 to about 6.0). In some embodiments, the heavy chain constant region nucleotide sequence encodes a human $C_H3$ amino acid sequence, wherein the $C_H3$ amino acid sequence comprises at least one modification between amino acid residues at positions 433 and 436 by EU numbering (i.e., at least one modification between amino acid residues at positions 464 and 467 by Kabat numbering), wherein the modification increases the affinity of the $C_H3$ amino acid sequence to FcRn in an acidic environment (e.g., in an endosome where pH ranges from about 5.5 to about 6.0). In some embodiments, the heavy chain constant region nucleotide sequence encodes a human heavy chain constant region amino acid sequence comprising a mutation selected from the group consisting of M428L by EU numbering (459 by Kabat numbering), N434S by EU numbering (465 by Kabat numbering), and a combination thereof. In some embodiments, the heavy chain constant region nucleotide sequence encodes a human heavy chain constant region amino acid sequence comprising a mutation selected from the group consisting of M428L by EU numbering (M459L by Kabat numbering), V259I by EU numbering (V272I by Kabat numbering), V308F by EU numbering (V327 by Kabat numbering), and a combination thereof. In some embodiments, the heavy chain constant region nucleotide sequence encodes a human heavy chain constant region amino acid sequence comprising an N434A mutation by EU numbering (an N465A mutation by Kabat numbering). In some embodiments, the heavy chain constant region nucleotide sequence encodes a human heavy chain constant region amino acid sequence comprising a mutation selected from the group consisting of M252Y by EU numbering (M265Y by Kabat numbering), S254T by EU numbering (S267T by Kabat numbering), T256E by EU numbering (T269E by Kabat numbering), and a combination thereof. In some embodiments, the heavy chain constant region nucleotide sequence encodes a human heavy chain constant region amino acid sequence comprising a mutation selected from the group consisting of T250Q by EU numbering (T263Q by Kabat numbering), M428L by EU numbering (M459L by Kabat numbering), and a combination thereof. In some embodiments, the heavy chain constant region nucleotide sequence encodes a human heavy chain constant region amino acid sequence comprising a mutation selected from the group consisting of H433K by EU numbering (H464K by Kabat numbering), N434Y by EU numbering (N465Y by Kabat numbering), and a combination thereof.

In various embodiments, Fc domains are modified (in the non-human animal; or, in an expression system that expresses together in a single polypeptide a light chain variable domain derived from a heavy chain of a non-human animal as described herein and a heavy chain constant sequence (e.g., a human sequence)) to have altered Fc receptor binding, which in turn affects effector function. In some embodiments, an engineered heavy chain constant region ($C_H$), which includes the Fc domain, is chimeric. As such, a chimeric $C_H$ region combines $C_H$ domains derived from more than one immunoglobulin isotype. For example, a chimeric $C_H$ region comprises part or all of a $C_H2$ domain derived from a human IgG1, human IgG2 or human IgG4 molecule, combined with part or all of a $C_H3$ domain derived from a human IgG1, human IgG2 or human IgG4 molecule. In some embodiments, a chimeric $C_H$ region contains a chimeric hinge region. For example, a chimeric hinge may comprise an "upper hinge" amino acid sequence (amino acid residues from positions 216 to 227 according to EU numbering; amino acid residues from positions 226 to 240 according to Kabat numbering) derived from a human IgG1, a human IgG2 or a human IgG4 hinge region, combined with a "lower hinge" sequence (amino acid residues from positions 228 to 236 according to EU numbering; amino acid positions from positions 241 to 249 according to Kabat numbering) derived from a human IgG1, a human IgG2 or a human IgG4 hinge region. In some embodiments, the chimeric hinge region comprises amino acid residues derived from a human IgG1 or a human IgG4 upper hinge and amino acid residues derived from a human IgG2 lower hinge.

In some embodiments, the Fc domain may be engineered to activate all, some, or none of the normal Fc effector functions, without affecting the Fc-containing protein's (e.g. antibody's) desired pharmacokinetic properties. For examples of proteins comprising chimeric $C_H$ regions and having altered effector functions, see International Patent Application No. PCT/US2014/14175, filed Jan. 31, 2014, which is herein incorporated in its entirety.

In various aspects, the genome of the non-human animals is modified (i) to delete or render nonfunctional (e.g., via insertion of a nucleotide sequence (e.g., an exogenous nucleotide sequence)) in the immunoglobulin locus or via non-functional rearrangement or inversion of all, or substantially all, endogenous functional immunoglobulin $V_H$, D, $J_H$ gene segments; and (ii) to comprise unrearranged human immunoglobulin light chain variable region gene segments, wherein the gene segments are present at an endogenous locus (i.e., where the gene segments are located in a wild type non-human animal). In some embodiments, the unrearranged human immunoglobulin light chain variable region gene segments are integrated in the genome (e.g., at a locus different from the endogenous immunoglobulin heavy chain locus in its genome, or within its endogenous locus, e.g., within an immunoglobulin variable locus, wherein the endogenous locus is placed or moved to a different location in the genome). In some embodiments, e.g., about 80% or more, about 85% or more, about 90% or more, about 95% or more, about 96% or more, about 97% or more, about 98% or more, or about 99% or more of all endogenous functional heavy chain V, D, or J gene segments are deleted or rendered non-functional. In some embodiments, e.g., at least 95%, 96%, 97%, 98%, or 99% of endogenous functional heavy chain V, D, or J gene segments are deleted or rendered non-functional. In some embodiments, the unrearranged human immunoglobulin light chain variable region gene segments are operably linked to a human or non-human heavy chain constant region gene sequence.

In some embodiments, the genetically modified non-human animal comprises a modification that deletes or renders non-functional endogenous functional $V_H$, D, and $J_H$ heavy chain variable gene segments and endogenous functional light chain variable $V_L$ and $J_L$ gene segments; and comprises (i) a rearranged human immunoglobulin light chain variable region nucleotide sequence (or a limited number of human $V_L$ gene segments, e.g., two or more but less than the wild type number of human $V_L$ gene segments) and (ii) a nucleotide sequence encoding unrearranged human immunoglobulin light chain V gene segments ($V_L$) and unrearranged human immunoglobulin light chain J gene segments ($J_L$) at an endogenous immunoglobulin locus (e.g., an endogenous immunoglobulin heavy chain locus comprising one or more heavy chain constant region genes each one comprising a sequence encoding a functional $C_H1$ domain, e.g., comprising at least an intact Igµ gene and at least one of an intact Igδ gene, an intact Igγ gene, an intact Igε gene, and an intact Igα gene) or integrated elsewhere in the genome (e.g., at a locus different from the endogenous immunoglobulin locus in its genome, or within its endogenous locus, e.g., within an immunoglobulin variable region locus, wherein the endogenous locus is placed or moved to a different location in the genome). In some embodiments, the genetically modified non-human animal comprises a modification that deletes or renders non-functional endogenous $V_H$, D, and $J_H$ heavy chain variable gene segments and endogenous light chain variable $V_L$ and $J_L$ gene segments; and comprises (i) a rearranged human immunoglobulin light chain variable region nucleotide sequence (or a limited number of human $V_L$ gene segments, e.g., two or more but less than the wild type number of human $V_L$ gene segments) and (ii) one or more unrearranged human immunoglobulin light chain variable region gene segments ($V_L$ and $J_L$) at an endogenous location (e.g., an endogenous immunoglobulin heavy chain locus) or integrated elsewhere in the genome (e.g., at a locus different from the endogenous immunoglobulin chain locus in its genome, or within its endogenous locus, e.g., within an immunoglobulin variable region locus, wherein the endogenous locus is placed or moved to a different location in the genome). In some embodiments, e.g., about 80% or more, about 85% or more, about 90% or more, about 95% or more, about 96% or more, about 97% or more, about 98% or more, or about 99% or more of all endogenous functional heavy chain V, D, or J gene segments are deleted or rendered non-functional. In some embodiments, e.g., at least 95%, 96%, 97%, 98%, or 99% of endogenous functional heavy chain V, D, or J gene segments are deleted or rendered non-functional. In some embodiments, the unrearranged human immunoglobulin light chain variable region gene segments are operably linked to a human or non-human heavy chain constant region gene sequence comprising one or more heavy chain constant region genes each one comprising a sequence encoding a functional $C_H1$ domain, e.g., comprising at least an intact Igµ gene and at least one of an intact Igδ gene, an intact Igγ gene, an intact Igε gene, and an intact Igα gene. In some embodiments, the rearranged human immunoglobulin light chain variable region nucleotide sequence (or a limited number of human $V_L$ gene segments, e.g., two or more but less than the wild type number of human $V_L$ gene segments) is operably linked to a human or non-human light chain constant region gene sequence, either kappa or lambda.

Various embodiments encompass light chain variable domains derived from immunoglobulin hybrid chains encoded by a hybrid immunoglobulin locus. Nucleic acid sequences encoding light chain variable domains may be used in making the genetically modified non-humans described herein, may be expressed by such animals, and/or may encode amino acids present in antibodies produced by (or derived from sequences diversified by) such animals. In some embodiments, the light chain variable domain is a human Vκ domain. In some embodiments, the light chain variable domain is a mouse Vκ domain. In some embodiments, the light chain variable domain is a rat Vκ domain. In some embodiments, the light chain variable domain is a human Vλ domain. In some embodiments, the light chain variable domain is a mouse Vλ domain. In some embodiments, the light chain variable domain is a rat Vλ domain.

In various embodiments, the light chain variable domains produced by the genetically modified non-human animals described herein are encoded by one or more mouse or human immunoglobulin κ light chain variable gene segments. In some embodiments, the one or more mouse immunoglobulin κ light chain variable gene segments comprise about three megabases of the mouse immunoglobulin κ light chain locus. In some embodiments, the one or more mouse immunoglobulin κ light chain variable gene segments comprises at least 137 Vκ gene segments, at least five Jκ gene segments or a combination thereof of the mouse immunoglobulin κ light chain locus. In some embodiments, the one or more human immunoglobulin κ light chain variable gene segments comprises about one-half megabase of a human immunoglobulin κ light chain locus. In specific embodiments, the one or more human immunoglobulin κ light chain variable gene segments comprise the proximal repeat (with respect to the immunoglobulin κ constant region) of a human immunoglobulin κ light chain locus. In some embodiments, the one or more human immunoglobulin κ light chain variable gene segments comprises at least 40 Vκ gene segments, at least five Jκ gene segments or a combination thereof of a human immunoglobulin κ light chain locus.

In particular embodiments, the genetically modified non-human animals further comprise a nucleotide sequence encoding an unrearranged human immunoglobulin light chain ($V_L$) gene segment and an unrearranged human immunoglobulin light chain ($J_L$) gene segment. In some embodiments, the nucleotide sequence encoding the unrearranged light chain V gene segment and the unrearranged light chain J gene segment is operably linked to an immunoglobulin heavy chain constant region gene sequence. In some embodiments, the unrearranged human immunoglobulin light chain V ($V_L$) gene segment and the unrearranged human immunoglobulin J ($J_L$) gene segment are operably linked, at an endogenous rodent locus, to a rodent immunoglobulin heavy chain constant region gene; e.g., an IgM or IgG heavy chain constant region gene, each of which encode a functional $C_H1$ domain.

In various embodiments, the unrearranged human variable region gene segments (e.g., human Vκ gene segments) are capable of rearranging and encoding human variable domains of an antibody. In some embodiments, the non-human animal does not comprise an endogenous $V_L$ gene segment. In some embodiments, the human Vκ gene segments expressed by the non-human animals are selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3. In some embodiments, the genetically modified non-human animals described herein express all functional human Vκ genes. In some embodiments, the human Vκ gene segments comprise Vκ4-1, Vκ5-2, Vκ7-3, Vκ2-4, Vκ1-5, and Vκ1-6. In some embodiments, the Vκ gene segments comprise Vκ3-7, Vκ1-8, Vκ1-9, Vκ2-10, Vκ3-11, Vκ1-12, Vκ1-13, Vκ2-14, Vκ3-15 and Vκ1-16. In some embodiments, the human Vκ gene segments comprise Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, and Vκ2-30. In some embodiments, the human Vκ gene segments comprise Vκ3-31, Vκ1-32, Vκ1-33, Vκ3-34, Vκ1-35, Vκ2-36, Vκ1-37, Vκ2-38, Vκ1-39, and Vκ2-40. In various embodiments, the non-human animal comprises five human Jκ gene segments, e.g., Jκ1, Jκ2, Jκ3, Jκ4, and Jκ5 gene segments. In specific embodiments, the Vκ gene segments comprise contiguous human immunoglobulin κ gene segments spanning the human immunoglobulin κ light chain locus from Vκ4-1 through Vκ2-40, and the Jκ1 gene segments comprise contiguous gene segments spanning the human immunoglobulin κ light chain locus from Jκ1 through Jκ5. In some embodiments, the immunoglobulin light chain locus of the non-human animal comprise two human $V_L$ gene segments, Vκ1-39 and Vκ3-20. In some embodiments, one or more (e.g., 2, 3, 4, 5, or more) human $V_L$ gene segments and two or more human $J_L$ gene segments are present at an endogenous heavy chain locus. In some embodiments, the genetically modified non-human animal is a mouse that comprises a functional λ light chain locus. In other embodiments, the mouse comprises a non-functional λ light chain locus.

In some embodiments, a genetically modified non-human animal (e.g., mouse or rat) as described herein expresses a rearranged human immunoglobulin light chain variable region nucleotide sequence (i.e., produces an antigen-binding protein comprising a rearranged light chain variable domain) and one or more, two or more, three or more, four or more, five or more, etc. light chain variable domains encoded by Vκ genes selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3.

In various embodiments, the rearranged human light chain variable region nucleotide sequence encodes one or more histidine codons that are not encoded by a corresponding human germ line light chain variable gene segment. In some embodiments, the light chain variable domain as described herein exhibits a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In some embodiments, the decrease in $t_{1/2}$ at an acidic pH as compared to a neutral pH is about 30 fold or more. In some embodiments, the rearranged human light chain variable region nucleotide sequence (or at least one of the limited number of human $V_L$ gene segments) comprises a substitution of at least one non-histidine codon encoded by the corresponding human germ line $V_L$ gene segment with a histidine codon. In some embodiments, the substitution is of one, two, three, or four codons (e.g., three or four codons). In some embodiments, the substitution is in the CDR3 codon(s). In some embodiments, the human $V_L$ gene segments is a human Vκ1-39 or human Vκ3-20 gene segment, and the human Vκ1-39 or human Vκ3-20 gene segment comprises a substitution of at least one non-histidine codon encoded by a corresponding human germ line $V_L$ gene segment with the histidine codon. In some embodiments, the human Vκ1-39 or human Vκ3-20 gene segment comprises a substitution of three or four histidine codons. In some embodiments, the three or four substitutions are in the CDR3 region. In some embodiments, the substitution is of three non-histidine codons of the human Vκ1-39 gene segment, wherein the substitution is designed to express histidines at positions 106, 108, and 111. In some embodiments, the substitution is of four non-histidine codons of the human Vκ1-39 gene segment, and the substitution is designed to express histidines at positions 105, 106, 108, and 111 (see, e.g., U.S. Patent Application Publication No. 2013-0247234 A1 and WO 2013/138680, incorporated by reference herein). In some embodiments, the substitution is of three non-histidine codons of the human Vκ3-20 gene segment, and the substitution is designed to express histidines at positions 105, 106, and 109. In yet additional embodiments, the substitution is of four non-histidine codons of the human Vκ3-20 gene segment, and the substitution is designed to express histidines at positions 105, 106, 107, and 109. In some embodiments, the immunoglobulin light chain locus comprises a rearranged human light chain variable region nucleotide sequence (or a limited number of human $V_L$ gene segments, e.g., two or more but less than the wild type number of human $V_L$ gene segments), wherein the nucleotide sequence (or at least one of the limited number of human $V_L$ gene segments) comprises at least one histidine codon that is not encoded by the corresponding human germ line $V_L$ gene segment. In various embodiments, the non-human animal comprising the genetically modified immunoglobulin loci as described herein, upon stimulation by an antigen of interest, expresses an antigen-binding protein comprising an amino acid sequence derived from human $V_L$ gene segments, wherein the antigen-binding protein retains at least one histidine residue at an amino acid position encoded by the at least one histidine codon introduced into the rearranged human light chain variable region nucleotide sequence (or the at least one of the limited number of human $V_L$ gene segments). In some embodiments, the animal expresses a population of antigen-binding proteins in response to an antigen, wherein all antigen-binding proteins in the population comprise (a) immunoglobulin light chain variable domains derived from a rearrangement of the human $V_L$ gene segments and the $J_L$ gene segments, and (b) immunoglobulin light chains comprising human light chain variable domains encoded by the rearranged human immunoglobulin light chain variable region nucleotide sequence (or encoded by one of the limited number of human $V_L$ gene segments), wherein rearranged human immunoglobulin light chain variable region nucleotide sequence (or at least one of the limited number of human $V_L$ gene segments) encodes one or more histidine codons that are not encoded by the corresponding human germ line $V_L$ gene segment.

Various embodiments encompass light chain constant region sequences. In some embodiments, for example, a first nucleotide sequence that encodes a human light chain variable domain (i.e., where the first nucleotide sequence contains unrearranged human immunoglobulin light chain variable region gene segments) is operably linked to a heavy chain constant region gene sequence, and a second nucleotide sequence that encodes a human light chain variable domain (i.e., where the second nucleotide sequence is a rearranged human immunoglobulin light chain variable nucleotide sequence or where the second sequence includes a limited number of human $V_L$ gene segments, e.g., two or more but less than the wild type number of human $V_L$ gene segments) is operably linked to a light chain constant region gene sequence. In various embodiments, the light chain constant region sequence operably linked to the rearranged human immunoglobulin light chain variable region nucleotide sequence (or limited number of human $V_L$ gene segments) is a human κ light chain constant region sequence. In some embodiments, the light chain constant region sequence operably linked to the rearranged light chain variable region nucleotide sequence (limited number of human $V_L$ gene segments) is a mouse κ light chain constant region sequence. In some embodiments, the light chain constant region sequence operably linked to the rearranged light chain variable region nucleotide sequence (limited number of human $V_L$ gene segments) is a rat κ light chain constant region sequence. In some embodiments, the light chain constant region sequence operably linked to the rearranged light chain variable region nucleotide sequence (limited number of human $V_L$ gene segments) is a human λ light chain constant region sequence. In some embodiments, the light chain constant region sequence operably linked to the rearranged light chain variable region nucleotide sequence (limited number of human $V_L$ gene segments) is a mouse light chain constant region sequence. In some embodiments, the light chain constant region sequence operably linked to the rearranged light chain variable region nucleotide sequence (limited number of human $V_L$ gene segments) is a rat λ light chain constant region sequence.

In various aspects, non-human animals are provided comprising a genetically modified immunoglobulin locus that encodes a rearranged light chain variable domain (e.g., where an immunoglobulin locus comprises a rearranged human immunoglobulin light chain variable region nucleotide sequence or a restricted (limited) number of human $V_L$ gene segments), wherein the rearranged light chain variable domain comprises a light chain variable ($V_L$) sequence that is operably linked to a light chain J segment ($J_L$) sequence. In some embodiments, the rearranged human immunoglobulin light chain variable region nucleotide sequence (or limited number of human $V_L$ gene segments) is operably linked to a non-human light chain constant region gene sequence. In some embodiments, the non-human light chain constant region gene sequence is a mouse or a rat constant region gene sequence. In some embodiments, the rearranged human immunoglobulin light chain variable region nucleotide sequence (or limited number of human $V_L$ gene segments) is operably linked to a human light chain constant region gene sequence.

In another aspect, genetically modified non-human animals and methods for making said animals are provided in which the animals comprise a functional universal light chain ("ULC") immunoglobulin locus (see, e.g., 2011-0195454 A1, US 2012-0021409A1, US 2012-0192300A1, US 2013-0045492A1, US 2013-0185821A1 and US 2013-0302836A1, incorporated by reference herein in their entireties) or a functional dual light chain ("DLC") immunoglobulin locus (see, e.g., U.S. Patent Application Publication No. US-2013-0198880-A1, incorporated by reference herein in its entirety). In some embodiments, such animals further comprise unrearranged light chain variable region gene segments operably linked to a human or non-human heavy chain constant region gene sequence (i.e., human $V_L$ and $J_L$ gene segments operably linked to an IgM, IgG, etc.). A ULC or DLC as used in the embodiments described herein can also be used to generate antibody variable chain sequences whose diversity results primarily from the processes of somatic mutation, thereby elucidating antibody variable chain sequences whose antigen-binding capacity benefits from post-genomic events.

Methods of Making and Using Non-Human Animals Comprising a High Diversity Hybrid Chain Locus Containing Unrearranged Light Chain Variable Region Gene Segments and a Low Diversity Light Chain Locus Containing a Rearranged Light Chain Variable Region Sequence Methods of making and using the genetically modified non-human animals described herein are provided. Methods are provided for placing a rearranged human light chain variable region nucleic acid sequence (or a limited number of human $V_L$ gene segments, e.g., two or more but less than the wild type number of human $V_L$ gene segments) in operable linkage with an immunoglobulin light chain constant region nucleic acid sequence in the genome of a non-human animal. In various embodiments, the constant region nucleic acid sequence is human or non-human, and the non-human animal is a rodent. In various embodiments, the methods comprise making a non-human animal that further comprises a hybrid immunoglobulin chain locus, e.g., an immunoglobuliln locus comprising one or more human light chain variable region gene segments, e.g., 40 human Vκ gene segments and five human Jκ gene segments, operably linked to a human or non-human heavy chain constant region nucleic acid sequence. In various aspects, the methods comprise placing the aforementioned sequences in the germ line of a non-human animal, e.g., a rodent, employing, e.g., transgenic technology including, e.g., employing modified pluripotent or totipotent donor cells (e.g., ES cells or iPS cells) with host embryos, germ cells (e.g., oocytes), etc. Thus, embodiments include a non-human hybrid immunoglobulin chain locus., e.g., an immunoglobulin chain locus in a genome of a non-human germ cell comprising unrearranged human immunoglobulin light chain variable region gene segments operably linked to a heavy chain constant region gene sequence, wherein the constant region gene sequence comprises a non-human sequence, a human sequence, or a combination thereof. In some embodiments, the rearranged human immunoglobulin light chain variable region nucleotide sequence (or a limited number of human $V_L$ gene segments) is operably linked to an endogenous non-human immunoglobulin constant region gene sequence. In some embodiments, the endogenous non-human immunoglobulin constant region gene sequence is a mouse or a rat light chain constant region gene sequence.

In various aspects, a method of making a non-human animal that comprises a genetically modified immunoglobulin locus is provided, wherein the method comprises: (a) modifying a genome of a non-human animal to delete or render non-functional endogenous functional immunoglobulin heavy chain V, D, and J gene segments; and (b) placing in the genome unrearranged human immunoglobulin light chain variable region gene segments. In one such aspect, a method is provided for making a non-human animal that expresses a single immunoglobulin light chain from a rearranged light chain gene sequence in the germ line of the non-human animal (or expressing an immunoglobulin light chain from a limited number of human $V_L$ gene segments, e.g., two or more but less than the wild type number of human $V_L$ gene segments), the method comprising a step of genetically modifying a non-human animal such that its entire antibody-expressing mature B cell population expresses a light chain derived from (i) a single $V_L$ gene segment, and (ii) a single $J_L$ gene segment or from (iii) a limited number of human $V_L$ gene segments (e.g., two or more but less than the wild type number of human $V_L$ gene segments). In some aspects, the method comprises inactivating or replacing an endogenous light chain immunoglobulin variable locus with a single rearranged light chain gene (or limited number of human $V_L$ gene segments) as described herein.

In another aspect, methods of making a non-human animal that comprises a genetically modified immunoglobulin heavy chain locus are provided, such methods comprising: (a) modifying a genome of a non-human animal to delete or render non-functional endogenous functional immunoglobulin heavy chain V, D, and J gene segments; and (b) placing in the genome unrearranged human immunoglobulin light chain variable region gene segments. In some embodiments, substantially all endogenous functional $V_H$, D, and $J_H$ gene segments are deleted from the immunoglobulin heavy chain locus of the non-human animal or rendered non-functional (e.g., via insertion of a nucleotide sequence (e.g., an exogenous nucleotide sequence in the immunoglobulin locus) or via non-functional rearrangement, or inversion of, endogenous $V_H$, D, $J_H$ segments). In some embodiments, the method comprises inserting unrearranged human immunoglobulin light chain variable region gene segments into an endogenous location (e.g., an endogenous immunoglobulin heavy chain locus). In some embodiments, the unrearranged human immunoglobulin light chain variable region gene segments are present elsewhere in the genome (e.g., at a locus different from the endogenous immunoglobulin chain locus in its genome, or within its endogenous locus, e.g., within an immunoglobulin variable locus, wherein the endogenous locus is placed or moved to a different location in the genome). In some embodiments, e.g., about 80% or more, about 85% or more, about 90% or more, about 95% or more, about 96% or more, about 97% or more, about 98% or more, or about 99% or more of all endogenous functional V, D, or J gene segments are deleted or rendered non-functional. In some embodiments, e.g., at least 95%, 96%, 97%, 98%, or 99% of endogenous functional heavy chain V, D, or J gene segments are deleted or rendered non-functional.

In another aspect, methods are provided for making a non-human animal that comprises a genetically modified immunoglobulin locus, comprising: (a) modifying a genome of a non-human animal to delete or render non-functional endogenous functional immunoglobulin light chain V and J gene segments; and (b) placing in an endogenous immunoglobulin light chain locus a rearranged human or non-human immunoglobulin light chain variable region nucleotide sequence (i.e., a nucleotide sequence that encodes a rearranged light chain variable domain) or a limited number of human or non-human $V_L$ gene segments (e.g., two or more but less than the wild type number of human $V_L$ gene segments), wherein the nucleotide sequence (or limited number of human or non-human $V_L$ gene segments) is operably linked to a light chain constant region gene sequence. In some embodiments, the genetically engineered immunoglobulin locus is present in the germ line genome of the non-human animal. In some embodiments, the rearranged human or non-human immunoglobulin light chain variable region nucleotide sequence (or limited number of human or non-human $V_L$ gene segments) is operably linked to a κ light chain constant region gene sequence. In some embodiments, the rearranged human or non-human immunoglobulin light chain variable region nucleotide sequence (or limited number of human or non-human $V_L$ gene segments) is operably linked to a mouse or rat κ light chain constant region gene sequence. In some embodiments, the rearranged human or non-human immunoglobulin light chain variable region nucleotide sequence (or limited number of human or non-human $V_L$ gene segments) is operably linked to a human κ light chain constant region gene sequence. In some embodiments, the rearranged human or non-human immunoglobulin light chain variable region nucleotide sequence (or limited number of human or non-human $V_L$ gene segments) is operably linked to a λ light chain constant region gene sequence. In some embodiments, rearranged human or non-human immunoglobulin light chain variable region nucleotide sequence (or limited number of human or non-human $V_L$ gene segments) is operably linked to a mouse or rat λ light chain constant region gene sequence. In some embodiments, the rearranged human or non-human immunoglobulin light chain variable region nucleotide sequence (or limited number of human or non-human $V_L$ gene segments) is operably linked to a human λ light chain constant region gene sequence.

In some embodiments, the limited number of human or non-human $V_L$ gene segments are operably linked to one or more human or non-human $J_L$ gene segments.

In another aspect, methods are provided for making a non-human animal that comprises a genetically modified immunoglobulin locus, comprising: (a) modifying a genome of a non-human animal to delete or render non-functional: (i) endogenous functional immunoglobulin heavy chain V, D, and J gene segments, and (ii) endogenous functional immunoglobulin light chain V and J gene segments; and (b) placing in the genome: (i) a first nucleotide sequence that encodes a rearranged light chain variable domain (e.g., where the first nucleotide sequence is a rearranged human immunoglobulin light chain variable region nucleotide sequence or where the first nucleotide sequence contains a limited number of human $V_L$ gene segments, e.g., two or more but less than the wild type number of human $V_L$ gene segments), wherein the first nucleotide sequence is operably linked to a light chain constant region gene sequence, and (ii) a second nucleotide sequence that encodes a human immunoglobulin light chain variable domain (i.e., where the second nucleotide sequence is an unrearranged human immunoglobulin light chain variable region nucleotide sequence), wherein the second nucleotide sequence is operably linked to a heavy chain constant region gene sequence comprising one or more heavy chain constant region genes each one comprising a sequence encoding a functional $C_H1$ domain, e.g., comprising at least an intact Igμ gene and at least one of an intact Igδ gene, an intact Igγ gene, an intact Igε gene, and an intact Igα gene. In some embodiments, the genetically engineered immunoglobulin locus is present in the germ line genome of the non-human animal. In some embodiments, the first nucleotide sequence that encodes the rearranged light chain variable domain (or contains a limited number of human $V_L$ gene segments) is operably linked to a κ light chain constant region gene sequence. In some embodiments, the first nucleotide sequence that encodes the rearranged light chain variable domain (or contains a limited number of human $V_L$ gene segments) is operably linked to a mouse or rat κ light chain constant region gene sequence. In some embodiments, the first nucleotide sequence that encodes the rearranged light chain variable domain (or contains a limited number of human $V_L$ gene segments) is operably linked to a human κ light chain constant region gene sequence. In some embodiments, the first nucleotide sequence that encodes the rearranged light chain variable domain (or contains a limited number of human $V_L$ gene segments) is operably linked to a λ light chain constant region gene sequence. In some embodiments, the first nucleotide sequence that encodes the rearranged light chain variable domain (or contains a limited number of human $V_L$ gene segments) is operably linked to a mouse or rat λ light chain constant region gene sequence. In some embodiments, the first nucleotide sequence that encodes the rearranged light chain variable domain (or contains a limited number of human $V_L$ gene segments) is operably linked to a human λ light chain constant region gene sequence. In some embodiments, the human immunoglobulin light chain variable domain is a κ light chain variable domain. Thus, in some embodiments, the second nucleotide sequence is a human kappa light chain variable region nucleotide sequence. In some embodiments, the human immunoglobulin light chain variable domain is a λ light chain variable domain. Thus, in some embodiments, the second nucleotide sequence is a human lambda light chain variable region nucleotide sequence. In some embodiments, the heavy chain constant region gene sequence is a non-human immunoglobulin heavy chain constant region gene sequence. In some embodiments, the non-human immunoglobulin heavy chain constant region gene sequence is a mouse or a rat heavy chain constant region gene sequence. In some embodiments, the non-human immunoglobulin heavy chain constant region gene sequence comprises an intact Igμ gene, an intact Igδ gene, an intact Igγ gene, an intact Igα gene, and/or an intact Igε gene.

Methods are provided for making a non-human animal, comprising: (a) modifying a genome of a non-human animal to delete or render non-functional (i) endogenous immunoglobulin heavy chain $V_H$, D, and and/or $J_H$ gene segments, and (ii) endogenous immunoglobulin light chain V and J gene segments; and (b) placing (i) a rearranged light chain variable region nucleotide sequence (or a limited number of human $V_L$ gene segments, e.g., two or more but less than the wild type number of human $V_L$ gene segments) at a light chain locus, wherein the rearranged light chain variable region nucleotide sequence (or limited number of human $V_L$ gene segments) comprises a light chain V gene segment ($V_L$) sequence that is operably linked to a light chain J gene segment ($J_L$) sequence; and (ii) one or more unrearranged human immunoglobulin light chain variable region gene segments (e.g., 40 human Vκ gene segments and at least one human Jκ gene segments) at a heavy chain locus so that the gene segments are operably linked to a human or non-human heavy chain constant region nucleotide sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene. In some embodiments, the rearranged light chain variable region nucleotide sequence encodes one or more histidine codons that are not encoded by a corresponding human germ line light chain variable gene segment.

In some aspects, a method for making a non-human animal comprising a genetically modified immunoglobulin locus is provided, comprising: (a) modifying a genome of a non-human animal to delete or render non-functional endogenous immunoglobulin light chain V and J gene segments; and (b) placing in the genome of the non-human animal a rearranged human or non-human light chain variable region nucleotide sequence (or a limited number of human or non-human $V_L$ gene segments) in operable linkage to a light chain constant region nucleotide sequence.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region.

In another aspect, a method for making a non-human animal comprising a genetically modified immunoglobulin locus is provided, comprising: (a) modifying a genome of a non-human animal to delete or render non-functional: (i) endogenous immunoglobulin heavy chain V, D, and/or J gene segments, and (ii) endogenous immunoglobulin light chain V and J gene segments; and (b) placing in the genome of the non-human animal: (i) a first nucleotide sequence that encodes a rearranged light chain variable domain (e.g., where the first nucleotide sequence is a rearranged human or non-human immunoglobulin light chain variable region nucleotide sequence or where the first nucleotide sequence contains a limited number of human $V_L$ gene segments; e.g., two or more but less than the wild type number of human $V_L$ gene segments), wherein the first nucleotide sequence is operably linked to a light chain constant region gene sequence, and (ii) a second nucleotide sequence that encodes a human or non-human light chain variable domain (i.e., where the second nucleotide sequence is an unrearranged human immunoglobulin light chain variable region nucleotide sequence), wherein the second nucleotide sequence is operably linked to a heavy chain constant region gene sequence. In some embodiments, the heavy chain constant region gene sequence comprises an intact Igμ gene, an intact Igδ gene, an intact Igγ gene, an intact Igα gene, and/or an intact Igε gene.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region. In some embodiments, the second nucleotide sequence is operably linked to a mouse or rat heavy chain constant region gene sequence comprising a nucleotide sequence encoding a $C_H1$, a hinge, a $C_H2$, a $C_H3$, or a combination thereof. In some embodiments, the second nucleotide sequence is operably linked to a human heavy chain constant region gene sequence comprising a nucleotide sequence encoding a $C_H1$, a hinge, a $C_H2$, a $C_H3$, or a combination thereof.

In another aspect, a method is provided for making a non-human animal that comprises a genetically modified immunoglobulin locus, comprising: (a) modifying a genome of a non-human animal to delete or render non-functional: (i) endogenous immunoglobulin heavy chain V, D, and/or J gene segments, and (ii) endogenous immunoglobulin light chain V and J gene segments; and (b) placing in the genome of the non-human animal: (i) a first allele comprising a first nucleotide sequence that encodes a rearranged light chain variable domain (e.g., where the first nucleotide sequence is a rearranged human immunoglobulin light chain variable region nucleotide sequence or where the first nucleotide sequence contains a limited number of human $V_L$ gene segments; e.g., two or more but less than the wild type number of human $V_L$ gene segments) operably linked to a light chain constant region gene sequence, and (ii) a second allele comprising a second nucleotide sequence that encodes a light chain variable domain (i.e., where the second nucleotide sequence is an unrearranged human immunoglobulin light chain variable region nucleotide sequence) operably linked to a heavy chain constant region gene sequence.

In another aspect, a method of making a non-human animal that comprises a genetically modified immunoglobulin heavy chain locus (e.g., hybrid immunoglobulin chain locus) and a modified immunoglobulin light chain locus is provided comprising: (a) modifying a genome of a non-human animal to delete or render non-functional endogenous immunoglobulin heavy chain V, D, and and/or J gene segments; (b) placing in an endogenous heavy chain locus of the non-human animal unrearranged human immunoglobulin light chain variable region gene segments in operable linkage with a heavy chain constant region, wherein the unrearranged human immunoglobulin light chain variable region gene segments comprise human Vκ and human Jκ gene segments; (c) modifying a genome of a non-human animal to delete or render non-functional endogenous immunoglobulin light chain V and and/or J gene segments; and (d) placing in an endogenous light chain locus of the non-human animal a rearranged human immunoglobulin light chain variable region nucleotide sequence (or a limited number of human $V_L$ gene segments, e.g., two or more but less than the wild type number of human $V_L$ gene segments) in operable linkage with a light chain constant region, wherein the rearranged human immunoglobulin light chain variable region nucleotide sequence (or limited number of human $V_L$ gene segments) comprises a rearranged human VκCκ sequence (or 2, 3, or 4 human $V_L$ gene segments). In some embodiments, the rearranged human VκJκ sequence is a human Vκ1-39Jκ5 sequence (e.g., set forth in SEQ ID NO: 1). In some embodiment, the rearranged human VκJκ sequence is a human Vκ3-20Jκ1 sequence (e.g., set forth in SEQ ID NO:2). In some embodiments, the limited number of human $V_L$ gene segments includes a human Vκ1-39 gene segment and a human Vκ3-20 gene segment. In some embodiments, the heavy chain constant region gene sequence comprises an intact Igμ gene, an intact Igδ gene, an intact Igγ gene, an intact Igα gene, and/or an intact Igε gene.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region. In some embodiments, the unrearranged human light chain variable region gene segments are operably linked to a mouse or rat heavy chain constant region gene sequence comprising a nucleotide sequence encoding $C_H1$, a hinge, a $C_H2$, a $C_H3$, or a combination thereof. In some embodiments, the unrearranged light chain variable region gene segments are operably linked to a human heavy chain constant region gene sequence comprising a nucleotide sequence encoding a $C_H1$, a hinge, a $C_H2$, a $C_H3$, or a combination thereof. In some embodiments, the unrearranged light chain variable region gene segments are operably linked to a human heavy chain constant region gene sequence comprising a nucleotide sequence encoding each of a $C_H1$, a hinge, a $C_H2$, and a $C_H3$ domain.

In another aspect, a method for making a non-human animal comprising a genetically modified immunoglobulin locus is provided, comprising: (a) modifying a genome of a non-human animal to delete or render non-functional: (i) endogenous immunoglobulin heavy chain V, D, and/or J gene segments, and (ii) endogenous immunoglobulin light chain V and J gene segments; and (b) placing in the genome of the non-human animal: (i) a rearranged human immunoglobulin light chain variable region nucleotide sequence (or a limited number of human $V_L$ gene segments, e.g., two or more but less than the wild type number of human $V_L$ gene segments) in operable linkage to a light chain constant region nucleotide sequence; and (ii) one or more human immunoglobulin light chain variable $V_L$ and $J_L$ gene segments in operable linkage to a heavy chain constant region nucleic acid sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene.

In various embodiments, the non-human animal is a rodent, e.g., a mouse, a rat, or a hamster. In some embodiments, the rodent is a mouse. In some embodiments, the light chain constant region is a rat or a mouse constant region, e.g., a rat or a mouse Cκ constant region.

In another aspect, nucleic acid sequences encoding rearranged light chain variable domains are provided. In some embodiments, the nucleic acid sequence is derived from a human Vκ and Jκ gene segments. In some embodiments, the nucleic acid sequence is derived from a human germ line Vκ segment and a human germ line Jκ segment. In some embodiments, the human Vκ segment corresponds to observed variants in the human population. In various embodiments, the nucleic acid sequence comprises a human Vκ gene selected from the group consisting of Vκ1-5, Vκ1-6, Vκ1-8, Vκ1-9, Vκ1-12, Vκ1-13, Vκ1-16, Vκ1-17, Vκ1-22, Vκ1-27, Vκ1-32, Vκ1-33, Vκ1-35, Vκ1-37, Vκ1-39, Vκ1D-8, Vκ1D-12, Vκ1D-13, Vκ1D-16, Vκ1D-17, Vκ1D-22, Vκ1D-27, Vκ1D-32, Vκ1D-33, Vκ1D-35, Vκ1D-37, Vκ1D-39, Vκ1D-42, Vκ1D-43, Vκ1-NL1, Vκ2-4, Vκ2-10, Vκ2-14, Vκ2-18, Vκ2-19, Vκ2-23, Vκ2-24, Vκ2-26, Vκ2-28, Vκ2-29, Vκ2-30, Vκ2-36, Vκ2-38, Vκ2-40, Vκ2D-10, Vκ2D-14, Vκ2D-18, Vκ2D-19, Vκ2D-23, Vκ2D-24, Vκ2D-26, Vκ2D-28, Vκ2D-29, Vκ2D-30, Vκ2D-36, Vκ2D-38, Vκ2D-40, Vκ3-7, Vκ3-11, Vκ3-15, Vκ3-20, Vκ3-25, Vκ3-31, Vκ3-34, Vκ3D-7, Vκ3D-7, Vκ3D-11, Vκ3D-15, Vκ3D-15, Vκ3D-20, Vκ3D-25, Vκ3D-31, Vκ3D-34, Vκ3-NL1, Vκ3-NL2, Vκ3-NL3, Vκ3-NL4, Vκ3-NL5, Vκ4-1, Vκ5-2, Vκ6-21, Vκ6D-21, Vκ6D-41, and Vκ7-3, and a polymorphic variant thereof. In some embodiments, the nucleic acid sequence further comprises a human or non-human animal heavy chain constant region gene sequence selected from a nucleotide sequence encoding a $C_H1$, a hinge, a $C_H2$, a $C_H3$, and a combination thereof. In specific embodiments, the nucleic acid comprises a constant region gene sequence comprising a nucleotide sequence encoding a $C_H1$, a hinge, a $C_H2$, and a $C_H3$. In various embodiments, the nucleic acid sequence comprises a human Jκ gene segment is selected from the group consisting of Jκ1, Jκ2, Jκ3, Jκ4, Jκ5, and a polymorphic variant thereof.

In another aspect, a nucleic acid construct is provided comprising an unrearranged human immunoglobulin light chain variable region nucleotide sequence (e.g., a nucleotide sequence that contains unrearranged human $V_L$ and $J_L$ gene segments) as described herein. In some embodiments, the nucleic acid construct is designed in such a way that the unrearranged human immunoglobulin light chain variable region nucleotide sequence is operably linked to a human or non-human animal heavy chain constant region gene sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene. In some embodiments, the nucleic acid construct contains two, three, four, or more unrearranged human immunoglobulin light chain variable region gene segments operably linked to a heavy chain constant region gene sequence. In some embodiments, the heavy chain constant region gene sequence comprises an intact Igμ gene, an intact Igδ gene, an intact Igγ gene, an intact Igα gene, and/or an intact Igε gene. In some embodiments, the nucleic acid construct is a targeting vector. In some embodiments, the targeting vector comprises an Adam6a gene, an Adam6b gene, or both, in order to prevent fertility problems associated with the deletion of the Adam6a/6b genes (see, for example, U.S. Pat. No. 8,642,835, incorporated by reference in its entirety). In some embodiments, the Adam6a and the Adam6b genes are placed at 5' upstream of the transcriptional unit of the unrearranged human light chain gene segments. In some embodiments, the targeting vector comprises a selection cassette flanked by recombination sites. In some embodiments, the targeting vector comprises one or more site-specific recombination sites (e.g., a loxP or a FRT site).

In another aspect, methods are provided for obtaining a light chain variable region ($V_{L/CH \times ULC}$) amino acid sequence capable of binding an antigen independently from a heavy chain variable region amino acid sequence, comprising: (a) immunizing a genetically modified non-human animal as described herein (e.g., a genetically modified animal whose genome comprises unrearranged human light chain variable region gene segments in operable linkage with a heavy chain constant region gene and a rearranged human or non-human light chain variable region nucleotide sequence (or a limited number of human or non-human $V_L$ gene segments) in operable linkage with a light chain constant region gene) with an antigen of interest, wherein the non-human animal mounts an immune response to the antigen; and (b) obtaining a rearranged light chain (VJ) nucleic acid sequence of a light chain variable domain that specifically binds the antigen from a cell (e.g., a B cell) of the genetically modified non-human animal. In various embodiments, the light chain variable regions produced by such methods are provided.

In some aspects, methods for obtaining a nucleic acid sequence that encodes an immunoglobulin light chain variable region ($V_{L/CH \times ULC}$) domain, comprise: (a) optionally immunizing a non-human animal with an antigen of interest or an immunogen thereof, wherein the non-human animal comprises in its genome (i) unrearranged human light chain variable region gene segments operably linked to a heavy chain constant region gene comprising one or more heavy chain constant region genes, each one comprising a sequence encoding a functional $C_H1$ domain, e.g., comprising an intact Ig gene, an intact Igδ gene, an intact Igγ gene, an intact Igε gene, and/or an intact Igα gene, and (ii) a rearranged human or non-human immunoglobulin light chain variable region nucleotide sequence (or a limited number of human or non-human $V_L$ gene segments) operably linked to a light chain constant region gene, (b) allowing the non-human animal to mount an immune response, (c) isolating from the immunized non-human animal a cell comprising a nucleic acid sequence that encodes a light chain variable domain that binds the antigen of interest, and (d) obtaining from the cell a nucleic acid sequence that encodes the light chain variable domain ($V_{L/CH \times ULC}$ domain) that binds the antigen of interest. In some embodiments, the heavy chain constant region gene sequence is a mouse or rat heavy chain constant region gene sequence. In some embodiments, the heavy chain constant region gene sequence is a human heavy chain constant region gene sequence. In some embodiments, the rearranged light chain variable domain expressed by the genetically modified locus is not autoreactive, i.e., non-immunogenic to the non-human animal. In some embodiments, the non-human animal comprises in its genome one or more (e.g., 6, 16, 30 or 40) unrearranged human $V_L$ gene segments and one or more (e.g., 5) human $J_L$ gene segments. In some certain embodiments, the unrearranged human $V_L$ and $J_L$ gene segments are Vκ and Jκ gene segments. In some embodiments, the isolating step (c) is carried out via fluorescence-activated cell sorting (FACS) or flow cytometry. In some embodiments, the cell comprising the nucleic acid sequence that encodes the light chain variable domain that binds the antigen of interest is a lymphocyte. In some embodiments, the lymphocyte comprises natural killer cells, T cells, or B cells. In some embodiments, the method further comprises a step of (c)' fusing the lymphocyte with a cancer cell. In certain embodiments, the cancer cell is a myeloma cell.

Thus, in various aspects, methods are provided for obtaining a nucleic acid sequence that encodes an immunoglobulin light chain variable domain ($V_{L/CH \times ULC}$) capable of binding an antigen independently from a heavy chain variable domain, comprising: (a) optionally immunizing a non-human animal with an antigen of interest or an immunogen thereof, wherein the non-human animal comprises in its genome (i) a rearranged human or non-human immunoglobulin light chain variable region nucleotide sequence (or a limited number of human or non-human $V_L$ gene segments) operably linked to a light chain constant region nucleic acid sequence; and (ii) unrearranged human immunoglobulin light chain variable region gene segments ($V_L$ and $J_L$) operably linked to a heavy chain constant region nucleotide sequence; (b) allowing the non-human animal to mount an immune response; (c) isolating from the immunized non-human animal a cell comprising a nucleic acid sequence that encodes a light chain variable domain that can bind the antigen; and (d) obtaining from the cell a nucleic acid sequence that encodes the light chain variable domain ($V_{L/CH \times ULC}$ domain) that can bind the antigen.

In some embodiments, the isolating step (c) is carried out via fluorescence-activated cell sorting (FACS) or flow cytometry. In some embodiments, the cell comprising the nucleic acid sequence that encodes the light chain variable domain that binds the antigen is a lymphocyte. In particular embodiments, the lymphocyte comprise natural killer cells, T cells, or B cells. In some embodiments, the methods further comprise a step of (c)' fusing the lymphocyte with a cancer cell. In particular embodiments, the cancer cell is a myeloma cell. In some embodiments, the nucleic acid sequence of (d) is fused with a nucleic acid sequence encoding an immunoglobulin constant region nucleic acid sequence. In some embodiments, the light chain constant region nucleic acid sequence is a human kappa sequence or a human lambda sequence. In some embodiments, the light chain constant region nucleic acid sequence is a mouse kappa sequence or a mouse lambda sequence. In some embodiments, the light chain constant region nucleic acid sequence is a rat kappa sequence or a rat lambda sequence. In some embodiments, the heavy chain constant region nucleic acid sequence is a human sequence comprising one or more heavy chain constant region genes, each one comprising a sequence encoding a functional $C_H1$ domain, e.g., comprising an intact Ig gene, an intact Igδ gene, an intact Igγ gene, an intact Igε gene, and/or an intact Igα gene. In some embodiments, the heavy chain constant region nucleic acid sequence is a mouse or rat sequence comprising one or more heavy chain constant region genes, each one comprising a sequence encoding a functional $C_H1$ domain, e.g., comprising an intact Ig gene, an intact Igδ gene, an intact Igγ gene, an intact Igε gene, and/or an intact Igα gene. In some embodiments, the nucleic acid sequence of (d) comprises one or more histidine codon substitutions or insertions that are derived from the unrearranged $V_L$ gene segment in the genome of the animal.

In some aspects, methods are provided for obtaining a nucleic acid sequence that encodes an immunoglobulin light chain variable domain ($V_{L/CH \times ULC}$), comprising: (a) optionally immunizing a non-human animal containing a genetically modified immunoglobulin loci as described herein with an antigen of interest, wherein the non-human animal comprises in its genome a rearranged human immunoglobulin light chain variable region nucleic acid sequence (or a limited number of human $V_L$ gene segments) operably linked to a light chain constant region nucleic acid sequence and unrearranged human immunoglobulin light chain variable region gene segments operably linked to a heavy chain constant region nucleic acid sequence comprising one or more heavy chain constant region genes, each one comprising a sequence encoding a functional $C_H1$ domain, e.g., comprising an intact Ig gene, an intact Igδ gene, an intact Igγ gene, an intact Igε gene, and/or an intact Igα gene; (b) allowing the non-human animal to mount an immune response; (c) harvesting a lymphocyte (e.g., a B cell) from the immunized non-human animal; (d) fusing the lymphocyte with a myeloma cell to form a hybridoma cell; and (e) obtaining from the hybridoma cell a nucleic acid sequence that encodes a light chain variable domain ($V_{L/CH \times ULC}$ domain) that can bind the antigen.

In another aspect, methods are provided for obtaining an immunoglobulin light chain variable region ($V_{L/CH \times ULC}$) amino acid sequence, comprising: (a) optionally immunizing a non-human animal containing genetically modified immunoglobulin loci as described herein with an antigen of interest, wherein the non-human animal comprises in its genome (i) a first nucleotide sequence that encodes a rearranged light chain variable domain (i.e., where the first nucleotide sequence is a rearranged human immunoglobulin light chain variable region nucleotide sequence or where the first nucleotide sequence contains a limited number of human $V_L$ gene segments, e.g., two or more but less than the wild type number of human $V_L$ gene segments), wherein the first nucleotide sequence is operably linked to a light chain constant region gene sequence; and (ii) a second nucleotide sequence that encodes a human or non-human light chain variable domain (i.e., where the second nucleotide sequence is an unrearranged human immunoglobulin light chain variable nucleotide sequence), wherein the second nucleotide sequence is operably linked to a heavy chain constant region gene sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene; (b) allowing the non-human animal to mount an immune response; (c) harvesting a lymphocyte (e.g., a B cell) from the immunized non-human animal; (d) fusing the lymphocyte with a myeloma cell to form a hybridoma cell; and (e) obtaining from the hybridoma cell a nucleic acid sequence that encodes a light chain variable domain ($V_L$ domain) that can bind the antigen.

In another aspect, methods are provided for obtaining an immunoglobulin light chain variable region ($V_{L/CH \times ULC}$) nucleic acid sequence of an immunoglobulin hybrid chain, comprising: (a) optionally immunizing a non-human animal containing genetically modified immunoglobulin loci as described herein with an antigen of interest, wherein the non-human animal comprises in its genome (i) a rearranged human immunoglobulin light chain variable region nucleic acid sequence (or a limited number of human $V_L$ gene segments, e.g., two or more but less than the number of wild type number of human $V_L$ gene segments) operably linked to a light chain constant region nucleic acid sequence; and (ii) one or more (e.g., 6, 16, 30, 40 or more) unrearranged human immunoglobulin light chain variable region gene segments ($V_L$ and $J_L$); (b) allowing the non-human animal to mount an immune response; (c) identifying a lymphocyte (e.g., a B cell) from the immunized non-human animal that expresses a $V_{L/CH \times ULC}$ amino acid sequence that binds the antigen independently from a heavy chain variable region; and, (d) cloning a nucleic acid sequence encoding the $V_{L/CH \times ULC}$ amino acid sequence of (c) from the lymphocyte of (c).

In additional aspects, a genetically modified immunoglobulin locus obtainable by any of the methods as described herein is provided. In various embodiments, the light chain variable regions produced by the methods as described herein and the nucleic acid sequence encoding such light chain variable regions are also provided.

In some aspects, an immunoglobulin heavy chain (e.g., hybrid immunoglobulin chain locus) and light chain locus in a germline genome of a non-human animal are provided, said light chain locus comprising (1) a rearranged human immunoglobulin light chain variable region nucleotide sequence (or a limited number of human $V_L$ gene segments) that is operably linked to a light chain constant region gene sequence, and said heavy chain locus (e.g., hybrid immunoglobulin chain locus) comprising (2) an unrearranged human immunoglobulin light chain variable region nucleotide sequence that is operably linked to a heavy chain constant region gene sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene. In some embodiments, the light chain constant region gene sequence is a κ light chain constant region gene sequence. In some embodiments, the light chain constant region gene sequence is a λ light chain constant region gene sequence. In some embodiments, the light chain constant region gene sequence is a mouse or rat light chain constant region gene sequence. In some embodiments, the rearranged light chain variable region nucleotide sequence is a κ light chain variable region gene sequence. In some embodiments, the rearranged light chain variable region nucleotide sequence is a light chain variable region gene sequence. In some embodiments, the rearranged light chain variable region nucleotide sequence is a mouse or rat light chain variable region gene sequence. In some embodiments, the heavy chain constant region gene sequence comprises an intact Igμ gene, an intact Igδ gene, an intact Igγ gene, an intact Igα gene, and/or an intact Igε gene.

In various embodiments, a limited number of human or non-human $V_L$ gene segments includes two human or non human $V_L$ gene segments. In some embodiments, the two human or non-human $V_L$ gene segments are operably linked to one or more, or five, human or non-human $J_L$ gene segments. In some certain embodiments, a limited number of human or non-human $V_L$ gene segments include two Vκ gene segments. In some certain embodiments, the two Vκ gene segments are operably linked to one or more, or five, Jκ gene segments.

Antigen-Binding Proteins

Additional aspects include antigen-binding proteins (e.g. antibodies) made by the genetically modified non-human animals described herein. Likewise, antigen-binding proteins (e.g., recombinant antibodies) with light chain variable region ($V_{L/CH\times ULC}$) sequences derived from or produced by (i.e., expressed from the unrearranged human immunoglobulin light chain variable region gene segments) the genetically modified non-human animals described herein are also provided. In some embodiments, the antigen-binding proteins as described herein include an immunoglobulin light chain that can specifically bind an antigen of interest with an affinity ($K_D$) lower than $10^{-6}$, $10^{-7}$, $10^{-8}$, $10^{-9}$ or $10^{-10}$. In some embodiments, the immunoglobulin light chain produced by the methods are capable of specifically binding an antigen of interest in the absence of a heavy chain variable region with an affinity ($K_D$) lower than $10^{-6}$, $10^{-7}$, $10^{-8}$, $10^{-9}$, or $10^{-10}$.

In various embodiments, the light chain variable domains generated as described herein specifically bind a target molecule ("T"). In one embodiment, a target molecule is any protein, polypeptide, or other macromolecule whose activity or extracellular concentration is desired to be attenuated, reduced or eliminated. In many instances, the target molecule to which a light chain variable region binds is a protein or polypeptide (i.e., a "target protein"); however, also provided are embodiments wherein the target molecule ("T") is a carbohydrate, glycoprotein, lipid, lipoprotein, lipopolysaccharide, or other non-protein polymer or molecule to which a light chain variable region binds. In various embodiments, T can be a cell surface-expressed target protein or a soluble target protein. Target binding by the antigen-binding molecule may take place in an extracellular or cell surface context. In certain embodiments, however, the antigen-binding molecule binds a target molecule inside the cell, for example within an intracellular component such as the endoplasmic reticulum, Golgi, endosome, lysosome, etc. Examples of cell surface-expressed target molecules include cell surface-expressed receptors, membrane-bound ligands, ion channels, and any other monomeric or multimeric polypeptide component with an extracellular portion that is attached to or associated with a cell membrane.

In another aspect, methods are provided for making an antigen-binding protein that comprises an immunoglobulin light chain variable $V_{L/CH\times ULC}$ domain that can bind an antigen independently from a heavy chain variable domain. Such methods comprise (a) optionally immunizing a genetically modified non-human animal with an antigen that comprises an epitope or immunogenic portion thereof, wherein the non-human animal comprises in its genome: (i) a rearranged human light chain variable region nucleic acid sequence (or a limited number of human $V_L$ gene segments, e.g., two or more but less than the wild type number of human $V_L$ gene segments) operably linked to a light chain constant region nucleic acid sequence; and (ii) unrearranged human immunoglobulin light chain variable region gene segments ($V_L$ and $J_L$) operably linked to an immunoglobulin heavy chain constant region nucleic acid sequence; (b) allowing the non-human animal to mount an immune response to the epitope or immunogenic portion thereof; (c) isolating from the non-human animal a cell comprising a nucleic acid sequence that encodes a light chain variable domain that specifically binds the epitope or immunogenic portion thereof and/or (d) obtaining from the cell of (c) the nucleic acid sequence that encodes the light chain variable domain that specifically binds the epitope or immunogenic portion thereof; and (e) employing the nucleic acid sequence of (d) in an expression construct, fused to a human immunoglobulin constant region nucleic acid sequence. e.g., a human heavy chain constant region nucleic acid sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene.

In some embodiments, at least one of the unrearranged human light chain $V_L$ or $J_L$ gene segments encode one or more histidine codons that are not encoded by a corresponding human germline light chain variable gene segment. In some embodiments, rearranged human light chain variable region nucleic acid sequence (or at least one of the limited number of human $V_L$ gene segments) encodes one or more histidine codons that are not encoded by a corresponding human germ line light chain variable gene segment. In some embodiments, the epitope is derived from a cell surface receptor.

In some embodiments, at least one of the human light chain $V_L$ or $J_L$ gene segments encode one or more histidine codons that are not encoded by a corresponding human germline light chain variable gene segment.

As will be clear throughout the specification, in some embodiments, provided protein variable domains are or comprise immunoglobulin-type variable domains (e.g., are or comprise immunoglobulin variable domains). In some embodiments, provided protein variable domains are or comprise heavy chain variable domains; in some embodiments, provided protein variable domains are or comprise light chain variable domains.

Figure 19:
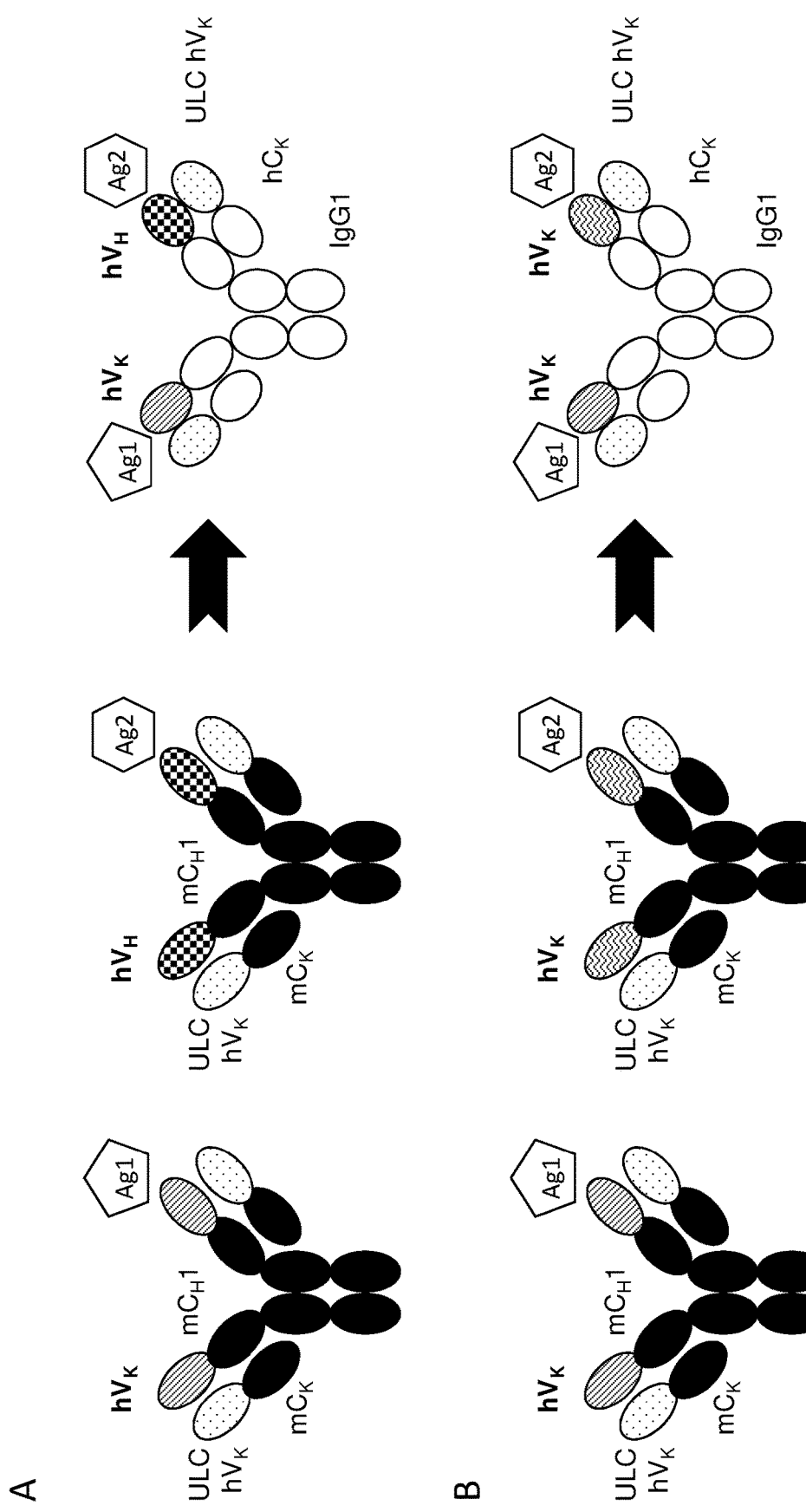

Those skilled in the art, reading the present specification, will readily appreciate that any of a variety of technologies can be utilized to produce, generate, and/or assemble antigen-binding proteins comprising light chain that can bind antigen independently from heavy chain variable domain. In some embodiments described herein, the antigen-binding proteins that are produced include antigen-binding proteins depicted in FIG. 19. These antigen-binding proteins comprise variable domains that are generated in non-human animals described herein, and nucleic acid sequences comprising sequences that encode these variable domains are co-expressed in a cell line to produce the antigen-binding proteins.

Genetically Modified Non-Human Cells and Embryos

In various aspects, a pluripotent cell, induced pluripotent, or totipotent stem cells derived from a non-human animal comprising the various genomic modifications herein are provided. In some embodiments, the pluripotent or totipotent cell is derived from a non-human animal. In some embodiments, the non-human animal is a rodent, e.g., a mouse, a rat, or a hamster. In some embodiments, the rodent is a mouse. In specific embodiments, the pluripotent cell is an embryonic stem (ES) cell. In some embodiments, the pluripotent cell comprises in its genome: (i) an immunoglobulin light chain locus that comprises a rearranged human or non-human light chain variable region nucleic acid sequence (or a limited number of human or non-human $V_L$ gene segments, e.g., two or more but less than the number of wild type human or non-human $V_L$ gene segments) operably linked to a light chain constant region nucleic acid sequence; and (ii) an immunoglobulin heavy chain locus (e.g., hybrid immunoglobulin chain locus) comprising one or more unrearranged human immunoglobulin $V_L$ and $J_L$ gene segments, operably linked to a heavy chain constant region nucleic acid sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene. In some embodiments, the heavy chain constant region gene sequence comprises an intact Igμ gene, an intact Igδ gene, an intact Igγ gene, an intact Igα gene, and/or an intact Igε gene. In specific embodiments, the pluripotent, induced pluripotent, or totipotent stem cells are mouse or rat embryonic stem (ES) cells. In some embodiments, the pluripotent, induced pluripotent, or totipotent stem cells have an XX karyotype or an XY karyotype.

Cells that comprise a nucleus containing a genetic modification as described herein are also provided, e.g., a modification introduced into a cell by pronuclear injection. In another aspect, a hybridoma or quadroma is provided, derived from a cell of the non-human animal as described herein. In some embodiments, the non-human animal is a rodent, such as a mouse, a rat, or a hamster.

In another aspect, a lymphocyte isolated from a genetically modified non-human animal as described herein is provided. In some embodiments, the lymphocyte is a B cell, wherein the B cell comprises an immunoglobulin genomic locus comprising a rearranged human or non-human immunoglobulin light chain variable region nucleotide sequence (or a limited number of human or non-human $V_L$ gene segments) operably linked to a human or a non-human animal (e.g., mouse or rat) light chain constant region gene sequence. In some embodiments, the B cell further comprises an immunoglobulin genomic locus comprising a rearranged human immunoglobulin light chain variable region nucleotide sequence operably linked to a human or non-human animal (e.g., mouse or rat) heavy chain constant region gene sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene. In some embodiments, the B cell is capable of producing antibodies wherein the rearranged light chain variable domain as described herein is operably linked to a heavy chain or light chain constant domain.

In another aspect, a non-human animal embryo comprises a cell whose genome comprises: (i) an immunoglobulin heavy chain locus (e.g., hybrid immunoglobulin chain locus) comprising unrearranged human light chain variable region gene segments operably linked to a constant region nucleic acid sequence comprising one or more heavy chain constant region genes, each one comprising a sequence encoding a functional $C_H1$ domain, e.g., comprising an intact Igμ gene, an intact Igδ gene, an intact Igγ gene, an intact Igε gene, and/or an intact Igα gene; and (ii) an immunoglobulin light chain locus comprising a rearranged human or non-human immunoglobulin light chain variable region nucleotide sequence (or a limited number of human or non-human $V_L$ gene segments) operably linked to a light chain constant region nucleic acid sequence. In some embodiments, the hybrid immunoglobulin locus comprising unrearranged human light chain variable region gene segments operably linked to a constant region nucleic acid sequence is operably linked to a heavy chain constant region nucleic acid sequence, and the heavy chain constant region gene sequence comprises an intact Igμ gene, an intact Igδ gene, an intact Igγ gene, an intact Igα gene, and/or an intact Igε gene.

In various embodiments, the genetically modified non-human animals express an antibody repertoire (e.g., an IgG repertoire) that is derived from the nucleotide sequence that encodes the rearranged light chain variable domain (or the nucleotide sequence that contains a limited number of human $V_L$ gene segments), and a plurality of light chain V segments (and a plurality of light chain J segments). In some embodiments, the genetically modified locus produces an antibody population that comprises an immunoglobulin light chain that is capable of specifically binding an antigen of interest with an affinity ($K_D$) lower than $10^{-6}$, $10^{-7}$, $10^-$, $10^{-9}$ or $10^{-10}$. In some embodiments, the immunoglobulin light chain expressed by the genetically modified locus is capable of specifically binding an antigen of interest in the absence of a heavy chain variable region with an affinity ($K_D$) lower than $10^{-6}$ $10^{-7}$, $10^{-8}$, $10^{-9}$, or $10^{-10}$.

In various embodiments, the genetic modifications described herein do not affect fertility of the non-human animal (see, for example, U.S. Pat. No. 8,642,835, incorporated by reference in its entirety). In some embodiments, the heavy chain locus, e.g., hybrid chain locus, comprises an endogenous Adam6a gene, Adam6b gene, or both, and the genetic modification does not affect the expression and/or function of the endogenous Adam6a gene, Adam6b gene, or both. In some embodiments, the genome of the genetically modified non-human animal comprises an Adam6a gene, Adam6b gene, or both integrated in the genome at location outside the heavy chain locus or hybrid chain locus. In some embodiments, an Adam6a and/or Adam6b gene is placed 5' upstream of the unrearranged light chain variable region gene segments. In some embodiments, the Adam6a and/or the Adam6b gene is placed 3' downstream of the unrearranged light chain variable region gene segments. In some embodiments, the heavy chain locus comprises a functional ectopic mouse Adam6 gene.

The capabilities of the genetically modified non-human animals described herein to apply selective pressure to genes or polynucleotides encoding light chain variable regions or domains (e.g., light chain CDR3s) can be applied to a variety of variable light chain gene sequences. In other words, the rearranged light chain variable region nucleotide sequences disclosed herein can be paired with one or more genetic modifications of a heavy chain locus and/or the insertion of nucleotide sequences encoding light chain variable domains into a heavy chain locus. This can be accomplished by, for example, mating (i.e., cross-breeding or intercrossing of animals with single modification) the non-human animals described herein (restricted to a common or universal light chain variable domain) with non-human animals comprising genetic modifications within one or more heavy chain-encoding loci. Genetically modified non-human animals comprising immunoglobulin light chain loci with a rearranged light chain variable region nucleotide sequence (or a limited number of human $V_L$ gene segments) and one or more heavy chain loci modifications can also be generated by targeted gene replacement of multiple loci, either simultaneously or sequentially (e.g., by sequential recombination in embryonic stem cells). Neither the type nor method of modification at the heavy chain loci limits embodiments described herein unless specifically noted. Rather, the selective pressure facilitated by embodiments described herein can be applied to virtually any polynucleotide sequence capable of being expressed and functioning as a heavy chain antigen-binding sequence, thereby driving the evolution of fitter antibody variable regions.

For example, as described herein, genetically modified non-human animals comprising an immunoglobulin locus with a rearranged light chain variable region nucleotide sequence (or a limited number of human $V_L$ gene segments) may further comprise (e.g., via cross-breeding or multiple gene targeting strategies) one or more modifications as described in WO 2011/072204, WO 2011/163311, WO 2011/163314, WO 2012/018764, WO 2012/141798, WO 2013/022782, WO 2013/059230, WO 2013/096142, WO 2013/116609, WO 2013/187953; these publications are incorporated herein by reference in their entirety. In particular embodiments, a genetically modified mouse comprising a rearranged light chain variable region nucleic acid sequence, or a limited number of $V_L$ gene segments, in a light chain locus (e.g., a rearranged light chain variable domain gene sequence, or two $V_L$ gene segments, operably linked to a human or non-human κ light chain constant region gene sequence) is crossed to a genetically modified mouse comprising an immunoglobulin heavy chain locus (e.g., hybrid immunoglobulin chain locus) comprising human light chain variable region gene segments (e.g., 40 human Vκ genes and all human Jκ genes inserted into a mouse heavy chain locus; see, e.g., U.S. Patent Application Publication no. 2012-0096572 A1, incorporated herein by reference). In specific embodiments, a genetically modified mouse comprising a rearranged light chain variable region nucleic acid sequence, or a limited number of $V_L$ gene segments, in a light chain locus (e.g., a rearranged light chain variable region nucleotide sequence, or two $V_L$ gene segments, operably linked to a human or non-human κ light chain constant region gene sequence) is crossed to a genetically modified mouse comprising an immunoglobulin heavy chain locus (e.g., hybrid immunoglobulin chain locus) comprising one or more human light chain variable region gene segments. The resulting mice are able to produce Igκ⁺B cells with variable heavy chains derived from genomic light chain variable sequences, thus facilitating the identification of Vκ domains that bind to specific targets.

EXAMPLES

The following non-limiting examples are set forth so as to provide those of ordinary skill in the art with a complete disclosure and description of how to make and use non-human animals described herein and aid in the understanding thereof, and are not intended to limit the scope of what the inventors regard as their invention nor are they intended to represent that the experiments below are all or the only experiments performed. The Examples do not include detailed descriptions of conventional methods that would be well known to those of ordinary skill in the art (molecular cloning techniques, etc.). Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Generation of Non-Human Animals Having Modified Immunoglobulin Loci

This example illustrates exemplary methods of engineering immunoglobulin heavy chain loci of non-human animals to contain (a) an immunoglobulin heavy chain locus comprising unrearranged human immunoglobulin light chain $V_L$ and $J_L$ gene segments operably linked to an immunoglobulin heavy chain constant region nucleic acid sequence (e.g., hybrid immunoglobulin chain locus); and (b) an immunoglobulin light chain locus comprising a rearranged human immunoglobulin light chain variable region nucleotide sequence operably linked to an immunoglobulin light chain constant region nucleic acid sequence.

Construction of Immunoglobulin Heavy Chain Loci with Light Chain Gene Segments

Figure 2:
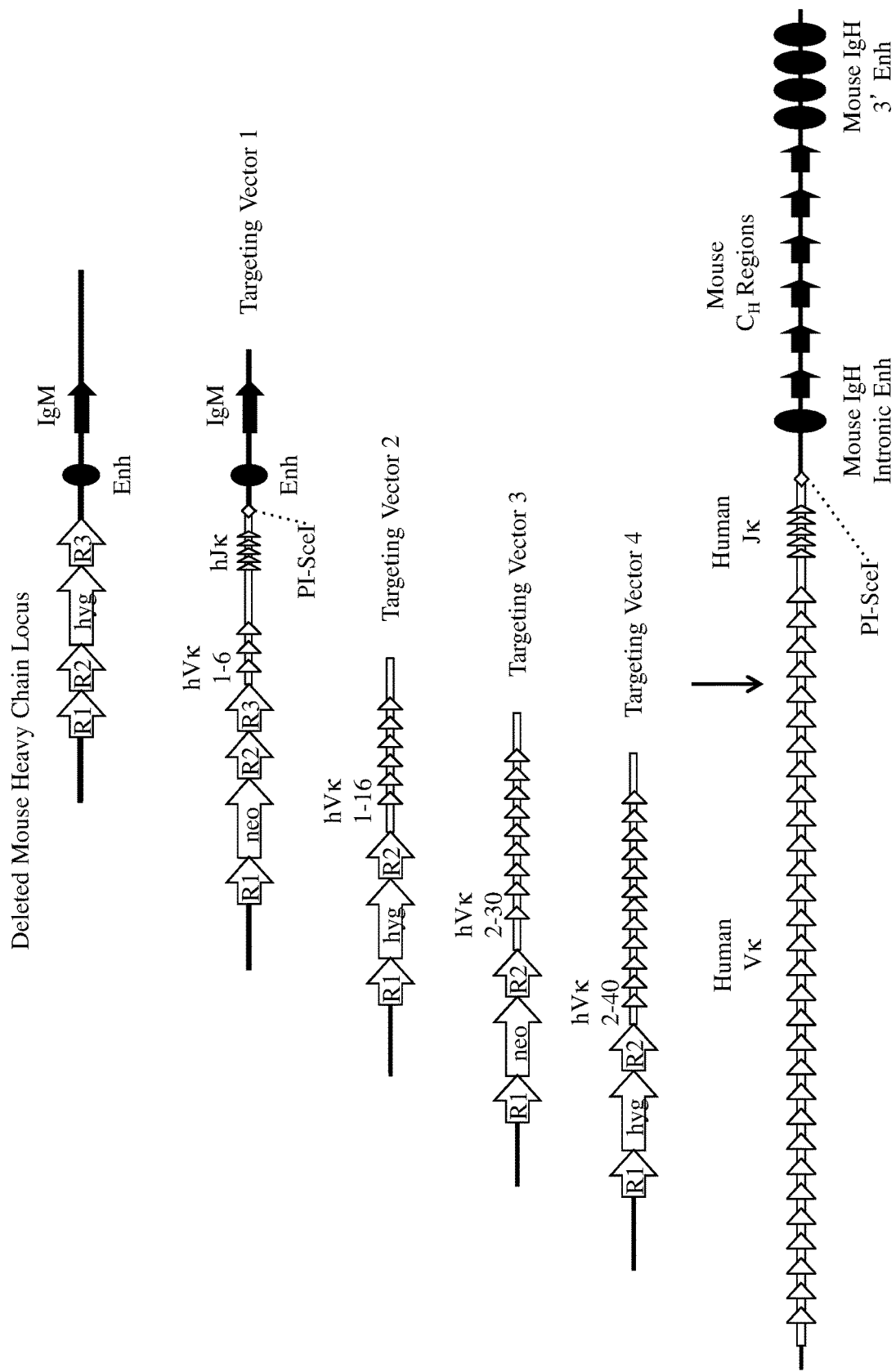
FIG. 2 shows a targeting strategy for progressive insertion of 40 human Vκ and 5 human Jκ gene segments into a mouse heavy chain locus. Hygromycin (hyg) and Neomycin (neo) selection cassettes are shown with recombinase recognition sites (R1, R2, etc.). A modified mouse heavy chain locus, e.g., a hybrid immunoglobulin locus comprising human Vκ and Jκ gene segments operably linked to mouse $C_H$ regions, is shown at the bottom.

Wild type mouse heavy chain and human κ light chain loci are depicted in FIG. 1. Construction of exemplary targeting vectors for the insertion of human light chain V and J gene segments (e.g., Vκ and Jκ) into a murine immunoglobulin heavy chain locus is described below. FIG. 2 illustrates four exemplary targeting vectors that contain a plurality of human κ light chain gene segments for insertion into a murine immunoglobulin heavy chain locus using homologous recombination.

Various targeting constructs were made using VELOCIGENE® genetic engineering technology (see, e.g., U.S. Pat. No. 6,586,251 and Valenzuela, D. M., Murphy, A. J., Frendewey, D., Gale, N. W., Economides, A. N., Auerbach, W., Poueymirou, W. T., Adams, N. C., Rojas, J., Yasenchak, J., Chernomorsky, R., Boucher, M., Elsasser, A. L., Esau, L., Zheng, J., Griffiths, J. A., Wang, X., Su, H., Xue, Y., Dominguez, M. G., Noguera, I., Torres, R., Macdonald, L. E., Stewart, A. F., DeChiara, T. M., Yancopoulos, G. D. (2003). High-throughput engineering of the mouse genome coupled with high-resolution expression analysis. Nat Biotechnol 21, 652-659) to modify mouse genomic Bacterial Artificial Chromosome (BAC) libraries. Mouse BAC DNA may be modified by homologous recombination to deletion the endogenous $V_H$, $D_H$ and $J_H$ gene segments for the subsequent insertion of unrearranged human $V_L$ and $J_L$ gene segments. Alternatively, the endogenous $V_H$, $D_H$ and $J_H$ gene segments may be left intact and inactivated so that recombination of endogenous gene segments to form a functional variable region is inhibited (e.g., by inversion or disruption of gene segments).

Genetically modified mice, and methods of making the same, whose genome contains an immunoglobulin hybrid chain locus comprising unrearranged human immunoglobulin light chain $V_L$ and $J_L$ gene segments operably linked to an immunoglobulin heavy chain constant region nucleic acid sequence are described in U.S. Patent Application Publication No. 2012-0096572 A1, incorporated herein by reference in its entirety. As shown in FIG. 2, four targeting vectors were engineered to progressively insert 40 human Vκ gene segments and five human Jκ gene segments into an non-human ES cell comprising an inactivated heavy chain locus (e.g., deleted endogenous $V_H$, $D_H$ and $J_H$ gene segments) and/or a light chain locus comprising a single rearranged human $V_L/J_L$ gene sequence operably linked to a light chain constant region, e.g., a non-human light chain constant region, e.g., at an endogenous non-human light chain locus, using standard molecular techniques recognized in the art. Table 1 sets forth the size of human DNA included in each targeting vector which contains various human κ light chain gene segments for insertion into a mouse immunoglobulin heavy chain locus. Any number of human Vκ and Jκ gene segments may be included in the targeting vectors. The exemplary targeting vectors set forth in FIG. 2 include human κ light chain gene segments that are naturally found in the proximal contig of the germ line human κ light chain locus (FIG. 1). The resulting endogenous heavy chain locus after successive insertion of all four targeting vectors is shown in the bottom of FIG. 2.

TABLE 1

| Targeting Vector | Size of Human κ Sequence | Human κ Gene Segments Added Vκ | Jκ |
|---|---|---|---|
| 1 | ~110.5 kb | 4-1, 5-2, 7-3, 2-4, 1-5, 1-6 | 1-5 |
| 2 | ~140 kb | 3-7, 1-8, 1-9, 2-10, 3-11, 1-12, 1-13, 2-14, 3-15, 1-16 | — |
| 3 | ~161 kb | 1-17, 2-18, 2-19, 3-20, 6-21, 1-22, 1-23, 2-24, 3-25, 2-26, 1-27, 2-28, 2-29, 2-30 | — |
| 4 | ~90 kb | 3-31, 1-32, 1-33, 3-34, 1-35, 2-36, 1-37, 2-38, 1-39, 2-40 | — |

Using a similar approach, other combinations of human light chain variable domains in the context of murine heavy chain constant regions may be constructed. Additional light chain variable domains may be derived from human Vλ and Jλ gene segments. Exemplary targeting vectors that include human DNA that include various numbers of human Vλ and Jλ gene segments are set forth in FIG. 3.

Figure 3:
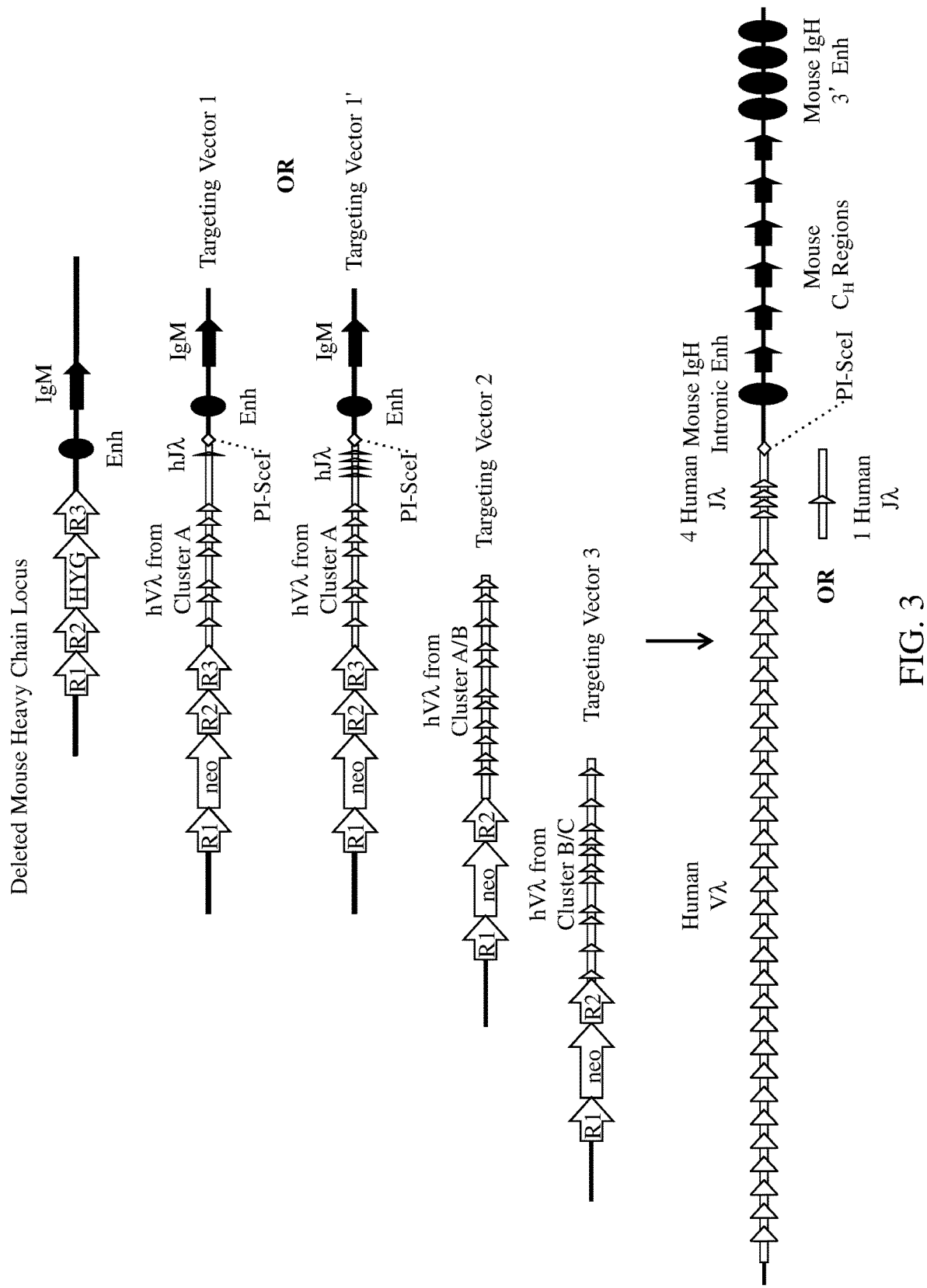
FIG. 3 shows an exemplary targeting strategy for progressive insertion of human Vλ and a human Jλ gene segment (or four human Jλ gene segments) into the mouse heavy chain locus. Hygromycin (hyg) and Neomycin (neo) selection cassettes are shown with recombinase recognition sites (R1, R2, etc.). A modified mouse heavy chain locus, e.g., a hybrid immunoglobulin locus, comprising human Vλ and Jλ gene segments (one or four) operably linked to mouse $C_H$ regions is shown at the bottom.

The human λ light chain locus extends over 1,000 kb and contains over 80 genes that encode variable (V) or joining (J) segments. Among the 70 Vλ gene segments of the human λ light chain locus, anywhere from 30-38 appear to be functional gene segments according to published reports. The 70 Vλ sequences are arranged in three clusters, all of which contain different members of distinct V gene family groups (clusters A, B and C). Within the human λ light chain locus, over half of all observed Vλ domains are encoded by the gene segments 1-40, 1-44, 2-8, 2-14, and 3-21. There are seven Jλ gene segments, only four of which are regarded as generally functional Jλ gene segments Jλ1, Jλ2, Jλ3, and Jλ7. In some alleles, a fifth Jλ-Cλ gene segment pair is reportedly a pseudo gene (Cλ6). Incorporation of multiple human Jλ gene segments into a hybrid heavy chain locus, as described herein, may be constructed by de novo synthesis. In this way, a genomic fragment containing multiple human Jλ gene segments in germline configuration is engineered with multiple human Vλ gene segments and allows for normal V-J recombination in the context of a heavy chain constant region. An exemplary targeting vector that includes multiple Jλ gene segments is shown in FIG. 3 (Targeting Vector 1').

Coupling light chain variable domains with heavy chain constant regions represents a potentially rich source of diversity for generating unique $V_L$ binding proteins with human $V_L$ regions in non-human animals. Exploiting this diversity of the human λ light chain locus (or human κ locus as described above) in mice results in the engineering of unique hybrid heavy chains and gives rise to another dimension of binding proteins to the immune repertoire of genetically modified animals and their subsequent use as a next generation platform for the generation of therapeutics.

The targeting vectors described above are used to electroporate mouse embryonic stem (ES) cells to created modified ES cells for generating chimeric mice that express $V_L$ binding proteins (i.e., human light chain gene segments operably linked to mouse heavy chain constant regions). ES cells containing an insertion of unrearranged human light chain gene segments are identified by the quantitative PCR assay, TAQMAN® (Lie and Petropoulos, 1998. Curr. Opin. Biotechnology 9:43-48). Specific primers sets and probes are designed for insertion of human sequences and associated selection cassettes, loss of mouse heavy chain sequences and retention of mouse sequences flanking the endogenous heavy chain locus.

ES cells bearing the human light chain gene segments (e.g., Vκ and Jκ) operably linked to a heavy chain constant region sequence can be transfected with a construct that expresses a recombinase in order to remove any undesired selection cassette introduced by the insertion of the human light chain gene segments. Optionally, the selection cassette may be removed by breeding to mice that express the recombinase (e.g., U.S. Pat. No. 6,774,279). Optionally, the selection cassette is retained in the mice.

Targeted ES cells described above are used as donor ES cells and introduced into an 8-cell stage mouse embryo by the VELOCIMOUSE® method (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N. C., Dominguez, M. G., Gale, N. W., Yancopoulos, G. D., DeChiara, T. M., Valenzuela, D. M. (2007). F0 generation mice fully derived from gene-targeted embryonic stem cells allowing immediate phenotypic analyses. Nat Biotechnol 25, 91-99). VELOCIMICE® (F0 mice fully derived from the donor ES cell) independently bearing human light chain gene segments at a mouse immunoglobulin heavy chain locus are identified by genotyping using a modification of allele assay (Valenzuela et al., supra) that detects the presence of the unique human light chain gene segments at an endogenous immunoglobulin heavy chain locus. Pups are genotyped and a pup heterozygous or homozygous for the genetically modified immunoglobulin heavy chain locus is selected for characterizing expression of $V_L$-containing heavy chains.

Mice whose genome comprises an immunoglobulin heavy chain allele that contains an insertion of forty (40) unrearranged human Vκ and five (5) Jκ gene segments into an endogenous locus so that said human Vκ and Jκ gene segments are operably linked to endogenous heavy chain constant regions are referred to as MAID1713 (see U.S. Patent Application Publication no. 2012-0096572 A1, incorporated herein by reference in its entirety). Mice having the same and also an integrated mouse Adam6 gene are referred to as MAID1994 (see U.S. Patent Application Publication no. 2013-0212719 A1, herein incorporated by reference in its entirety).

Figure 4:
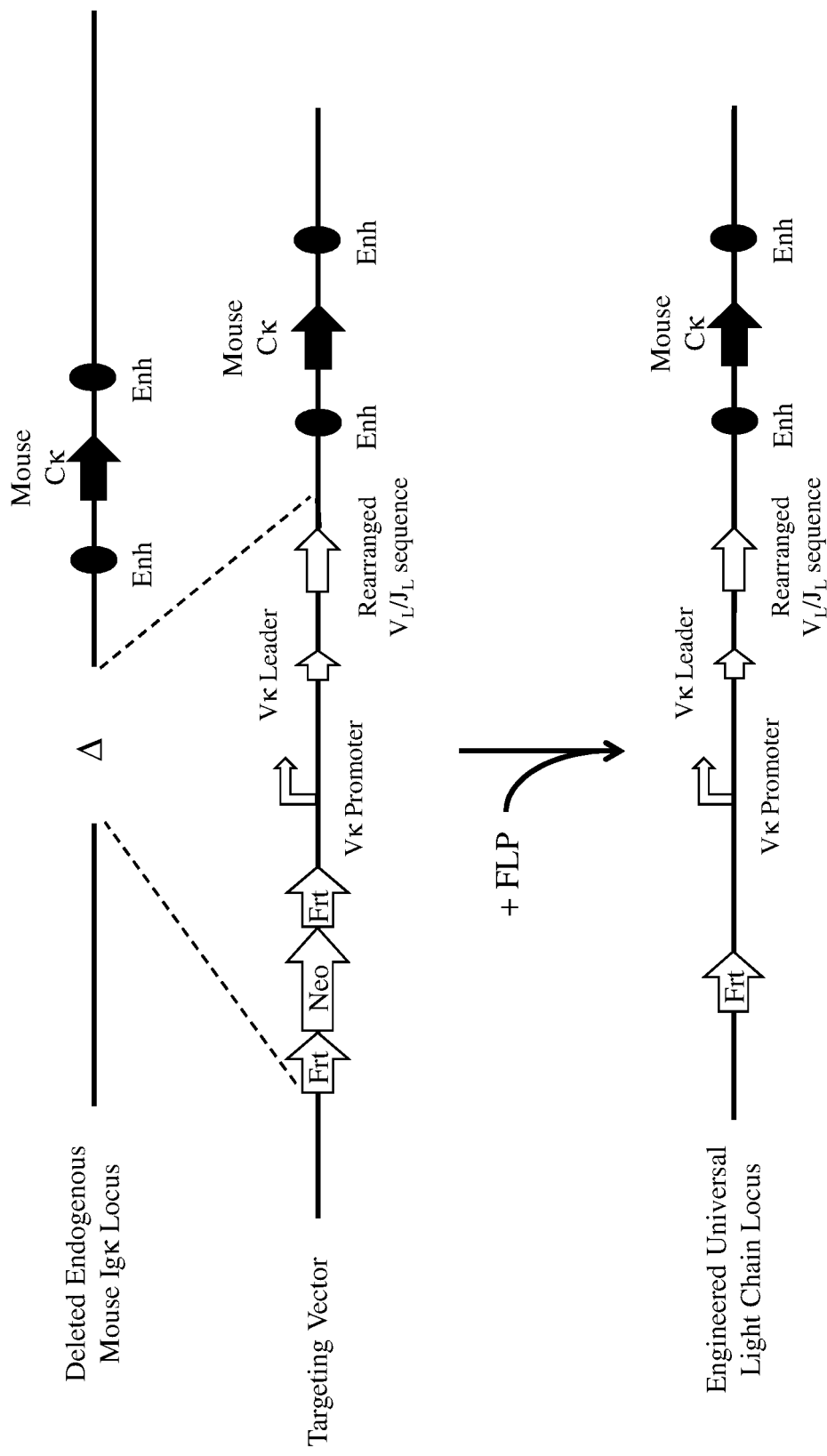
FIG. 4 illustrates an exemplary targeting strategy for replacing endogenous mouse immunoglobulin κ light chain variable region gene segments with a rearranged human $V_L/J_L$ sequence.

Construction of Immunoglobulin Light Chain Loci with a Rearranged Human Light Chain Nucleotide Sequence Construction of exemplary targeting vectors for the insertion of a single rearranged human light chain nucleotide sequence (e.g., a single human rearranged $V_L/J_L$ nucleotide sequence) into a murine immunoglobulin light chain locus are described below. FIG. 4 illustrates a targeting vector that contains a single rearranged human light chain nucleotide sequence for insertion into a murine immunoglobulin light chain locus using homologous recombination.

Figure 5:
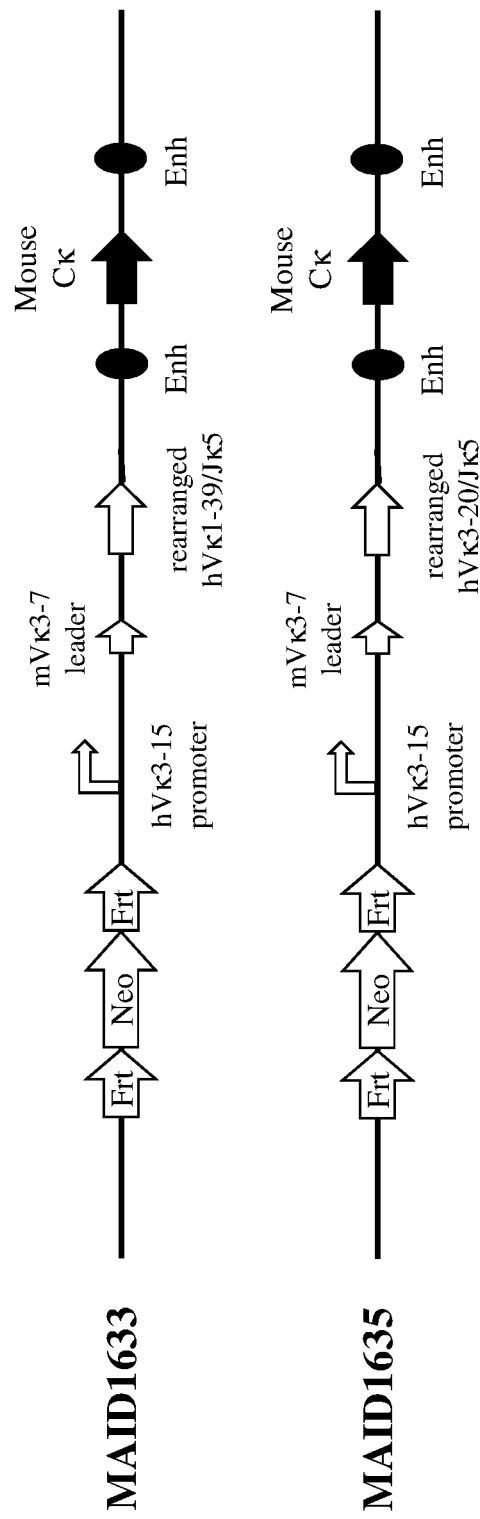
FIG. 5 illustrates two exemplary targeting vectors for replacing endogenous mouse immunoglobulin light chain Vκ and Jκ gene segments with a rearranged human Vκ1-39Jκ5 sequence (MAID 1633; SEQ ID NO:1) or a rearranged human Vκ3-20Jκ1 sequence (MAID 1635; SEQ ID NO:2).

Genetically modified mice, and methods of making the same, whose genome contains an immunoglobulin light chain locus comprising a rearranged human immunoglobulin light chain variable region nucleotide sequence operably linked to an immunoglobulin light chain constant region nucleic acid sequence are described in U.S. Patent Application Publication No. US 2011-0195454A1, incorporated herein by reference in its entirety. As shown in FIG. 4, a targeting vector was engineered to contain a single rearranged human light chain (i.e., a rearranged human $V_L/J_L$) nucleotide sequence for insertion into an ES cell comprising an inactivated mouse κ light chain locus (e.g., deleted endogenous Vκ and Jκ gene segments) and, optionally, a hybrid immunoglobulin locus, using standard molecular techniques recognized in the art. The single rearranged human light chain nucleotide sequence may include any human $V_L$ and human $J_L$ sequence. Suitable exemplary rearranged human light chain nucleotide sequences that can be employed include those derived from a rearranged human Vκ1-39Jκ5 nucleotide sequence (MAID1633, FIG. 5), a rearranged human Vκ3-20Jκ1 nucleotide sequence (MAID1635, FIG. 5).

Alternatively, as described above, in some embodiments, a mouse may also be engineered to comprise an insertion of human Vλ and Jλ gene segments into an endogenous immunoglobulin heavy chain locus so that said human Vλ and Jλ gene segments are operably linked to heavy chain constant regions. In such embodiments, to achieve optimal expression and usage of the inserted human Vλ and Jλ gene segments, those skilled in the art are aware that one might use a rearranged sequence such as a rearranged human VλJλ nucleotide sequence. Such rearranged human VλJλ nucleotide sequence would provide a better ability of the rearranged human VλJλ sequences in the context of a heavy chain constant region to pair with the rearranged human VλJλ sequence in the context of a light chain constant region. Rearranged human VκJκ sequences in the context of heavy chain constant regions may not be able to effectively associate with rearranged VλJλ sequences in the context of light chain constant regions (see US 2012-0096572 A1). Therefore, an exemplary rearranged human VλJλ sequence includes a rearranged human Vλ2-14Jλ1 nucleotide sequence.

The targeting vector described above is used to electroporate mouse embryonic stem (ES) cells, which may optionally comprise a hybrid immunoglobulin locus, to create modified ES cells for generating chimeric mice that express light chains encoded by a single rearranged human light chain nucleotide sequence (i.e., a single human $V_L/J_L$ nucleotide sequence operably linked to mouse light chain constant regions). ES cells containing an insertion of a single rearranged human light chain nucleotide sequence is identified by the quantitative PCR assay, TAQMAN® (Lie and Petropoulos, 1998. Curr. Opin. Biotechnology 9:43-48). Specific primers sets and probes are designed for insertion of the single rearranged human light chain nucleotide sequence and associated selection cassettes, loss of mouse light chain sequences and retention of mouse sequences flanking an endogenous light chain locus.

ES cells bearing the single rearranged human light chain nucleotide sequence can be transfected with a construct that expresses a recombinase in order to remove any undesired selection cassette introduced by the insertion of the single rearranged human light chain nucleotide sequence. Optionally, the selection cassette may be removed by breeding to mice that express the recombinase (e.g., U.S. Pat. No. 6,774,279). Optionally, the selection cassette is retained in the mice.

Targeted ES cells described above are used as donor ES cells and introduced into an 8-cell stage mouse embryo by the VELOCIMOUSE® method (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N. C., Dominguez, M. G., Gale, N. W., Yancopoulos, G. D., DeChiara, T. M., Valenzuela, D. M. (2007). F0 generation mice fully derived from gene-targeted embryonic stem cells allowing immediate phenotypic analyses. Nat Biotechnol 25, 91-99). VELOCIMICE® (F0 mice fully derived from the donor ES cell) independently bearing a single rearranged human light chain nucleotide sequence at a mouse immunoglobulin light chain locus are identified by genotyping using a modification of allele assay (Valenzuela et al., supra) that detects the presence of the unique rearranged human light chain nucleotide sequence at an endogenous immunoglobulin light chain locus. Pups are genotyped and a pup heterozygous or homozygous for the genetically modified immunoglobulin light chain locus is selected for characterizing expression of the single human light chain.

Example 2. Characterization of Mice Comprising a Single Rearranged Human Immunoglobulin Light Chain Nucleotide Sequence and a Plurality of Human κ Light Chain Gene Segments Mice comprising a rearranged light chain variable region nucleic acid sequence in a light chain locus (ULC Mouse: MAID1633, single rearranged human Vκ1-39/Jκ5 or MAID1635, single rearranged human Vκ3-20Jκ1) were generated as described above. Briefly, in the ULC mouse, all endogenous functional light chain variable gene segments were deleted and replaced with a single rearranged light chain variable region nucleic acid sequence (e.g., a sequence that encodes a human Vκ1-39/Jκ5 or a human Vκ3-20Jκ1), which is operably linked to an endogenous light chain constant region nucleic acid sequence.

Mice comprising genetically engineered heavy chain loci containing unrearranged human immunoglobulin light chain $V_L$ and $J_L$ gene segments in a heavy chain locus (KOH Mouse: MAID1713: 40 human Vκ gene segments and five human Jκ gene segments; MAID1994: 40 human Vκ gene segments and five human Jκ gene segments, and an integrated Adam6 gene) were generated as described above. Briefly, in the KOH Mouse, all endogenous functional heavy chain variable gene segments were deleted and replaced with 40 unrearranged human Vκ gene segments and five (5) unrearranged human Jκ gene segments, which are operably linked to an immunoglobulin heavy chain constant region nucleic acid sequence.

Figure 6:
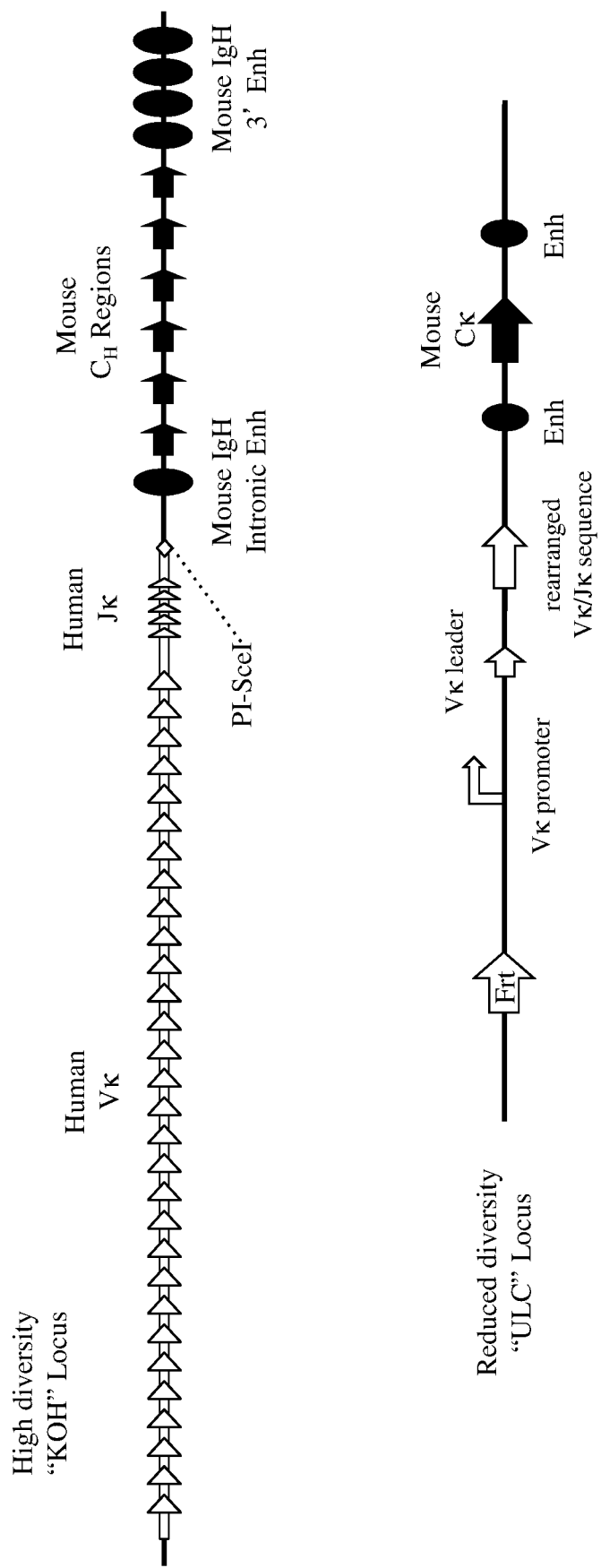
FIG. 6 shows a modified mouse heavy chain locus, e.g., a hybrid immunoglobulin locus comprising human Vκ and Jκ gene segments operably linked to mouse $C_H$ regions and a modified mouse κ light chain locus comprising a rearranged human VκJκ sequence. In one particular embodiment, a mouse having the modified heavy chain locus and modified κ light chain locus as shown (KOH×ULC) is created by breeding a "KOH" mouse and a "ULC" mouse.

Homozygous ULC mice (MAID1633 or MAID 1635) described above were bred to homozygous KOH mice (MAID1713 or MAID 1994) mice to produce a mouse heterozygous for the ULC allele and the KOH allele. F1 heterozygous mice generated from this cross were bred to each other to obtain mice homozygous for each allele (MAID1713HO 1633HO, MAID1713HO 1635HO, MAID1994HO 1633HO, or MAID1994HO 1635HO; "KOH×ULC"). Such mice express $V_L$ binding proteins that have a structure that resembles that of immunoglobulins, but yet are distinct in that such binding proteins lack heavy chain variable domains. The presence of the genetically modified alleles in the immunoglobulin heavy chain and light chain loci was confirmed by TAQMAN™ screening and karyotyping using specific probes and primers described above. The homozygous KOH×ULC mice comprise an insertion of unrearranged human light chain gene segments as described herein (e.g., human Vκ and Jκ) into the mouse heavy chain locus in which all endogenous variable heavy chain VDJ gene segments have been deleted and an insertion of a single rearranged human light chain variable region nucleotide sequence (MAID1633: rearranged human Vκ1-39Jκ5; MAID1635: rearranged human Vκ3-20Jκ1) into the mouse kappa (κ) light chain locus in which all mouse Vκ and Jκ genes have been deleted (FIG. 6). In some embodiments, KOH×ULC mouse further comprise an integrated Adam6 gene.

Alternatively, to generate mice comprising both ULC allele and KOH allele, ES cells harboring a ULC modification or ES cells harboring a KOH modification are targeted with KOH or ULC targeting vector, respectively. Mice are generated from ES cells harboring both modifications by introducing ES cells into an 8 stage mouse embryo by VELOCIMMUNE® method and screening as described above in Example 3. F1 heterozygous mice are bred to obtain homozygous mice.

All mice were housed and bred in specific pathogen-free conditions at Regeneron Pharmaceuticals, Inc. Three KOH (MAID1994HO 1242HO; see U.S. Patent Application Publication No. US 2013-0212719 A1, incorporated by reference herein) mice (~11 weeks old, male) and two groups of three KOH×ULC (MAID1994HO 1633HO, ~12 weeks old, female; MAID1994HO 1635HO, ~11 weeks old, 2 male and 1 female) mice were sacrificed, and spleens and bone marrow were harvested from the animals. Bone marrow was collected from femurs by flushing with complete RPMI medium (RPMI medium supplemented with fetal calf serum, sodium pyruvate, Hepes, 2-mercaptoethanol, non-essential amino acids, and gentamycin). Red blood cells from spleen and bone marrow preparations were lysed with ACK lysis buffer and washed with complete RPMI medium.

Flow Cytometry

In order to examine the ability of the genetically modified homozygous "KOH×ULC" (MAID1994HO 1633HO and MAID1994HO 1635HO) mice described herein to produce $V_L$ binding proteins derived from the genetically modified alleles (e.g., from the allele that contains a single copy of the rearranged human light chain nucleotide sequence in the light chain locus and the allele that contains unrearranged human Vκ and Jκ gene segments in the heavy chain locus), fluorescence-activated cell sorting (FACS) analysis was performed. KOH mice comprising an unrearranged light chain locus comprising unrearranged human $V_L$ and $J_L$ gene segments (1994 HO 1242 HO), as well as VELOCIMMUNE® mice comprising unrearranged human heavy and light chain gene segments on mouse heavy and light chain loci, respectively (VI3) were used as controls.

Briefly, 1×10⁶ cells were incubated with anti-mouse CD16/CD32 (clone 2.4G2, BD Pharmigen) on ice for 10 minutes, followed by labeling with the following antibody cocktail for 30 minutes on ice: APC-H7 conjugated anti-mouse CD19 (clone 1D3, BD Pharmigen), Pacific Blue conjugated anti-mouse CD3 (clone 17A2, BioLegend), FITC conjugated anti-mouse Igκ (clone 187.1, BD Pharmigen) or anti-mouse CD43 (clone 1B11, BioLegend), PE conjugated anti-mouse Igλ (clone RML-42, BioLegend) or anti-mouse c-kit (clone 2B8, BioLegend), PerCP-Cy5.5 conjugated anti-mouse IgD (BioLegend), PE-Cy7 conjugated anti-mouse IgM (clone II/41, eBioscience), APC conjugated anti-mouse B220 (clone RA3-6B2, eBioscience). Following staining, cells were washed and fixed in 2% formaldehyde. Data acquisition was performed on an LSRII flow cytometer and analyzed with FlowJo (Tree Star, Inc.). Gating: total B cells (CD19⁺CD3⁻), Igκ⁺B cells (Igκ⁺Igλ⁻CD19⁺CD3⁻), Igλ⁺B cells (Igκ⁻Igλ⁺CD19⁺CD3⁻). Results for the bone marrow compartment are shown in FIGS. 7-10. Results for the splenic compartment are shown in FIGS. 11-15.

Only mature B lymphocytes can enter the lymphoid follicles of spleen and lymph nodes and thus efficiently participate in the immune response. Mature, long-lived B lymphocytes derive from short-lived precursors generated in the bone marrow. Selection into the mature pool is an active process and takes place in the spleen. Two populations of splenic B cells have been identified as precursors for mature B cells. Transitional B cells of type 1 (T1) are recent immigrants from the bone marrow. They develop into the transitional B cells of type 2 (T2), which are cycling and found exclusively in the primary follicles of the spleen. Mature B cells can be generated from T1 or T2 B cells. Loder, F. et al., J. Exp. Med., 190(1): 75-89, 1999.

Figure 7:
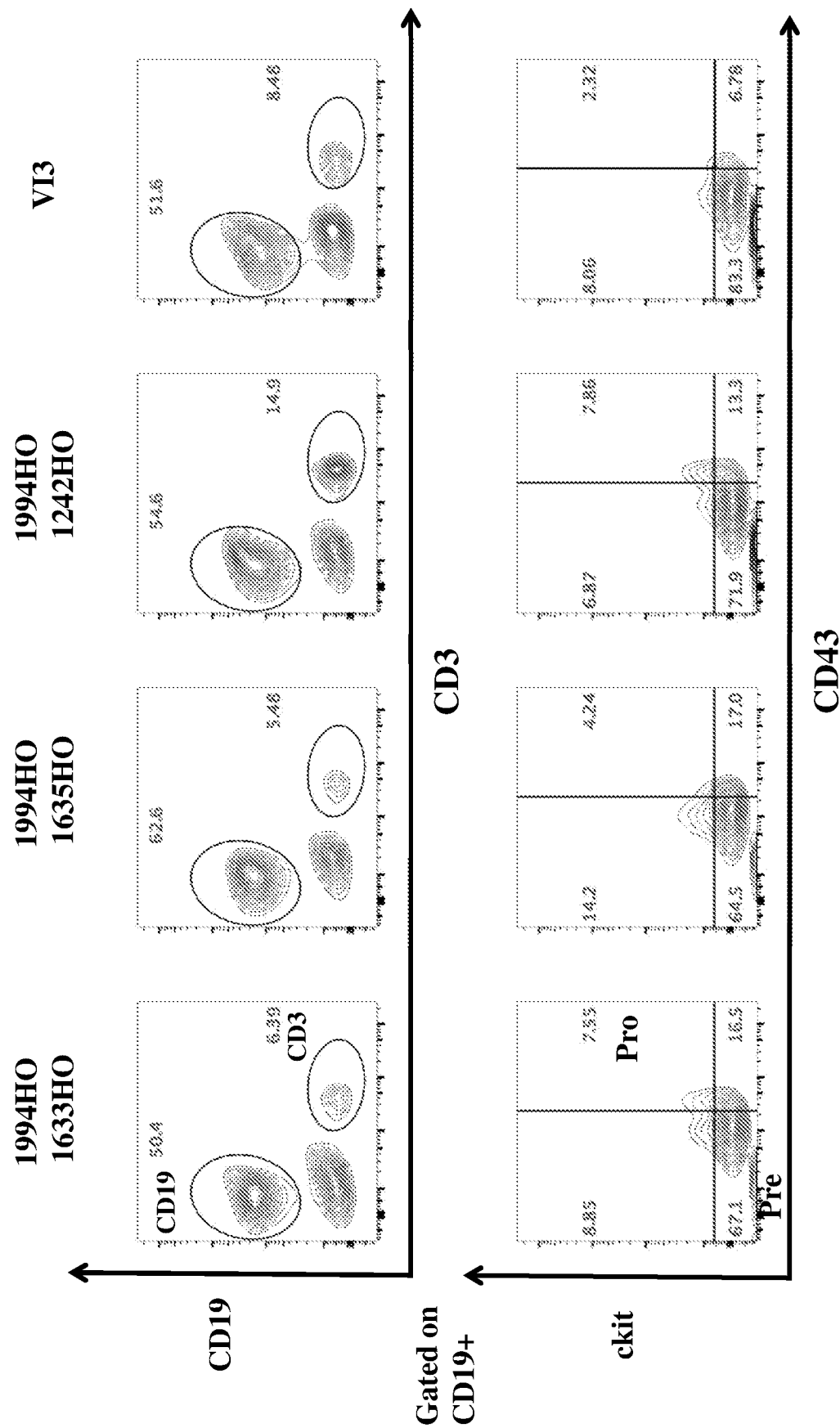
FIG. 7 shows representative contour plots of bone marrow stained for B and T cells (top row; $CD19^+$ and $CD3^+$, respectively) and bone marrow gated on $CD19^+$ and stained for $ckit^+$ and $CD43^+$ (bottom row) from a VELOCIMMUNE® mouse (VI3), a mouse homozygous for unrearranged human immunoglobulin light chain variable Vκ and Jκ gene segments at the heavy chain locus, homozygous for unrearranged human immunoglobulin Vκ and Jκ gene segments at the κ light chain locus and an integrated Adam6 gene ("KOH" mouse; 1994HO 1242HO), and a mouse homozygous for a rearranged light chain variable region nucleotide sequence at the κ light chain locus (either $V_K3$-$20J_K1$ or $V_K1$-$39J_K5$) and homozygous for unrearranged human immunoglobulin Vκ and Jκ gene segments at the heavy chain locus and an integrated Adam6 gene (1994HO 1635HO for $V_K3$-$20J_K1$; 1994HO 1633HO for $V_K1$-$39J_K5$; "KOH×ULC" mouse). Pro and Pre B cells are noted on the contour plots. Percentage of cells within each gated region is shown.
Figure 8:
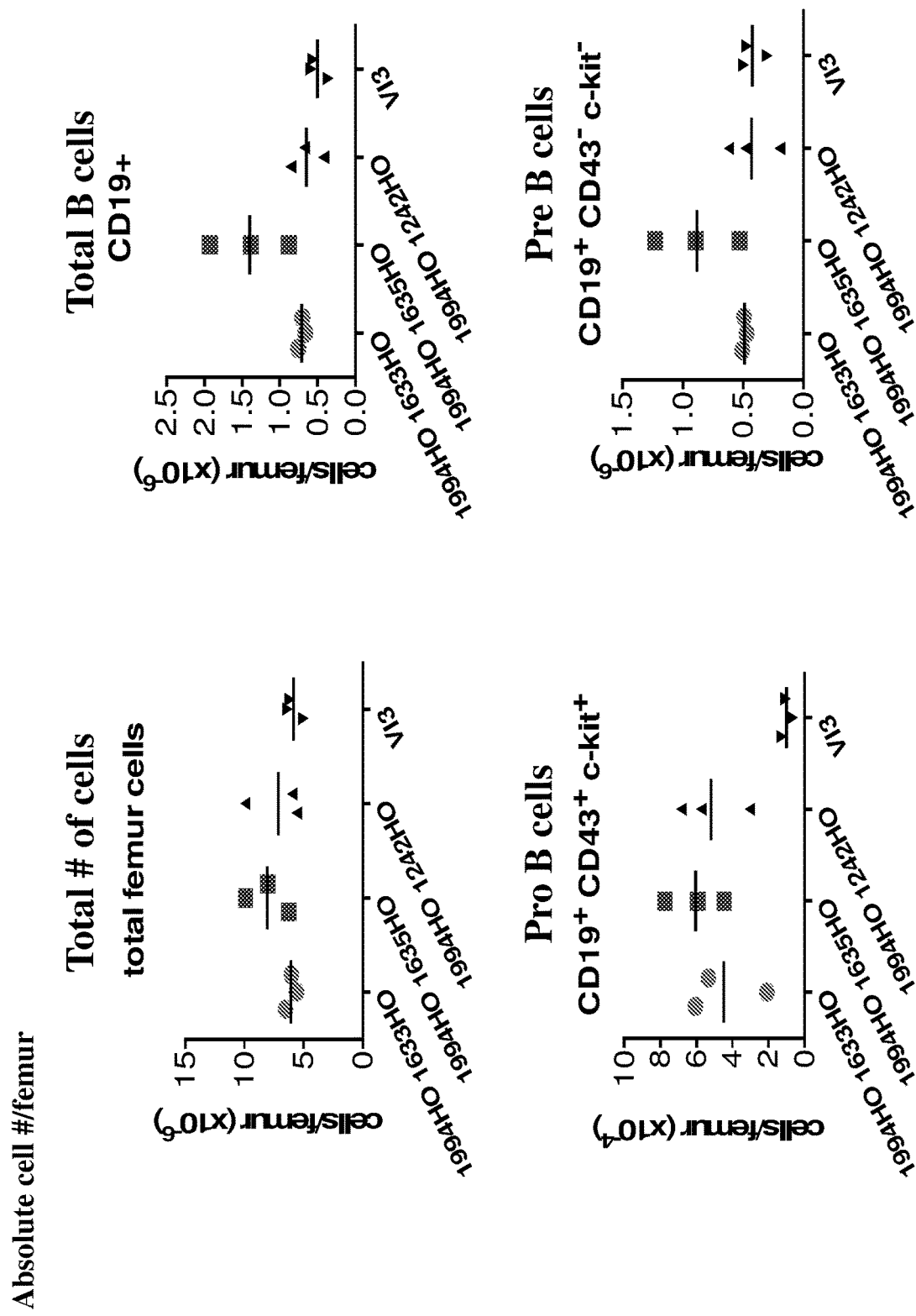
FIG. 8 shows the total number of cells (top left), the total number of B ($CD19^+$) cells (top, right), the number of Pro B cells ($CD19^+CD43^+ckit^+$), and the number of Pre B cells ($CD19^+CD43^-ckit^-$) in bone marrow isolated from the femurs of KOH×ULC mice (1994HO 1633HO:Vκ1-39Jκ5; 1994HO 1635HO:Vκ3-20Jκ1), KOH mice (1994HO 1242HO) and VELOCIMMUNE® humanized mice (VI3).
Figure 9:
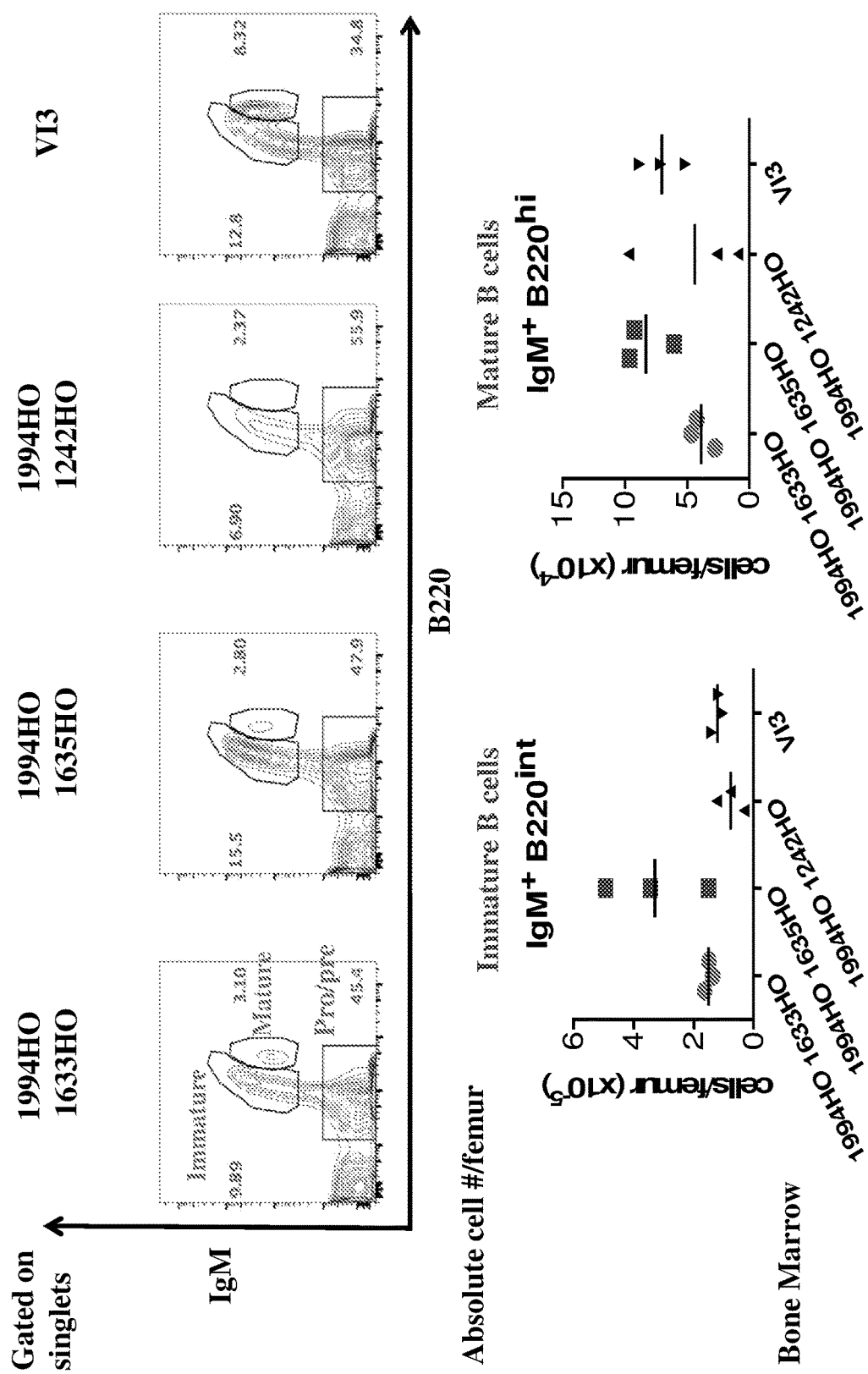
FIG. 9 shows representative contour plots (top row) of bone marrow gated on singlets stained for immunoglobulin M (IgM) and B220 from KOH×ULC mice (1994HO 1633HO, 1994HO 1635HO), a KOH mouse (1994HO 1242HO) and a VELOCIMMUNE® humanized mouse (VI3). Immature, mature and pro/pre B cells are noted on each of the contour plots. Percentage of cells within each gated region is shown; the bottom row shows the total number and immature B (left, $IgM^+B220^{int}$) cells and mature B ($IgM^+B220^{hi}$) in bone marrow isolated from the femurs of KOH×ULC mice (1994HO 1633HO:Vκ1-39Jκ5; 1994HO 1635HO:Vκ3-20Jκ1), KOH mice (1994HO 1242HO) and VELOCIMMUNE® humanized mice (VI3).
Figure 10:
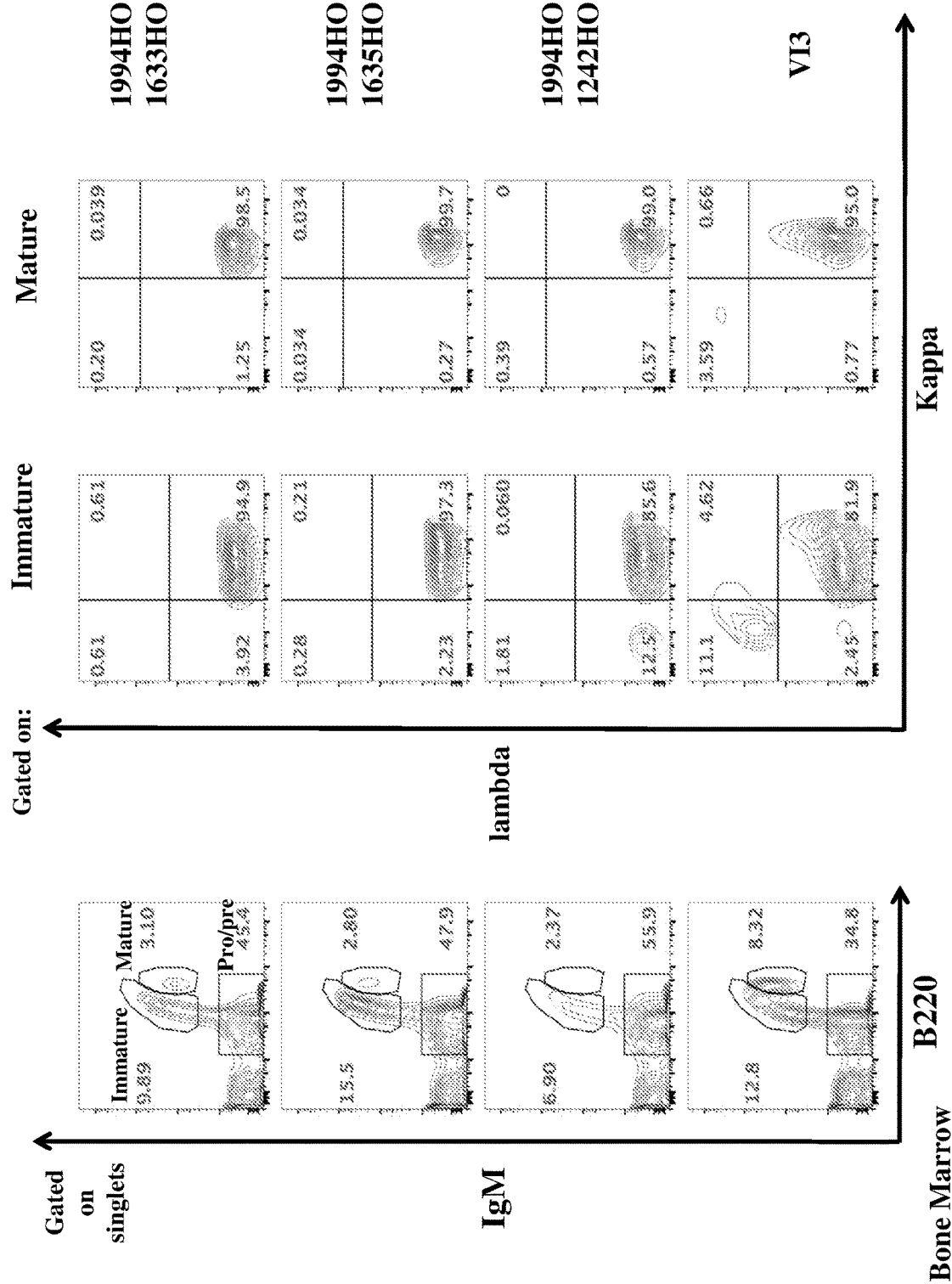
FIG. 10 shows representative contour plots (left column) of bone marrow gated on singlets stained for immunoglobulin M (IgM) and B220 from KOH×ULC mice (1994HO 1633HO, 1994HO 1635HO), a KOH mouse (1994HO 1242HO) and a VELOCIMMUNE® humanized mouse (VI3). Immature, mature and pro/pre B cells are noted on each of the contour plots; the right two columns shows representative contour plots of bone marrow gated on immature B cells (left, $IgM^+B220^{int}$) and mature B cells (right, $IgM^+B220^{hi}$) stained for Igκ and Igλ expression isolated from the femurs of KOH×ULC mice (1994HO 1633HO:Vκ1-39Jκ5; 1994HO 1635HO:Vκ3-20Jκ1), a KOH mouse (1994HO 1242HO) and VELOCIMMUNE® humanized mouse (VI3). Percentage of cells within each gated region is shown.

The FACS analysis (FIGS. 7-15) suggested that the KOH×ULC mice were able to produce nearly normal B cell populations in the bone marrow compartment (FIGS. 7-8). Interestingly, KOH×ULC mice demonstrate a lack of lambda (λ) expression in the bone marrow (FIG. 10).

Figure 11:
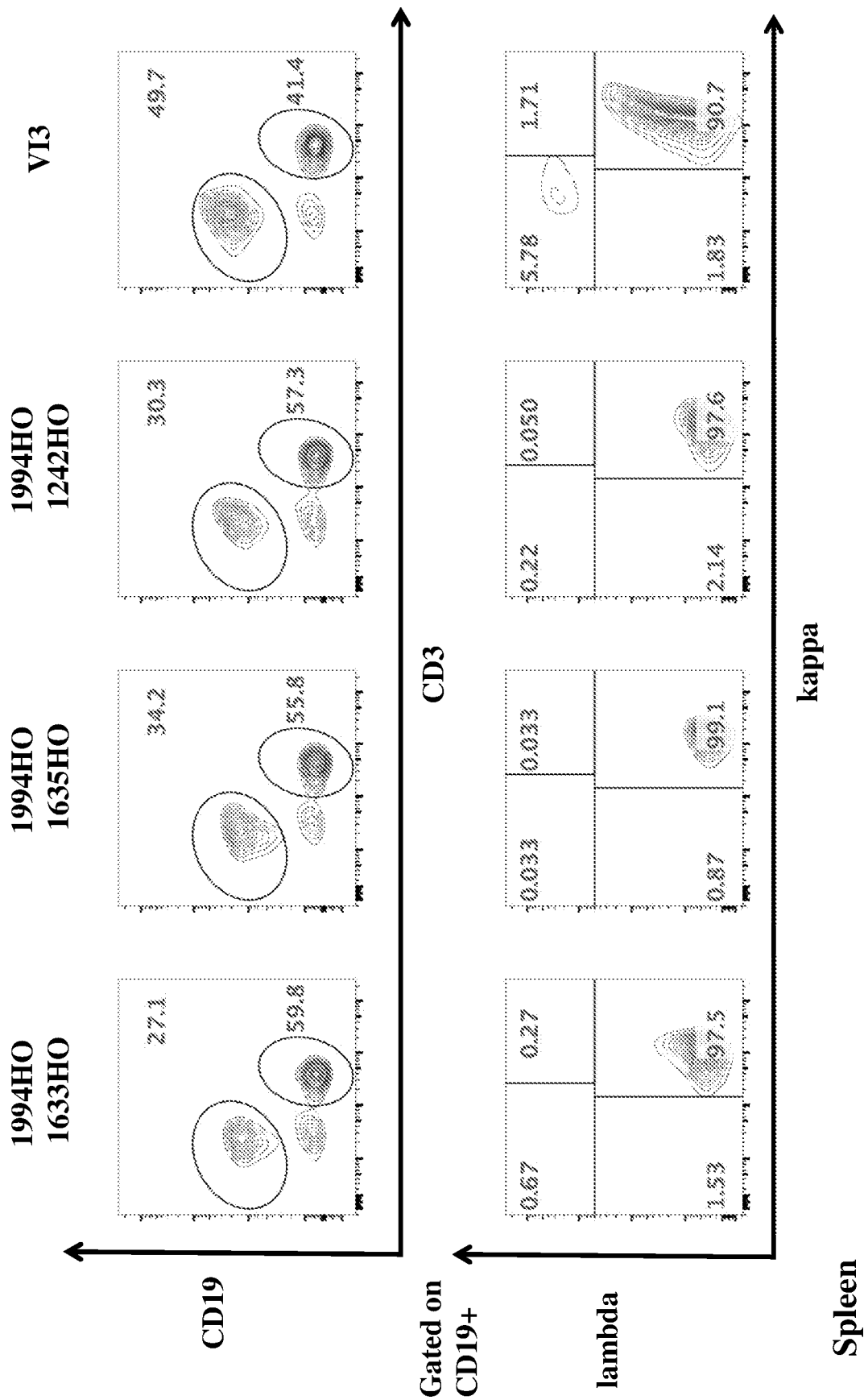
FIG. 11 shows representative contour plots of splenocytes stained for B and T cells (top row; $CD19^+$ and $CD3^+$, respectively) and splenocytes gated on $CD19^+$ and stained for $Ig\kappa^+$ and $Ig\lambda^+$ expression from KOH×ULC mice (1994HO 1633HO:Vκ1-39Jκ5; 1994HO 1635HO:Vκ3-20Jκ1), a KOH mouse (1994HO 1242HO) and a VELOCIMMUNE® humanized mouse (VI3). Percentage of cells within each gated region is shown.
Figure 12:
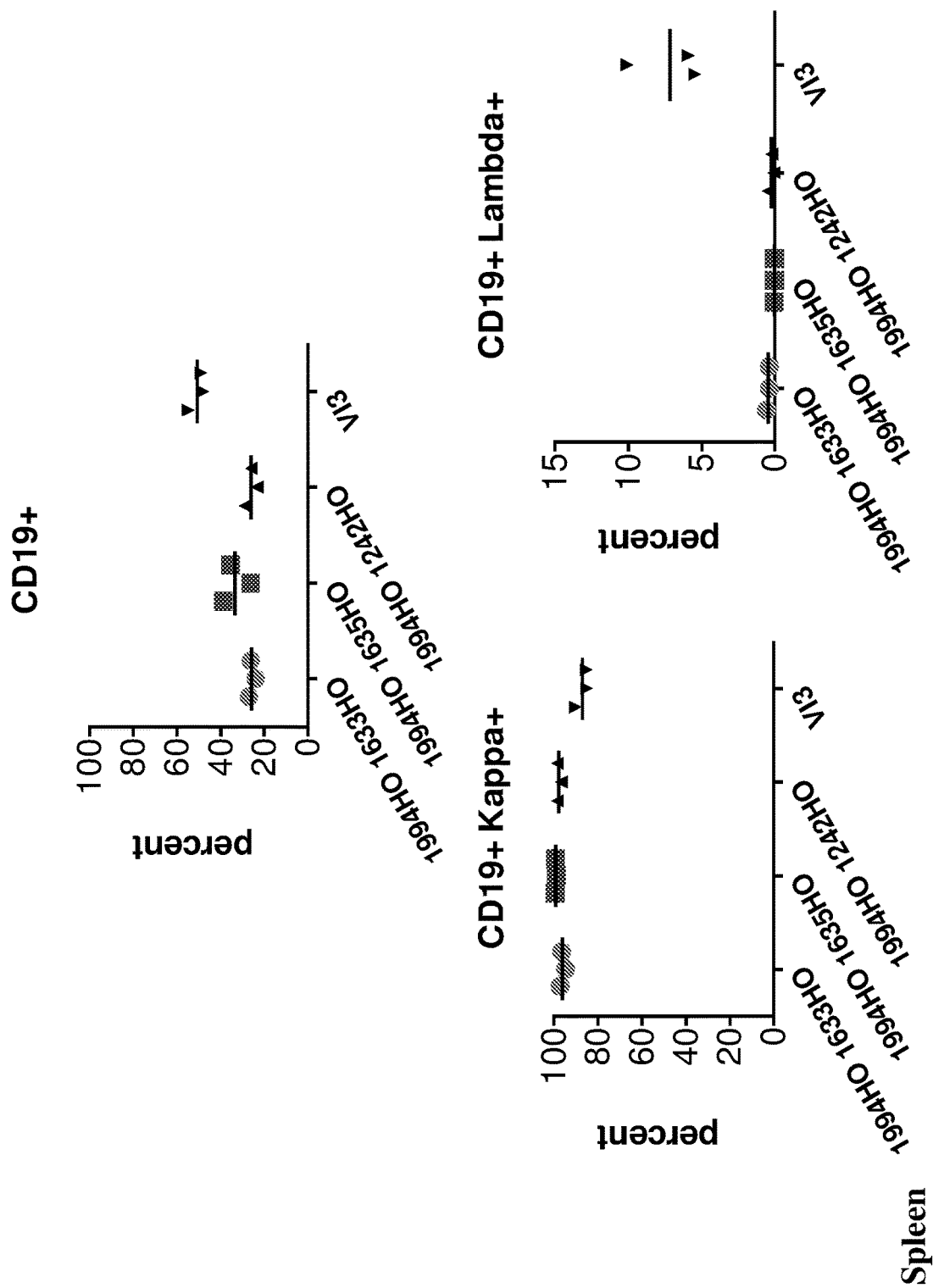
FIG. 12 shows the total number of B cells ($CD19^+$), $Ig\kappa^+B$ cells ($CD19^+Kappa^+$) and $Ig\lambda+B$ cells ($CD19^+Lambda^+$) in harvested spleens from KOH×ULC mice (1994HO 1633HO:Vκ1-39Jκ5; 1994HO 1635HO:Vκ3-20Jκ1), KOH mice (1994HO 1242HO) and VELOCIMMUNE® humanized mice (VI3).
Figure 13:
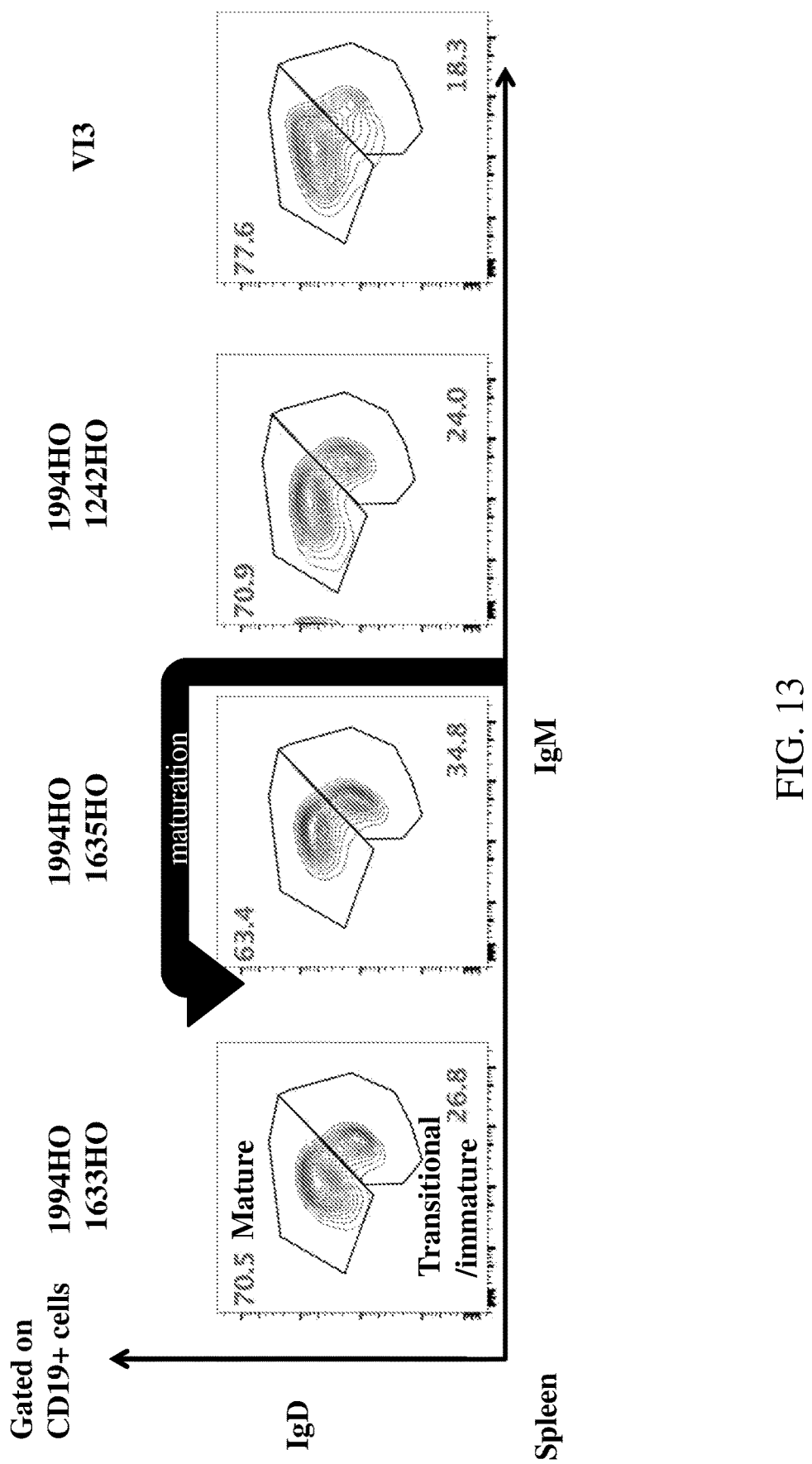
FIG. 13 shows representative contour plots of splenocytes gated on CD19+ and stained for immunoglobulin D (IgD) and immunoglobulin M (IgM) from KOH×ULC mice (1994HO 1633HO:Vκ1-39Jκ5; 1994HO 1635HO:Vκ3-20Jκ1), a KOH mouse (1994HO 1242HO) and a VELOCIMMUNE® humanized mouse (VI3). Percentage of cells within each gated region is shown. Mature ($CD19^+IgM^{lo}IgD^{hi}$) and transitional/immature ($CD19^+IgD^{int}IgM^{hi}$) B cells are noted in each contour plot. Percentage of cells within each gated region is shown.
Figure 14:
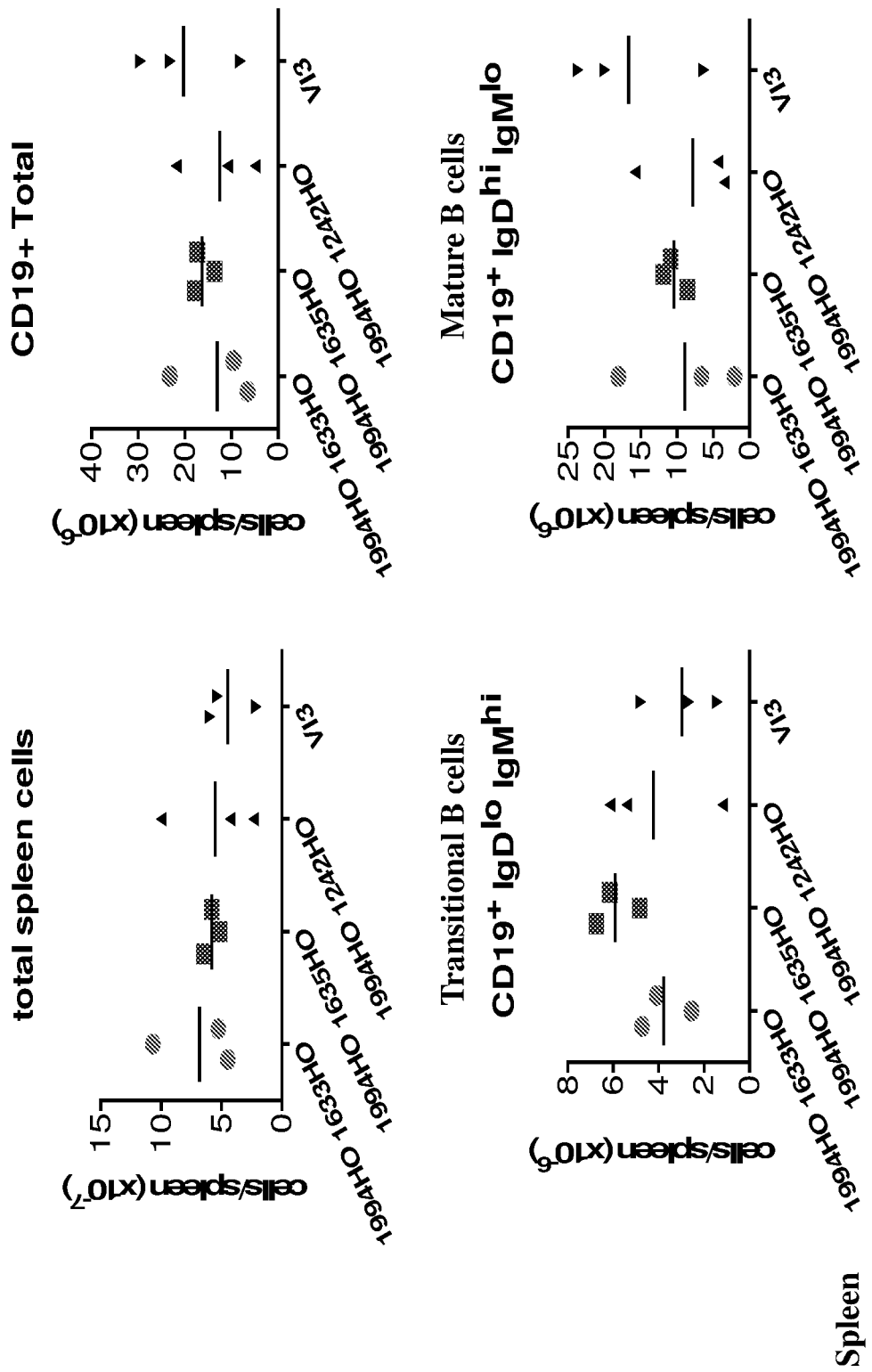
FIG. 14 shows the absolute number of splenocytes (top left), the total number of B cells (top right; $CD19^+$), Transitional B cells (bottom left; $CD19^+IgD^{lo}IgM^{hi}$), and mature B cells ($CD19^+IgD^{hi}IgM^{lo}$) in harvested spleens from KOH×ULC mice (1994HO 1633HO:Vκ1-39Jκ5; 1994HO 1635HO:Vκ3-20Jκ1), a KOH mouse (1994HO 1242HO) and a VELOCIMMUNE® humanized mouse (VI3).
Figure 15:
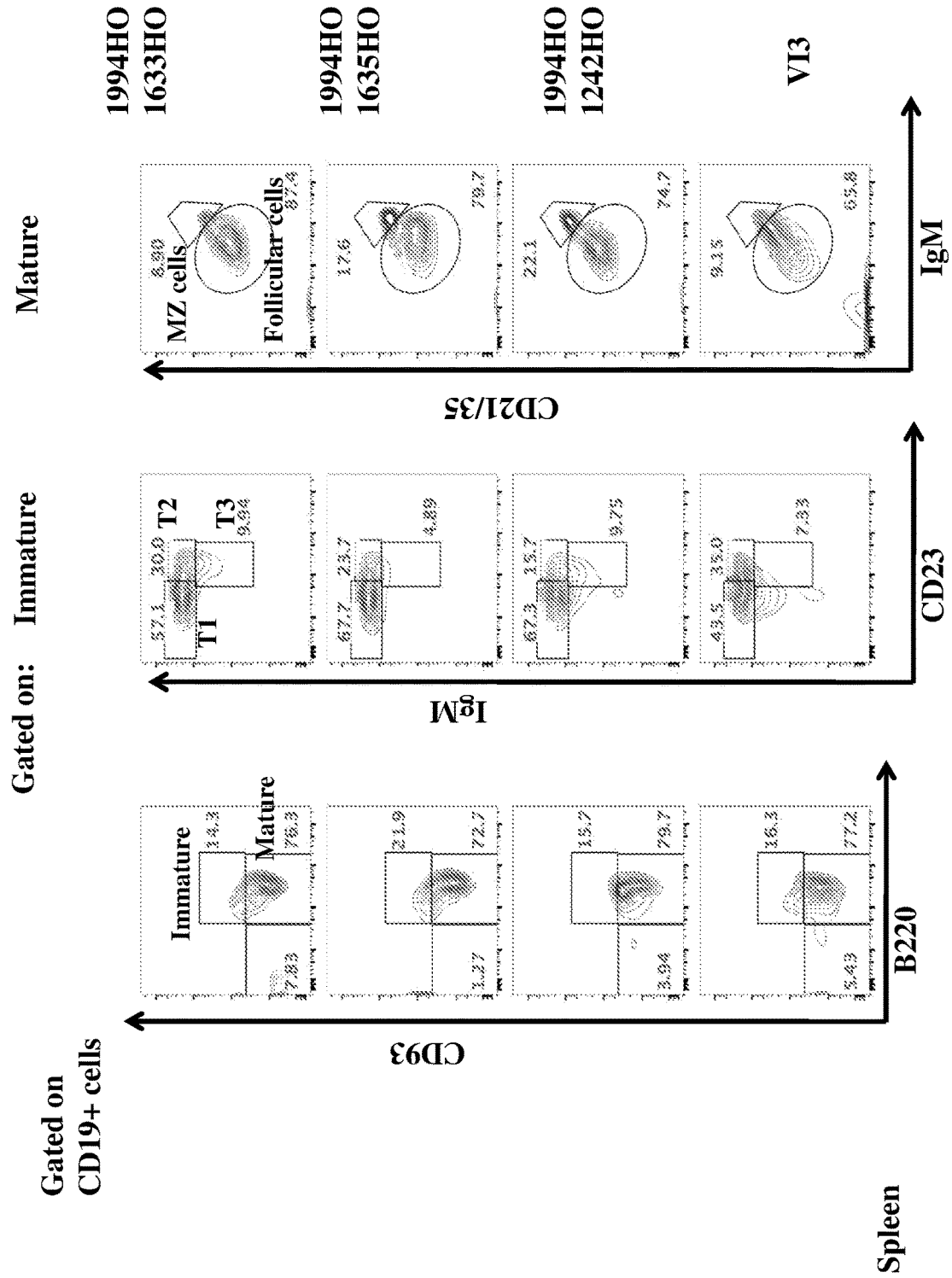
FIG. 15 shows representative contour plots of the peripheral B cell development KOH×ULC mice (1994HO 1633HO:Vκ1-39Jκ5; 1994HO 1635HO:Vκ3-20Jκ1), a KOH mouse (1994HO 1242HO) and a VELOCIMMUNE® humanized mouse (VI3). The first column (left) of contour plots show $CD93^+$ and $B220^+$ splenocytes gated on $CD19^+$ indicating immature and mature B cells. The second column (middle) of contour plot shows $IgM^+$ and $CD23^+$ expression in immature B cells indicating T1 ($IgD$-$IgM^+CD21^{lo}CD23^-$), T2 ($IgD^{hi}IgM^{hi}CD21^{mid}CD23^+$) and T3 B cell populations. The third column (right) of contour plots shows $CD21^+$ ($CD35^+$) and $IgM^+$ expression of mature B cells indicating a smaller first population that give rise to marginal zone B cells and a second population that gives rise to follicular (FO) B cells. Percentage of cells within each gated region is shown.

In the splenic compartment, KOH×ULC mice produced nearly normal B cell populations (FIGS. 11, 12, and 14). As in the bone marrow compartment, KOH×ULC mice demonstrated a lack of lambda (λ) expression in the spleen (FIGS. 11 and 12). Also in the splenic compartment, KOH×ULC mice demonstrated nearly normal transitional and mature B cell populations as compared to VELOCIMMUNE® (VI3) mice (FIGS. 13-15).

Taken together, these data show that the KOH×ULC mice provided by the present invention, such as those with the genetic modifications described in Example 1, are healthy and demonstrate a near wild-type B cell development. Moreover, such mice express binding proteins that resemble natural antibodies in structure, but yet lack heavy chain variable region sequences.

Figure 16:
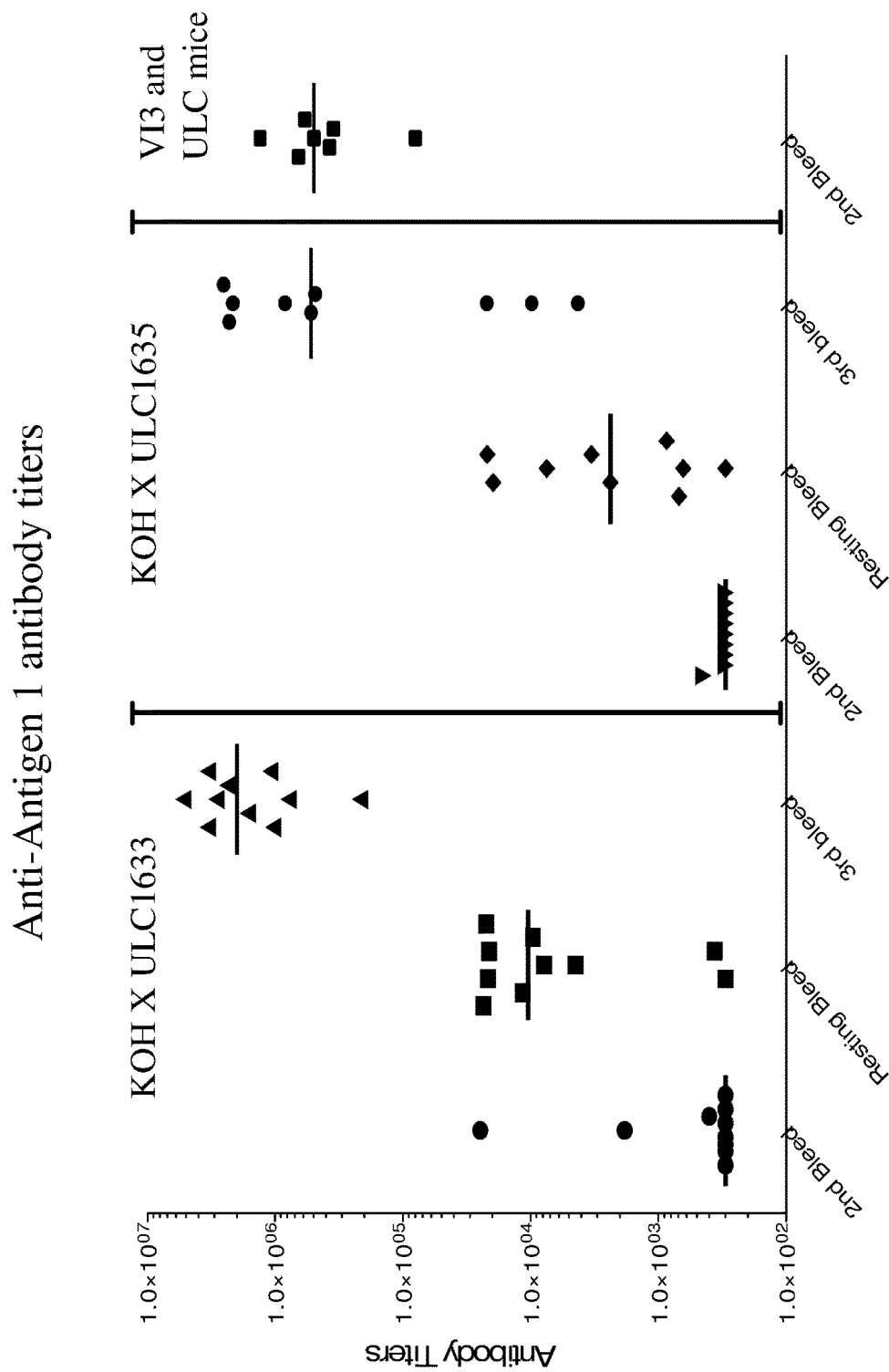
FIG. 16 shows anti-Antigen 1 antibody titers in different KOH×ULC mice following immunization, resting phase and boost protocols. KOH×ULC mice mount a strong, high titer antigen-specific antibody response comparable to VI3 and ULC mice following a resting phase and additional boosts. Mice were immunized by the footpad route. The $2^{nd}$ bleed is following six boosts; $3^{rd}$ bleed is following four additional boosts. Mice were resting for 4.5 weeks after the $2^{nd}$ bleed. Antigen 1 is a carrier protein. VI3 mice are disclosed in U.S. Pat. No. 8,642,835, herein incorporated by reference. 1633 is a ULC mouse with Vκ1-39. 1635 is a ULC mouse with Vκ3-20.

Finally, as depicted in FIG. 16, mice comprising the genetic modifications described herein were capable of generating antigen-specific titers when immunized with Antigen 1 (a cell surface receptor).

Example 3. Antigen-Binding Characterization of $V_{L/CH\times ULC}$ Domains from KOH×ULC Mice This example illustrates exemplary methods of obtaining nucleic acid sequences that encode an immunoglobulin light chain variable domain ($V_{L/CH\times ULC}$) that can detectably bind an antigen independently from a cognate variable domain, e.g., a cognate universal light chain variable domain. Exemplary $V_{L/CH\times ULC}$ domains that detectably bind an antigen independently from a cognate variable domain are obtained from genetically modified non-human animals (e.g., mice) whose genome includes an immunoglobulin heavy chain locus (hybrid immunoglobulin chain locus) containing unrearranged human light chain gene segments (e.g., $V_L$ and $J_L$ gene segments) operably linked to a heavy chain constant region sequence and an immunoglobulin light chain locus containing a rearranged immunoglobulin light chain variable sequence (i.e., a universal or common light chain variable region) operably linked to a light chain constant region sequence. Such non-human animals express binding proteins that contain immunoglobulin light chain $V_{L/CH\times ULC}$ variable domains operably linked to a heavy chain constant regions and common immunoglobulin light chain variable domains operably linked to a light chain constant regions, wherein the $V_{L/CH\times ULC}$ light chains are derived from the unrearranged human light chain gene segments, and wherein the common light chain variable domains are encoded by the single rearranged light chain variable gene sequence.

Figure 17:
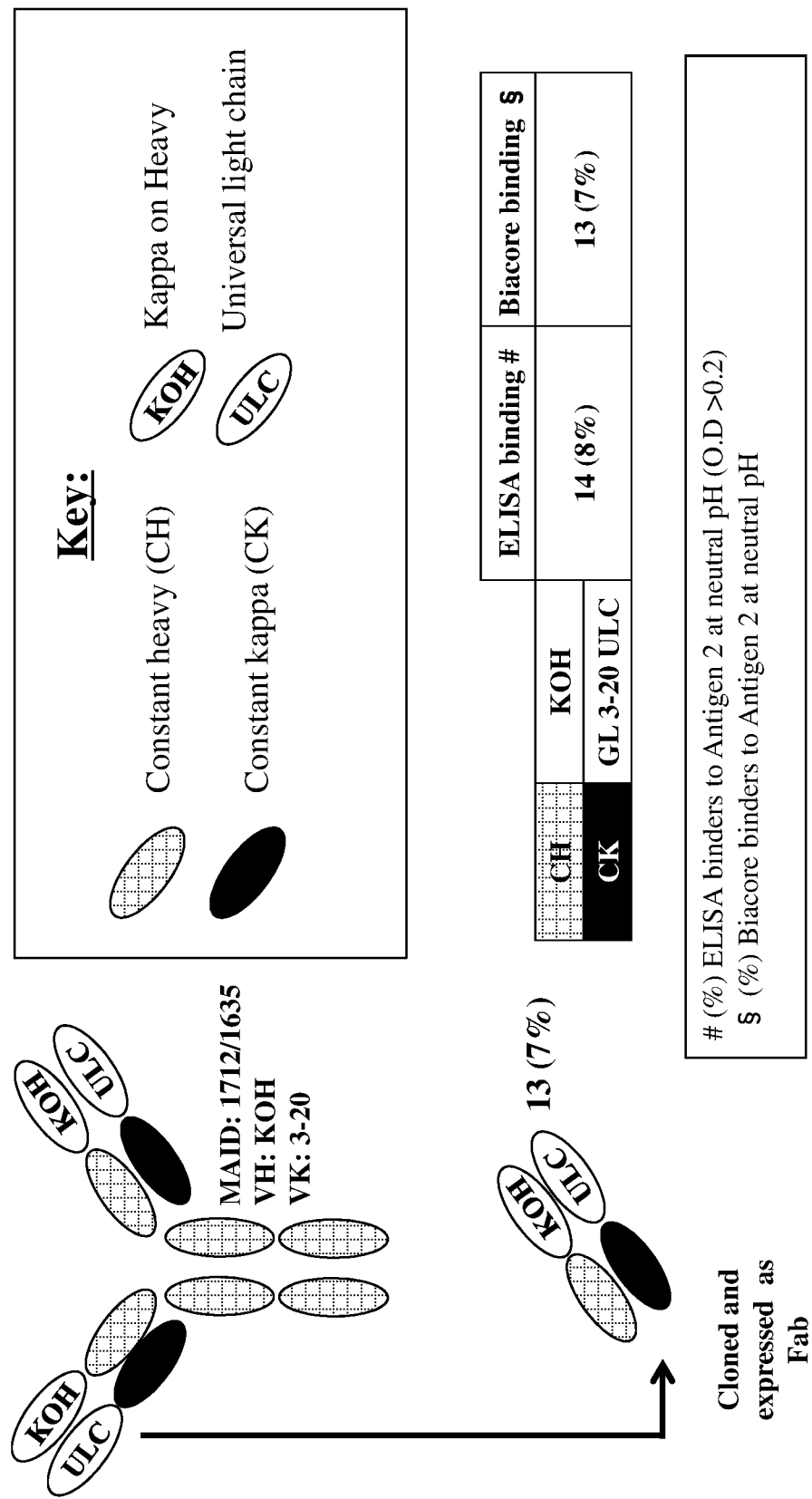
FIG. 17 shows a schematic of antigen specific binding protein Fabs constructed from KOH×ULC mice. Antigen positive B cells were sorted from two KOH×ULC mice following immunization protocol with immunogen Antigen 2. Positive KOH variable domains were cloned into Fab plasmids. KOH variable domains were cloned into heavy constants. Transient transfections were carried out to produce protein for antigen positive screening by ELISA.

Preparation of a $V_{L/CH\times ULC}$, specifically a $V_{\kappa OH\times ULC}$ immunoglobulin light chain variable domain, that retains antigen binding when paired with an unrelated, e.g., non-cognate, human $V_H$ domain was performed. KOH×ULC mice were immunized with a cell surface protein (Antigen 2). Antigen positive B-cells were sorted from two KOH×ULC mice; MAID1712 1635 (KOH×ULC:Vκ3-20Jκ1). Cells were sorted based on Antigen 2 and 1536 B-cells were collected. 384 B-cells were processed from the "best" mouse as judged during sorting. 176 KOH $V_L$ domains, e.g., $V_{\kappa/CH\kappa ULC}$ domains were cloned into Fab plasmids. Individual sequences encoding one of 176 KOH VL domains were cloned into Fab plasmids along with a sequence encoding a human Vκ3-20 germline ULC sequence. Each sequence encoding a KOH VL ($V_{\kappa OH\kappa ULC}$) domain was cloned operably linked with a heavy chain constant region sequence (i.e. CH1) and the ULC sequence was closed operably linked with a light chain constant κ gene sequence. Transient transfections were carried out to produce protein for Ag+ screening. Screening for Antigen 2 binding was assayed by ELISA and BIACORE™. Fourteen (14) samples bound Antigen 2 at neutral pH as determined by ELISA, as shown in FIG. 17. Binding was confirmed by BIACORE™ for 13 of the 14 ELISA binders.

Subsequently, two KOH derived $V_L$ ($V_{\kappa OH\kappa ULC}$) domains were chosen and independently cloned and reformatted with light chain constant regions (i.e., Cκ). Each of the reformatted KOH $V_L$/Cκ chains were independently paired with non-cognate $V_H$ domain formatted with a heavy chain $C_H$ to form a typical antibody structure. Notably, the non-cognate $V_H$ domain was generated in a mouse that was genetically modified to generate all $V_H$ domains from a single rearranged heavy chain variable region sequence, see, e.g., U.S. Patent Publication No. 20140245468, incorporated herein in its entirety by reference, and immunized with an unrelated enzyme (Antigen 3). The reformatted $V_L$ domains were tested for Antigen 2 binding by BIACORE™. Results are shown in FIG. 18.

In FIG. 18, antibodies A and B each comprise an immunoglobulin light chain comprising a distinct KOH $V_L$ ($V_{\kappa OHxULC}$) fused with a Cκ constant domain and an immunoglobulin heavy chain comprising a $V_H$ domain fused with an intact $C_H$ domain. In contrast, while antibody C comprises the same immunoglobulin heavy chain as antibodies A and B, antibody C comprises an immunoglobulin light chain comprising a $V_L$ domain that is cognate to the $V_H$ domain fused with a Cκ domain.

The results show that when a $V_H$ domain derived from a single rearranged heavy chain variable region and raised against Antigen 3 is paired with cognate light chain variable domains, antigen binding to Antigen 3 is maintained (see, FIG. 18; showing antibody C binds to Antigen 3 as expected). Not surprising, when the same $V_H$ domain was paired with a noncognate KOH $V_L$ domain, Antigen 3 binding was undetectable (FIG. 18).

In contrast, Antigen 2 binding was maintained for both KOH $V_L$ ($V_{\kappa OHxULC}$) domains (i.e., antibody A and B $V_L$ domains) despite being (1) reformatted onto a Cκ domain and (2) paired with a non-cognate $V_H$ domain.

The results suggest that KOH antibodies isolated from KOH×ULC mice can bind antigen solely through one $V_L$ domain (i.e., a Vκ domain). This is confirmed by reformatting a KOH $V_L$ ($V_{\kappa OHxULC}$) domain onto a light chain backbone (i.e., a Cκ region) and pairing with a $V_H$ domain raised against a different antigen. Such a molecule was shown to retain binding to the antigen to which the parental KOH antibody (i.e., $V_{\kappa OHxULC}$ domain) was raised.

Taken together, this Example demonstrates that KOH×ULC mice provide a robust in vivo system to select for "antibody-like" molecules that bind antigen solely through a $V_{L/CHxULC}$ domain (e.g., $V\kappa_{/CHxULC}$), i.e., independent of a cognate variable domain. Such mice provide the opportunity to select $V_L$ domains ($V\kappa_{/CHxULC}$ or $V\lambda_{/CHxULC}$) that bind antigen in the absence of a cognate variable domain and/or when paired with a noncognate variable domain. The $V_L$ binding proteins expressed by the mice described herein may provide a novel paratope or binding surface to targets that evolve to avoid conventional antibodies (e.g., HIV and influenza).

Example 4. Making a Multi-Specific Antigen Binding Protein Comprising a $V_{L/CHxULC}$ Domain This example illustrates an exemplary method of making a multi-specific antigen-binding protein comprising a light chain variable $V_{L/CHxULC}$ domain derived from an immunoglobulin hybrid chain that is cognate with a universal light chain. As described in Example 3, a first nucleic acid sequence encoding a KOH $V_L$ domain, e.g., a $V_{\kappa/CHxULC}$, is isolated from a non-human animal genetically modified to comprise in its genome an immunoglobulin hybrid chain locus containing unrearranged human light chain gene segments (e.g., $V_\kappa$ and $J_\kappa$ gene segments) operably linked to a heavy chain constant region sequence and an immunoglobulin light chain locus containing a rearranged immunoglobulin light chain variable sequence (i.e., a universal or common light chain variable region) operably linked to a light chain constant region sequence. A second nucleic acid encoding a second $V_{L/CHxULC}$ domain may also be isolated from a non-human animal genetically modified to comprise in its genome an immunoglobulin hybrid chain locus containing unrearranged human light chain gene segments (e.g., $V_L$ and $J_L$ gene segments) operably linked to a heavy chain constant region sequence and an immunoglobulin light chain locus containing a rearranged immunoglobulin light chain variable sequence (i.e., a universal or common light chain variable region) operably linked to a light chain constant region sequence. Alternatively, a second nucleic acid encoding a heavy chain variable $V_{HxULC}$ domain that binds the second antigen and is cognate to a universal light chain may be isolated from a non-human animal genetically modified with a universal light chain ("ULC"), see, e.g., 2011-0195454 A1, US 2012-0021409A1, US 2012-0192300A1, US 2013-0045492A1, US 2013-0185821A1 and US 2013-0302836A1, incorporated by reference herein in their entireties) or a restricted (limited) immunoglobulin light chain variable region gene segment repertoire (e.g., a restricted immunoglobulin light chain variable segment repertoire comprising two or more but less than the wild type number of human $V_L$ gene segments; for example, a dual light chain, or "DLC", U.S. Patent Application Publication No. US-2013-0198880-A1, incorporated by reference herein in its entirety).

A first binding component encoded by a nucleic acid comprising the first nucleic acid sequence encoding the first a $V_{L/CHxULC}$ domain that binds the first antigen may be co-expressed in a cell with a second binding component encoded by the second nucleic acid comprising a nucleic acid sequence encoding the second variable $V_{L/CHxULC}$ domain or $V_{H/CHxULC}$ domain that binds the second antigen such that the first and second binding components are expressed as a multi-specific, e.g., a bi-specific antigen-binding protein. Exemplary pairing formats include the first and second binding components respectively pairing in an Fv format, an scFv format, a Fab format, an scFab format, a tetrameric antibody format wherein the first and second binding components are each heavy chains comprising a functional $C_H1$ domain associated with a universal light chain, or a tetrameric antibody format wherein one of the first or second binding components is a heavy chains comprising a functional $C_H1$ domain and is associated with the other of the first or second binding component as a light chain KOH×ULC mice comprising unrearranged human light chain variable region gene segments were immunized with Antigen A, a multivalent high molecular weight protein, to form $V_{\kappa/CH\times ULC}$ variable domains specific for Antigen A. ULC mice comprising unrearranged human heavy chain variable region gene segments as described in e.g., 2011-0195454 A1, US 2012-0021409A1, US 2012-0192300A1, US 2013-0045492A1, US 2013-0185821A1 and US 2013-0302836A1, incorporated by reference herein in their entireties, were immunized with Antigen B, a monomeric lower molecular weight protein, to form $V_{H\times ULC}$ variable domains specific for antigen B.

B-cells expressing antigen-binding proteins capable of binding Antigen A or Antigen B were respectively sorted from KOH×ULC or ULC mice as described in U.S. Pat. No. 7,582,298, incorporated herein by reference. Both KOH× ULC and ULC mice used in this study were genetically modified with a ULC encoded by a rearranged immunoglobulin light chain comprising a human Vκ3-20 gene segment rearranged with a human Jκ1 gene segment.

Briefly, red blood cells were removed by lysis followed by pelleting the harvested splenocytes. Resuspended splenocytes were first incubated with a cocktail of human IgG, FITC-anti-mFc, and Antigen A labeled with biotin or Antigen B labeled with biotin (as appropriate) for 1 hour. The stained cells were washed twice with PBS, then stained with a cocktail of human and rat IgG, APC-anti-mIgM, and SA-PE for one hour. The stained cells were washed once with PBS and were analyzed by flow cytometry on a Reflection (Sony). Each IgG positive, IgM negative, and antigen positive B cell was sorted and plated into a separate well on a 384-well plate. RT-PCR of antibody genes from these B cells was performed according to a method described by Wang et al. (2000) (J Immunol Methods 244:217-225).

Briefly, cDNAs for each single B cell were synthesized via reverse transcription (RT). The $V_{\kappa OH\times ULC}$ region DNA sequences from Antigen A immunized κOH×ULC mice were amplified by PCR using a 5' degenerate primer specific for human kappa chain variable region leader sequence and a 3' primer specific for mouse heavy chain constant region, to form an amplicon. The amplicon was then amplified again by PCR using a 5' degenerate primer set specific for framework 1 of human kappa variable region sequence and a nested 3' primer specific for mouse heavy chain constant region. The $V_{KOHXULC}$ PCR product was cloned into a first Sap I-linearized antibody vector containing human IgG1 heavy chain constant region and an expression cassette for the universal light chain derived from the rearranged Vκ3-20Jκ1. The heavy chain variable region DNA sequences from Antigen B immunized ULC mice were amplified by PCR using a 5' degenerate primer specific for human IgG heavy chain variable region leader sequence and a 3' primer specific for mouse heavy chain constant region, to form an amplicon. The amplicon was then amplified again by PCR using a 5' degenerate primer set specific for framework 1 of human IgG heavy chain variable region sequence and a nested 3' primer specific for mouse heavy chain constant region. The $V_{H/CH\times ULC}$ PCR products were cloned into a second Sap I-linearized antibody vectors containing a human IgG1 heavy chain constant region.

Purified recombinant plasmid having a rearranged gene encoding the universal light chain derived from the rearranged Vκ3-20Jκ1 sequence operably linked to a human κ constant gene and a $V_{L/CH\times ULC}$ sequence operably linked with the human IgG1 constant region sequence, and a purified plasmid having a $V_{H/CH\times ULC}$ sequence operably linked with the human IgG1 constant region sequence were combined and transfected into a CHO host cell line. Stably transfected CHO cell pools were isolated after selection with 400 μg/ml hygromycin for 12 days. The CHO cell pools were used to produce the antigen-binding proteins as shown in FIG. 19A.

Equilibrium dissociation constants ($K_D$) for selected antibody supernatants or purified antibodies were determined by SPR (Surface Plasmon Resonance) using a Biacore T200 or 4000 instrument (GE Healthcare). All data was obtained using HBS-EP (10 mM Hepes, 150 mM NaCl, 0.3 mM EDTA, 0.05% Surfactant P20, pH 7.4) as both the running and sample buffers, at 25° C. or 37° C. Antibodies were captured from crude supernatant samples or purified mAbs on a CM4 or CM5 sensor chip surface previously derivatized with a high density of anti-human Fc antibodies using standard amine coupling chemistry. During the capture step, supernatants or purified mAbs were injected across the anti-human Fc surface at a flow rate of 10 μL/min, for a total of 0.5-2.0 minutes. The capture step was followed by an injection of either running buffer or Antigen A at a concentration range from 3.125 nM-100 nM for 1.5-3.0 minutes at a flow rate of 30 μL/min or Antigen B at a concentration range from 0.37 nM-90 nM for for 3.0 minutes. Dissociation of antigens from the captured antibody was monitored for 3.0-5.0 minutes. The captured antibody was removed by a brief injection of 10 mM glycine, pH 1.5. All sensorgrams were double referenced by subtracting sensorgrams from buffer injections from the analyte sensorgrams, thereby removing artifacts caused by dissociation of the antibody from the capture surface. Binding data for each antibody was fitted to a 1:1 binding model with mass transport limitation.

The binding affinities of universal light chain antibodies are shown in FIG. 20, which exhibits $K_D$ values in the nanomolar range. Specifically, all bispecific antibodies (B1-B3) comprising a $V_{\kappa/CH\times ULC}$ binding component, a $V_{H\times ULC}$ binding component, and universal light chain bound to Antigen A with affinities ranging from 6.8 to 9.6 nM at 25° C. (FIG. 20) and with affinities ranging from 100-140 nM and $t_{1/2}$ values of less than about 1 min at 37° C. (data not shown). The bispecific antibodies also bound to Antigen B with affinities ranging from about 5-100 nM at 25° C. (FIG. 20) and with affinities ranging from 174-178 nM at 37° C. (data not shown).

Control monospecific antibodies (antibodies $C_{KOH}1$-$C_{KOH}3$), which were raised against Antigen A and included universal light chain variable domains paired with bivalent $V_{\kappa/CH\times ULC}$ domains, which were respectively cloned to produce the bispecific antibodies B1-B3, bound to Antigen A with affinities ranging from 2-8 nM at 25° C., but not Antigen B (FIG. 20). Without wishing to be bound by theory, it is possible that the differences in the $t_{1/2}$ values at 25° C. observed for Antigen A interactions with the bivalent antibodies ($C_{KOH}1$-$C_{KOH}3$) compared to the bispecific antibodies (B1-B3) may be due to the multivalent nature of Antigen A, which may contribute to a predominantly avidity driven interaction. Dissociation constants ($t_{1/2}$) were not determined for $C_{KOH}1$-$C_{KOH}3$ antibodies at 37° C.

A control monospecific antibody (antibody $C_{VH}$), which was raised against antigen B and included universal light chain variable domains paired with a bivalent $hV_{H\times ULC}$ domain, which was cloned to produce each of bispecific antibodies B1-B3, bound antigen B with an affinity of 5.2 nM at 25° C. and a $t_{1/2}$ value (41.1 min) that was similar to $t_{1/2}$ values (23-31 min) with which Antigen B dissociated from the bispecific antibodies (FIG. 20). Binding of $C_{VH}$ to Antigen B at 37° C. was not tested.

An isotype control antibody (C₁) did not bind to either antigen A or antigen B (FIG. 20). Another control anti-B antibody (C) in typical antibody format, e.g., having two heavy chains, each comprising a $V_H$ domain fused with a $C_H$ domain, and two light chains, each having a $V_L$ domain fused with a $C_L$ domain, bound to antigen B with affinity of 1.4 nM and did not bind to antigen A (FIG. 20).

Taken together, this Example demonstrates that a $V_{L/CH \times ULC}$ domain generated in a KOH×ULC non-human animal is capable of binding antigen in a multi-specific format with another variable domain specific for a second distinct epitope.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

What is claimed is:

1. A mouse comprising in its germline genome:
   (i) at an endogenous immunoglobulin (Ig) heavy chain locus, an unrearranged human Ig light chain variable kappa (Vκ) gene segment and an unrearranged human Ig light chain joining kappa (Jκ) gene segment operably linked to an endogenous Ig heavy chain constant region nucleic acid sequence comprising at least one intact Ig heavy chain constant region gene encoding a functional $C_H1$ domain, wherein the at least one intact Ig heavy chain constant region gene is an Igμ gene, Igδ gene, Igγ gene, Igα gene or an Igε gene, wherein the unrearranged human Ig Vκ gene segment and the unrearranged human Ig Jκ gene segment rearrange in a B cell to form a hybrid sequence comprising a rearranged human Ig Vκ/Jκ gene sequence operably linked to the endogenous Ig heavy κ chain constant region nucleic acid sequence;
   (ii) at an endogenous Ig light chain κ locus, a human universal Ig light chain variable region nucleotide sequence comprising a single human Ig Vκ gene segment rearranged with a single human Ig Jκ gene segment operably linked to an endogenous Ig light chain κ constant region nucleic acid sequence;
   wherein the mouse expresses an antigen-binding protein that comprises a human Ig hybrid chain derived from the rearranged human Ig Vκ/Jκ gene sequence operably linked to the endogenous Ig heavy chain constant region nucleic acid sequence and a cognate light chain derived from the human universal Ig light chain variable region nucleotide sequence at the endogenous Ig light chain locus, wherein the human Ig hybrid chain comprises a human Ig light chain variable κ (hVκ/$_{CHxULC}$) domain fused to an endogenous heavy chain constant IgM, IgD, IgG, IgE or IgA region comprising a functional $C_H1$ domain, and wherein the cognate light chain comprises a human Ig light variable κ domain chain fused to an endogenous light chain κ constant domain.

2. A B cell expressing the antigen-binding protein obtained from the mouse of claim 1.

3. A method of making the mouse of claim 1, comprising modifying a genome of a mouse embryonic stem (ES) cell to comprise
   (i) at an endogenous Ig heavy chain locus, an unrearranged human Ig Vκ gene segment and an unrearranged human Ig Jκ gene segment operably linked to an endogenous Ig heavy chain constant region nucleic acid sequence comprising at least one intact Ig heavy chain constant region gene encoding a functional $CH_1$ domain, wherein the intact Ig heavy chain constant region gene is an Igμ gene, an Igδ gene, an Igγ gene, an Igα gene, or an Igε gene,
   wherein the unrearranged human Ig Vκ gene segment and the unrearranged human Ig Jκ gene segment rearrange in a B cell to form a hybrid sequence comprising a rearranged human Ig Vκ/Jκ gene sequence operably linked to the endogenous Ig heavy chain constant region nucleic acid sequence; and
   (ii) at an endogenous Ig light chain κ locus, a human universal Ig light chain variable region nucleotide sequence comprising a single human Ig Vκ gene segment rearranged with a single human Ig Jκ gene segment operably linked to an endogenous Ig light chain κ constant region nucleic acid sequence.

4. The method of claim 3, wherein modifying the genome of the mouse ES cell comprises
   (i) replacing endogenous Ig VH gene segments, endogenous Ig $D_H$ gene segments and endogenous Ig $J_H$ gene segments at the endogenous Ig heavy chain locus with the unrearranged human Ig Vκ gene segment and Jκ gene segment, and
   (ii) replacing endogenous Ig Vκ gene segments and Jκ gene segments at the endogenous Ig light chain κ locus with the human universal Ig light chain variable region nucleotide sequence.

5. A method of obtaining an hVκ/$_{CHxULC}$ domain or a nucleic acid encoding the hVκ/$_{CHxULC}$ domain, the method comprising
   isolating from the mouse of claim 1 a cell expressing the nucleic acid that encodes the hVκ/$_{CHxULC}$ domain, and obtaining from the cell the hVκ/$_{CHxULC}$ domain or the nucleic acid encoding the hVκ/$_{CHxULC}$ domain.

6. The mouse of claim 1, wherein the unrearranged human Ig Vκ gene segment and the unrearranged human Ig Jκ gene segment comprises a plurality of unrearranged human Ig Vκ gene segments and a plurality of unrearranged human Ig Jκ gene segments, respectively, and wherein the pluralities of unrearranged human Ig Vκ ene segments and unrearranged human Ig Jκ gene segments replace endogenous Ig $V_H$ gene segments, endogenous Ig $D_H$ gene segments, and endogenous Ig $J_H$ gene segments at the endogenous Ig heavy chain locus.

7. The mouse of claim 1, wherein the unrearranged human Ig Vκ gene segment and the unrearranged human Ig Jκ gene segment comprises a plurality of unrearranged human Ig Vκ gene segments and all unrearranged human Ig Jκ gene segments, respectively, and wherein the plurality of unrearranged human Ig Vκ gene segments and all unrearranged human Ig Jκ gene segments replace endogenous Ig $V_H$ gene segments, endogenous Ig $D_H$ gene segments, and endogenous Ig $J_H$ gene segments at the endogenous Ig heavy chain locus.

8. The mouse of claim 1, wherein the unrearranged human Ig Vκ gene segment and the unrearranged human Ig Jκ gene segment comprises at least 40 unrearranged human Ig Vκ gene segments and all unrearranged human Ig Jκ gene segments, respectively, and wherein the at least 40 unrearranged human Ig Vκ gene segments and all unrearranged human Ig Jκ gene segments replace endogenous Ig $V_H$ gene segments, endogenous Ig $D_H$ gene segments, and endogenous Ig $J_H$ gene segments at the endogenous Ig heavy chain locus.

9. The mouse of claim 1, wherein the human universal Ig light chain variable region nucleotide sequence is a rearranged Vκ1-39/Jκ gene sequence or a rearranged Vκ3-20/Jκ gene sequence.

10. The mouse of claim 1,
wherein endogenous Ig Vκ gene segments and/or endogenous Ig Jκ gene segments at the endogenous Ig light chain κ locus are replaced with the human universal Ig light chain variable region nucleotide sequence.

11. The mouse of claim 10, wherein the human universal Ig light chain variable region nucleotide sequence is a rearranged Vκ1-39/Jκ gene sequence or a rearranged Vκ3-20/Jκ gene sequence.

12. The mouse of claim 8, wherein endogenous Ig Vκ gene segments and/or endogenous Ig Jκ gene segments at the endogenous Ig light chain κ locus are replaced with the human universal Ig light chain variable region nucleotide sequence.

13. The mouse of claim 12, wherein the human universal Ig light chain variable region nucleotide sequence is a rearranged Vκ1-39/Jκ gene sequence or a rearranged Vκ3-20/Jκ gene sequence.

14. The method of claim 4, comprising replacing endogenous Ig $V_H$ gene segments, endogenous Ig $D_H$ gene segments, and endogenous Ig $J_H$ gene segments at the endogenous Ig heavy chain locus with a plurality of unrearranged human Ig Vκ gene segments and a plurality of unrearranged human Ig Jκ gene segments.

15. The method of claim 4, comprising replacing endogenous Ig $V_H$ gene segments, endogenous Ig $D_H$ gene segments, and endogenous Ig $J_H$ gene segments at the endogenous Ig heavy chain locus with a plurality of unrearranged human Ig Vκ gene segments and all unrearranged human Ig Jκ gene segments.

16. The method of claim 4, comprising replacing endogenous Ig $V_H$ gene segments, endogenous Ig $D_H$ gene segments, and endogenous Ig $J_H$ gene segments at the endogenous Ig heavy chain locus with at least 40 unrearranged human Ig Vκ gene segments and all unrearranged human Ig Jκ gene segments.

17. The method of claim 4, wherein the human universal Ig light chain variable region nucleotide sequence is a rearranged Vκ1-39/Jκ gene sequence or a rearranged Vκ3-20/Jκ gene sequence.

18. The method of claim 5, wherein the unrearranged human Ig Vκ gene segment and the unrearranged human Jκ gene segment of the mouse comprises a plurality of unrearranged human Ig Vκ gene segments and a plurality of unrearranged human Ig Jκ gene segments, respectively, and wherein the pluralities of unrearranged human Ig Vκ gene segments and unrearranged human Ig Jκ gene segments replace endogenous Ig $V_H$ gene segments, endogenous Ig $D_H$ gene segments, and endogenous Ig $J_H$ gene segments at the endogenous Ig heavy chain locus.

19. The method of claim 5, wherein the unrearranged human Ig Vκ gene segment and the unrearranged human Jκ gene segment of the mouse comprises a plurality of unrearranged human Ig Vκ gene segments and all unrearranged human Ig Jκ gene segments, respectively, and wherein the plurality of unrearranged human Ig Vκ gene segments and all unrearranged human Ig Jκ gene segments replace endogenous Ig $_{VH}$ gene segments, endogenous Ig $D_H$ gene segments, and endogenous Ig $J_H$ gene segments at the endogenous Ig heavy chain locus.

20. The method of claim 5, wherein the unrearranged human Ig Vκ gene segment and the unrearranged human Jκ gene segment of the mouse comprises at least 40 unrearranged human Ig Vκ gene segments and all unrearranged human Ig Jκ gene segments, respectively, and wherein the at least 40 unrearranged human Ig Vκ gene segments and all unrearranged human Ig Jκ gene segments replace endogenous Ig $V_H$ gene segments, endogenous Ig $D_H$ gene segments, and endogenous Ig $J_H$ gene segments at the endogenous Ig heavy chain locus.

21. The method of claim 5, wherein the human universal Ig light chain variable region nucleotide sequence of the mouse is a rearranged Vκ1-39/Jκ gene sequence or a rearranged Vκ3-20/Jκ gene sequence.

22. The method of claim 5,
wherein endogenous Ig Vκ gene segments and/or endogenous Ig Jκ gene segments at the endogenous Ig light chain κ locus are replaced with the human universal Ig light chain variable region nucleotide sequence.

23. The method of claim 22, wherein the human universal Ig light chain variable region nucleotide sequence of the mouse is a rearranged Vκ1-39/Jκ gene sequence or a rearranged Vκ3-20/Jκ gene sequence.

24. The method of claim 20, wherein endogenous Ig Vκ gene segments and/or endogenous Ig Jκ gene segments at the endogenous Ig light chain κ locus are replaced with the human universal Ig light chain variable region nucleotide sequence.

25. The mouse of claim 24, wherein the human universal Ig light chain variable region nucleotide sequence of the mouse is a rearranged Vκ1-39/Jκ gene sequence or a rearranged Vκ3-20/Jκ gene sequence.

* * * * *

UNITED STATES PATENT AND TRADEMARK OFFICE
CERTIFICATE OF CORRECTION

| | |
|---|---|
| PATENT NO. | : 11,111,314 B2 |
| APPLICATION NO. | : 15/559358 |
| DATED | : September 7, 2021 |
| INVENTOR(S) | : Macdonald et al. |

Page 1 of 1

It is certified that error appears in the above-identified patent and that said Letters Patent is hereby corrected as shown below:

In the Claims

Claim 1, Line 16, Column 105, Line 37:
endogenous Ig heavy κ chain constant region nucleic
Should be:
--endogenous Ig heavy chain constant region nucleic--

Claim 6, Line 6, Column 106, Line 63:
unrearranged human Ig Vκ ene segments and unrearranged
Should be:
--unrearranged human Ig Vκ gene segments and unrearranged--

Signed and Sealed this
Twenty-fourth Day of May, 2022

Katherine Kelly Vidal
*Director of the United States Patent and Trademark Office*